US012509449B2

(12) United States Patent
Berger et al.

(10) Patent No.: US 12,509,449 B2
(45) Date of Patent: Dec. 30, 2025

(54) ANTHELMINTIC COMPOUNDS COMPRISING A QUINOLINE STRUCTURE

(71) Applicant: Intervet Inc., Madison, NJ (US)

(72) Inventors: Michael Berger, Wiesbaden (DE); Michael R. Linder, Ingelheim (DE); Carolin Schneider, Hofheim (DE); Janina Tanzler, Nierder-Olm (DE); Ulrich Sondern, Dortmund (DE)

(73) Assignee: Intervet Inc., Rahway, NJ (US)

( * ) Notice: Subject to any disclaimer, the term of this patent is extended or adjusted under 35 U.S.C. 154(b) by 733 days.

(21) Appl. No.: 17/785,656

(22) PCT Filed: Dec. 17, 2020

(86) PCT No.: PCT/EP2020/086666

§ 371 (c)(1),
(2) Date: Jun. 15, 2022

(87) PCT Pub. No.: WO2021/122911

PCT Pub. Date: Jun. 24, 2021

(65) Prior Publication Data

US 2023/0148316 A1 May 11, 2023

(30) Foreign Application Priority Data

Dec. 18, 2019 (EP) .................................... 19217685
Dec. 11, 2020 (EP) .................................... 20213298

(51) Int. Cl.
*C07D 405/12* (2006.01)
*A61P 33/10* (2006.01)
*C07D 215/38* (2006.01)

(52) U.S. Cl.
CPC ............ *C07D 405/12* (2013.01); *A61P 33/10* (2018.01); *C07D 215/38* (2013.01)

(58) Field of Classification Search
CPC .................................................... C07D 405/12
USPC ....................................................... 514/235.2
See application file for complete search history.

(56) References Cited

U.S. PATENT DOCUMENTS

| | | | |
|---|---|---|---|
| 5,399,582 | A | 3/1995 | Endris et al. |
| 5,595,991 | A | 1/1997 | Shoop et al. |
| 5,834,260 | A | 11/1998 | Byrne et al. |
| 5,945,317 | A | 8/1999 | Byrne et al. |
| 5,962,499 | A | 10/1999 | Meinke et al. |
| 6,221,894 | B1 | 4/2001 | Meinke et al. |
| 7,312,248 | B2 | 12/2007 | Meyer et al. |
| 7,361,689 | B2 | 4/2008 | Shuster et al. |
| 8,106,212 | B2 | 1/2012 | Jeschke et al. |
| 2005/0182059 | A1 | 8/2005 | Winzenberg et al. |
| 2006/0128779 | A1 | 6/2006 | Winzenberg et al. |
| 2006/0281695 | A1 | 12/2006 | Meyer et al. |

FOREIGN PATENT DOCUMENTS

| | | | |
|---|---|---|---|
| EP | 0539588 | A1 | 5/1993 |
| WO | 1996029073 | A1 | 9/1996 |
| WO | 2007115643 | A1 | 10/2007 |
| WO | 2010053517 | A2 | 5/2010 |
| WO | 2010075591 | A2 | 7/2010 |
| WO | 2016033341 | A1 | 3/2016 |
| WO | 2017178416 | A1 | 10/2017 |
| WO | 2017192385 | A1 | 11/2017 |
| WO | 2018087036 | A1 | 5/2018 |
| WO | 2019025341 | A1 | 2/2019 |
| WO | 2019170626 | A1 | 9/2019 |
| WO | 2019197468 | A1 | 10/2019 |
| WO | 2019201835 | A1 | 10/2019 |
| WO | 2019206799 | A1 | 10/2019 |
| WO | 2019215182 | A1 | 11/2019 |
| WO | 2019215198 | A1 | 11/2019 |
| WO | 2020053364 | A1 | 3/2020 |
| WO | 2020053365 | A2 | 3/2020 |
| WO | 2020070049 | A1 | 4/2020 |
| WO | 2020079198 | A1 | 4/2020 |
| WO | 2020094363 | A1 | 5/2020 |
| WO | 2020131631 | A1 | 6/2020 |
| WO | 2020169445 | A1 | 8/2020 |
| WO | 2020193341 | A1 | 10/2020 |
| WO | 2020201079 | A1 | 10/2020 |
| WO | 2020201398 | A1 | 10/2020 |
| WO | 2020208036 | A1 | 10/2020 |
| WO | 2020212235 | A1 | 10/2020 |
| WO | 2020219871 | A1 | 10/2020 |

OTHER PUBLICATIONS

Cheng, Jie-Fei et al., Heteroaryl substituted bis-trifluoromethyl carbinols as malonyl-CoA decarboxylase inhibitors, Bioorganic & Medicinal Chemistry Letters, 2006, 3484-3488, 16.
Gerster, John F. et al., Synthesis and Structure-Activity-Relationships of 1H-Imidazo[4,5-c]quinolines That Induce Interferon Production, J. Med. Chem., 2005, 3481-3491, 48.
Higuchi, T., et al., "Pro-drugs as NovelDelivery Systems", A.C.S. Symposium Series, 1987, 14, pp. 1-6.
Kokatla, Hari Prasad et al., Structure-Based Design of Novel Human Toll-like Receptor 8 Agonists, ChemMedChem, 2014, 719-723, 9.
Kotha, Sambasivarao et al., Recent applications of the Suzuki-Miyaura cross-coupling reaction in organic synthesis, Tetrahedron, 2002, 9633-9695, 58.
Pfister, Jurg R. et al., A Useful Variant of the Curtius Reaction, Synthesis, 1983, 38-40, N/A.
Zhang, Jiankang et al., Discovery of a series of N-(5-(quinolin-6-yl)pyridin-3-yl) benzenesulfonamides as PI3K/mTOR dual inhibitors, Eur. J. Med. Chem., 2017, 509-520, 127.
Bastin, R.J.; et al., Salt Selection and Optimization Procedures for Pharmaceutical New Chemical Entities, Organic Process Research and Development, 4, pp. 427-435, 2000.

(Continued)

*Primary Examiner* — Taofiq A Solola
(74) *Attorney, Agent, or Firm* — David J. Kerwick

(57) ABSTRACT

The present invention relates to new anthelmintic compounds. These compounds can for example be used in the treatment of the kind of worm disease caused by helminths such as *Dirofilaria*, in particular *Dirofilaria immitis*.

21 Claims, No Drawings

(56) References Cited

OTHER PUBLICATIONS

Belikov, V.G., Pharmaceutical Chemistry, Moscow MEDpress-inform, 4th Edition, 27-29, 2007, English translation.
Bernstein, J., Bioavailability, Polymorphism of molecular crystals, Ch. 7.3.2, 324-330 (translated pp. 1-9), 2007, English translation.
Dyson, G. and May, P., Chemistry of Synthetic Medicinal Substances, M: World, N/A, 12-19, 1964, English Translation.
Knunyants, I.L. (Editor), Chemical Encyclopedic Dictionary, Moscow, Soviet Encyclopaedia, N/A, 130-131, 1983, Machine translation.
Kummerer, K., Pharmaceuticals in the environment, Annual Review of Environment and Resources, 35, 57-75, 2010.
Pinto M.A.L. et al., Thermoanalytical studies of carbamazepine: hydration/dehydration, thermal decomposition, and solid phase transitions, Brazilian Journal of Pharmaceutical Sciences, 50, 877-884 (English abstract), 2014.
Zawilska, Jolanta B. et al., Prodrugs: A challenge for the drug development, Pharmaceutical Reports, 65(1), 1-14, 2013.
Nagano, Tetsuo et al., Methods for structural optimization, Soyakukagaku, Tokyokagakudojinn Co., Ltd, N/A, 133-136, 2004, machine translation.

ANTHELMINTIC COMPOUNDS COMPRISING A QUINOLINE STRUCTURE

CROSS-REFERENCE TO RELATED APPLICATIONS

This application is a national stage entry under 35 U.S.C. § 371 of PCT/EP2020/086666 filed Dec. 17, 2020, which published as WO 2021/122911 A1 on Jun. 24, 2021, which claims priority to EP Application Serial No. 19217685.7 filed Dec. 18, 2019, and EP Application Serial No. 20213298.1 filed Dec. 11, 2020.

The present invention relates to new anthelmintic compounds. These compounds can for example be used in the treatment of the kind of worm disease caused by helminths such as *Dirofilaria*, in particular *Dirofilaria immitis.*

BACKGROUND

Several severe animal diseases are caused by helminths, wherein the helminths can be categorized in the following groups of a) cestodes: e.g. *Anaplocephala* spp.; *Dipylidium* spp.; *Diphyllobothrium* spp.; *Echinococcus* spp.; *Moniezia* spp.; *Taenia* spp.; b) trematodes e.g. *Dicrocoelium* spp.; *Fasciola* spp.; *Paramphistomum* spp.; *Schistosoma* spp.; or c) nematodes, e.g. *Acanthocheilonema* spp.; *Ancylostoma* spp.; *Anecator* spp.; *Ascaridia* spp.; *Ascaris* spp.; *Brugia* spp.; *Bunostomum* spp.; *Capillaria* spp.; *Chabertia* spp.; *Cooperia* spp.; *Cyathostomum* spp.; *Cylicocyclus* spp.; *Cylicodontophorus* spp.; *Cylicostephanus* spp.; *Craterostomum* spp.; *Dictyocaulus* spp.; *Dipetalonema* spp; *Dirofilaria* spp.; *Dracunculus* spp.; *Enterobius* spp.; *Filaroides* spp.; *Habronema* spp.; *Haemonchus* spp.; *Heterakis* spp.; *Hyostrongylus* spp.; *Metastrongylus* spp.; *Meullerius* spp. *Necator* spp.; *Nematodirus* spp.; *Nippostrongylus* spp.; *Oesophagostomum* spp.; *Onchocerca* spp.; *Onchocercidae* spp; *Ostertagia* spp.; *Oxyuris* spp.; *Parascaris* spp.; *Stephanurus* spp.; *Strongylus* spp.; *Syngamus* spp.; *Toxocara* spp.; *Strongyloides* spp.; *Teladorsagia* spp.; *Toxascaris* spp.; *Trichinella* spp.; *Trichuris* spp.; *Trichostrongylus* spp.; *Triodontophorous* spp.; *Uncinaria* spp., *and/or Wuchereria* spp.

The above helminths cause helminthiasis also known as worm infection. These helminths often live in the gastrointestinal tract of their host, but they may also burrow into other organs, where they induce physiological damage. For example, *Ascaridia* spp. are reported to cause from infections of the small intestine to partial or even total obstruction of the gastrointestinal tract of the affected animal, in particular feather animals such as birds. Further, another helminth, *Haemonchus* spp., are known to affect animals like sheep and goats, wherein such infestation often results in the attachment in the abomasal mucosa for sucking blood from the host. Thus, the affected animal can get anaemic and short of breath. Even further, *Oesophagostomum* spp. are known to cause a nodule formation in the intestines of its infected hosts, which may result in dysentery.

Furthermore, heartworm disease, also known as cardiovascular dirofilariasis, is a serious and mostly fatal disease that may affect inner organs such as lung and heart in pets and certain other mammals. The disease is caused by parasitic nematodes, *Dirofilaria immitis*, which in the adult state can have a length up to about 30 centimetres and a thickness of about 1 millimetre. These nematodes live in the heart, the lung and associated blood vessels causing severe lung disease, heart failure and damage to other inner organs such as the liver and kidneys. Thus, heartworm infection may result in complication for the host, typically culminating in the host's death.

The heartworm disease is known to affect pets, in particular dogs, which are considered as the definitive host. However, also cats, ferrets, wolves, coyotes, jackals, foxes, bears, sea lions and in very rare case even humans (zoonosis) may be affected by heartworms.

Heartworms have to go through different stages before they become adults infecting the host animal. The mosquito plays an essential role in the heartworm's life cycle since it is required as an intermediate host. Adult female heartworms living in an infected host birth to larvae called microfilaria, which can circulate in the bloodstream for as long as two years and are ingested by bloodsucking mosquitos. When a mosquito bites and takes up blood from such an infected host, it picks up said microfilariae, which start to develop in the mosquito such that the first and second larval stages ($L_1$) and ($L_2$) of the heartworm development occurs within the body of a mosquito. Once said larvae have matured into the third larval stage ($L_3$), the infective larval stage, and the mosquito locates and bites a host, these infective larvae are deposited onto the surface of the host's skin and enter the new host through the mosquito's bite such that they are under the skin at the site of the bite. After a short period of about 2 weeks for further growth, they develop into the fourth larval stage ($L_4$) and migrate to the muscles of the chest and abdomen. 45 to 60 days after infection the larvae become immature adults (fifth larval stage; $L_5$) and between 75 and 120 days after infection (bite of the mosquito), these immature heartworms then enter the bloodstream and are carried to the heart and the pulmonary system, where they significantly increase in size over the next about three months. By seven months after the infection (bite of the mosquito) the adult worms have mated, and the females begin giving birth to the above-mentioned microfilaria. The matured heartworms can live for up to about 7 years in dogs and up to about 3 years in cats. Due to the longevity of these worms, each mosquito season can lead to an increasing number of heartworms in an infected pet.

Due to the extensive use of anthelmintic compounds, a highly resistant worm population is reported to have occurred. The occurrence of this resistance against known anthelmintics is considered to cause growing problems for a successful treatment of the above-mentioned diseases.

WO 2018/087036 A1 and WO 2019/025341 A1 both disclose a compound considered as anthelmintic, namely a quinoline 3-carboxamide derivative of the following structure

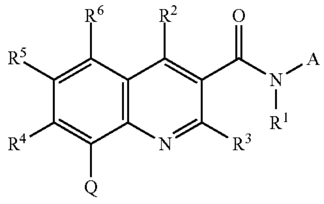

wherein residues $R^1$, $R^2$, $R^3$, $R^4$, $R^5$, $R^6$, A and Q are defined correspondingly.

The molecules are considered as modulators of the calcium-activated potassium channel slo-1 of nematodes, wherein slo-1 can be regarded as the helminth's ortholog of the human KCa1.1 channel (potassium calcium-activated channel subfamily M alpha 1), which is encoded by the KCNMA1 gene (KCa1.1 and KCNMA1 are often used synonymously. Slo-1 exhibits calcium-activated potassium channel activity and voltage-gated potassium channel activity. Slo-1 channels play an important role in the neuromuscular system as well as in secretory cells among others. Thus, slo-1 modulators are reported to be involved in several processes including behavioural response to ethanol, locomotion and pharyngeal pumping. More particularly they disrupt neuromuscular transmission causing a flaccid paralysis and also affect feeding and egg-laying. Further, they slow the development of the larvae and the adults of the corresponding helminth.

Nevertheless, especially in view of the occurrence of resistance to known anthelmintics compounds there is still an urgent need for new active pharmaceutical ingredients that are able to address infections by helminths.

Hence, it is an object of the present invention to overcome one or more of the drawbacks of the prior art.

It is an object to provide new anthelmintic compounds which can be used to address infections in mammals, in particular in pets such as cats and dogs, especially in dogs. In particular, it is an object to provide new anthelmintic compounds which can be used to address infections in mammals by parasitic helminths such as *Ostertagia ostertagi, Cooperia oncophora, Cooperia punctata, Trichostrongylus axei, Haemonchus placei, Haemonchus contortus, Nematodirus helvetianus, Nematodirus spathiger, Trichostrongylus colubriformis, Trichostrongylus circumcincta, Oesophagostomum venulosum, Chabertia ovina, Dictyocaulus viviparous, Dictyocaulus filaria, Dirofilaria immitis, Dirofilaria repens*; b) *Trematodes: Fasciola hepatica, Fascioloides magna, Dicrocoelium dentriticum, Paramphistomum cervi*, c) *Cestodes:Monezia expansai*, especially *Ascaridia galli, Haemonchus contortus, Oesophagostomum dentatum*, and *Acanthocheilonema viteae* and by *Dirofilaria immitis*, in particular infections by *Dirofilaria immitis* (heartworm).

Another object is to provide new anthelmintic compounds which can be used to address infections in mammals, wherein these compounds are compatible with standard antiparasitic treatments in pets, in particular in cats and dogs, especially in dogs. In particular, it is an object to provide new anthelmintic compounds which can be used to address infections in pets such as cats and dogs and which can be administered orally or topically.

More specifically, it is an object to provide new anthelmintic compounds which can be used to address infections in mammals by parasitic helminths, in particular infections by *Dirofilaria immitis* (heartworm), but does not negatively affect the host by undesired side-effects.

Moreover, it an object that said new anthelmintic compounds can be used in different treatment schedules, in particular in monthly or longer treatment schedules.

SUMMARY OF THE INVENTION

Surprisingly it was found that at least one of the objects can be met by providing a compound according to Formula (I)

Formula (I)

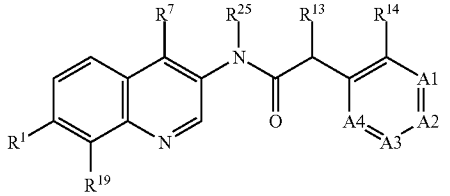

wherein $R^1$ is independently selected from the group consisting of hydrogen, $C_{1-6}$-alkyl, $C_{2-6}$-alkenyl, $C_{2-6}$-alkynyl, $C_{3-10}$-cycloalkyl, 5- to 10-membered heterocyclyl, $C_{6-10}$ aryl, 5- to 10-membered heteroaryl, $C_{1-6}$-alkoxy, $C_{1-6}$-alkylmercapto, halogen, cyano, nitro, hydroxy, mercapto, $NR^2R^3$, COOH, $C(=O)OR^4$, $SR^4$, $SOR^4$, $SO_2R^4$, $SO_2NR^5R^6$ and $C(=O)NR^5R^6$,
 wherein each $C_{1-6}$-alkyl, $C_{2-6}$-alkenyl, $C_{2-6}$-alkynyl, $C_{3-10}$-cycloalkyl, 5- to 10-membered heterocyclyl, $C_{6-10}$ aryl, 5- to 10-membered heteroaryl, $C_{1-6}$-alkoxy or $C_{1-6}$-alkylmercapto, is optionally substituted with one or more substituent(s) independently selected from the group consisting of
 $C_{1-6}$-alkyl, $C_{2-6}$-alkenyl, $C_{2-6}$-alkynyl, $C_{3-10}$-cycloalkyl, 5- to 10-membered heterocyclyl, $C_{6-10}$-aryl, 5- to 10-membered heteroaryl, $C_{1-6}$-alkoxy, $C_{1-6}$-alkylmercapto, halogen, cyano, nitro, hydroxy, mercapto, $NR^{2'}R^{3'}$, $C(=O)OR^{4'}$, $SR^{4'}$, $SOR^{4'}$, $SO_2R^{4'}$, $SO_2NR^{5'}R^{6'}$ and $C(=O)NR^{5'}R^{6'}$, $R^2$ and $R^3$ are independently selected from the group consisting of
 hydrogen, $C_{1-6}$-alkyl, $C_{2-6}$-alkenyl, $C_{2-6}$-alkynyl, $C_{3-10}$-cycloalkyl, 5- to 10-membered heterocyclyl, $C_{6-10}$-aryl, 5- to 10-membered heteroaryl, $C_{1-6}$-alkoxy-$C_{1-6}$-alkyl, $C_{1-6}$-alkyl substituted with $C_{3-10}$-cycloalkyl, $C_{1-6}$-alkyl substituted with 5- to 10-membered heterocyclyl, $C_{1-6}$-alkyl substituted with $C_{6-10}$-aryl and $C_{1-6}$-alkyl substituted with 5- to 10-membered heteroaryl, or $R^2$ and $R^3$ together with the N atom to which they are attached form a saturated or unsaturated heterocyclic ring having 3 to 12 ring atoms, wherein 0, 1, 2 or 3 further ring atoms are selected from N, S and O,
 wherein each $C_{1-6}$-alkyl, $C_{2-6}$-alkenyl, $C_{2-6}$-alkynyl, $C_{3-10}$-cycloalkyl, 5- to 10-membered heterocyclyl, $C_{6-10}$-aryl, 5- to 10-membered heteroaryl, $C_{1-6}$-alkoxy-$C_{1-6}$-alkyl, $C_{1-6}$-alkyl substituted with $C_{3-10}$-cycloalkyl, $C_{1-6}$-alkyl substituted with 5- to 10-membered heterocyclyl, $C_{1-6}$-alkyl substituted with $C_{6-10}$-aryl or $C_{1-6}$-alkyl substituted with 5- to 10-membered heteroaryl or the heterocyclic ring formed by $R^2$ and $R^3$ together with the N atom to which they are attached is optionally substituted with one or more substituent(s) independently selected from the group consisting of
 $C_{1-6}$-alkyl, $C_{2-6}$-alkenyl, $C_{2-6}$-alkynyl, $C_{3-10}$-cycloalkyl, 5- to 10-membered heterocyclyl, $C_{6-10}$-aryl, 5- to 10-membered heteroaryl, $C_{1-6}$-alkoxy, carbonyl, halogen, cyano, hydroxy, mercapto, $NR^{2''}R^{3''}$, $C(=O)OR^{4''}$, $SR^{4''}$, $SOR^4$, $SO_2R^{4''}$, $SO_2NR^{5''}R^{6''}$ and $C(=O)NR^{5''}R^{6''}$;

$R^4$, $R^5$ and $R^6$ are independently selected from hydrogen and $C_{1-6}$-alkyl, $R^{2'}$, $R^{3'}$, $R^{4'}$, $R^{5'}$ and $R^{6'}$ are independently selected from hydrogen and $C_{1-6}$-alkyl, $R^{2''}$, $R^{3''}$, $R^{4''}$, $R^{5''}$ and $R^{6''}$ are independently selected from hydrogen and $C_{1-6}$-alkyl, $R^7$ is independently selected from the group consisting of hydrogen, $C_{1-6}$-alkyl, $C_{2-6}$-alkenyl, $C_{2-6}$-alkynyl, $C_{3-10}$-cycloalkyl, 4- to 10-membered heterocyclyl, $C_{6-10}$ aryl, 5- to 10-membered heteroaryl, $C_{1-6}$-alkoxy, $C_{1-6}$-alkylmercapto, halogen, cyano, nitro, hydroxy, mercapto, $NR^8R^9$, COOH, $C(=O)OR^{10}$, $SR^{10}$, $SOR^{10}$, $SO_2R^{10}$, $SO_2NR^{11}R^{12}$ and $C(=O)NR^{11}R^{12}$ wherein each $C_{1-6}$-alkyl, $C_{2-6}$-alkenyl, $C_{2-6}$-alkynyl, $C_{3-10}$-cycloalkyl, 4- to 10-membered heterocyclyl, $C_{6-10}$ aryl, 5- to 10-membered heteroaryl, $C_{1-6}$-alkoxy or $C_{1-6}$-alkylmercapto, is optionally substituted with one or more substituent(s) independently selected from the group consisting of $C_{1-6}$-alkyl, $C_{2-6}$-alkenyl, $C_{2-6}$-alkynyl, $C_{3-10}$-cycloalkyl, 5- to 10-membered heterocyclyl, $C_{6-10}$-aryl, 5- to 10-membered heteroaryl, $C_{1-6}$-alkoxy, $C_{1-6}$-alkylmercapto, halogen, cyano, nitro, hydroxy, mercapto, $NR^{8'}R^{9'}$, $C(=O)OR^{10'}$, $SR^{10'}$, $SOR^{10'}$, $SO_2R^{10'}$, $SO_2NR^{11'}R^{12'}$ and $C(=O)NR^{11'}R^{12'}$, $R^8$ and $R^9$ are independently selected from the group consisting of hydrogen, $C_{1-6}$-alkyl, $C_{2-6}$-alkenyl, $C_{2-6}$-alkynyl, $C_{3-10}$-cycloalkyl, 5- to 10-membered heterocyclyl, $C_{6-10}$-aryl, 5- to 10-membered heteroaryl, $C_{1-6}$-alkoxy-$C_{1-6}$-alkyl, $C_{1-6}$-alkyl substituted with $C_{3-10}$-cycloalkyl, $C_{1-6}$-alkyl substituted with 5- to 10-membered heterocyclyl, $C_{1-6}$-alkyl substituted with $C_{6-10}$-aryl, $C_{1-6}$-alkyl substituted with 5- to 10-membered heteroaryl, or $R^8$ and $R^9$ together with the N atom to which they are attached form a saturated or unsaturated heterocyclic ring having 3 to 12 ring atoms, wherein 0, 1, 2, or 3 further ring atoms are selected from N, S and O, wherein each $C_{1-6}$-alkyl, $C_{2-6}$-alkenyl, $C_{2-6}$-alkynyl, $C_{3-10}$-cycloalkyl, 5- to 10-membered heterocyclyl, $C_{6-10}$-aryl, 5- to 10-membered heteroaryl, $C_{1-6}$-alkoxy-$C_1$-6-alkyl, $C_{1-6}$-alkyl substituted with $C_{3-10}$-cycloalkyl, $C_{1-6}$-alkyl substituted with 5- to 10-membered heterocyclyl, $C_{1-6}$-alkyl substituted with $C_{6-10}$-aryl or $C_{1-6}$-alkyl substituted with 5- to 10-membered heteroaryl or the heterocyclic ring formed by $R^8$ and $R^9$ together with the N atom to which they are attached is optionally substituted with one or more substituent(s) independently selected from the group consisting of $C_{1-6}$-alkyl, $C_{2-6}$-alkenyl, $C_{2-6}$-alkynyl, $C_{3-10}$-cycloalkyl, 5- to 10-membered heterocyclyl, $C_{6-10}$-aryl, 5- to 10-membered heteroaryl, $C_{1-6}$-alkoxy, carbonyl, halogen, cyano, hydroxy, mercapto, $NR^{8''}R^{9''}$, $C(=O)OR^{10''}$, $SR^{10''}$, $SOR^{10''}$, $SO_2R^{10''}$, $SO_2NR^{11''}R^{12''}$ and $C(=O)NR^{11''}R^{12''}$;

$R^{10}$, $R^{11}$ and $R^{12}$ are independently selected from hydrogen and $C_{1-6}$-alkyl, $R^{8'}$, $R^{9'}$, $R^{10'}$, $R^{11'}$ and $R^{12'}$ are independently selected from hydrogen and $C_{1-6}$-alkyl, $R^{8''}$, $R^{9''}$, $R^{10''}$, $R^{11''}$ and $R^{12''}$ are independently selected from hydrogen and $C_{1-6}$-alkyl, $R^{13}$ is hydrogen or $C_{1-3}$ alkyl, $R^{14}$ is hydrogen, $C_{1-3}$ alkyl, $C_{1-3}$ alkoxy, $NR^{14'}R^{14''}$, wherein $R^{14'}$ and $R^{14''}$ are independently $C_{1-3}$-alkyl or $R^{13}$ and $R^{14}$ together with the atoms to which they are attached form a 5 or 6-carbon atoms containing non-aromatic ring, wherein the 5 or 6-carbon atoms containing ring is optionally substituted with one or more $C_{1-3}$-alkyl or =O, and/or wherein one or more of the ring forming carbon atoms are optionally replaced by —NH—, —N=, =N—, —O—, —S(O)—, —S(O)$_2$— or —S—, or $R^{13}$ and $R^{14}$ together with the atoms to which they are attached form a 5 or 6-carbon atoms containing aromatic ring, wherein the 5 or 6-carbon atoms containing ring is optionally substituted with one or more $C_{1-3}$-alkyl and/or wherein one or more of the ring forming carbon atoms are optionally replaced by —NH—, —N=, =N—, —O— or —S—, A1 is N or $CR^{15}$, wherein $R^{15}$ is independently hydrogen, halogen, $C_{1-3}$ alkyl, $C_{1-3}$ alkoxy, or $NR^{15'}R^{15''}$, wherein $R^{15'}$ and $R^{15''}$ are independently $C_{1-3}$-alkyl, A2 is N or $CR^{16}$, wherein $R^{16}$ is independently hydrogen, halogen, $C_{1-3}$ alkyl, $C_{1-3}$ alkoxy, or $NR^{16'}R^{16''}$, wherein $R^{16'}$ and $R^{16''}$ are independently $C_{1-3}$-alkyl, A3 is N or $CR^{17}$, wherein $R^{17}$ is independently hydrogen, halogen, $C_{1-3}$ alkyl, $C_{1-3}$ alkoxy, or $NR^{17'}R^{17''}$, wherein $R^{17'}$ and $R^{17''}$ are independently $C_{1-3}$-alkyl, A4 is N or $CR^{18}$, wherein $R^{18}$ is independently hydrogen, halogen $C_{1-3}$ alkyl, $C_{1-3}$ alkoxy, or $NR^{18''}R^{18''}$, wherein $R^{18'}$ and $R^{18''}$ are independently $C_{1-3}$-alkyl, $R^{19}$ is independently selected from the group consisting of $C_{6-10}$-aryl and 5- to 10-membered heteroaryl, wherein each $C_{6-10}$-aryl or 5- to 10-membered heteroaryl is optionally substituted with one or more substituent(s) independently selected from the group consisting of $C_{1-6}$-alkyl, $C_{2-6}$-alkenyl, $C_{3-10}$-cycloalkyl, 5- to 10-membered heterocyclyl, $C_{6-10}$-aryl, 5- to 10-membered heteroaryl, $C_{1-6}$-alkoxy, $C_{1-6}$-alkylmercapto, halogen, cyano, nitro, hydroxy, mercapto, $NR^{20}R^{21}$, $C(=O)OR^{22}$, $SR^{22}$, $SOR^{22}$, $SO_2R^{22}$, $SO_2NR^{23}R^{24}$ and $C(=O)NR^{23}R^{24}$, $R^{20}$ and $R^{21}$ are independently selected from the group consisting of hydrogen, $C_{1-6}$-alkyl, $C_{3-10}$-cycloalkyl, $C_{6-10}$-aryl, 5- to 10-membered heteroaryl, $C_{1-6}$-alkoxy-$C_{1-6}$-alkyl, $C_1$-$C_6$-alkyl substituted with $C_{6-10}$-aryl, $C_{1-6}$-alkyl substituted with 5- to 10-membered heteroaryl, or $R^{20}$ and $R^{21}$ together with the N atom to which they are attached form a saturated or unsaturated heterocyclic ring having 3 to 12 ring atoms, wherein 0, 1, 2, or 3 further ring atoms are selected from N, S and O;

wherein each $C_{1-6}$-alkyl, $C_{2-6}$-alkenyl, $C_{3-10}$-cycloalkyl, 5- to 10-membered heterocyclyl, $C_{6-10}$-aryl, 5- to 10-membered heteroaryl, $C_{1-6}$-alkoxy or $C_{1-6}$-alkylmercapto or the heterocyclic ring formed by $R^{20}$ and $R^{21}$ together with the N atom to which they are attached is optionally substituted with one or more substituents independently selected from the group consisting of $C_{1-6}$-alkyl, $C_{2-6}$-alkenyl, $C_{2-6}$-alkynyl, $C_{3-10}$-cycloalkyl, 5- to 10-membered heterocyclyl, $C_{6-10}$-aryl, 5- to 10-membered heteroaryl, $C_{1-6}$-alkoxy, carbonyl, halogen, cyano, hydroxy, mercapto, $NR^{20'}R^{21'}$, $C(=O)OR^{22'}$ $SR^{22'}$, $SOR^{22'}$, $SO_2R^{22'}$, $SO_2NR^{23'}R^{24'}$ and $C(=O)NR^{23'}R^{24'}$ $R^{22}$, $R^{23}$ and $R^{24}$ are independently selected from hydrogen and $C_{1-6}$-alkyl, $R^{20'}$, $R^{21'}$, $R^{22'}$, $R^{23'}$ and $R^{24'}$ are independently selected from hydrogen and $C_{1-6}$-alkyl, $R^{25}$ is independently selected from hydrogen and $C_{1-6}$-alkyl, or a stereoisomer, physiologically acceptable salt, ester, solvate, polymorph, prodrug or mixtures thereof.

In one embodiment of the invention and/or embodiments thereof, $R^1$ is independently selected from the group consisting of hydrogen, $C_{1-6}$-alkyl, $C_{1-6}$-alkoxy, halogen, cyano, nitro, hydroxy, $NR^2R^3$, $C(=O)OR^4$ and $C(=O)NR^5R^6$, wherein each $C_{1-6}$-alkyl or $C_{1-6}$-alkoxy is optionally substituted with one or more substituents independently selected from the group consisting of $C_{1-6}$-alkyl, $C_{1-6}$-alkoxy, halogen, cyano, nitro, hydroxy and $NR^{2'}R^{3'}$, $R^2$ and $R^3$ are independently selected from the group consisting of hydrogen, $C_{1-6}$-alkyl, $C_{3-10}$-cycloalkyl, $C_{6-10}$-aryl and 5 to 10-membered heteroaryl, or $R^2$ and $R^3$ together with the N atom to which they are attached form a saturated or unsaturated heterocyclic ring having 3 to 12 ring atoms, wherein 1 ring atom is N and wherein 0, 1, 2 or 3 further ring atoms are selected from N, S and O;

wherein each $C_{1-6}$-alkyl, $C_{3-10}$-cycloalkyl, $C_{6-10}$-aryl or 5 to 10-membered heteroaryl or the heterocyclic ring formed by $R^2$ and $R^3$ together with the N atom to which they are attached is optionally substituted with one or more substituent(s) independently selected from the group consisting of $C_{1-6}$-alkyl, $C_{3-10}$-cycloalkyl and $C_{1-6}$-alkoxy, $R^4$, $R^5$ and $R^6$ are independently selected from hydrogen and $C_{1-6}$-alkyl, $R^{2'}$ and $R^{3'}$ are independently selected from hydrogen and $C_{1-6}$-alkyl.

In one embodiment of the invention and/or embodiments thereof, $R^1$ is independently selected from the group consisting of hydrogen, $C_{1-6}$-alkyl, $C_{1-6}$-alkoxy and halogen, wherein each $C_{1-6}$-alkyl or $C_{1-6}$-alkoxy is optionally substituted with one or more substituent(s) independently selected from the group consisting of $C_{1-6}$-alkyl, $C_{1-6}$-alkoxy, halogen, cyano, hydroxy and $NR^{2'}R^{3'}$, wherein $R^{2'}$ and $R^{3'}$ are independently selected from hydrogen and $C_{1-3}$-alkyl.

In one embodiment of the invention and/or embodiments thereof, $R^1$ is independently selected from the group consisting of hydrogen, methyl, trifluoromethyl, ethyl, methoxy, ethoxy, fluoride and chloride.

In one embodiment of the invention and/or embodiments thereof, $R^7$ is independently selected from the group consisting of hydrogen, $C_{1-6}$-alkyl, $C_{2-6}$-alkenyl, $C_{3-10}$-cycloalkyl, 4- to 10 membered heterocyclyl, $C_{1-6}$-alkoxy, halogen, cyano, hydroxy, $NR^8R^9$, $C(=O)OR^{10}$, $SR^{10}$, $SOR^{10}$, $SO_2R^{10}$ and $C(=O)NR^{11}R^{12}$, wherein each $C_{1-6}$-alkyl, $C_{2-6}$-alkenyl, $C_{3-10}$-cycloalkyl, 4- to 10 membered heterocyclyl or $C_{1-6}$-alkoxy is optionally substituted with one or more substituent(s) independently selected from the group consisting of $C_{1-6}$-alkyl, $C_{3-10}$-cycloalkyl, 5- to 10 membered heterocyclyl, $C_{1-6}$-alkoxy, halogen, cyano, hydroxy, $NR^{8'}R^{9'}$, $C(=O)OR^{10'}$, and $C(=O)NR^{11'}R^{12'}$, $R^8$ and $R^9$ are independently selected from the group consisting of hydrogen, $C_{1-6}$-alkyl, $C_{3-10}$-cycloalkyl, $C_{6-10}$-aryl, 5- to 10 membered heterocyclyl and 5- to 10 membered heteroaryl, or $R^8$ and $R^9$ together with the N atom to which they are attached form a saturated or unsaturated heterocyclic ring having 3 to 12 ring atoms, wherein 1 ring atom is N and wherein 0, 1, 2, or 3 further ring atoms are selected from N, S and O;

wherein each $C_{1-6}$-alkyl, $C_{3-10}$-cycloalkyl, $C_{6-10}$-aryl, 5- to 10 membered heterocyclyl, and 5- to 10 membered heteroaryl or the heterocyclic ring formed by $R^8$ and $R^9$ together with the N atom to which they are attached is optionally substituted with one or more substituent(s) independently selected from the group consisting of $C_{1-6}$-alkyl, $C_{1-6}$-alkoxy, halogen, cyano, hydroxy, $NR^{8''}R^{9''}$, $C(=O)-OR^{10''}$ and $C(=O)NR^{11''}R^{12''}$;

$R^{10}$, $R^{11}$ and $R^{12}$ are independently selected from hydrogen and $C_{1-6}$-alkyl, $R^{8'}$, $R^{9'}$, $R^{10'}$, $R^{11'}$ and $R^{12'}$ are independently selected from hydrogen and $C_{1-6}$-alkyl, $R^{8''}$, $R^{9''}$, $R^{10''}$, $R^{11''}$ and $R^{12''}$ are independently selected from hydrogen and $C_{1-6}$-alkyl.

In one embodiment of the invention and/or embodiments thereof, $R^7$ is independently selected from the group consisting of hydrogen, $C_{1-6}$-alkyl, $C_{2-6}$-alkenyl, 4- to 10 membered heterocyclyl, $C_{1-6}$-alkoxy, hydroxy, $NR^8R^9$, $C(=O)OR^{10}$, $SR^{10}$, $SOR^{10}$, $SO_2R^{10}$ and $C(=O)NR^{11}R^{12}$, wherein each $C_{1-6}$-alkyl, $C_{2-6}$-alkenyl, 4- to 10 membered heterocyclyl or $C_{1-6}$-alkoxy is optionally substituted with one or more substituent(s) independently selected from the group consisting of $C_{1-6}$-alkyl, 5- to 10 membered heterocyclyl, $C_{1-6}$-alkoxy, halogen, cyano, hydroxy, $NR^{8'}R^{9'}$, $C(=O)OR^{10'}$ and $C(=O)NR^{11'}R^{12'}$, $R^8$ and $R^9$ are independently selected from the group consisting of hydrogen, $C_{1-6}$-alkyl, $C_{6-10}$-aryl, and 5- to 10 membered heteroaryl, or $R^8$ and $R^9$ together with the N atom to which they are attached form a saturated or unsaturated heterocyclic ring having 3 to 12 ring atoms, wherein 1 ring atom is N and wherein 0, 1, 2 or 3 further ring atoms are selected from N, S and O;

wherein the $C_{1-6}$-alkyl, $C_{6-10}$-aryl, and 5- to 10 membered heteroaryl or the heterocyclic ring formed by $R^8$ and $R^9$ together with the N atom to which they are attached is optionally substituted with one or more substituent(s) independently selected from the group consisting of $C_{1-6}$-alkyl, $C_{1-6}$-alkoxy, hydroxy and $NR^{8''}R^{9''}$;

$R^{10}$, $R^{11}$ and $R^{12}$ are independently selected from hydrogen or $C_{1-6}$-alkyl, $R^{8'}$, $R^{9'}$, $R^{10'}$, $R^{11'}$ and $R^{12'}$ are independently selected from hydrogen or $C_{1-6}$-alkyl.

$R^{8''}$ are $R^{9''}$ are independently selected from hydrogen or $C_{1-6}$-alkyl.

In one embodiment of the invention and/or embodiments thereof, $R^7$ is independently selected from the group consisting of methyl, ethyl, propyl, isopropyl, isopropenyl, methoxy, ethoxy, isopropoxy, hydroxy, methyl sulfoxyl, methyl sulfonyl methylthio, amino, methylamino, ethylamino, (ethyl)(methyl)amino, isopropylamino, dimethylamino, (isopropyl)(methyl)amino, hydroxyethylamino, (hydroxyethyl)(methyl)amino methoxyethylamino, (methoxyethyl)(methyl)amino, morpholin-4-yl, pyrrolidin-1-yl, 3-hydroxy-pyrrolidin-1-yl 3-fluoroazetidinyl and 3,3-difluoroazetidinyl.

In one embodiment of the invention and/or embodiments thereof, $R^{13}$ and $R^{14}$ together with the atoms to which they are attached form a 5 or 6-carbon atoms containing non-aromatic ring, wherein the 5 or 6-carbon atoms containing ring is optionally substituted with one or more $C_{1-3}$-alkyl or =O, and/or wherein one or more of the ring forming carbon atoms are optionally replaced by —NH—, —N=, =N—, —O—, —S(O)—, —$S(O)_2$— or —S—, A1 is N or $CR^{15}$, wherein $R^{15}$ is independently hydrogen, halogen, $C_{1-3}$ alkyl, $C_{1-3}$ alkoxy, or $NR^{15'}R^{15''}$, wherein $R^{15'}$ and $R^{15''}$ are independently $C_{1-3}$-alkyl, A2 is N or $CR^{16}$, wherein $R^{16}$ is independently hydrogen, halogen, $C_{1-3}$ alkyl, $C_{1-3}$ alkoxy, or $NR^{16'}R^{16''}$, wherein $R^{16'}$ and $R^{16''}$ are independently $C_{1-3}$-alkyl, A3 is N or $CR^{17}$, wherein $R^{17}$ is independently hydrogen, halogen, $C_{1-3}$ alkyl, $C_{1-3}$ alkoxy, or $NR^{17'}R^{17''}$, wherein $R^{17'}$ and $R^{17''}$ are independently $C_{1-3}$-alkyl, A4 is N or $CR^{18}$, wherein $R^{18}$ is independently hydrogen, halogen $C_{1-3}$ alkyl, $C_{1-3}$ alkoxy, or $NR^{18'}R^{18''}$, wherein $R^{18'}$ and $R^{18''}$ are independently $C_{1-3}$-alkyl, In one embodiment of the invention and/or embodiments thereof, $R^{13}$ and $R^{14}$ together with the atoms to which they are attached form a 5 or 6-carbon atoms containing aromatic ring, wherein the 5 or 6-carbon atoms containing ring is optionally substituted with one or more $C_{1-3}$-alkyl, and/or wherein one or more of the ring forming carbon atoms are optionally replaced by —NH—, —N=, =N—, —O— or —S—, A1 is N or $CR^{15}$, wherein $R^{15}$ is independently hydrogen, halogen, $C_{1-3}$ alkyl, $C_{1-3}$ alkoxy, or $NR^{15'}R^{15''}$, wherein $R^{15'}$ and $R^{15''}$ are independently $C_{1-3}$-alkyl, A2 is N or $CR^{16}$, wherein $R^{16}$ is independently hydrogen, halogen, $C_{1-3}$ alkyl, $C_{1-3}$ alkoxy, or $NR^{16'}R^{16''}$, wherein $R^{16'}$ and $R^{16''}$ are independently $C_{1-3}$-alkyl, A3 is N or $CR^{17}$, wherein $R^{17}$ is independently hydrogen, halogen, $C_{1-3}$ alkyl, $C_{1-3}$ alkoxy, or $NR^{17'}R^{17''}$, wherein $R^{17'}$ and $R^{17''}$ are independently $C_{1-3}$-alkyl, A4 is N or $CR^{18}$, wherein $R^{18}$ is independently hydrogen, halogen $C_{1-3}$ alkyl, $C_{1-3}$ alkoxy, or $NR^{18'}R^{18''}$, wherein $R^{18'}$ and $R^{18''}$ are independently $C_{1-3}$-alkyl.

In one embodiment of the invention and/or embodiments thereof, none, one or two residues of A1, A2, A3 and A4 is N.

In one embodiment of the invention and/or embodiments thereof,

A1 is $CR^{15}$, A2 is $CR^{16}$, A3 is $CR^{17}$ and A4 is $CR^{1''}$.

In one embodiment of the invention and/or embodiments thereof, $R^{19}$ is independently selected from the group consisting of $C_{6-10}$-aryl and 5- to 10-membered heteroaryl, wherein each $C_{6-10}$-aryl or 5- to 10-membered heteroaryl is optionally substituted with one or more substituent(s) independently selected from the group consisting of $C_{1-6}$-alkyl, $C_{3-10}$-cycloalkyl, 5- to 10-membered heterocyclyl, $C_{6-10}$-aryl, 5- to 10-membered heteroaryl, $C_{1-6}$-alkoxy, halogen, cyano, nitro, hydroxy, $NR^{20}R^{21}$, C(=O)$OR^{22}$ and C(=O)$NR^{23}R^{24}$, $R^{20}$ and $R^{21}$ are independently selected from the group consisting of hydrogen, $C_{1-6}$-alkyl, $C_{3-10}$-cycloalkyl and $C_{6-10}$-aryl or $R^{20}$ and $R^{21}$ together with the N atom to which they are attached form a saturated or unsaturated heterocyclic ring having 3 to 12 ring atoms, wherein 0, 1, 2, or 3 further ring atoms are selected from N, S and O;

wherein each $C_{1-6}$-alkyl, $C_{3-10}$-cycloalkyl or $C_{6-10}$-aryl or the heterocyclic ring formed by $R^{20}$ and $R^{21}$ together with the N atom to which they are attached is optionally substituted with one or more substituents independently selected from the group consisting of $C_{1-6}$-alkyl, $C_{3-10}$-cycloalkyl, 5- to 10-membered heterocyclyl, $C_{6-10}$-aryl, 5- to 10-membered heteroaryl, $C_{1-6}$-alkoxy, halogen, cyano, hydroxy, $NR^{20'}R^{21'}$, C(=O)$OR^{22'}$ and C(=O)$NR^{23'}R^{24'}$ $R^{22}$, $R^{23}$ and $R^{24}$ are independently selected from hydrogen and $C_{1-6}$-alkyl, $R^{20'}$, $R^{21'}$, $R^{22'}$, $R^{23'}$ and $R^{24'}$ are independently selected from hydrogen and $C_{1-6}$-alkyl.

In one embodiment of the invention and/or embodiments thereof, $R^{19}$ is independently selected from the group consisting of $C_{6-10}$-aryl and 5- to 10-membered heteroaryl wherein each $C_{6-10}$-aryl or 5- to 10-membered heteroaryl is optionally substituted with one or more substituent(s) independently selected from the group consisting of $C_{1-6}$-alkyl, $C_{1-6}$-alkoxy, halogen, cyano, nitro and hydroxy.

In one embodiment of the invention and/or embodiments thereof, $R^{19}$ is $C_{6-10}$-aryl, wherein the $C_{6-10}$-aryl is optionally substituted with one or more substituent(s) independently selected from the group consisting of $C_{1-6}$-alkyl, halogen, cyano and nitro.

In one embodiment of the invention and/or embodiments thereof, $R^{19}$ is $C_{6-10}$-aryl, wherein the $C_{6-10}$-aryl is phenyl substituted with one, two or three substituents independently selected from the group consisting of fluoride, chloride and bromide.

In one embodiment of the invention and/or embodiments thereof, $R^{25}$ is hydrogen.

In one embodiment of the invention and/or embodiments thereof the compound according to Formula (I) is present in form of the (S)-enantiomer.

Further, the present invention provides a process for preparing the compound according to Formula (I) comprising the step of reacting a compound of Formula (A)

Formula (A)

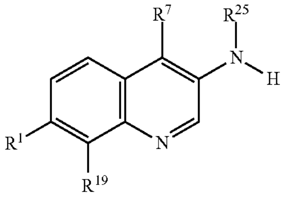

with a compound of Formula (B)

Formula (B)

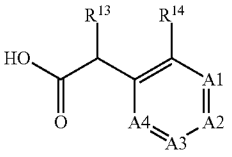

wherein $R^1$, $R^7$, $R^{13}$, $R^{14}$, A1, A2, A3, A4, $R^9$ and $R^{25}$ are defined as in any one of embodiments as disclosed herein to obtain the compound according to Formula (I).

Further, the present invention provides a veterinary composition comprising compound according to Formula (I) as defined in any one of the embodiments as described herein, and one or more physiologically acceptable excipient(s).

In one embodiment of the invention and/or embodiments thereof, the one or more physiologically acceptable excipient(s) are selected from carriers, fillers, flavours, binders, antioxidants, buffers, sugar components, lubricants, surfactants, stabilizers, flow agents, disintegration agents and preservatives and mixtures thereof.

Further, the present invention provides compounds according to Formula (I) as defined in any one of the embodiments as described herein or the veterinary composition according to the invention for use as a medicament.

Further, the present invention provides compounds according to Formula (I) or the veterinary composition according to the invention for use in the treatment of disorders/diseases caused by helminths.

In one embodiment of the invention and/or embodiments thereof, the disease is the filariasis and in particular heartworm disease.

In one embodiment of the invention and/or embodiments thereof, the helminths are *Dirofilaria immitis.*

DETAILED DESCRIPTION

It was found that compounds according to Formula (I) or a stereoisomer, physiologically acceptable salt, ester, solvate, polymorph, prodrug and mixtures thereof are useful in the treatment of disorders/diseases caused by helminths such as *Ostertagia ostertagi, Cooperia oncophora, Cooperia punctata, Trichostrongylus axei, Haemonchus placei, Haemonchus contortus, Nematodirus helvetianus, Nematodirus spathiger, Trichostrongylus colubriformis, Trichostrongylus circumcincta, Oesophagostomum venulosum, Chabertia ovina, Dictyocaulus viviparous, Dictyocaulus filaria, Dirofilaria immitis, Dirofilaria repens*; b) *Trematodes: Fasciola hepatica, Fascioloides magna, Dicrocoelium dentriticum, Paramphistomum cervi*, c) *Cestodes:Monezia expansa*. In particular, *Ascaridia galli, Haemonchus contortus, Oesophagostomum dentatum* and by *Dirofilaria immitis*. In particular, the compounds according to the invention and/or any embodiments thereof are useful in the treatment of the helminth infection such as filariasis and in particular heartworm disease. Optionally, the compounds according to the invention and/or any embodiments thereof are useful in the treatment of the disorders/diseases caused by helminths, such as nematodes, in particular *Dirofilaria immitis*, wherein the disorder/disease caused by *Dirofilaria immitis* is the heartworm disease.

Advantageously the compounds according to the invention and/or any embodiments thereof are effective against helminths such as *Dirofilaria immitis*, but not effective against bacteria that are especially relevant in the mammal's, in particular the dog's, health, such as Acinetocbacter *baumanii* or *Staphylococcus* spp. or *Streptococcus* spp.

The inventors found that the compounds of the invention meet such needs and are therefore very useful in the treatment (and prevention) of diseases caused by helminths such as the heartworm disease.

The following abbreviations and definitions are used throughout this application.

Generally, reference to a certain element is meant to include all isotopes of that element. For example, if a group is defined to include hydrogen or a residue is hydrogen, it also includes deuterium and tritium.

The term "$C_{1-6}$-alkyl" refers to alkyl groups having 1 to 6 carbon atoms that do not contain heteroatoms. Thus, the term includes straight chain alkyl groups such as methyl, ethyl, propyl, butyl, pentyl and hexyl. The term also includes branched chain isomers of straight chain alkyl groups, including but not limited to, the following that are provided by way of example: $—CH(CH_3)_2$, $—CH(CH_3)(CH_2CH_3)$, $—CH(CH_2CH_3)_2$, $—C(CH_3)_3$, $—CH_2CH(CH_3)_2$, $—CH_2CH(CH_2CH_3)_2$, $—CH_2C(CH_3)_3$, $—CH(CH_3)CH(CH_3)(CH_2CH_3)$, $—CH_2CH_2CH(CH_3)_2$, $—CH_2CH_2CH(CH_3)(CH_2CH_3)$, $—CH_2CH_2C(CH_3)_3$ and others. Thus, the term "$C_{1-6}$-alkyl' includes primary alkyl groups having 1 to 6 carbon atoms, secondary alkyl groups having 3 to 6 carbon atoms and tertiary alkyl groups having 4 to 6 carbon atoms.

Correspondingly, the term "$C_{1-3}$-alkyl" refers to alkyl groups having 1 to 3 carbon atoms that do not contain heteroatoms. Thus, the term includes straight chain alkyl groups such as methyl, ethyl, and propyl. The term also includes branched chain isomers of straight chain alkyl groups, namely $CH(CH_3)_2$. Thus, the term "$C_{1-3}$-alkyl' includes primary alkyl groups having 1 to 3 carbon atoms, and a secondary alkyl groups having 3 carbon atoms.

The term "$C_{2-6}$-alkenyl" refers to straight and branched chain alkenyl groups such as those described with respect to the "$C_{2-6}$-alkyl" defined above, except that at least one double bond exists between two carbon atoms. Examples include, but are not limited to $—CH{=}CH_2$, $—C(CH_3){=}CH_2$, $—CH{=}CH(CH_3)$, $—CH{=}C(CH_3)_2$, $—CH{=}CH(CH_3)$, $—C(CH_3){=}CH(CH_3)$, $—C(CH_2CH_3)H{=}CH_2$, $—CH_2{=}CH(CH_2CH_3)$, $—CH_2CH_2—CH{=}CH_2$, $CH_2CH_2—C(CH_3){=}CH_2$, $CH_2CH_2—CH{=}C(CH_3)H$, $—CH{=}CH—(CH_2)_2CH_3$, $—CH{=}C(CH_3)—CH_2CH_3$, $—(CH_2)_3—CH{=}CH_2$, $—(CH_2)_4—CH{=}CH_2$, $—(CH_2)_2—CH{=}C(CH_3)_2$, butadienyl, pentadienyl, and hexadienyl among others.

The term "$C_{2-6}$-alkynyl" refers to straight and branched chain alkynyl groups such as those described with respect to the "$C_{2-6}$-alkyl" defined above, except that at least one triple bond exists between two carbon atoms. Examples include, but are not limited to, $—C{\equiv}CH$, $—C{\equiv}CCH_3$, $—C{\equiv}C—CH_2CH_3$, $—CH_2—C{\equiv}CH$, $—CH(CH_3)—C{\equiv}CH$, $—C(CH_3)_2—C{\equiv}CH$, $—CH_2—C{\equiv}CCH_3$, $—CH(CH_3)—C{\equiv}CCH_3$, $—C(CH_3)_2—C{\equiv}CCH_3$, $—CH_2—C{\equiv}C{\equiv}CH_2CH_3$, $—CH(CH_3)—C{\equiv}C—CH_2CH_3$, $—C(CH_3)_2—C{\equiv}C—CH_2CH_3$, $—(CH_2)_2—C{\equiv}C—CH_2CH_3$, $—(CH_2)_3—C{\equiv}C—CH_3$ among others.

The term "$C_{3-10}$-cycloalkyl" refers to non-aromatic monocyclic alkyl groups having 3 to 10 carbon atoms or non-aromatic polycyclic alkyl groups having 3 to 10 carbons atoms, wherein said groups consist solely of carbon and hydrogen atoms. Cycloalkyl may include fused or bridged ring systems having 3 to 10 carbon atoms. Non-aromatic monocyclic alkyl groups having 3 to 10 carbon atoms include, but are not limited to, cyclopropyl, cyclobutyl, cyclopentyl, cyclohexyl, cycloheptly, cyclooctyl and the like. Non-aromatic polycyclic alkyl groups having 3 to 10 carbon atoms include, but are not limited to, adamantine, norbornane, decalinyl, 7,7-dimethyl-bicyclo[2.2.1]heptanyl and the like.

The term "5 to 10-membered heterocyclyl" refers to cyclic groups wherein 5 to 10 members (atoms) form the skeleton, wherein the skeleton of said cyclic compounds comprises at least one carbon atom and at least one heteroatom. Examples of heteroatoms include, but are not limited to, N, O and S. Unless specifically stated otherwise in the specification, the "5 to 10-membered heterocyclyl" may be a monocyclic, bicyclic or polycyclic group which may include fused or bridged ring systems, wherein a part of the fused ring system may be aromatic; the nitrogen, carbon or sulphur atoms in the "5 to 10-membered heterocyclyl" may be optionally oxidized; the nitrogen atom may be optionally quaternized; and the heterocyclyl residue radical may be partially saturated.

Examples of heterocyclyl groups include, but are not limited, to pyrrolinyl, 3H-pyrazolyl, 4H-pyrazolyl dihydropyridyl, pyrrolidinyl, imidazolidinyl, piperidinyl, piperazinyl, homopiperazinyl, indolinyl, quinuclidinyl, morpholinyl, thiomorpholinyl thiazolodinyl, dihydrodithiinyl, dihydrodithionyl, tetrahydrothiophene, tetrahydrothiopyran, benzothiazinyl such as 2H-1,4-benzothiazinyl, dihydrobenzothiazinyl such a 2H-3,4-dihydrobenzothiazinyl, benzodioxolyl such as 1,3-benzodioxoyl, dihydrooxathiinyl, 1,4-oxathianyl. Further examples of heterocyclyl groups include, but are not limited to, those described above in which one or more S atoms in the ring is double-bonded to one or two oxygen atoms (sulfoxides and sulfones) such as tetrahydrothiophene, tetrahydrothiophene oxide and tetrahydrothiophene-1,1-dioxid as well as thiomorpholine, thiomorpholine oxide and thiomorpholine-1,1 dioxiide.

The term "$C_{6-10}$ aryl" refers to a group with an aromatic skeletal structure, wherein the ring atoms of the aromatic skeletal structure are carbon atoms. In other words, the "$C_{6-10}$ aryl" does not contain heteroatoms such as N, S, O in the aromatic skeletal structure.

Examples for aryl groups include, but are not limited, to phenyl, biphenyl and naphthyl.

The term "5 to 10-membered heteroaryl" refers to an aromatic group wherein 5 to 10 members (atoms) form the skeleton, wherein the skeleton of said cyclic compound comprises at least one carbon atom and at least one heteroatom. Examples of heteroatoms include, but are not limited to, N, O and S. Unless specifically stated otherwise in the specification, the "5 to 10-membered heterocyclyl" may be a monocyclic or bicyclic or polycyclic group, which may include fused ring systems.

Examples of 5 to 10-membered heteroaryl groups include, but are not limited to, pyrrolyl, imidazolyl, pyrazolyl, pyridyl, pyrimidyl, pyrazinyl, pyridazinyl, triazolyl such as 1H-1,2,3-triazolyl, 2H-1,2,3-triazolyl,1H-1,2,4-triazolyl and 4H-1,2,4-triazlyl, tetrazolyl such as 1H-tetrazolyl, 2H tetrazolyl and 5H-tetrazoyl, indolyl, isoindolyl, indolinyl, indolizinyl, benzimidazolyl, quinolyl, isoquinolyl, indazolyl, naphthyridinyl, benzotriazolyl, oxazolyl, isoxazolyl, oxadiazolyl such as 1,2,4-oxadiazolyl, 1,3,4-oxadiazolyl, 1,2,5-oxadiazolyl, benzoxazolyl, benzoxadiazolyl, benzoxazinyl such as 2H-1,4-benzoxazinyl thiazolyl, isothiazolyl, thiadiazolyl such 1,2,3-thiadiazolyl, 1,2,4-thiadiazolyl, 1,3,4-thiadiazolyl, 1,2,5-thiadiazolyl, thienyl, benzothiazolyl, benzothiadiazolyl, benzothiazinyl, benzofuranyl, quinolinyl, isoquinolin, cinnolinyl, quinaxolinyl quinoxalinyl, triazinyl, tetrazinyl, purinyl, pteridinyl, furyl, benzodioxolyl such as 1,3-benzodioxoyl, benzothienyl, benzodithiinyl and benzoxathiinyl.

The term "$C_{1-6}$-alkoxy" refers to a group which based on an alkyl group having 1 to 6 carbon atoms bound to an oxygen. The alkyl group having 1 to 6 carbon atoms refers to straight and branched chains such as those described with respect to the "$C_{1-6}$-alkyl" defined above.

Correspondingly, the term "$C_{1-3}$-alkoxy" refers to a group which is based on an alkyl group having 1 to 3 carbon atoms bound to an oxygen. The alkyl group having 1 to 3 carbon atoms refers to straight and branched chains such as those described with respect to the "$C_{1-3}$-alkyl" defined above.

The term "$C_{1-6}$-alkylmercapto" refers to a group which is based on an alkyl group having 1 to 6 carbon atoms bound to a sulfur The alkyl group having 1 to 6 carbon atoms refers to straight and branched chains such as those described with respect to the "$C_{1-6}$-alkyl" defined above.

"Optionally substituted" refers to the optional replacement of one or more hydrogen(s) of the group to be substituted with one or more of the defined substituent(s).

Further amines, hydroxyl and mercapto groups may be protected. The term "protected" with regard to these groups refers to forms of these functionalities with a protecting group to prevent said groups from undesirable reaction. Such protecting groups are known to those skilled in the art for example from Protective Groups in Organic Synthesis; Wuts, P. G. M. John Wiley & Sons, New York, NY, ($53^{th}$ Edition, 2014). The protecting groups can be added or removed using the procedures set forth therein.

Examples of protected hydroxyl groups include, but are not limited to, silyl ethers such as those obtained by reaction of a hydroxyl group with a reagent such as, but not limited to, t-butyldimethyl-chlorosilane, trim ethyl chlorosilane, triisopropylchlorosilane, tri ethyl chlorosilane; substituted methyl and ethyl ethers such as, but not limited to, methoxymethyl ether, methythiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate and trifluoracetate.

Examples of protected amine groups include, but are not limited to, amides such as formamide, acetamide, trifluoroacetamide and benzamide; imides, such as phthalimide and dithiosuccinimide; carbamate such as tert-butyloxycarbonyl (Boc) and others.

Examples of protected mercapto groups include, but are not limited to, thioether such as S-benzyl thioether, and S-4-picolyl thioether; substituted S-methyl derivatives such as hemithio, dithio and aminothio acetals and others.

Stereoisomers include compounds which are made of the same atoms connected in the same sequence, but the atoms are positioned differently in space. Stereoisomers include diastereoisomers and enantiomers.

A "physiologically acceptable salt" it referred to as salt with an inorganic base, organic base, inorganic acid, organic acid or basic or acidic amino acid.

Examples of suitable inorganic acids for making (physiologically acceptable) salts include, but are not limited to, hydrochloric, hydrobromic, hydroiodic, nitric, carbonic, sulfuric and phosphoric acid.

Examples of suitable organic acids for making (pharmaceutically acceptable) salts include, but are not limited to, cholic acid, sorbic acid, lauric acid, acetic acid, trifluoroacetic acid, formic acid, propionic acid, succinic acid, glycolic acid, gluconic acid, digluconic acid, lactic acid, malic acid, tartaric acid, citric acid, ascorbic acid, glucuronic acid, maleic acid, fumaric acid, pyruvic acid, aspartic acid, glutamic acid, benzoic acid, anthranilic acid, mesylic acid, stearic acid, salicylic acid, p-hydroxybenzoic acid, phenylacetic acid, mandelic acid, embonic acid, ethanesulfonic acid, benzenesulfonic acid, toluene sulfonic acid, pantothenic acid, 2-hydroxyethanesulfonic acid, sulfanilic acid, cyclohexylaminosulfonic acid, β-hydroxybutyric acid, galactaric acid, galacturonic acid, adipic acid, alginic acid, butyric acid, camphoric acid, camphorsulfonic acid, cyclopentanepropionic acid, dodecylsulficacid, glycoheptanoic acid, glycerophosphic acid, heptanoic acid, hexanoic acid, nicotinic acid, 2-naphthalesulfonic acid, oxalic acid, palmoic acid, pectinic acid, 3-phenylpropionic acid, picric acid, pivalic acid, thiocyanic acid, tosylic acid, undecanoic acid and acidic amino acids such as aspartic acid and glutamic acid.

Examples of base addition salts may include, for example, metallic salts and organic salts.

Metallic salts include, but are not limited to, alkali metal (group Ia) salts, alkaline earth metal (group Ha) salts and other physiologically acceptable metal salts. Examples of such salts may be made from aluminium, calcium, lithium, magnesium, potassium, sodium, and zinc. For example, a free acid compound may be mixed with sodium hydroxide to form such a base addition salt.

Organic salts may be made from amines, such as trimethylamine, diethylamine, N,N'-dibenzyl-ethylenediamine, chloroprocaine, ethanolamine, diethanolamine, ethylenediamine, N-methyl-glucamine, procaine and basic amino acids such as arginine, lysine and ornithine.

As used herein, the term "pharmaceutically acceptable ester" refers to esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids in which each alkyl or alkenyl moiety advantageously has not more than 6 carbon atoms. Representative examples of particular esters include, but are not limited to, formates, acetates, propionates, butyrates, acrylates and ethylsuccinates.

A solvate of a compound can be regarded as a compound in which an organic solvent or water adheres to said compound. Organic solvents refer to the ones which are known by the skilled person. In case that water is adhered to the compound the corresponding compound is known as a hydrate.

The term "polymorph" as used herein and as generally understood by the skilled person refers to different crystalline forms of the same molecular entity. Therefore, due to their different chemical compositions, solvates and hydrates as discussed above are not included in the definition of polymorphism but are rather designated "pseudopolymorphs" instead.

The term "prodrug" refers to compounds that are rapidly transformed in vivo to yield the parent compound of the above Formula ((I), for example by hydrolysis in blood. A thorough discussion is provided in T. Higuchi and V. Stella, Pro-drugs as Novel Delivery Systems, Vol. 14 of the A. C. S. Symposium Series, and in Edward B. Roche, Bioreversible Carriers in Drug Design, American Pharmaceutical Association and Pergamon Press, 1987.

The term "pharmaceutically acceptable prodrugs" as used herein refers to those prodrugs of the compounds of the present invention that are, within the scope of sound medical judgment, suitable for use in contact with the tissues of humans and lower animals without undue toxicity, irritation, allergic response and the like, commensurate with a reasonable benefit/risk ratio and effective for their intended use, as well as the zwitterionic forms, where possible, of the compounds of the invention.

The invention provides a compound according to the invention and/or embodiments thereof, wherein $R^1$ is defined as above.

In an embodiment of the invention and/or embodiments thereof, $R^1$ is independently selected from the group consisting of hydrogen, $C_{1-6}$-alkyl, $C_{1-6}$-alkoxy, halogen, cyano, nitro, hydroxy, $NR^2R^3$, $C(=O)OR^4$ and $C(=O)NR^5R^6$, wherein each $C_{1-6}$-alkyl or $C_{1-6}$-alkoxy is optionally substituted with one or more substituents independently selected from the group consisting of $C_{1-6}$-alkyl, $C_{1-6}$-alkoxy, halogen, cyano, nitro, hydroxy and $NR^{2'}R^{3'}$, $R^2$ and $R^3$ are independently selected from the group consisting of hydrogen, $C_{1-6}$-alkyl, $C_{3-10}$-cycloalkyl, $C_{6-10}$-aryl and 5 to 10-membered heteroaryl, or $R^2$ and $R^3$ together with the N atom to which they are attached form a saturated or unsaturated heterocyclic ring having 3 to 12 ring atoms, wherein 1 ring atom is N and wherein 0, 1, 2 or 3 further ring atoms are selected from N, S and O;

wherein each $C_{1-6}$-alkyl, $C_{3-10}$-cycloalkyl, $C_{6-10}$-aryl or 5 to 10-membered heteroaryl or the heterocyclic ring formed by $R^2$ and $R^3$ together with the N atom to which they are attached is optionally substituted with one or more substituent(s) independently selected from the group consisting of $C_{1-6}$-alkyl, $C_{3-10}$-cycloalkyl and $C_{1-6}$-alkoxy, $R^4$, $R^5$ and $R^6$ are independently selected from hydrogen and $C_{1-6}$-alkyl, preferably from hydrogen and $C_{1-3}$-alkyl, $R^{2'}$ and $R^{3'}$ are independently selected from hydrogen and $C_{1-6}$-alkyl, preferably from hydrogen and $C_{1-3}$-alkyl.

Optionally, in an embodiment of the invention and/or embodiments thereof, $R^1$ is independently selected from the group consisting of hydrogen, $C_{1-6}$-alkyl, $C_{1-6}$-alkoxy, halogen, cyano, nitro and $C(=O)NR^5R^6$, wherein each $C_{1-6}$-alkyl or $C_{1-6}$-alkoxy is optionally substituted with one or more substituents independently selected from the group consisting of $C_{1-6}$-alkyl, $C_{1-6}$-alkoxy, halogen, cyano, nitro, hydroxy and $NR^{2'}R^{3'}$, $R^5$ and $R^6$ are independently selected from hydrogen and $C_{1-3}$-alkyl, $R^{2'}$ and $R^{3'}$ are independently selected from hydrogen and $C_{1-3}$-alkyl.

Optionally, in an embodiment of the invention and/or embodiments thereof, $R^1$ is independently selected from the group consisting of hydrogen, $C_{1-6}$-alkyl, $C_{1-6}$-alkoxy and halogen, wherein $C_{1-6}$-alkyl and $C_{1-6}$-alkoxy is optionally substituted with one or more substituent(s) independently selected from the group consisting of $C_{1-6}$-alkyl, $C_{1-6}$-alkoxy, halogen, cyano, hydroxy and $NR^{2'}R^{3'}$, wherein $R^{2'}$ and $R^{3'}$ are independently selected from hydrogen and $C_{1-3}$-alkyl, more preferably from hydrogen and methyl.

In one embodiment of the invention and/or embodiments thereof, $R^1$ is independently selected from the group consisting of hydrogen, methyl, trifluoromethyl, ethyl, methoxy, ethoxy, fluoride and chloride.

In an embodiment of the invention and/or embodiments thereof, the compounds are according to Formula (Iai), (Iaii), (Iaiii), (Iaiv), (Iav) or (Iavi)

Formula (Iai)

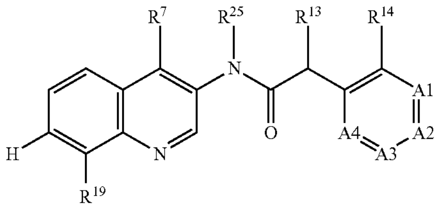

Formula (Iaii)

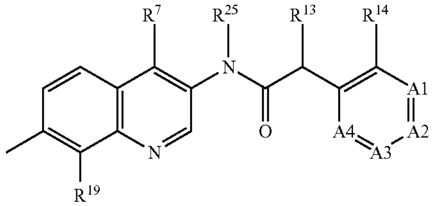

Formula (Iaiii)

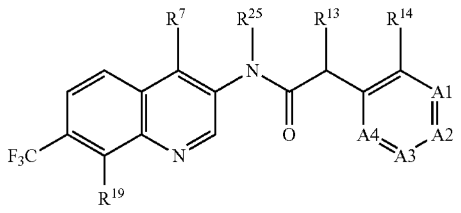

Formula (Iaiv)

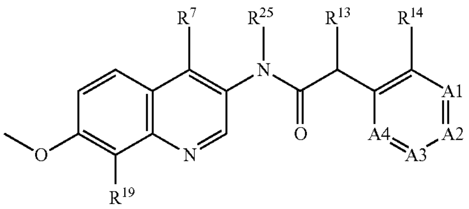

Formula (Iav)

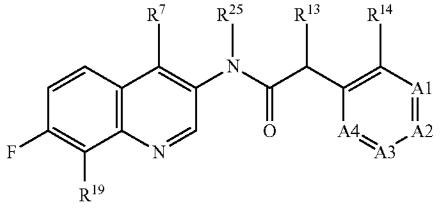

Formula (Iavi)

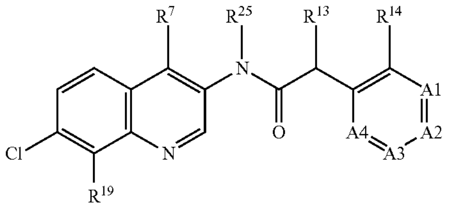

or a stereoisomer, physiologically acceptable salt, ester, solvate, polymorph, prodrug and mixtures thereof, wherein $R^7$, $R^{13}$, $R^{14}$, A1, A2, A3, A4, $R^{19}$ and $R^{25}$ are defined as in any of the embodiments described herein.

In an embodiment of the invention and/or embodiments thereof, the compounds are according to Formula (Iai), preferably in form of the (S)-enantiomer. In an embodiment of the invention and/or embodiments thereof, the compounds are according to Formula (Iaii), preferably in form of the (S)-enantiomer. In an embodiment of the invention and/or embodiments thereof, the compounds are according to Formula (Iaiii), preferably in form of the (S)-enantiomer. In an embodiment of the invention and/or embodiments thereof, the compounds are according to Formula (Iaiv), preferably in form of the (S)-enantiomer. In an embodiment of the invention and/or embodiments thereof, the compounds are according to Formula (Iav), preferably in form of the (S)-enantiomer. In an embodiment of the invention and/or embodiments thereof, the compounds are according to Formula (Iavi), preferably in form of the (S)-enantiomer.

The invention provides a compound according to the invention and/or embodiments thereof, wherein $R^7$ is defined as above.

In an embodiment of the invention and/or embodiments thereof, $R^7$ is independently selected from the group consisting of hydrogen, $C_{1-6}$-alkyl, $C_{2-6}$-alkenyl, $C_{3-10}$-cycloalkyl, 4 to 10-membered heterocyclyl, $C_{1-6}$-alkoxy, halogen, cyano, hydroxy, $NR^8R^9$, C(=O)$OR^{10}$, $SR^{10}$, $SOR^{10}$, $SO_2R^{10}$ and C(=O)$NR^{11}R^{12}$, wherein each $C_{1-6}$-alkyl, $C_{2-6}$-alkenyl, $C_{3-10}$-cycloalkyl, 4 to 10-membered heterocyclyl or $C_{1-6}$-alkoxy is optionally substituted with one or more substituent(s) independently selected from the group consisting of $C_{1-6}$-alkyl, $C_{3-10}$-cycloalkyl, 5 to 10-membered heterocyclyl, $C_{1-6}$-alkoxy, halogen, cyano, hydroxy, $NR^{8'}R^{9'}$, C(=O)$OR^{10'}$ and C(=O)$NR^{11'}R^{12'}$, $R^8$ and $R^9$ are independently selected from the group consisting of hydrogen, $C_{1-6}$-alkyl, $C_{3-10}$-cycloalkyl, $C_{6-10}$-aryl, 5 to 10-membered heterocyclyl and 5 to 10-membered heteroaryl, or $R^8$ and $R^9$ together with the N atom to which they are attached form a saturated or unsaturated heterocyclic ring having 3 to 12 ring atoms, wherein 1 ring atom is N and wherein 0, 1, 2, or 3 further ring atoms are selected from N, S and O;

wherein the $C_{1-6}$-alkyl, $C_{3-10}$-cycloalkyl, $C_{6-10}$-aryl, 5 to 10-membered heterocyclyl or 5 to 10-membered heteroaryl or the heterocyclic ring formed by $R^8$ and $R^9$ together with the N atom to which they are attached is optionally substituted with one or more substituent(s) independently selected from the group consisting of $C_{1-6}$-alkyl, $C_{1-6}$-alkoxy, halogen, cyano, hydroxy, $NR^{8''}R^{9''}$, C(=O)$OR^{10''}$ and C(=O)$NR^{11''}R^{12''}$;

$R^{10}$, $R^{11}$ and $R^{12}$ are independently selected from hydrogen and $C_{1-6}$-alkyl, $R^{8''}$, $R^{9''}$, $R^{10''}$, $R^{11''}$ and $R^{12''}$ are independently selected from hydrogen and $C_{1-6}$-alkyl.

In an embodiment of the invention and/or embodiments thereof, wherein $R^7$ is independently selected from the group consisting of hydrogen, $C_{1-6}$-alkyl, $C_{2-6}$-alkenyl, 4 to 10-membered heterocyclyl, $C_{1-6}$-alkoxy, hydroxy, $NR^8R^9$, C(=O)$OR^{10}$, $SR^{10}$, $SOR^{10}$, $SO_2R^{10}$ and C(=O)$NR^{11}R^{12}$, wherein each $C_{1-6}$-alkyl, $C_{2-6}$-alkenyl, 4- to 10-membered heterocyclyl or $C_{1-6}$-alkoxy is optionally substituted with one or more substituent(s) independently selected from the group consisting of $C_{1-6}$-alkyl, 5 to 10-membered heterocyclyl, $C_{1-6}$-alkoxy, halogen, cyano, hydroxy, $NR^{8'}R^{9'}$, C(═O)$OR^{10'}$ and C(═O)$NR^{11'}R^{12'}$, $R^8$ and $R^9$ are independently selected from the group consisting of hydrogen, $C_{1-6}$-alkyl, $C_{6-10}$-aryl and 5 to 10-membered heteroaryl, or $R^8$ and $R^9$ together with the N atom to which they are attached form a saturated or unsaturated heterocyclic ring having 3 to 12 ring atoms, wherein 1 ring atom is N and wherein 0, 1, 2, or 3 further ring atoms are selected from N, S and O;

wherein the $C_{1-6}$-alkyl, $C_{6-10}$-aryl or 5 to 10-membered heteroaryl or the heterocyclic ring formed by $R^8$ and $R^9$ together with the N atom to which they are attached is optionally substituted with one or more substituent(s) independently selected from the group consisting of $C_{1-6}$-alkyl, $C_{1-6}$-alkoxy, hydroxy and $NR^{8''}R^{9''}$;

$R^{10}$, $R^{11}$ and $R^{12}$ are independently selected from hydrogen or $C_{1-6}$-alkyl, preferably from hydrogen or $C_{1-3}$-alkyl, $R^{8'}$, $R^{9'}$, $R^{10'}$, $R^{11'}$ and $R^{12'}$ are independently selected from hydrogen or $C_{1-6}$-alkyl, preferably from hydrogen or $C_{1-3}$-alkyl, $R^{8''}$ and $R^{9''}$ are independently selected from hydrogen or $C_{1-6}$-alkyl, preferably from hydrogen or $C_{1-3}$-alkyl.

In an embodiment of the invention and/or embodiments thereof, $R^7$ is independently selected from the group consisting of hydrogen, $C_{1-6}$-alkyl, $C_{2-6}$-alkenyl, 4 to 10-membered heterocyclyl, $C_{1-3}$-alkoxy, hydroxy, $NR^8R^9$, $SR^{10}$, $SOR^{10}$ and $SO_2R^{10}$, wherein each $C_{1-6}$-alkyl, $C_{2-6}$-alkenyl, 4 to 10-membered heterocyclyl or $C_{1-3}$-alkoxy is optionally substituted with one or more substituent(s) independently selected from the group consisting of $C_{1-3}$-alkyl, 5 to 10-membered heterocyclyl, $C_{1-6}$-alkoxy, halogen, cyano, hydroxy, $NR^{8'}R^{9'}$, C(═O)$OR^{10'}$ and C(═O)$NR^{11'}R^{12'}$, $R^8$ and $R^9$ are independently selected from the group consisting of hydrogen, $C_{1-6}$-alkyl, $C_{6-10}$-aryl and 5 to 10-membered heteroaryl, or $R^8$ and $R^9$ together with the N atom to which they are attached form a saturated or unsaturated heterocyclic ring having 3 to 12 ring atoms, wherein 1 ring atom is N and wherein 0, 1, 2, or 3 further ring atoms are selected from N, S and O;

wherein the $C_{1-6}$-alkyl, $C_{6-10}$-aryl or 5 to 10-membered heteroaryl or the heterocyclic ring formed by $R^8$ and $R^9$ together with the N atom to which they are attached is optionally substituted with one or more substituent(s) independently selected from the group consisting of $C_{1-6}$-alkyl, $C_{1-6}$-alkoxy, hydroxy and $NR^{8''}R^{9''}$;

$R^{10}$ is independently selected from hydrogen or $C_{1-3}$-alkyl, preferably from hydrogen, methyl or ethyl, $R^{8'}$, $R^{9'}$, $R^{10'}$, $R^{11'}$ and $R^{12'}$ are independently selected from hydrogen or $C_{1-3}$-alkyl, preferably from hydrogen, methyl or ethyl, $R^{8''}$ and $R^{9''}$ are independently selected from hydrogen or $C_{1-3}$-alkyl, preferably from hydrogen, methyl or ethyl.

In an embodiment of the invention and/or embodiments thereof, $R^7$ is independently selected from the group consisting of methyl, ethyl, propyl, isopropyl, isopropenyl methoxy, ethoxy, isopropoxy, hydroxy, methyl sulfoxyl, methyl sulfonyl, methylthio, amino, methylamino, ethylamino, (ethyl)(methyl)amino, isopropylamino, dimethylamino, (isopropyl)(methyl)amino, hydroxyethylamino, (hydroxyethyl)(methyl)amino, methoxyethylamino, (methoxyethyl)(methyl)amino, morpholin-4-yl, pyrrolidine-1-yl, 3-hydroxy-pyrrolidin-1yl 3-fluoroazetidinyl and 3,3-difluoroazetidinyl.

In an embodiment of the invention and/or embodiments thereof, the compounds are according to Formula (Ibi), (Ibii) (Ibiii). (Ibiv), (Ibv) (Ibvi), (Ibvii), (Ibviii) (Ibix), (Ibx), (Ibxi) or (Ibxii)

Formula (Ibi)

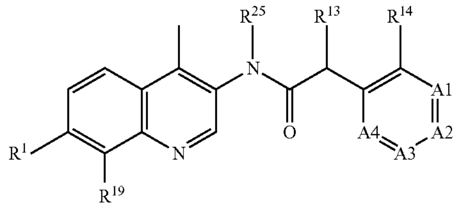

Formula (Ibii)

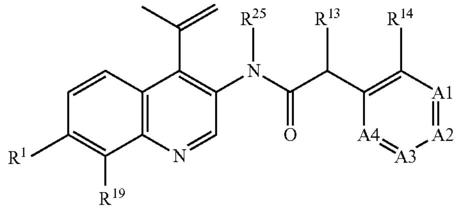

Formula (Ibiii)

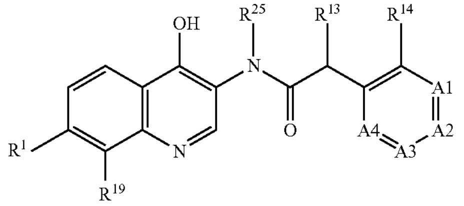

Formula (biv)

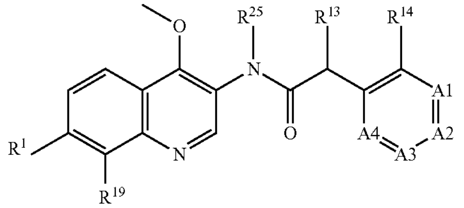

Formula (bv)

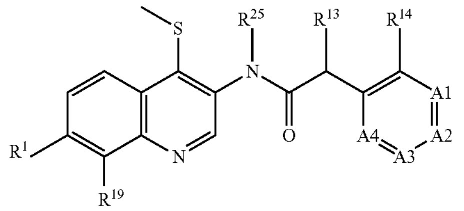

Formula (bvi)

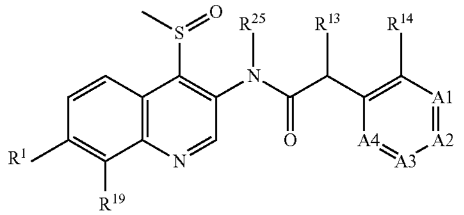

-continued

Formula (bvii)

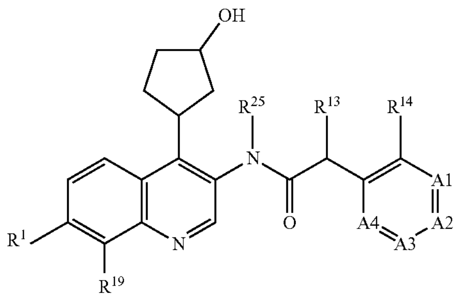

Formula (bviii)

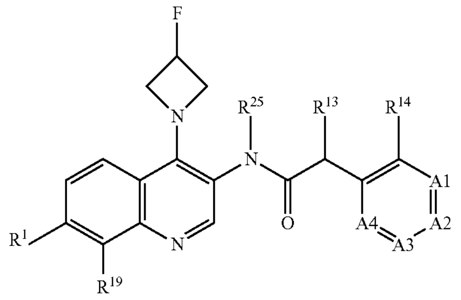

Formula (bix)

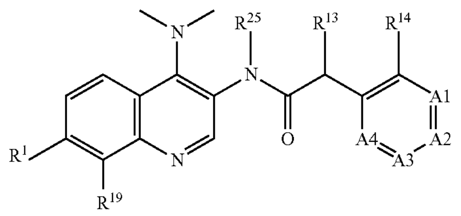

Formula (bx)

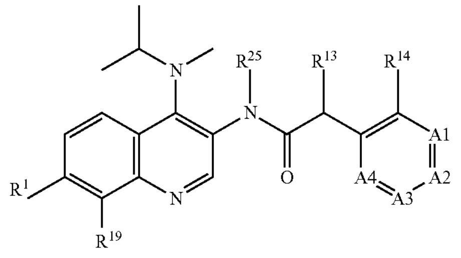

Formula (bxi)

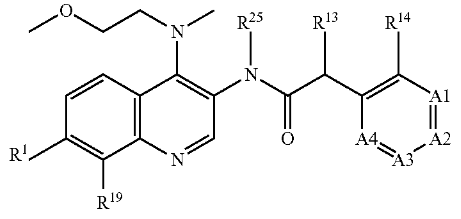

-continued

Formula (bxii)

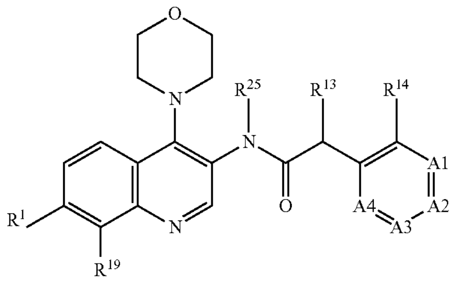

or a stereoisomer, physiologically acceptable salt, ester, solvate, polymorph, prodrug and mixtures thereof, wherein $R^1$, $R^{13}$, $R^{14}$, A1, a2, A3, A4, $R^{19}$ and $R^{25}$ are defined as in any of the embodiments described herein.

In an embodiment of the invention and/or embodiments thereof, the compounds are according to Formula (Ibi), preferably in form of the (S)-enantiomer). In an embodiment of the invention and/or embodiments thereof, the compounds are according to Formula (Ibii), preferably in form of the (S)-enantiomer. In an embodiment of the invention and/or embodiments thereof, the compounds are according to Formula (Ibiii), preferably in form of the (S)-enantiomer. In an embodiment of the invention and/or embodiments thereof, the compounds are according to Formula (Ibiv), preferably in form of the (S)-enantiomer). In an embodiment of the invention and/or embodiments thereof, the compounds are according to Formula (Ibv), preferably in form of the (S)-enantiomer. In an embodiment of the invention and/or embodiments thereof, the compounds are according to Formula (Ibvi), preferably in form of the (S)-enantiomer. In an embodiment of the invention and/or embodiments thereof, the compounds are according to Formula (Ibvii), preferably in form of the (S)-enantiomer). In an embodiment of the invention and/or embodiments thereof, the compounds are according to Formula (Ibviii), preferably in form of the (S)-enantiomer. In an embodiment of the invention and/or embodiments thereof, the compounds are according to Formula (Ibix), preferably in form of the (S)-enantiomer. In an embodiment of the invention and/or embodiments thereof, the compounds are according to Formula (Ibx), preferably in form of the (S)-enantiomer). In an embodiment of the invention and/or embodiments thereof, the compounds are according to Formula (Ibxi), preferably in form of the (S)-enantiomer. In an embodiment of the invention and/or embodiments thereof, the compounds are according to Formula (Ibxii), preferably in form of the (S)-enantiomer.

The invention provides a compound according to the invention and/or embodiments thereof, wherein $R^{13}$ and $R^{14}$ as well as A1, A2, A3, A4 are defined as above.

In an embodiment of the invention and/or embodiments thereof, $R^{13}$ is hydrogen or $C_{1-3}$ alkyl and $R^{14}$ is hydrogen, $C_{1-3}$ alkyl or $C_{1-3}$ alkoxy.

More suitably, in an embodiment of the invention and/or embodiments thereof, $R^{13}$ is hydrogen or $C_{1-3}$ alkyl and $R^{14}$ is hydrogen or $C_{1-3}$ alkyl.

More suitably, in an embodiment of the invention and/or embodiments thereof, $R^{13}$ is hydrogen, methyl or ethyl, preferably hydrogen or methyl and $R^{14}$ is hydrogen or methyl, preferably hydrogen.

A1 is N or $CR^{15}$, wherein $R^{15}$ is independently hydrogen, halogen, $C_{1-3}$ alkyl, $C_{1-3}$ alkoxy, or $NR^{15'}R^{15''}$, wherein $R^{15'}$ and $R^{15''}$ are independently $C_{1-3}$-alkyl, A2 is N or $CR^{16}$, wherein $R^{16}$ is independently hydrogen, halogen, $C_{1-3}$ alkyl, $C_{1-3}$ alkoxy, or $NR^{16'}R^{16''}$, wherein $R^{16'}$ and $R^{16''}$ are independently $C_{1-3}$-alkyl, A3 is N or $CR^{17}$, wherein $R^{17}$ is independently hydrogen, halogen, $C_{1-3}$ alkyl, $C_{1-3}$ alkoxy, or $NR^{17'}R^{17''}$, wherein $R^{17'}$ and $R^{17''}$ are independently $C_{1-3}$-alkyl, A4 is N or $CR^{18}$, wherein $R^{18}$ is independently hydrogen, halogen $C_{1-3}$ alkyl, $C_{1-3}$ alkoxy, or $NR^{18'}R^{18''}$, wherein $R^{18'}$ and $R^{18''}$ are independently $C_{1-3}$-alkyl.

More suitably, in an embodiment of the invention and/or embodiments thereof, $R^{13}$ is hydrogen or $C_{1-3}$ alkyl and $R^{14}$ is hydrogen or $C_{1-3}$ alkyl, A1 is N or $CR^{15}$, wherein $R^{15}$ is independently hydrogen, $C_{1-3}$ alkyl, $C_{1-3}$ alkoxy, A2 is N or $CR^{16}$, wherein $R^{16}$ is independently hydrogen, $C_{1-3}$ alkyl, $C_{1-3}$ alkoxy, A3 is N or $CR^{17}$, wherein $R^{17}$ is independently hydrogen, $C_{1-3}$ alkyl, $C_{1-3}$ alkoxy, A4 is N or $CR^{18}$, wherein $R^{18''}$ is independently hydrogen, $C_{1-3}$ alkyl, $C_{1-3}$ alkoxy, wherein none, one or two of residues A1, A2, A3 and A4 is N.

More suitably, in an embodiment of the invention and/or embodiments thereof, $R^{13}$ is hydrogen, methyl or ethyl, preferably hydrogen or methyl and $R^{14}$ is hydrogen or methyl, preferably hydrogen, A1 is N or $CR^{15}$, wherein $R^{15}$ is independently hydrogen or $C_{1-3}$ alkyl, A2 is N or $CR^{16}$, wherein $R^{16}$ is independently hydrogen or $C_{1-3}$ alkyl, A3 is N or $CR^{17}$, wherein $R^{17}$ is independently hydrogen or $C_{1-3}$ alkyl, A4 is N or $CR^{18}$, wherein $R^{18}$ is independently hydrogen or $C_{1-3}$ alkyl, wherein none, one or two of residues A1, A2, A3 and A4 is N.

In another embodiment of the invention and/or embodiments thereof,

A1 is $CR^{15}$, wherein $R^1$ is independently hydrogen, halogen, $C_{1-3}$ alkyl, $C_{1-3}$ alkoxy or $NR^{15'}R^{15''}$, wherein $R^{15'}$ and $R^{15''}$ are independently $C_{1-3}$-alkyl, A2 is $CR^{16}$, wherein $R^{16}$ is independently hydrogen, halogen, $C_{1-3}$ alkyl, $C_{1-3}$ alkoxy or $NR^{16'}R^{16''}$, wherein $R^{16'}$ and $R^{16''}$ are independently $C_{1-3}$-alkyl, A3 is $CR^{17}$, wherein $R^{17}$ is independently hydrogen, $C_{1-3}$ alkyl or $C_{1-3}$ alkoxy, A4 is $CR^{18}$, wherein $R^{18}$ is independently hydrogen, $C_{1-3}$ alkyl or $C_{1-3}$ alkoxy.

In another embodiment of the invention and/or embodiments thereof, $R^{13}$ is hydrogen or $C_{1-3}$-alkyl, $R^{14}$ is hydrogen, $C_{1-3}$-alkyl, or $C_{1-3}$-alkoxy, A1 is $CR^{15}$, wherein $R^{15}$ is hydrogen, halogen, $C_{1-3}$-alkyl, $C_{1-3}$-alkoxy, or $NR^{15'}R^{15''}$, wherein $R^{15'}$ and $R^{15''}$ are independently $C_{1-3}$-alkyl, A2 is $CR^{16}$, wherein $R^{16}$ is hydrogen, halogen, $C_{1-3}$-alkyl, $C_{1-3}$-alkoxy, or $NR^{16'}R^{16''}$, wherein $R^{16'}$ and $R^{16''}$ are independently $C_{1-3}$-alkyl, A3 is $CR^{17}$, wherein $R^{17}$ is hydrogen or $C_{1-3}$-alkyl, A4 is $CR^{18}$, wherein $R^{18}$ is hydrogen or $C_{1-3}$-alkyl.

In another embodiment of the invention and/or embodiments thereof, $R^{13}$ is hydrogen, methyl or ethyl, preferably hydrogen or methyl, $R^{14}$ is hydrogen or methyl, preferably hydrogen, A1 is $CR^{15}$, wherein $R^{15}$ is hydrogen or $C_{1-3}$ alkyl, preferably hydrogen or methyl, A2 is $CR^{16}$, wherein $R^{16}$ hydrogen or $C_{1-3}$ alkyl, preferably hydrogen or methyl, A3 is $CR^{17}$ and A4 is $CR^{18}$, wherein $R^{17}$ and $R^{18}$ are hydrogen.

In another embodiment of the invention and/or embodiments thereof, $R^{13}$ is hydrogen, methyl or ethyl, preferably hydrogen or methyl, $R^{14}$ is hydrogen or methyl, preferably hydrogen, A1 is $CR^{15}$, A2 is $CR^{16}$, A3 is $CR^{17}$ and A4 is $CR^{18}$, wherein $R^{15}$, $R^{16}$, $R^{17}$ and $R^{18}$ are hydrogen.

In an embodiment of the invention and/or embodiments thereof, the compounds are according to Formula (Ic).

Formula (Ic)

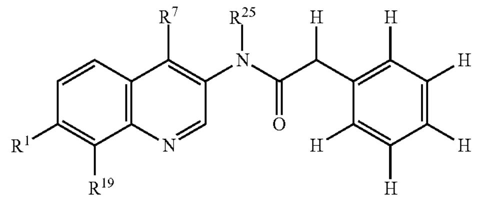

or a stereoisomer, physiologically acceptable salt, ester, solvate, polymorph, prodrug and mixtures thereof, wherein $R^1$, $R^7$, $R^{19}$ and $R^{25}$ are defined as in any of the embodiments described herein.

In an embodiment of the invention and/or embodiments thereof, the compounds are according to Formula (Ic), preferably in form of the (S)-enantiomer.

In one embodiment of the invention and/or embodiments thereof, $R^{13}$ and $R^{14}$ together with the atoms to which they are attached form a 5 or 6 carbon atoms-containing, non-aromatic ring, wherein the 5 or 6 carbon atoms-containing ring is optionally substituted with one or more $C_{1-3}$-alkyl or =O, and/or wherein one or more of the ring forming carbon atoms are optionally replaced by —NH—, —N=, =N—, —O—, —S(O)—, —$S(O)_2$— or —S—, or $R^{13}$ and $R^{14}$ together with the atoms to which they are attached form a 5 or 6-carbon atoms containing aromatic ring, wherein the aromatic ring is optionally substituted with one or more $C_{1-3}$-alkyl, and/or wherein one or more of the ring-forming carbon atoms are optionally replaced by —NH—, —N=, =N—, —O— or —S—.

Examples of the 5 or 6 carbon atoms containing non-aromatic or aromatic ring, wherein the 5 or 6 carbon atoms-containing non-aromatic ring is optionally substituted with one or more $C_{1-3}$-alkyl or =O, and/or wherein one or more of the ring forming carbon atoms are optionally replaced by —NH—, —N=, =N—, —O—, —S(O)—, —$S(O)_2$— or —S—; or wherein the 5 or 6 carbon atoms-containing aromatic ring is optionally substituted with one or more $C_{1-3}$-alkyl, and/or wherein one or more of the ring forming carbon atoms are optionally replaced by —NH—, —N=, =N—, —O— or —S-include, but are not limited to, the residues which are represented by the below structures.

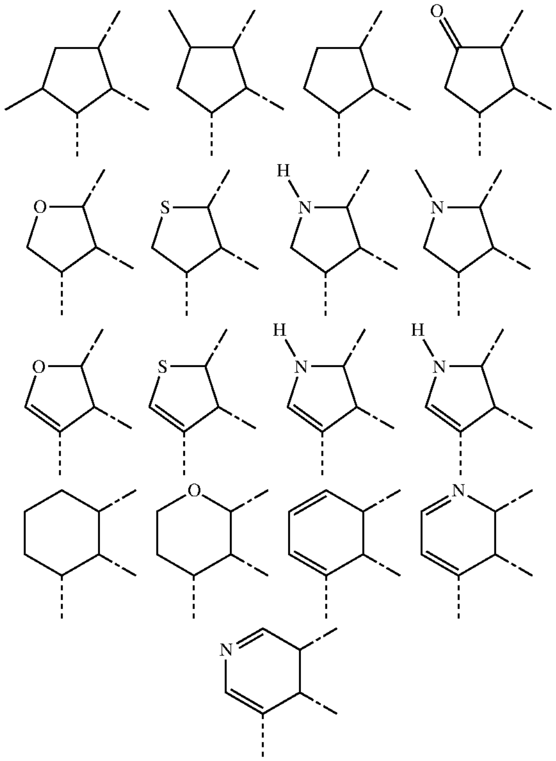

wherein

------ denotes the bond to the amide group; and

—·— denotes the bond with which the above ring system is fused with the aromatic ring inter alia comprising A1, A2, A3 and A4.

In one embodiment of the invention and/or embodiments thereof, $R^{13}$ and $R^{14}$ together with the atoms to which they are attached form a 5 or 6-carbon atoms containing non-aromatic ring, wherein the non-aromatic ring is optionally substituted with one or more $C_{1-3}$-alkyl or =O, and/or wherein one or more of the ring-forming carbon atoms are optionally replaced by —NH—, —O—, —S(O)—, —$S(O)_2$— or —S—, A1 is N or $CR^{15}$, wherein $R^{15}$ is independently hydrogen, halogen $C_{1-3}$ alkyl, $C_{1-3}$ alkoxy or $NR^{15'}R^{15''}$, wherein $R^{15'}$ and $R^{15''}$ are independently $C_{1-3}$-alkyl, A2 is N or $CR^{16}$, wherein $R^{16}$ is independently hydrogen, halogen, $C_{1-3}$ alkyl, $C_{1-3}$ alkoxy or $NR^{16'}R^{16''}$, wherein $R^{16'}$ and $R^{16''}$ are independently $C_{1-3}$-alkyl, A3 is N or $CR^{17}$, wherein $R^{17}$ is independently hydrogen, halogen, $C_{1-3}$ alkyl, $C_{1-3}$ alkoxy or $NR^{15'}R^{15''}$, wherein $R^{15'}$ and $R^{15''}$ are independently $C_{1-3}$-alkyl, A4 is N or $CR^{18}$, wherein $R^{18}$ is independently hydrogen, halogen, $C_{1-3}$ alkyl, $C_{1-3}$ alkoxy or $NR^{15'}R^{15''}$, wherein $R^{15'}$ and $R^{15''}$ are independently $C_{1-3}$-alkyl.

In one embodiment of the invention and/or embodiments thereof, $R^{13}$ and $R^{14}$ together with the atoms to which they are attached form a 5 or 6-carbon atoms containing non-aromatic ring, wherein one or more of the ring-forming carbon atoms are optionally replaced by —NH—, —O—, or —S—, A1 is N or $CR^{15}$, wherein $R^{15}$ is independently hydrogen, $C_{1-3}$ alkyl or $C_{1-3}$ alkoxy, A2 is N or $CR^{16}$, wherein $R^{16}$ is independently hydrogen, $C_{1-3}$ alkyl or $C_{1-3}$ alkoxy, A3 is N or $CR^{17}$, wherein $R^{17}$ is independently hydrogen, $C_{1-3}$ alkyl or $C_{1-3}$ alkoxy, A4 is N or $CR^{18}$, wherein $R^{18}$ is independently hydrogen, $C_{1-3}$ alkyl or $C_{1-3}$ alkoxy, wherein none, one or two of A1, A2, A3 and A4 are N.

In one embodiment of the invention and/or embodiments thereof, $R^{13}$ and $R^{14}$ together with the atoms to which they are attached form a 5 or 6-carbon atoms containing non-aromatic ring, wherein the non-aromatic ring is optionally substituted with one or more $C_{1-3}$-alkyl or =O, and/or wherein one or more of the ring-forming carbon atoms are optionally replaced by —NH— or —O—, A1 is N or $CR^{15}$, wherein $R^{15}$ is independently hydrogen or $C_{1-3}$ alkoxy, A2 is N or $CR^{16}$, wherein $R^{16}$ is independently hydrogen or $C_{1-3}$ alkoxy, A3 is N or $CR^{17}$, wherein $R^{17}$ is independently hydrogen or $C_{1-3}$ alkoxy, A4 is N or $CR^{18}$, wherein $R^{18}$ is independently hydrogen or $C_{1-3}$ alkoxy, wherein none, one or two of A1, A2, A3 and A4 are N.

In one embodiment of the invention and/or embodiments thereof, none of A1, A2, A3 and A4 is N.

In one embodiment of the invention and/or embodiments thereof, A1 is N. In one embodiment of the invention and/or embodiments thereof, A2 is N. In one embodiment of the invention and/or embodiments thereof, A3 is N. In one embodiment of the invention and/or embodiments thereof, A4 is N.

In an embodiment of the invention and/or embodiments thereof, the compounds are according to Formula (Idi), (Idii) (Idiii) (Idiv), (Idv), (Idvi) or (Idvii)

Formula (Idi)

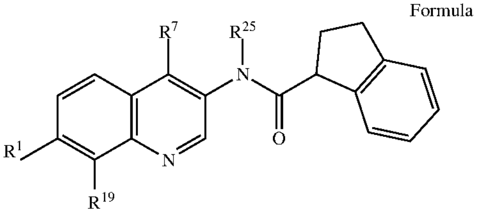

Formula (Idii)

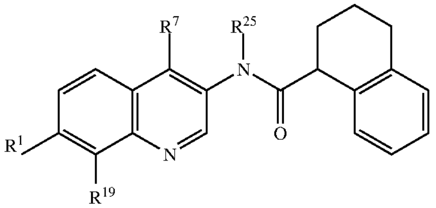

Formula (Idiii)

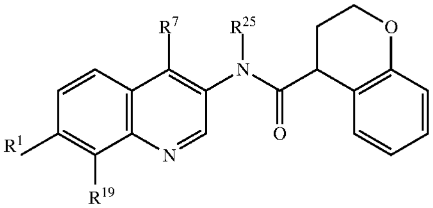

-continued

Formula (Idiv)

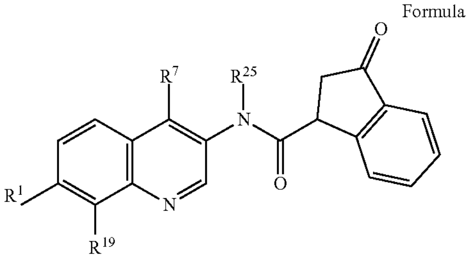

Formula (Idv)

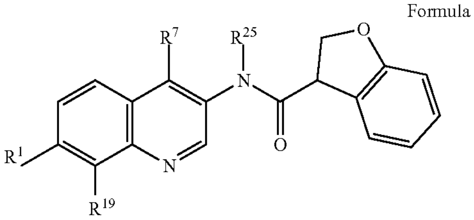

Formula (Idvi)

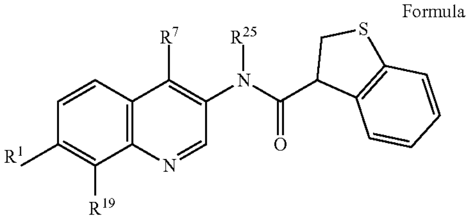

Formula (Idvii)

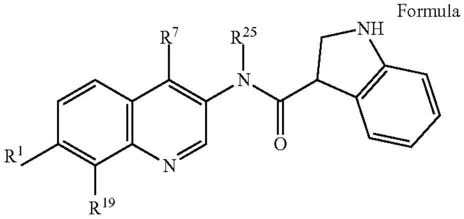

or a stereoisomer, physiologically acceptable salt, ester, solvate, polymorph, prodrug and mixtures thereof, wherein $R^1$, $R^7$, $R^9$ and $R^{25}$ are defined as in any of the embodiments described herein.

In an embodiment of the invention and/or embodiments thereof, the compounds are according to Formula (Idi), preferably in form of the (S)-enantiomer. In an embodiment of the invention and/or embodiments thereof, the compounds are according to Formula (Idii), preferably in form of the (S)-enantiomer. In an embodiment of the invention and/or embodiments thereof, the compounds are according to Formula (Idiii), preferably in form of the (S)-enantiomer. In an embodiment of the invention and/or embodiments thereof, the compounds are according to Formula (Idiv), preferably in form of the (S)-enantiomer. In an embodiment of the invention and/or embodiments thereof, the compounds are according to Formula (Idv), preferably in form of the (S)-enantiomer. In an embodiment of the invention and/or embodiments thereof, the compounds are according to Formula (Idvi), preferably in form of the (S)-enantiomer. In an embodiment of the invention and/or embodiments thereof, the compounds are according to Formula (Idvii), preferably in form of the (S)-enantiomer.

In one embodiment of the invention and/or embodiments thereof, $R^{13}$ and $R^{14}$ together with the atoms to which they are attached form a 5 or 6-carbon atoms containing aromatic ring, wherein the aromatic ring is optionally substituted with one or more $C_{1-3}$-alkyl, and/or wherein one or more of the ring-forming carbon atoms are optionally replaced by —NH—, —N=, =N—, —O— or —S—, A1 is N or $CR^{15}$, wherein $R^{15}$ is independently hydrogen, halogen $C_{1-3}$ alkyl, $C_{1-3}$ alkoxy or $NR^{15'}R^{15''}$, wherein $R^{15'}$ and $R^{15''}$ are independently $C_{1-3}$-alkyl, A2 is N or $CR^{16}$, wherein $R^{16}$ is independently hydrogen, halogen, $C_{1-3}$ alkyl, $C_{1-3}$ alkoxy or $NR^{16'}R^{16''}$, wherein $R^{16'}$ and $R^{16''}$ are independently $C_{1-3}$-alkyl, A3 is N or $CR^{17}$, wherein $R^{17}$ is independently hydrogen, halogen, $C_{1-3}$ alkyl, $C_{1-3}$ alkoxy or $NR^{15'}R^{15''}$, wherein $R^{15'}$ and $R^{15''}$ are independently $C_{1-3}$-alkyl, A4 is N or $CR^{18}$, wherein $R^{18}$ is independently hydrogen, halogen, $C_{1-3}$ alkyl, $C_{1-3}$ alkoxy or $NR^{15'}R^{15''}$, wherein $R^{15'}$ and $R^{15''}$ are independently $C_{1-3}$-alkyl.

In one embodiment of the invention and/or embodiments thereof, $R^{13}$ and $R^{14}$ together with the atoms to which they are attached form a 5 or 6-carbon atoms containing aromatic ring, wherein one or more of the ring-forming carbon atoms are optionally replaced by —NH—, —N=, =N—, —O— or —S—, A1 is N or $CR^{15}$, wherein $R^{15}$ is independently hydrogen, $C_{1-3}$ alkyl or $C_{1-3}$ alkoxy, A2 is N or $CR^{16}$, wherein $R^{16}$ is independently hydrogen, $C_{1-3}$ alkyl or $C_{1-3}$ alkoxy, A3 is N or $CR^{17}$, wherein $R^{17}$ is independently hydrogen, $C_{1-3}$ alkyl or $C_{1-3}$ alkoxy, A4 is N or $CR^{18}$, wherein $R^{18}$ is independently hydrogen, $C_{1-3}$ alkyl or $C_{1-3}$ alkoxy, wherein none, one or two of A1, A2, A3 and A4 are N.

In one embodiment of the invention and/or embodiments thereof, $R^{13}$ and $R^{14}$ together with the atoms to which they are attached form a 5 or 6-carbon atoms containing aromatic ring, wherein one or more of the ring-forming carbon atoms are optionally replaced by —NH—, —N=, =N— or —S—, A1 is N or $CR^{15}$, wherein $R^{15}$ is independently hydrogen or $C_{1-3}$ alkoxy, A2 is N or $CR^{16}$, wherein $R^{16}$ is independently hydrogen or $C_{1-3}$ alkoxy, A3 is N or $CR^{17}$, wherein $R^{17}$ is independently hydrogen or $C_{1-3}$ alkoxy, A4 is N or $CR^{18}$, wherein $R^{18}$ is independently hydrogen or $C_{1-3}$ alkoxy, wherein none, one or two of A1, A2, A3 and A4 are N.

In an embodiment of the invention and/or embodiments thereof, the compounds are according to Formula (Idviii), (Idix), (Idx), (Idxi), (Idxii), (Idxiii), (Idxiv) or (Idxv)

Formula (Idviii)

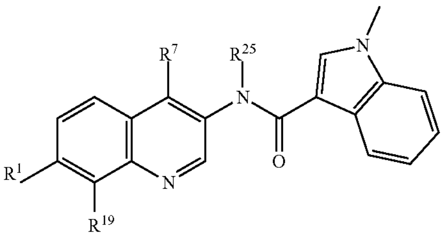

-continued

Formula (Idix)

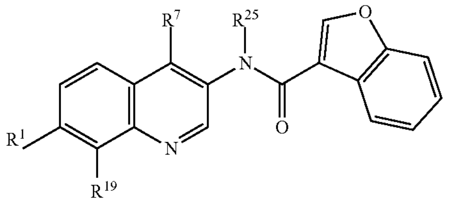

Formula (Idx)

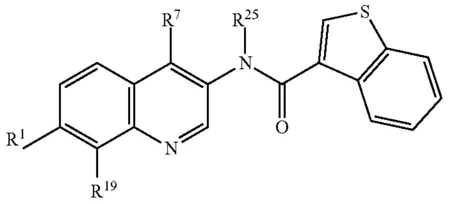

Formula (Idxi)

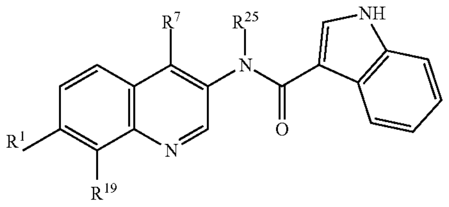

Formula (Idxii)

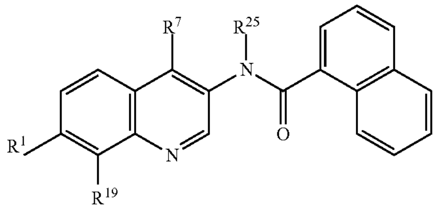

Formula (Idvi)

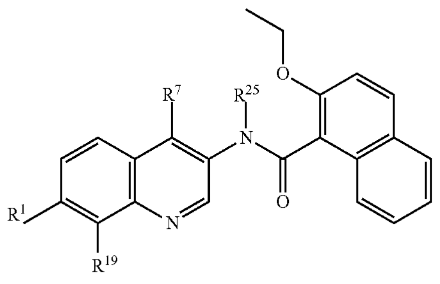

Formula (Idxiv)

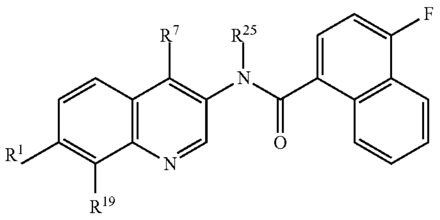

-continued

Formula (Idxv)

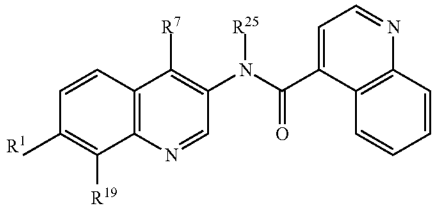

or a stereoisomer, physiologically acceptable salt, ester, solvate, polymorph, prodrug and mixtures thereof, wherein $R^1$, $R^7$, $R^9$ and $R^{25}$ are defined as in any of the embodiments described herein.

In an embodiment of the invention and/or embodiments thereof, the compounds are according to Formula (Idviii), preferably in form of the (S)-enantiomer. In an embodiment of the invention and/or embodiments thereof, the compounds are according to Formula (Idix), preferably in form of the (S)-enantiomer. In an embodiment of the invention and/or embodiments thereof, the compounds are according to Formula (Idx), preferably in form of the (S)-enantiomer. In an embodiment of the invention and/or embodiments thereof, the compounds are according to Formula (Idxi), preferably in form of the (S)-enantiomer. In an embodiment of the invention and/or embodiments thereof, the compounds are according to Formula (Idxii), preferably in form of the (S)-enantiomer. In an embodiment of the invention and/or embodiments thereof, the compounds are according to Formula (Idxiii), preferably in form of the (S)-enantiomer. In an embodiment of the invention and/or embodiments thereof, the compounds are according to Formula (Idxiv), preferably in form of the (S)-enantiomer. In an embodiment of the invention and/or embodiments thereof, the compounds are according to Formula (Idxv), preferably in form of the (S)-enantiomer.

The invention provides a compound according to the invention and/or embodiments thereof, wherein $R^{19}$ is defined as above.

In one embodiment of the invention and/or embodiments thereof, $R^{19}$ is independently selected from the group consisting of $C_{6-10}$-aryl and 5 to 10-membered heteroaryl, wherein each $C_{6-10}$-aryl or 5 to 10-membered heteroaryl is optionally substituted with one or more substituent(s) independently selected from the group consisting of $C_{1-6}$-alkyl, $C_{3-10}$-cycloalkyl, $C_{1-6}$-alkoxy, 5 to 10-membered heterocyclyl, $C_{6-10}$-aryl, 5 to 10-membered heteroaryl, halogen, cyano, nitro, hydroxy, $NR^{20}R^{21}$, $C(=O)OR^{22}$ and $C(=O)NR^{23}R^{24}$, $R^{20}$ and $R^{21}$ are independently selected from the group consisting of hydrogen, $C_{1-6}$-alkyl, $C_{3-10}$-cycloalkyl and $C_{6-10}$-aryl or $R^{20}$ and $R^{21}$ together with the N atom to which they are attached form a saturated or unsaturated heterocyclic ring having 3 to 12 ring atoms, wherein 0, 1, 2, or 3 further ring atoms are selected from N, S and O;

wherein each $C_{1-6}$-alkyl, $C_{3-10}$-cycloalkyl or $C_{6-10}$-aryl or the heterocyclic ring formed by $R^{20}$ and $R^{21}$ together with the N atom to which they are attached is optionally substituted with one or more substituents independently selected from the group consisting of $C_{1-6}$-alkyl, $C_{3-10}$-cycloalkyl, $C_{1-6}$-alkoxy, 5 to 10-membered heterocyclyl, $C_{6-10}$-aryl, 5 to 10-membered heteroaryl, halogen, cyano, hydroxy, $NR^{20'}R^{21'}$, $C(=O)OR^{22'}$ and $C(=O)NR^{23'}R^{24'}$ $R^{22}$, $R^{23}$ and $R^{24}$ are independently selected from hydrogen and $C_{1-6}$-alkyl, $R^{20'}$, $R^{21'}$, $R^{22'}$, $R^{23'}$ and $R^{24'}$ are independently selected from hydrogen and $C_{1-6}$-alkyl.

In an embodiment of the invention and/or embodiments thereof, $R^{19}$ is independently selected from the group consisting of $C_{6-10}$-aryl and 5 to 10-membered heteroaryl, wherein each $C_{6-10}$-aryl or 5 to 10-membered heteroaryl is optionally substituted with one or more substituent(s) independently selected from the group consisting of $C_{1-6}$-alkyl, $C_{1-6}$-alkoxy, halogen, cyano, nitro, hydroxy, $C(=O)OR^{22}$, $SO_2R^{22}$, $SO_2NR^{23}R^{24}$ and $C(=O)NR^{23}R^{24}$ $R^{22}$, $R^{23}$ and $R^{24}$ are independently selected from hydrogen and $C_{1-6}$-alkyl.

In an embodiment of the invention and/or embodiments thereof, $R^{19}$ is independently selected from the group consisting of $C_{6-10}$-aryl and 5 to 10-membered heteroaryl, wherein each $C_{6-10}$-aryl or 5 to 10-membered heteroaryl is optionally substituted with one or more substituent(s) independently selected from the group consisting of $C_{1-6}$-alkyl, $C_{1-6}$-alkoxy, halogen, cyano, nitro, $C(=O)OR^{22}$ and $C(=O)NR^{23}R^{24}$, $R^{22}$, $R^{23}$ and $R^{24}$ are independently selected from hydrogen and $C_{1-6}$-alkyl, preferably from hydrogen and $C_{1-3}$-alkyl.

In an embodiment of the invention and/or embodiments thereof, $R^{19}$ is independently selected from the group consisting of $C_{6-10}$-aryl and 5 to 10-membered heteroaryl wherein each $C_{6-10}$-aryl or 5 to 10-membered heteroaryl is optionally substituted with one or more substituent(s) independently selected from the group consisting of $C_{1-6}$-alkyl, $C_{1-6}$-alkoxy, halogen, cyano, nitro and hydroxy.

In an embodiment of the invention and/or embodiments thereof, $R^{19}$ is a 5 to 10-membered heteroaryl wherein the 5 to 10-membered heteroaryl is optionally substituted with one or more substituent(s) independently selected from the group consisting of $C_{1-6}$-alkyl, $C_{1-6}$-alkoxy, halogen, cyano, nitro and hydroxy.

In an embodiment of the invention and/or embodiments thereof, $R^{19}$ is a 5 to 10-membered heteroaryl wherein the 5 to 10-membered heteroaryl is optionally substituted with one or more substituent(s) independently selected from the group consisting of $C_{1-6}$-alkyl and halogen, preferably halogen.

Examples of 5 to 10-membered heteroaryl groups include, but are not limited to, pyrrolyl, imidazolyl, pyrazolyl, pyridin-2-yl, pyridin-3-yl, pyridin-4-yl, pyrimidin-2-yl, pyrimidin-3-yl, pyrimidin-4-yl, pyrazinyl, pyridazinyl, triazolyl such as 1H-1,2,3-triazolyl, 2H-1,2,3-triazolyl,1H-1,2,4-triazolyl and 4H-1,2,4-triazlyl, tetrazolyl such as 1H-tetrazolyl, 2H tetrazolyl and 5H-tetrazoyl, indolyl, isoindolyl, indolinyl, indolizinyl, benzimidazolyl, quinoline 4-yl, quinoline-8-yl, isoquinolyl, indazolyl, naphthyridinyl, benzotriazolyl, oxazolyl, isoxazolyl, oxadiazolyl such as 1,2,4-oxadiazolyl, 1,3,4-oxadiazolyl, 1,2,5-oxadiazolyl, benzoxazolyl, benzoxadiazolyl, benzoxazinyl such as 2H-1, 4-benzoxazinyl thiazolyl, isothiazolyl, thiadiazolyl such 1,2, 3-thiadiazolyl, 1,2,4-thiadiazolyl, 1,3,4-thiadiazolyl, 1,2,5-thiadiazolyl, thien-2-yl, thien-3-yl benzothiazolyl, benzothiadiazolyl, benzothiazinyl, benzofuranyl, quinolinyl, isoquinolin, cinnolinyl, quinaxolinyl quinoxalinyl, triazinyl, tetrazinyl, purinyl, pteridinyl, furyl, benzodioxolyl such as 1,3-benzodioxoyl, benzothienyl, benzodithiinyl and benzoxathiinyl. Preferred are pyridin-2-yl, pyridin-3-yl, pyridin-4-yl, pyrimidin-2-yl, pyrimidin-3-yl, pyrimidin-4-yl, quinoline-8-yl, thien-2-yl and thien-3-yl.

In an embodiment of the invention and/or embodiments thereof, $R^{19}$ is a 5 to 10-membered heteroaryl, wherein the 5 to 10-membered heteroaryl is substituted with one or more substituent(s) independently selected from the group consisting of $C_{1-6}$-alkyl and halogen, preferably halogen.

In an embodiment of the invention and/or embodiments thereof, $R^{19}$ is selected from the group consisting of pyridin-2-yl, pyridine-3-yl, pyridine-4-yl 2,5-dichloropyridin-4-yl, 2,6-dichloropyridn-4-yl, 5-chlorothien-2-yl, 5-chlorothien-3-yl, pyrimidin-4-yl, quinoline-4-yl, quinoline-8-yl and 2,6-difluoropyridin-yl.

In an embodiment of the invention and/or embodiments thereof, wherein $R^{19}$ is $C_{6-10}$-aryl, wherein the $C_{6-10}$ aryl is optionally substituted with one or more substituent(s) independently selected from the group consisting of $C_{1-6}$-alkyl, halogen, cyano and nitro.

In an embodiment of the invention and/or embodiments thereof, wherein $R^{19}$ is $C_{6-10}$-aryl, wherein $C_{6-10}$ aryl is phenyl substituted with one, two or three substituents independently selected from the group consisting of fluoride, chloride and bromide.

Examples of phenyl substituted with one, two or three substituents independently selected from the group consisting of fluoride, chloride and bromide include, but are not limited to, 2-fluoro-phenyl, 3-fluourophenyl, 4-fluorophenyl, 2-chlorophenyl, 3-chlorophenyl, 4-chlorophenyl, 2-bromophenyl, 3-bromophenyl, 4-bromophenyl, 2,3-difluorophenyl, 2,4-difluorophenyl, 2,5-di-fluorophenyl, 3,4-difluorophenyl, 3,5-difluorophenyl, 2,3-dichlorophenyl, 2,4-dichlorophenyl, 2,5-dichlorophenyl, 3,4-dichlorophenyl, 3,5-diclorophenyl, 2,3-dibromophenyl, 2,4-dibromophenyl, 2,5-dibromophenyl, 3,4-dibromophenyl, 3,5-dibromophenyl, 2,3,4-trifluorophenyl, 2,3,5-trifluorophenyl, 3,4,5-trifluorophenyl, 2,3,4-trichlorophenyl, 2,3,5-trichlorophenyl, 3,4,5-trichlorophenyl, 2,3,4-tribromophenyl, 2,3,5-tribromophenyl, 3,4,5-tribromophenyl, 2-chloro-3-fluorophenyl, 2-chloro-4-fluorophenyl, 2-chloro-5-fluorophenyl, 3-chloro-2-fluorophenyl, 3-chloro-4-fluorophenyl, 3-chloro-5-fluorophenyl, 4-chloro-2-fluorophenyl, 4-chloro-3-fluoro-phenyl, 4-chloro-5-fluorophenyl, 5-chloro-2-fluorophenyl, 5-chloro-3-fluorophenyl, 5-chloro-4-fluorophenyl, 3-bromo-2fluorophenyl, 4-bromo-2-chlorobromophenyl, 4-bromo-3-chlorophenyl, 3,4-dichloro-2-fluoro-phenyl, 3,5-dichloro-2-fluorophenyl, 3,5-dichloro-4-fluorophenyl, 4,5-dichloro-3-flurorophenyl, 3,4-dibromo-2-fluoro-phenyl, 3,5-dibromo-2-fluorophenyl, 4,5-dibromo-3-flurophenyl, 2-chloro-3,4-difluorophenyl, 2-chloro-3,5-difluorophenyl, 3-chloro-4,5-difluorophenyl, 3,4-dibromo-2-chlorophenyl, 3,5-dibromo-2-chlorophenyl, 4,5-dibromo-3-chlorophenyl, 2-bromo-3,4-difluorophenyl, 2-bromo-3,5-difluorophenyl, 3-bromo-4,5-difluorophenyl, 2-bromo-3,4-dichlorophenyl, 2-bromo-3,5-dichlorophenyl, 3-bromo-4,5-dichlorophenyl, 4-bromo-3-chloro-2-fluorophenyl, 4-bromo-2-chloro-3-fluorophenyl, 2-bromo-3-chloro-4-fluorophenyl, 5-bromo-3-chloro-2-fluorophenyl, 5-bromo-2-chloro-3-fluorophenyl, 2-bromo-3-chloro-5-fluourophenyl, 5-bromo-4-chloro-3-fluorophenyl, 5-bromo-3-chloro-4-fluorophenyl and 3-bromo-4-chloro-5 fluorophenyl.

Preferred are 3-flurorophenyl, 3-chlorophenyl, 2,3-diflurorophenyl 3,5-difluorophenyl, 2,3-dichlorophenyl, 3,5-dichlorophenyl, 2-chloro-3-fluorophenyl, 3-chloro-2-fluorophenyl, 5-chloro-3-fluorophenyl, 5-chlor-3-fluorophenyl, 5-chloro-2-fluorophenyl, 3,4,5-trifluorophenyl, 2,3,5-trifluorophenyl, 3,5-dichloro-4-fluorophenyl and 3,4,5-trichlorophenyl, more preferably 3-chlorophenyl, 2,3-dichlorophenyl, 3,5-dichlorophenyl, 3,5-difluorophenyl, 2,3,5-trifluorophenyl, 3,4,5-trifluorophenyl, 3-chloro-2-fluorophenyl, 5-chloro-3-fluorophenyl, 5-chloro-3-fluorophenyl, 3,5-dichloro-4-fluorophenyl, in particular 2,3,5-trifluorophenyl, 5-chloro-2-fluorophenyl, 2,3-dichlorophenyl and 3,5-dichlorophenyl.

In an embodiment of the invention and/or embodiments thereof, the compounds are according to Formula (Iei), (Ieii), (Ieiii) or (Ieiv)

Formula (Iei)

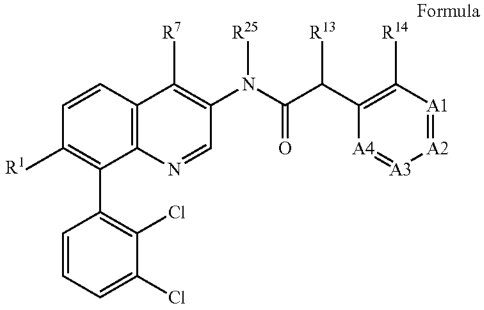

Formula (Ieii)

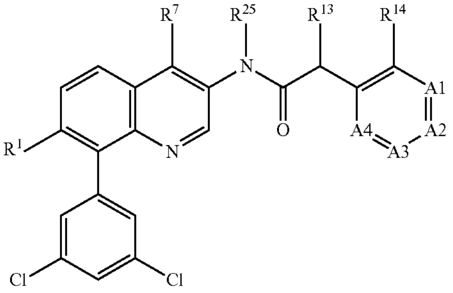

Formula (Ieiii)

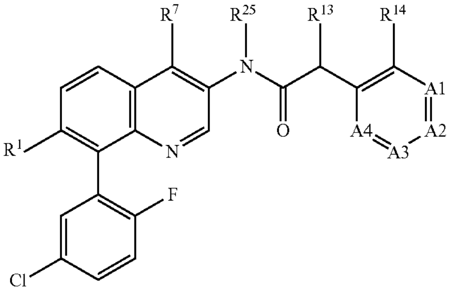

-continued

Formula (Ieiv)

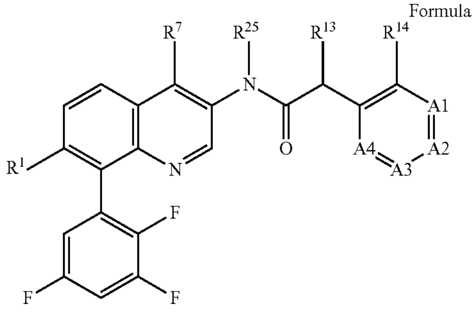

or a stereoisomer, physiologically acceptable salt, ester, solvate, polymorph, prodrug and mixtures thereof, wherein $R^1$, $R^7$, $R^{13}$, $R^{14}$, A1, A2, A3, A4 and $R^{25}$ are defined as in any of the embodiments described herein.

In an embodiment of the invention and/or embodiments thereof, the compounds are according to Formula (Iei), preferably in form of the (S)-enantiomer. In an embodiment of the invention and/or embodiments thereof, the compounds are according to Formula (Ieii), preferably in form of the (S)-enantiomer. In an embodiment of the invention and/or embodiments thereof, the compounds are according to Formula (Ieiii), preferably in form of the (S)-enantiomer. In an embodiment of the invention and/or embodiments thereof, the compounds are according to Formula (Ieiv), preferably in form of the (S)-enantiomer.

The invention provides a compound according to the invention and/or embodiments thereof, wherein $R^{25}$ is defined as above.

In an embodiment of the invention and/or embodiments thereof, $R^{25}$ is hydrogen or $C_{1-3}$-alkyl.

In an embodiment of the invention and/or embodiments thereof, $R^{25}$ is hydrogen or methyl.

In an embodiment of the invention and/or embodiments thereof, the compounds are according to Formula (Ifi) or (Ifii)

Formula (Ifi)

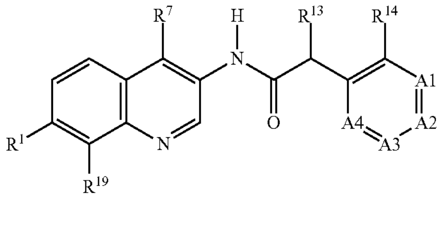

Formula (Ifii)

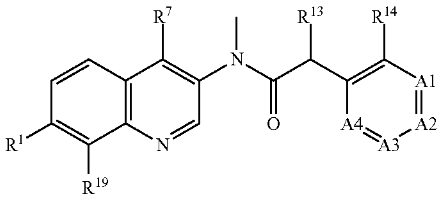

or a stereoisomer, physiologically acceptable salt, ester, solvate, polymorph, prodrug and mixtures thereof, wherein $R^1$, $R^7$, $R^{13}$, $R^{14}$, A1, A2, A3, A4 and $R^{19}$ are defined as in any of the embodiments described herein.

In an embodiment of the invention and/or embodiments thereof, the compounds are according to Formula (Ifi), preferably in form of the (S)-enantiomer. In an embodiment of the invention and/or embodiments thereof, the compounds are according to Formula (Ifii), preferably in form of the (S)-enantiomer.

The invention provides a compound according to the invention and/or embodiments thereof, wherein $R^1$ and $R^7$ are defined as above.

In an embodiment of the invention and/or embodiments thereof, $R^1$ is independently selected from the group consisting of hydrogen, $C_{1-6}$-alkyl, $C_{1-6}$-alkoxy, halogen, cyano, nitro, hydroxy, $NR^2R^3$, C(═O)$OR^4$ and C(═O)$NR^5R^6$, wherein each $C_{1-6}$-alkyl or $C_{1-6}$-alkoxy is optionally substituted with one or more substituents independently selected from the group consisting of $C_{1-6}$-alkyl, $C_{1-6}$-alkoxy, halogen, cyano, nitro, hydroxy and $NR^{2'}R^{3'}$, $R^2$ and $R^3$ are independently selected from the group consisting of hydrogen, $C_{1-6}$-alkyl, $C_{3-10}$-cycloalkyl, $C_{6-10}$-aryl and 5 to 10-membered heteroaryl, or $R^2$ and $R^3$ together with the N atom to which they are attached form a saturated or unsaturated heterocyclic ring having 3 to 12 ring atoms, wherein 1 ring atom is N and wherein 0, 1, 2 or 3 further ring atoms are selected from N, S and O;

wherein each $C_{1-6}$-alkyl, $C_{3-10}$-cycloalkyl, $C_{6-10}$-aryl or 5 to 10-membered heteroaryl or the heterocyclic ring formed by $R^2$ and $R^3$ together with the N atom to which they are attached is optionally substituted with one or more substituent(s) independently selected from the group consisting of $C_{1-6}$-alkyl, $C_{3-10}$-cycloalkyl and $C_{1-6}$-alkoxy, $R^4$, $R^5$ and $R^6$ are independently selected from hydrogen and $C_{1-6}$-alkyl, preferably from hydrogen and $C_{1-3}$-alkyl, $R^{2'}$ and $R^{3'}$ are independently selected from hydrogen and $C_{1-6}$-alkyl, preferably from hydrogen and $C_{1-3}$-alkyl, and $R^7$ is independently selected from the group consisting of hydrogen, $C_{1-6}$-alkyl, $C_{2-6}$-alkenyl, $C_{3-10}$-cycloalkyl, 4 to 10-membered heterocyclyl, $C_{1-6}$-alkoxy, halogen, cyano, hydroxy, $NR^8R^9$, C(═O)$OR^{10}$, $SR^{10}$, $SOR^{10}$, $SO_2R^{10}$ and C(═O)$NR^{11}R^{12}$, wherein each $C_{1-6}$-alkyl, $C_{2-6}$-alkenyl, $C_{3-10}$-cycloalkyl, 4 to 10-membered heterocyclyl or $C_{1-6}$-alkoxy is optionally substituted with one or more substituent(s) independently selected from the group consisting of $C_{1-6}$-alkyl, $C_{3-10}$-cycloalkyl, 5 to 10-membered heterocyclyl, $C_{1-6}$-alkoxy, halogen, cyano, hydroxy, $NR^{8'}R^{9'}$, C(═O)$OR^{10'}$ and C(═O)$NR^{11'}R^{12'}$, $R^8$ and $R^9$ are independently selected from the group consisting of hydrogen, $C_{1-6}$-alkyl, $C_{3-10}$-cycloalkyl, $C_{6-10}$-aryl, 5 to 10-membered heterocyclyl and 5 to 10-membered heteroaryl, or $R^8$ and $R^9$ together with the N atom to which they are attached form a saturated or unsaturated heterocyclic ring having 3 to 12 ring atoms, wherein 1 ring atom is N and wherein 0, 1, 2, or 3 further ring atoms are selected from N, S and O;

wherein the $C_{1-6}$-alkyl, $C_{3-10}$-cycloalkyl, $C_{6-10}$-aryl, 5 to 10-membered heterocyclyl or 5 to 10-membered heteroaryl or the heterocyclic ring formed by $R^8$ and $R^9$ together with the N atom to which they are attached is optionally substituted with one or more substituent(s) independently selected from the group consisting of $C_{1-6}$-alkyl, $C_{1-6}$-alkoxy, halogen, cyano, hydroxy, $NR^{8''}R^{9''}$, C(═O)—$OR^{10''}$ and C(═O)$NR^{11''}R^{12''}$;

$R^{10}$, $R^{11}$ and $R^{12}$ are independently selected from hydrogen and $C_{1-6}$-alkyl, $R^{8'}$, $R^{9'}$, $R^{10'}$, $R^{11'}$ and $R^{12'}$ are independently selected from hydrogen and $C_{1-6}$-alkyl, $R^{8''}$, $R^{9''}$, $R^{10''}$, $R^{11''}$ and $R^{12''}$ are independently selected from hydrogen and $C_{1-6}$-alkyl.

In an embodiment of the invention and/or embodiments thereof, $R^1$ is independently selected from the group consisting of hydrogen, $C_{1-6}$-alkyl, $C_{1-6}$-alkoxy and halogen, wherein $C_{1-6}$-alkyl and $C_{1-6}$-alkoxy is optionally substituted with one or more substituent(s) independently selected from the group consisting of $C_{1-6}$-alkyl, $C_{1-6}$-alkoxy, halogen, cyano, hydroxy and $NR^{2'}R^{3'}$, wherein $R^{2'}$ and $R^{3'}$ are independently selected from hydrogen and $C_{1-3}$-alkyl, more preferably from hydrogen and methyl, $R^7$ is independently selected from the group consisting of hydrogen, $C_{1-6}$-alkyl, $C_{2-6}$-alkenyl, 4 to 10-membered heterocyclyl, $C_{1-3}$-alkoxy, hydroxy, $NR^8R^9$, $SR^{10}$, $SOR^{10}$ and $SO_2R^{10}$, wherein each $C_{1-6}$-alkyl, $C_{2-6}$-alkenyl, 4 to 10-membered heterocyclyl or $C_{1-3}$-alkoxy is optionally substituted with one or more substituent(s) independently selected from the group consisting of $C_{1-3}$-alkyl, 5 to 10-membered heterocyclyl, $C_{1-6}$-alkoxy, halogen, cyano, hydroxy, $NR^{8'}R^{9'}$, C(═O)$OR^{10'}$ and C(═O)$NR^{11'}R^{12'}$, $R^8$ and $R^9$ are independently selected from the group consisting of hydrogen, $C_{1-6}$-alkyl, $C_{6-10}$-aryl and 5 to 10-membered heteroaryl, or $R^8$ and $R^9$ together with the N atom to which they are attached form a saturated or unsaturated heterocyclic ring having 3 to 12 ring atoms, wherein 1 ring atom is N and wherein 0, 1, 2, or 3 further ring atoms are selected from N, S and O;

wherein the $C_{1-6}$-alkyl, $C_{6-10}$-aryl or 5 to 10-membered heteroaryl or the heterocyclic ring formed by $R^8$ and $R^9$ together with the N atom to which they are attached is optionally substituted with one or more substituent(s) independently selected from the group consisting of $C_{1-6}$-alkyl, $C_{1-6}$-alkoxy, hydroxy and $NR^{8''}R^{9''}$;

$R^{10}$ is independently selected from hydrogen or $C_{1-3}$-alkyl, preferably from hydrogen, methyl or ethyl $R^{8'}$, $R^{9'}$, $R^{10'}$, $R^{11'}$ and $R^{12'}$ are independently selected from hydrogen or $C_{1-3}$-alkyl, preferably from hydrogen, methyl or ethyl, $R^{8''}$ and $R^{9''}$ are independently selected from hydrogen or $C_{1-3}$-alkyl, preferably from hydrogen, methyl or ethyl.

In one embodiment of the invention and/or embodiments thereof, $R^1$ is independently selected from the group consisting of hydrogen, methyl, trifluoromethyl, ethyl, methoxy, ethoxy, fluoride and chloride, and $R^7$ is independently selected from the group consisting of methyl, ethyl, propyl, isopropyl, isopropenyl methoxy, ethoxy, isopropoxy, hydroxy, methyl sulfoxyl, methyl sulfonyl methylthio, amino, methylamino, ethylamino, (ethyl)(methyl)amino, isopropylamino, dimethylamino, (isopropyl)(methyl)amino, hydroxyethylamino, (hydroxyethyl)(methyl)amino, methoxyethylamino, morpholin-4-yl, pyrrolin-1-yl, 3-hydroxy-pyrrolidin 3-fluoroazetidinyl and 3,3-difluoroazetidinyl.

In an embodiment of the invention and/or embodiments thereof, the compounds are according to Formula (Igi), (Igii), (Igiii), (Igiv), (Igv) or (Igvi)

Formula (Igi)

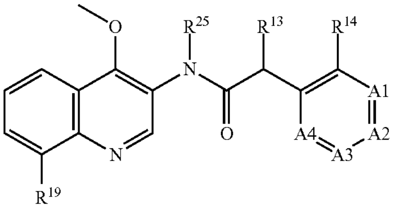

Formula (Igii)

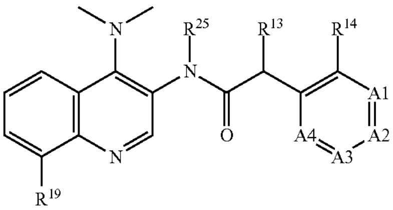

Formula (Igiii)

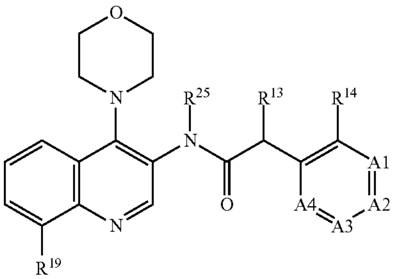

Formula (Igiv)

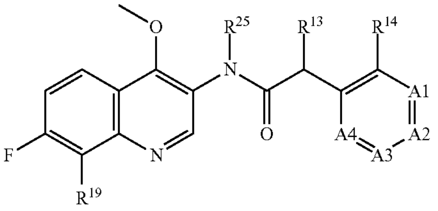

Formula (Igv)

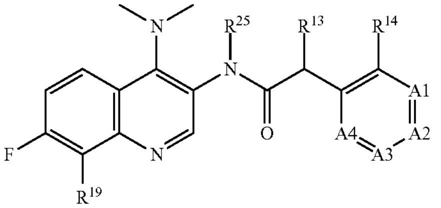

-continued

Formula (Igvi)

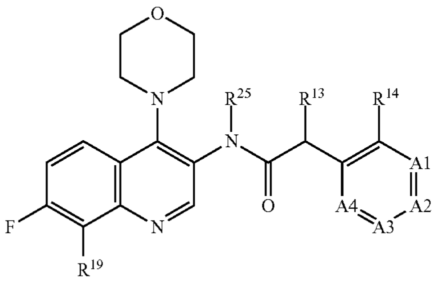

or a stereoisomer, physiologically acceptable salt, ester, solvate, polymorph, prodrug and mixtures thereof, wherein $R^{13}$, $R^{14}$, A1, A2, A3, A4, $R^{19}$ and $R^{25}$ are defined as in any of the embodiments described herein.

In an embodiment of the invention and/or embodiments thereof, the compounds are according to Formula (Igi), preferably in form of the (S)-enantiomer. In an embodiment of the invention and/or embodiments thereof, the compounds are according to Formula (Igii), preferably in form of the (S)-enantiomer. In an embodiment of the invention and/or embodiments thereof, the compounds are according to Formula (Igiii), preferably in form of the (S)-enantiomer. In an embodiment of the invention and/or embodiments thereof, the compounds are according to Formula (Igiv), preferably in form of the (S)-enantiomer. In an embodiment of the invention and/or embodiments thereof, the compounds are according to Formula (Igv, preferably in form of the (S)-enantiomer).

In an embodiment of the invention and/or embodiments thereof, the compounds are according to Formula (Igvi, preferably in form of the (S)-enantiomer).

The invention provides a compound according to the invention and/or embodiments thereof, wherein $R^1$ as well as $R^{13}$, $R^{14}$, A1, A2, A3 and A4 are defined as above.

In an embodiment of the invention and/or embodiments thereof, $R^1$ is independently selected from the group consisting of hydrogen, $C_{1-6}$-alkyl, $C_{1-6}$-alkoxy, halogen, cyano, nitro, hydroxy, $NR^2R^3$, $C(=O)OR^4$ and $C(=O)NR^5R^6$, wherein each $C_{1-6}$-alkyl or $C_{1-6}$-alkoxy is optionally substituted with one or more substituents independently selected from the group consisting of $C_{1-6}$-alkyl, $C_{1-6}$-alkoxy, halogen, cyano, nitro, hydroxy and $NR^{2'}R^{3'}$, $R^2$ and $R^3$ are independently selected from the group consisting of hydrogen, $C_{1-6}$-alkyl, $C_{3-10}$-cycloalkyl, $C_{6-10}$-aryl and 5 to 10-membered heteroaryl, or $R^2$ and $R^3$ together with the N atom to which they are attached form a saturated or unsaturated heterocyclic ring having 3 to 12 ring atoms, wherein 1 ring atom is N and wherein 0, 1, 2 or 3 further ring atoms are selected from N, S and O;

wherein each $C_{1-6}$-alkyl, $C_{3-10}$-cycloalkyl, $C_{6-10}$-aryl or 5 to 10-membered heteroaryl or the heterocyclic ring formed by $R^2$ and $R^3$ together with the N atom to which they are attached is optionally substituted with one or more substituent(s) independently selected from the group consisting of $C_{1-6}$-alkyl, $C_{3-10}$-cycloalkyl and $C_{1-6}$-alkoxy, $R^4$, $R^5$ and $R^6$ are independently selected from hydrogen and $C_{1-6}$-alkyl, preferably from hydrogen and $C_{1-3}$-alkyl, $R^{2'}$ and $R^{3'}$ are independently selected from hydrogen and $C_{1-6}$-alkyl, preferably from hydrogen and $C_{1-3}$-alkyl, and $R^{13}$ and $R^{14}$ together with the atoms to which they are attached form a 5 or 6-carbon atoms containing non-aromatic ring, wherein the non-aromatic ring is optionally substituted with one or more $C_{1-3}$-alkyl or =O, and/or wherein one or more of the ring-forming carbon atoms are optionally replaced by —NH—, —O—, —S(O)—, —S(O)$_2$— or —S—, A1 is N or $CR^{15}$, wherein $R^{15}$ is independently hydrogen, halogen, $C_{1-3}$ alkyl, $C_{1-3}$ alkoxy, or $NR^{15'}R^{15''}$, wherein $R^{15'}$ and $R^{15''}$ are independently $C_{1-3}$-alkyl, A2 is N or $CR^{16}$, wherein $R^{16}$ is independently hydrogen, halogen, $C_{1-3}$ alkyl, $C_{1-3}$ alkoxy, or $NR^{16'}R^{16''}$, wherein $R^{16'}$ and $R^{16''}$ are independently $C_{1-3}$-alkyl, A3 is N or $CR^{17}$, wherein $R^{17}$ is independently hydrogen, halogen, $C_{1-3}$ alkyl, $C_{1-3}$ alkoxy, or $NR^{17'}R^{17''}$, wherein $R^{17'}$ and $R^{17''}$ are independently $C_{1-3}$-alkyl, A4 is N or $CR^{18}$, wherein $R^{18}$ is independently hydrogen, halogen, $C_{1-3}$ alkyl, $C_{1-3}$ alkoxy, or $NR^{18'}R^{18''}$, wherein $R^{18'}$ and $R^{18''}$ are independently $C_{1-3}$-alkyl.

Optionally, in an embodiment of the invention and/or embodiments thereof, $R^1$ is independently selected from the group consisting of hydrogen, $C_{1-6}$-alkyl, $C_{1-6}$-alkoxy and halogen, wherein $C_{1-6}$-alkyl and $C_{1-6}$-alkoxy is optionally substituted with one or more substituent(s) independently selected from the group consisting of $C_{1-6}$-alkyl, $C_{1-6}$-alkoxy, halogen, cyano, hydroxy and $NR^{2'}R^{3'}$, wherein $R^{2'}$ and $R^{3'}$ are independently selected from hydrogen and $C_{1-3}$-alkyl, more preferably from hydrogen and methyl, and $R^{13}$ and $R^{14}$ together with the atoms to which they are attached form a 5 or 6-carbon atoms containing non-aromatic ring, wherein one or more of the ring-forming carbon atoms are optionally replaced by —NH—, —O— or —S—, A1 is N or $CR^{15}$, wherein $R^{15}$ is independently hydrogen, $C_{1-3}$ alkyl or $C_{1-3}$ alkoxy, A2 is N or $CR^{16}$, wherein $R^{16}$ is independently hydrogen, $C_{1-3}$ alkyl or $C_{1-3}$ alkoxy, A3 is N or $CR^{17}$, wherein $R^{17}$ is independently hydrogen, $C_{1-3}$ alkyl or $C_{1-3}$ alkoxy, A4 is N or $CR^{18}$, wherein $R^{18}$ is independently hydrogen, $C_{1-3}$ alkyl or $C_{1-3}$ alkoxy, wherein none, one or two of A1, A2, A3 and A4 are N.

In one embodiment of the invention and/or embodiments thereof, $R^1$ is independently selected from the group consisting of hydrogen, methyl, trifluoromethyl, ethyl, methoxy, ethoxy, fluoride and chloride, and $R^{13}$ and $R^{14}$ together with the atoms to which they are attached form a 5 or 6-carbon atoms containing non-aromatic ring, wherein one or more of the ring-forming carbon atoms are optionally replaced by —NH— or —O—, A1 is N or $CR^{15}$, wherein $R^{15}$ is independently hydrogen or $C_{1-3}$ alkoxy, A2 is N or $CR^{16}$, wherein $R^{16}$ is independently hydrogen or $C_{1-3}$ alkoxy, A3 is N or $CR^{17}$, wherein $R^{17}$ is independently hydrogen or $C_{1-3}$ alkoxy, preferably hydrogen, A4 is N or $CR^{18}$, wherein $R^{18}$ is independently hydrogen or $C_{1-3}$ alkoxy, preferably hydrogen, wherein none, one or two of A1, A2, A3 and A4 are N.

In an embodiment of the invention and/or embodiments thereof, the compounds are according to Formula (Ihi), (Ihii) (Ihiii), (Ihiv), (Ihv) or (Ihvi)

Formula (Ihi)

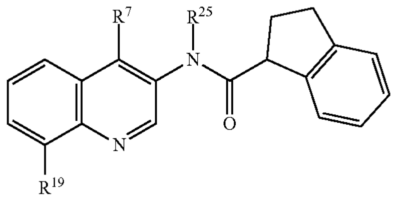

Formula (Ihii)

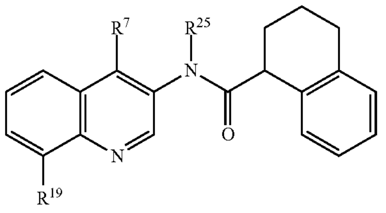

Formula (Ihiii)

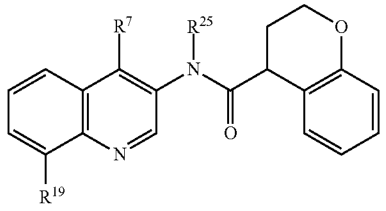

Formula (Ihiv)

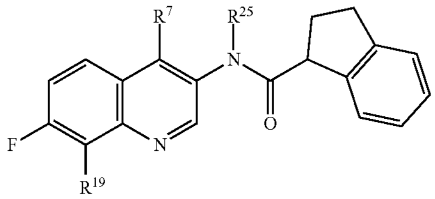

Formula (Ihv)

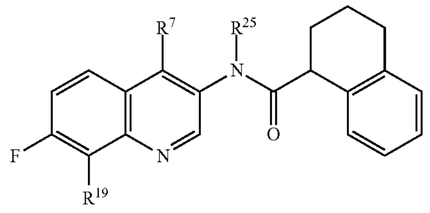

Formula (Ihvi)

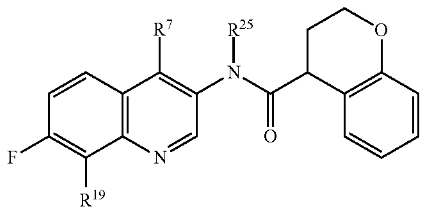

or a stereoisomer, physiologically acceptable salt, ester, solvate, polymorph, prodrug and mixtures thereof, wherein $R^7$, $R^{19}$ and $R^{25}$ are defined as in any of the embodiments described herein.

In an embodiment of the invention and/or embodiments thereof, the compounds are according to Formula (Ihi), preferably in form of the (S)-enantiomer. In an embodiment of the invention and/or embodiments thereof, the compounds are according to Formula (Ihii), preferably in form of the (S)-enantiomer. In an embodiment of the invention and/or embodiments thereof, the compounds are according to Formula (Ihiii), preferably in form of the (S)-enantiomer. In an embodiment of the invention and/or embodiments thereof, the compounds are according to Formula (Ihiv), preferably in form of the (S)-enantiomer. In an embodiment of the invention and/or embodiments thereof, the compounds are according to Formula (Ihv). In an embodiment of the invention and/or embodiments thereof, the compounds are according to Formula (Ihvi), preferably in form of the (S)-enantiomer.

In an embodiment of the invention and/or embodiments thereof, $R^1$ is independently selected from the group consisting of hydrogen, $C_{1-6}$-alkyl, $C_{1-6}$-alkoxy, halogen, cyano, nitro, hydroxy, $NR^2R^3$, C(=O)$OR^4$ and C(=O)$NR^5R^6$,
  wherein each $C_{1-6}$-alkyl or $C_{1-6}$-alkoxy is optionally substituted with one or more substituents independently selected from the group consisting of $C_{1-6}$-alkyl, $C_{1-6}$-alkoxy, halogen, cyano, nitro, hydroxy and $NR^{2'}R^{3'}$, $R^2$ and $R^3$ are independently selected from the group consisting of
  hydrogen, $C_{1-6}$-alkyl, $C_{3-10}$-cycloalkyl, $C_{6-10}$-aryl and 5 to 10-membered heteroaryl, or $R^2$ and $R^3$ together with the N atom to which they are attached form a saturated or unsaturated heterocyclic ring having 3 to 12 ring atoms, wherein 1 ring atom is N and wherein 0, 1, 2 or 3 further ring atoms are selected from N, S and O;
  wherein each $C_{1-6}$-alkyl, $C_{3-10}$-cycloalkyl, $C_{6-10}$-aryl or 5 to 10-membered heteroaryl or the heterocyclic ring formed by $R^2$ and $R^3$ together with the N atom to which they are attached is optionally substituted with one or more substituent(s) independently selected from the group consisting of
  $C_{1-6}$-alkyl, $C_{3-10}$-cycloalkyl and $C_{1-6}$-alkoxy, $R^4$, $R^5$ and $R^6$ are independently selected from hydrogen and $C_{1-6}$-alkyl, preferably from hydrogen and $C_{1-3}$-alkyl, $R^{2'}$ and $R^{3'}$ are independently selected from hydrogen and $C_{1-6}$-alkyl, preferably from hydrogen and $C_{1-3}$-alkyl, and $R^{13}$ and $R^{14}$ together with the atoms to which they are attached form a 5 or 6-carbon atoms containing aromatic ring, wherein the aromatic ring is optionally substituted with one or more $C_{1-3}$-alkyl, and/or wherein one or more of the ring-forming carbon atoms are optionally replaced by —NH—, —N=, =N—, —O— or —S—, A1 is N or $CR^{15}$, wherein $R^{15}$ is independently hydrogen, halogen $C_{1-3}$ alkyl, $C_{1-3}$ alkoxy or $NR^{15'}R^{15''}$, wherein $R^{15'}$ and $R^{15''}$ are independently $C_{1-3}$-alkyl, A2 is N or $CR^{16}$, wherein $R^{16}$ is independently hydrogen, halogen, $C_{1-3}$ alkyl, $C_{1-3}$ alkoxy or $NR^{16'}R^{16''}$, wherein $R^{16'}$ and $R^{16''}$ are independently $C_{1-3}$-alkyl, A3 is N or $CR^{17}$, wherein $R^{17}$ is independently hydrogen, halogen, $C_{1-3}$ alkyl, $C_{1-3}$ alkoxy or $NR^{15'}R^{15''}$, wherein $R^{15'}$ and $R^{15''}$ are independently $C_{1-3}$-alkyl, A4 is N or $CR^{18}$, wherein $R^{18}$ is independently hydrogen, halogen, $C_{1-3}$ alkyl, $C_{1-3}$ alkoxy or $NR^{15'}R^{15''}$, wherein $R^{15'}$ and $R^{15''}$ are independently $C_{1-3}$-alkyl.

Optionally, in an embodiment of the invention and/or embodiments thereof, $R^1$ is independently selected from the group consisting of hydrogen, $C_{1-6}$-alkyl, $C_{1-6}$-alkoxy and halogen,
  wherein $C_{1-6}$-alkyl and $C_{1-6}$-alkoxy is optionally substituted with one or more substituent(s) independently selected from the group consisting of $C_{1-6}$-alkyl, $C_{1-6}$-alkoxy, halogen, cyano, hydroxy and $NR^{2'}R^{3'}$, wherein $R^{2'}$ and $R^{3'}$ are independently selected from hydrogen and $C_{1-3}$-alkyl, more preferably from hydrogen and methyl, and $R^{13}$ and $R^{14}$ together with the atoms to which they are attached form a 5 or 6-carbon atoms containing aromatic ring, wherein one or more of the ring-forming carbon atoms are optionally replaced by —NH—, —N=, =N—, —O— or —S—, A1 is N or $CR^{15}$, wherein $R^{15}$ is independently hydrogen, $C_{1-3}$ alkyl or $C_{1-3}$ alkoxy, A2 is N or $CR^{16}$, wherein $R^{16}$ is independently hydrogen, $C_{1-3}$ alkyl or $C_{1-3}$ alkoxy, A3 is N or $CR^{17}$, wherein $R^{17}$ is independently hydrogen, $C_{1-3}$ alkyl or $C_{1-3}$ alkoxy, A4 is N or $CR^{18}$, wherein $R^{18}$ is independently hydrogen, $C_{1-3}$ alkyl or $C_{1-3}$ alkoxy, wherein none, one or two of A1, A2, A3 and A4 are N.

In one embodiment of the invention and/or embodiments thereof, $R^1$ is independently selected from the group consisting of hydrogen, methyl, trifluoromethyl, ethyl, methoxy, ethoxy, fluoride and chloride, and $R^{13}$ and $R^{14}$ together with the atoms to which they are attached form a 5 or 6-carbon atoms containing aromatic ring, wherein one or more of the ring-forming carbon atoms are optionally replaced by —NH—, —N=, =N— or —S—, A1 is N or $CR^{15}$, wherein $R^{15}$ is independently hydrogen or $C_{1-3}$ alkoxy, A2 is N or $CR^{16}$, wherein $R^{16}$ is independently hydrogen or $C_{1-3}$ alkoxy, A3 is N or $CR^{17}$, wherein $R^{17}$ is independently hydrogen or $C_{1-3}$ alkoxy, preferably hydrogen, A4 is N or $CR^{18}$, wherein $R^{18}$ is independently hydrogen or $C_{1-3}$ alkoxy, preferably hydrogen, wherein none, one or two of A1, A2, A3 and A4 are N.

In an embodiment of the invention and/or embodiments thereof, the compounds are according to Formula (Ihvii), (Ihviii) (Ihix), (Ihx), (Ihxi) or (Ihxii)

Formula (Ihvii)

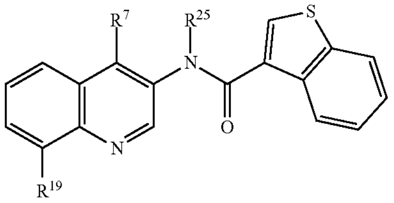

-continued

Formula (Ihviii)

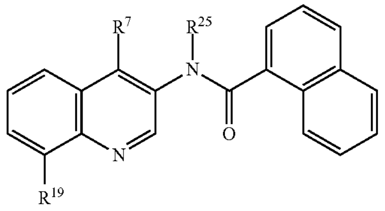

Formula (Ihix)

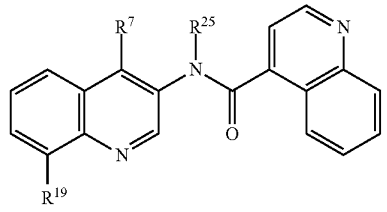

Formula (Ihx)

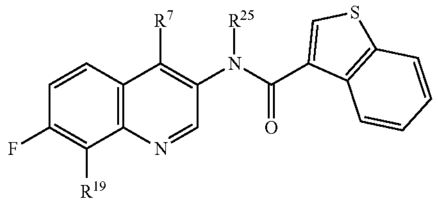

Formula (Ihxi)

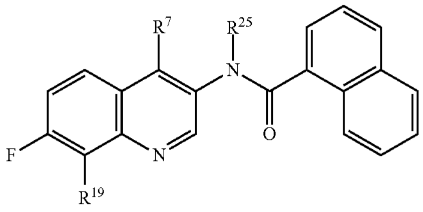

Formula (Ihxii)

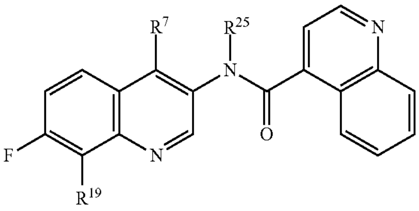

or a stereoisomer, physiologically acceptable salt, ester, solvate, polymorph, prodrug and mixtures thereof, wherein $R^7$, $R^{19}$ and $R^{25}$ are defined as in any of the embodiments described herein.

In an embodiment of the invention and/or embodiments thereof, the compounds are according to Formula (Ihvii), preferably in form of the (S)-enantiomer. In an embodiment of the invention and/or embodiments thereof, the compounds are according to Formula (Ihviii), preferably in form of the (S)-enantiomer. In an embodiment of the invention and/or embodiments thereof, the compounds are according to Formula (Ihix), preferably in form of the (S)-enantiomer. In an embodiment of the invention and/or embodiments thereof, the compounds are according to Formula (Ihx), preferably in form of the (S)-enantiomer. In an embodiment of the invention and/or embodiments thereof, the compounds are according to Formula (Ihxi). In an embodiment of the invention and/or embodiments thereof, the compounds are according to Formula (Ihxii), preferably in form of the (S)-enantiomer.

The invention provides a compound according to the invention and/or embodiments thereof, wherein $R^1$ and $R^{19}$ are defined as above.

In an embodiment of the invention and/or embodiments thereof, $R^1$ is independently selected from the group consisting of hydrogen, $C_{1-6}$-alkyl, $C_{1-6}$-alkoxy, halogen, cyano, nitro, hydroxy, $NR^2R^3$, $C(=O)OR^4$ and $C(=O)NR^5R^6$, wherein each $C_{1-6}$-alkyl or $C_{1-6}$-alkoxy is optionally substituted with one or more substituents independently selected from the group consisting of $C_{1-6}$-alkyl, $C_{1-6}$-alkoxy, halogen, cyano, nitro, hydroxy and $NR^{2'}R^{3'}$, $R^2$ and $R^3$ are independently selected from the group consisting of hydrogen, $C_{1-6}$-alkyl, $C_{3-10}$-cycloalkyl, $C_{6-10}$-aryl and 5 to 10-membered heteroaryl, or $R^2$ and $R^3$ together with the N atom to which they are attached form a saturated or unsaturated heterocyclic ring having 3 to 12 ring atoms, wherein 1 ring atom is N and wherein 0, 1, 2 or 3 further ring atoms are selected from N, S and O;

wherein each $C_{1-6}$-alkyl, $C_{3-10}$-cycloalkyl, $C_{6-10}$-aryl or 5 to 10-membered heteroaryl or the heterocyclic ring formed by $R^2$ and $R^3$ together with the N atom to which they are attached is optionally substituted with one or more substituent(s) independently selected from the group consisting of $C_{1-6}$-alkyl, $C_{3-10}$-cycloalkyl and $C_{1-6}$-alkoxy, $R^4$, $R^5$ and $R^6$ are independently selected from hydrogen and $C_{1-6}$-alkyl, preferably from hydrogen and $C_{1-3}$-alkyl, $R^{2'}$ and $R^{3'}$ are independently selected from hydrogen and $C_{1-6}$-alkyl, preferably from hydrogen and $C_{1-3}$-alkyl, and $R^{19}$ is independently selected from the group consisting of $C_{6-10}$-aryl and 5 to 10-membered heteroaryl, wherein each $C_{6-10}$-aryl or 5 to 10-membered heteroaryl is optionally substituted with one or more substituent(s) independently selected from the group consisting of $C_{1-6}$-alkyl, $C_{3-10}$-cycloalkyl, $C_{1-6}$-alkoxy, 5 to 10-membered heterocyclyl, $C_{6-10}$-aryl, 5 to 10-membered heteroaryl, halogen, cyano, nitro, hydroxy, $NR^{20}R^{21}$, $C(=O)OR^{22}$ and $C(=O)NR^{23}R^{24}$, $R^{20}$ and $R^{21}$ are independently selected from the group consisting of hydrogen, $C_{1-6}$-alkyl, $C_{3-10}$-cycloalkyl and $C_{6-10}$-aryl or $R^{20}$ and $R^{21}$ together with the N atom to which they are attached form a saturated or unsaturated heterocyclic ring having 3 to 12 ring atoms, wherein 0, 1, 2, or 3 further ring atoms are selected from N, S and O;

wherein each $C_{1-6}$-alkyl, $C_{3-10}$-cycloalkyl or $C_{6-10}$-aryl or the heterocyclic ring formed by $R^{20}$ and $R^{21}$ together with the N atom to which they are attached is optionally substituted with one or more substituents independently selected from the group consisting of $C_{1-6}$-alkyl, $C_{3-10}$-cycloalkyl, $C_{1-6}$-alkoxy, 5 to 10-membered heterocyclyl, $C_{6-10}$-aryl, 5 to 10-membered heteroaryl, halogen, cyano, hydroxy, $NR^{20'}R^{21'}$, $C(=O)OR^{22'}$ and $C(=O)NR^{23'}R^{24'}$ $R^{22}$, $R^{23}$ and $R^{24}$ are independently selected from hydrogen and $C_{1-6}$-alkyl, $R^{20'}$, $R^{21'}$, $R^{22'}$, $R^{23'}$ and $R^{24'}$ are independently selected from hydrogen and $C_{1-6}$-alkyl.

Optionally, in an embodiment of the invention and/or embodiments thereof, $R^1$ is independently selected from the group consisting of hydrogen, $C_{1-6}$-alkyl, $C_{1-6}$-alkoxy and halogen, wherein $C_{1-6}$-alkyl and $C_{1-6}$-alkoxy is optionally substituted with one or more substituent(s) independently selected from the group consisting of $C_{1-6}$-alkyl, $C_{1-6}$-alkoxy, halogen, cyano, hydroxy and $NR^{2'}R^{3'}$, wherein $R^{2'}$ and $R^{3'}$ are independently selected from hydrogen and $C_{1-3}$-alkyl, more preferably from hydrogen and methyl, and $R^{19}$ is independently selected from the group consisting of $C_{6-10}$-aryl and 5 to 10-membered heteroaryl wherein each $C_{6-10}$-aryl or 5 to 10-membered heteroaryl is optionally substituted with one or more substituent(s) independently selected from the group consisting of $C_{1-6}$-alkyl, $C_{1-6}$-alkoxy, halogen, cyano, nitro and hydroxy.

In one embodiment of the invention and/or embodiments thereof, $R^1$ is independently selected from the group consisting of hydrogen, methyl, trifluoromethyl, ethyl, methoxy, ethoxy, fluoride and chloride, and $R^{19}$ is independently selected from the group consisting of 3-chlorophenyl, 2,3-dichlorophenyl, 3,5-dichlorophenyl, 3,5-difluorophenyl, 2,3,5-trifluorophenyl, 3,4,5-trifluorophenyl, 3-chloro-2-fluorophenyl, 5-chloro-3-fluorophenyl, 5-chloro-3-fluorophenyl, 3,5-dichloro-4-fluorophenyl, in particular 2,3,5-trifluorophenyl, 5-chloro-2-fluorophenyl, 2,3-dichlorophenyl and 3,5-dichlorophenyl.

In an embodiment of the invention and/or embodiments thereof, the compounds are according to Formula (Iii), (Iiii), (Iiiii), (Iiiv), (Iiv) or (Iivi)

Formula (Iii)

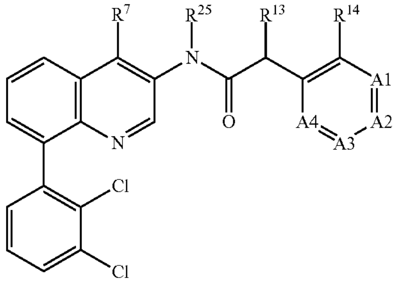

Formula (Iiii)

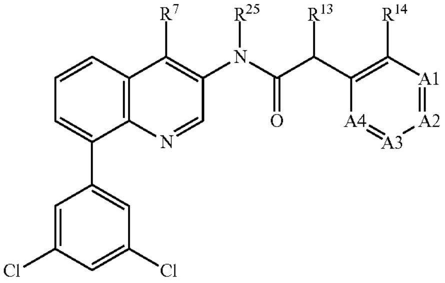

-continued

Formula (Iiiii)

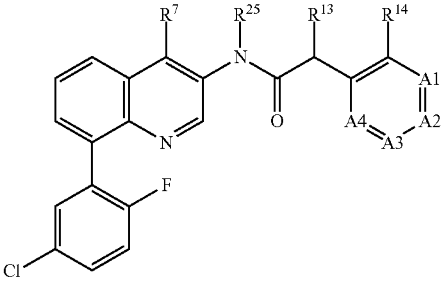

Formula (Iiiv)

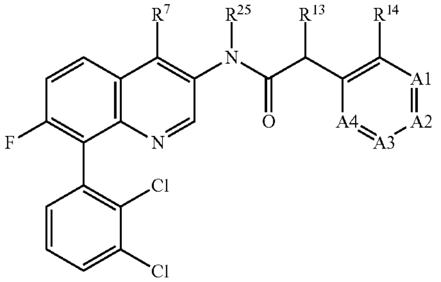

Formula (Iiv)

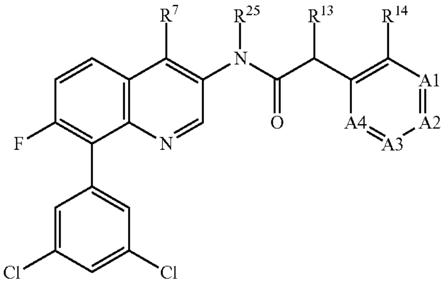

Formula (Iivi)

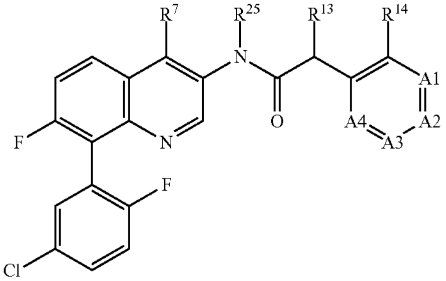

or a stereoisomer, physiologically acceptable salt, ester, solvate, polymorph, prodrug and mixtures thereof, wherein $R^7$, R, $R^{14}$, A1, A2, A3, A4 and $R^{25}$ are defined as in any of the embodiments described herein.

In an embodiment of the invention and/or embodiments thereof, the compounds are according to Formula (Iii), preferably in form of the (S)-enantiomer. In an embodiment of the invention and/or embodiments thereof, the compounds are according to Formula (Iiii), preferably in form of the (S)-enantiomer. In an embodiment of the invention and/or embodiments thereof, the compounds are according to Formula (Iiiii), preferably in form of the (S)-enantiomer. In an embodiment of the invention and/or embodiments thereof, the compounds are according to Formula (Iiiv), preferably in form of the (S)-enantiomer. In an embodiment of the invention and/or embodiments thereof, the compounds are according to Formula (Iiv), preferably in form of the (S)-enantiomer. In an embodiment of the invention and/or embodiments thereof, the compounds are according to Formula (Iivi), preferably in form of the (S)-enantiomer.

The invention provides a compound according to the invention and/or embodiments thereof, wherein $R^1$ and $R^{25}$ are defined as above.

In an embodiment of the invention and/or embodiments thereof, $R^1$ is independently selected from the group consisting of hydrogen, $C_{1-6}$-alkyl, $C_{1-6}$-alkoxy, halogen, cyano, nitro, hydroxy, $NR^2R^3$, $C(=O)OR^4$ and $C(=O)NR^5R^6$, wherein each $C_{1-6}$-alkyl or $C_{1-6}$-alkoxy is optionally substituted with one or more substituents independently selected from the group consisting of $C_{1-6}$-alkyl, $C_{1-6}$-alkoxy, halogen, cyano, nitro, hydroxy and $NR^{2'}R^{3'}$, $R^2$ and $R^3$ are independently selected from the group consisting of hydrogen, $C_{1-6}$-alkyl, $C_{3-10}$-cycloalkyl, $C_{6-10}$-aryl and 5 to 10-membered heteroaryl, or $R^2$ and $R^3$ together with the N atom to which they are attached form a saturated or unsaturated heterocyclic ring having 3 to 12 ring atoms, wherein 1 ring atom is N and wherein 0, 1, 2 or 3 further ring atoms are selected from N, S and O;

wherein each $C_{1-6}$-alkyl, $C_{3-10}$-cycloalkyl, $C_{6-10}$-aryl or 5 to 10-membered heteroaryl or the heterocyclic ring formed by $R^2$ and $R^3$ together with the N atom to which they are attached is optionally substituted with one or more substituent(s) independently selected from the group consisting of $C_{1-6}$-alkyl, $C_{3-10}$-cycloalkyl and $C_{1-6}$-alkoxy, $R^4$, $R^5$ and $R^6$ are independently selected from hydrogen and $C_{1-6}$-alkyl, preferably from hydrogen and $C_{1-3}$-alkyl, $R^{2'}$ and $R^{3'}$ are independently selected from hydrogen and $C_{1-6}$-alkyl, preferably from hydrogen and $C_{1-3}$-alkyl, and $R^{25}$ is hydrogen or $C_{1-3}$-alkyl.

In one embodiment of the invention and/or embodiments thereof, $R^1$ is independently selected from the group consisting of hydrogen, methyl, trifluoromethyl, ethyl, methoxy, ethoxy, fluoride and chloride, and $R^{25}$ is hydrogen or methyl.

In an embodiment of the invention and/or embodiments thereof, the compounds are according to Formula (Iji), (Ijii), (Ijiii) or (Ijiv)

Formula (Iji)

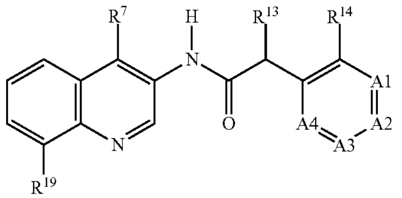

Formula (Ijii)

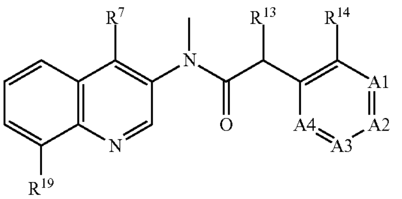

-continued

Formula (Ijiii)

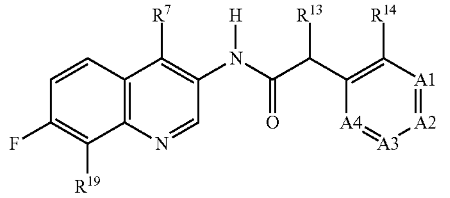

Formula (Ijiv)

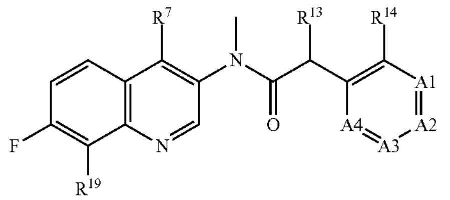

or a stereoisomer, physiologically acceptable salt, ester, solvate, polymorph, prodrug and mixtures thereof, wherein $R^7$, $R^3$, $R^{14}$, A1, A2, A3 and A4 are defined as in any of the embodiments described herein.

In an embodiment of the invention and/or embodiments thereof, the compounds are according to Formula (Iji), preferably in form of the (S)-enantiomer. In an embodiment of the invention and/or embodiments thereof, the compounds are according to Formula (Ijii), preferably in form of the (S)-enantiomer. In an embodiment of the invention and/or embodiments thereof, the compounds are according to Formula (Ijiii), preferably in form of the (S)-enantiomer. In an embodiment of the invention and/or embodiments thereof, the compounds are according to Formula (Ijiv), preferably in form of the (S)-enantiomer.

The invention provides a compound according to the invention and/or embodiments thereof, wherein $R^7$ as well as $R^{13}$, $R^{14}$, A1, A2; A3 and A4 are defined as above.

In an embodiment of the invention and/or embodiments thereof, $R^7$ is independently selected from the group consisting of hydrogen, $C_{1-6}$-alkyl, $C_{2-6}$-alkenyl, $C_{3-10}$-cycloalkyl, 4 to 10-membered heterocyclyl, $C_{1-6}$-alkoxy, halogen, cyano, hydroxy, $NR^8R^9$, $C(=O)OR^{10}$, $SR^{10}$, $SOR^{10}$, $SO_2R^{10}$ and $C(=O)NR^{11}R^{12}$ wherein each $C_{1-6}$-alkyl, $C_{2-6}$-alkenyl, $C_{3-10}$-cycloalkyl, 4 to 10-membered heterocyclyl or $C_{1-6}$-alkoxy is optionally substituted with one or more substituent(s) independently selected from the group consisting of $C_{1-6}$-alkyl, $C_{3-10}$-cycloalkyl, 5 to 10-membered heterocyclyl, $C_{1-6}$-alkoxy, halogen, cyano, hydroxy, $NR^{8'}R^{9'}$, $C(=O)OR^{10'}$ and $C(=O)NR^{11'}R^{12'}$, $R^8$ and $R^9$ are independently selected from the group consisting of hydrogen, $C_{1-6}$-alkyl, $C_{3-10}$-cycloalkyl, $C_{6-10}$-aryl, 5 to 10-membered heterocyclyl and 5 to 10-membered heteroaryl, or $R^8$ and $R^9$ together with the N atom to which they are attached form a saturated or unsaturated heterocyclic ring having 3 to 12 ring atoms, wherein 1 ring atom is N and wherein 0, 1, 2, or 3 further ring atoms are selected from N, S and O;

wherein the $C_{1-6}$-alkyl, $C_{3-10}$-cycloalkyl, $C_{6-10}$-aryl, 5 to 10-membered heterocyclyl or 5 to 10-membered heteroaryl or the heterocyclic ring formed by $R^8$ and $R^9$ together with the N atom to which they are attached is optionally substituted with one or more substituent(s) independently selected from the group consisting of $C_{1-6}$-alkyl, $C_{1-6}$-alkoxy, halogen, cyano, hydroxy, $NR^{8''}R^{9''}$, C(=O)—$OR^{10''}$ and C(=O)$NR^{11''}R^{12''}$;

$R^{10}$, $R^{11}$ and $R^{12}$ are independently selected from hydrogen and $C_{1-6}$-alkyl, $R^{8'}$, $R^{9'}$, $R^{10'}$, $R^{11'}$ and $R^{12'}$ are independently selected from hydrogen and $C_{1-6}$-alkyl, $R^{8''}$, $R^{9''}$, $R^{10''}$, $R^{11''}$ and $R^{12''}$ are independently selected from hydrogen and $C_{1-6}$-alkyl, and $R^{13}$ and $R^{14}$ together with the atoms to which they are attached form a 5 or 6-carbon atoms containing non-aromatic ring, wherein the non-aromatic ring is optionally substituted with one or more $C_{1-3}$-alkyl or =O, and/or wherein one or more of the ring-forming carbon atoms are optionally replaced by —NH—, —O—, —S(O)—, —$S(O)_2$— or —S—, A1 is N or $CR^{15}$, wherein $R^{15}$ is independently hydrogen, halogen, $C_{1-3}$ alkyl, $C_{1-3}$ alkoxy, or $NR^{15'}R^{15''}$, wherein $R^{15'}$ and $R^{15''}$ are independently $C_{1-3}$-alkyl, A2 is N or $CR^{16}$, wherein $R^{16}$ is independently hydrogen, halogen, $C_{1-3}$ alkyl, $C_{1-3}$ alkoxy, or $NR^{16'}R^{16''}$, wherein $R^{16'}$ and $R^{16''}$ are independently $C_{1-3}$-alkyl, A3 is N or $CR^{17}$, wherein $R^{17}$ is independently hydrogen, halogen, $C_{1-3}$ alkyl, $C_{1-3}$ alkoxy, or $NR^{17'}R^{17''}$, wherein $R^{17'}$ and $R^{17''}$ are independently $C_{1-3}$-alkyl, A4 is N or $CR^{18}$, wherein $R^{18}$ is independently hydrogen, halogen, $C_{1-3}$ alkyl, $C_{1-3}$ alkoxy, or $NR^{18'}R^{18''}$, wherein $R^{18'}$ and $R^{18''}$ are independently $C_{1-3}$-alkyl.

In an embodiment of the invention and/or embodiments thereof, $R^7$ is independently selected from the group consisting of hydrogen, $C_{1-6}$-alkyl, $C_{2-6}$-alkenyl, 4- to 10-membered heterocyclyl, $C_{1-3}$-alkoxy, hydroxy, $NR^8R^9$, $SR^{10}$, $SOR^{10}$ and $SO_2R^{10}$, wherein each $C_{1-6}$-alkyl, $C_{2-6}$-alkenyl, 4- to 10-membered heterocyclyl or $C_{1-3}$-alkoxy is optionally substituted with one or more substituent(s) independently selected from the group consisting of $C_{1-3}$-alkyl, 5 to 10-membered heterocyclyl, $C_{1-6}$-alkoxy, halogen, cyano, hydroxy, $NR^{8'}R^{9'}$, C(=O)$OR^{10'}$ and C(=O)$NR^{11'}R^{12'}$, $R^8$ and $R^9$ are independently selected from the group consisting of hydrogen, $C_{1-6}$-alkyl, $C_{6-10}$-aryl and 5 to 10-membered heteroaryl, or $R^8$ and $R^9$ together with the N atom to which they are attached form a saturated or unsaturated heterocyclic ring having 3 to 12 ring atoms, wherein 1 ring atom is N and wherein 0, 1, 2, or 3 further ring atoms are selected from N, S and O;

wherein the $C_{1-6}$-alkyl, $C_{6-10}$-aryl or 5 to 10-membered heteroaryl or the heterocyclic ring formed by $R^8$ and $R^9$ together with the N atom to which they are attached is optionally substituted with one or more substituent(s) independently selected from the group consisting of $C_{1-6}$-alkyl, $C_{1-6}$-alkoxy, hydroxy and $NR^{8''}R^{9''}$;

$R^{10}$ is independently selected from hydrogen or $C_{1-3}$-alkyl, preferably from hydrogen, methyl or ethyl $R^{8'}$, $R^{9'}$, $R^{10'}$, $R^{11'}$ and $R^{12'}$ are independently selected from hydrogen or $C_{1-3}$-alkyl, preferably from hydrogen, methyl or ethyl, $R^{8''}$ and $R^{9''}$ are independently selected from hydrogen or $C_{1-3}$-alkyl, preferably from hydrogen, methyl or ethyl, and $R^{13}$ and $R^{14}$ together with the atoms to which they are attached form a 5 or 6-carbon atoms containing non-aromatic ring, wherein one or more of the ring-forming carbon atoms are optionally replaced by —NH—, —O— or —S—, A1 is N or $CR^{15}$, wherein $R^{15}$ is independently hydrogen, $C_{1-3}$ alkyl or $C_{1-3}$ alkoxy, A2 is N or $CR^{16}$, wherein $R^{16}$ is independently hydrogen, $C_{1-3}$ alkyl or $C_{1-3}$ alkoxy, A3 is N or $CR^{17}$, wherein $R^{17}$ is independently hydrogen, $C_{1-3}$ alkyl or $C_{1-3}$ alkoxy, A4 is N or $CR^{18}$, wherein $R^{18}$ is independently hydrogen, $C_{1-3}$ alkyl or $C_{1-3}$ alkoxy, wherein none, one or two of A1, A2, A3 and A4 are N.

In an embodiment of the invention and/or embodiments thereof, $R^7$ is independently selected from the group consisting of methyl, ethyl, isopropyl, isopropenyl methoxy, ethoxy, propyl, isopropoxy, hydroxy, methyl sulfoxyl, methyl sulfonyl methylthio, amino, methylamino, ethylamino, (ethyl)(methyl)amino isopropylamino, dimethylamino, (isopropyl)(methyl)amino, hydroxyethylamino, (hydroxyethyl)(methyl)amino, methoxyethylamino, morpholin-4-yl, (methoxyethyl)(methyl)amino, pyrrolidin-1-yl, 3-hydroxy-pyrrolidin-1-yl 3-fluoroazetidinyl and 3,3-difluoroazetidinyl, and $R^{13}$ and $R^{14}$ together with the atoms to which they are attached form a 5 or 6-carbon atoms containing non-aromatic ring, wherein one or more of the ring-forming carbon atoms are optionally replaced by —NH— or —O—, A1 is N or $CR^{15}$, wherein $R^{15}$ is independently hydrogen or $C_{1-3}$ alkoxy, A2 is N or $CR^{16}$, wherein $R^{16}$ is independently hydrogen or $C_{1-3}$ alkoxy, A3 is N or $CR^{17}$, wherein $R^{17}$ is independently hydrogen or $C_{1-3}$ alkoxy, preferably hydrogen, A4 is N or $CR^{18}$, wherein $R^{18}$ is independently hydrogen or $C_{1-3}$ alkoxy, preferably hydrogen, wherein none, one or two of A1, A2, A3 and A4 are N.

In an embodiment of the invention and/or embodiments thereof, the compounds are according to Formula (Iki), (Ikii), (Ikiii), (Ikiv), (Ikv), (Ikvi), (Ikvii), (Ikviii) or (Ikix)

Formula (Iki)

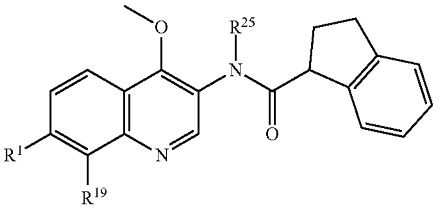

Formula (Ikii)

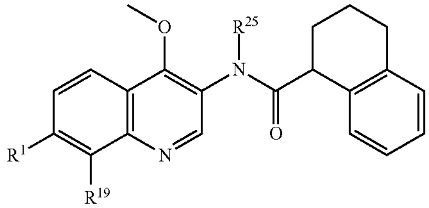

-continued

Formula (Ikiii)

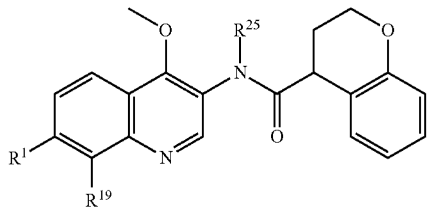

Formula (Ikiv)

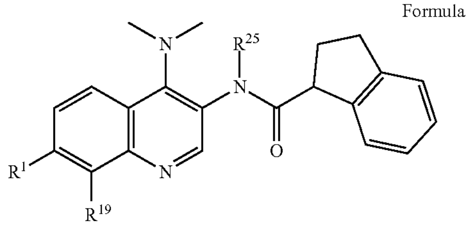

Formula (Ikv)

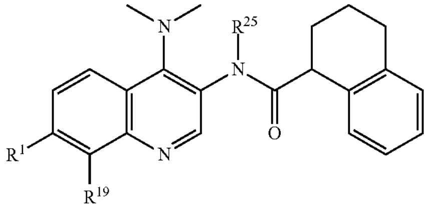

Formula (Ikvi)

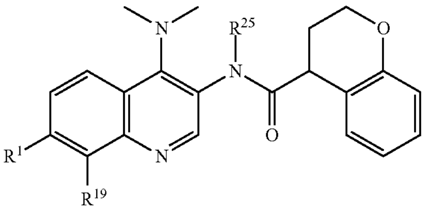

Formula (Ikvii)

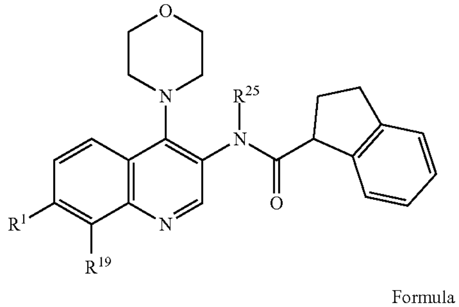

Formula (Ikviii)

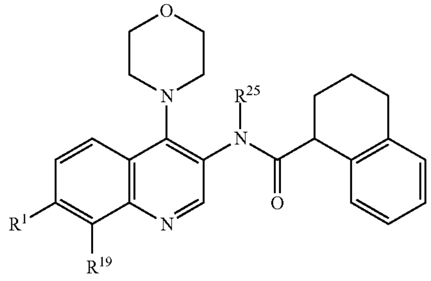

-continued

Formula (Ikix)

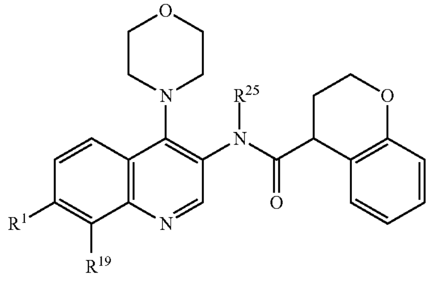

or a stereoisomer, physiologically acceptable salt, ester, solvate, polymorph, prodrug and mixtures thereof, wherein $R^1$, $R^{19}$ and $R^{25}$ are defined as in any of the embodiments described herein.

In an embodiment of the invention and/or embodiments thereof, the compounds are according to Formula (Iki), preferably in form of the (S)-enantiomer. In an embodiment of the invention and/or embodiments thereof, the compounds are according to Formula (Ikii), preferably in form of the (S)-enantiomer. In an embodiment of the invention and/or embodiments thereof, the compounds are according to Formula (Ikiii), preferably in form of the (S)-enantiomer. In an embodiment of the invention and/or embodiments thereof, the compounds are according to Formula (Ikiv), preferably in form of the (S)-enantiomer. In an embodiment of the invention and/or embodiments thereof, the compounds are according to Formula (Ikv), preferably in form of the (S)-enantiomer. In an embodiment of the invention and/or embodiments thereof, the compounds are according to Formula (Ikvi), preferably in form of the (S)-enantiomer. In an embodiment of the invention and/or embodiments thereof, the compounds are according to Formula (Ikvii), preferably in form of the (S)-enantiomer. In an embodiment of the invention and/or embodiments thereof, the compounds are according to Formula (Ikviii), preferably in form of the (S)-enantiomer. In an embodiment of the invention and/or embodiments thereof, the compounds are according to Formula (Ikix), preferably in form of the (S)-enantiomer.

In an embodiment of the invention and/or embodiments thereof, $R^7$ is independently selected from the group consisting of hydrogen, $C_{1-6}$-alkyl, $C_{2-6}$-alkenyl, $C_{3-10}$-cycloalkyl, 4 to 10-membered heterocyclyl, $C_{1-6}$-alkoxy, halogen, cyano, hydroxy, $NR^8R^9$, $C(=O)OR^{10}$, $SR^{10}$, $SOR^{10}$, $SO_2R^{10}$ and $C(=O)NR^{11}R^{12}$ wherein each $C_{1-6}$-alkyl, $C_{2-6}$-alkenyl, $C_{3-10}$-cycloalkyl, 4 to 10-membered heterocyclyl or $C_{1-6}$-alkoxy is optionally substituted with one or more substituent(s) independently selected from the group consisting of $C_{1-6}$-alkyl, $C_{3-10}$-cycloalkyl, 5 to 10-membered heterocyclyl, $C_{1-6}$-alkoxy, halogen, cyano, hydroxy, $NR^{8'}R^{9'}$, $C(=O)OR^{10'}$ and $C(=O)NR^{11'}R^{12'}$, $R^8$ and $R^9$ are independently selected from the group consisting of hydrogen, $C_{1-6}$-alkyl, $C_{3-10}$-cycloalkyl, $C_{6-10}$-aryl, 5 to 10-membered heterocyclyl and 5 to 10-membered heteroaryl, or $R^8$ and $R^9$ together with the N atom to which they are attached form a saturated or unsaturated heterocyclic ring having 3 to 12 ring atoms, wherein 1 ring atom is N and wherein 0, 1, 2, or 3 further ring atoms are selected from N, S and O;

wherein the $C_{1-6}$-alkyl, $C_{3-10}$-cycloalkyl, $C_{6-10}$-aryl, 5 to 10-membered heterocyclyl or 5 to 10-membered heteroaryl or the heterocyclic ring formed by $R^8$ and $R^9$ together with the N atom to which they are attached is optionally substituted with one or more substituent(s) independently selected from the group consisting of $C_{1-6}$-alkyl, $C_{1-6}$-alkoxy, halogen, cyano, hydroxy, $NR^{8''}R^{9''}$, C(═O)—$OR^{10''}$ and C(═O)$NR^{11''}R^{12''}$;

$R^{10}$, $R^{11}$ and $R^{12}$ are independently selected from hydrogen and $C_{1-6}$-alkyl, $R^{8'}$, $R^{9'}$, $R^{10'}$, $R^{11'}$ and $R^{12'}$ are independently selected from hydrogen and $C_{1-6}$-alkyl, $R^{8''}$, $R^{9''}$, $R^{10''}$, $R^{11''}$ and $R^{12''}$ are independently selected from hydrogen and $C_{1-6}$-alkyl, and $R^{13}$ and $R^{14}$ together with the atoms to which they are attached form a 5 or 6-carbon atoms containing aromatic ring, wherein the aromatic ring is optionally substituted with one or more $C_{1-3}$-alkyl, and/or wherein one or more of the ring-forming carbon atoms are optionally replaced by —NH—, —N═, ═N—, —O— or —S—, A1 is N or $CR^{15}$, wherein $R^{15}$ is independently hydrogen, halogen $C_{1-3}$ alkyl, $C_{1-3}$ alkoxy or $NR^{15'}R^{15''}$, wherein $R^{15'}$ and $R^{15''}$ are independently $C_{1-3}$-alkyl, A2 is N or $CR^{16}$, wherein $R^{16}$ is independently hydrogen, halogen, $C_{1-3}$ alkyl, $C_{1-3}$ alkoxy or $NR^{16'}R^{16''}$, wherein $R^{16'}$ and $R^{16''}$ are independently $C_{1-3}$-alkyl, A3 is N or $CR^{17}$, wherein $R^{17}$ is independently hydrogen, halogen, $C_{1-3}$ alkyl, $C_{1-3}$ alkoxy or $NR^{15'}R^{15''}$, wherein $R^{15'}$ and $R^{15''}$ are independently $C_{1-3}$-alkyl, A4 is N or $CR^{18}$, wherein $R^{18}$ is independently hydrogen, halogen, $C_{1-3}$ alkyl, $C_{1-3}$ alkoxy or $NR^{15'}R^{15''}$, wherein $R^{15'}$ and $R^{15''}$ are independently $C_{1-3}$-alkyl.

In an embodiment of the invention and/or embodiments thereof, $R^7$ is independently selected from the group consisting of hydrogen, $C_{1-6}$-alkyl, $C_{2-6}$-alkenyl, 4- to 10-membered heterocyclyl, $C_{1-3}$-alkoxy, hydroxy, $NR^8R^9$, $SR^{10}$, $SOR^{10}$ and $SO_2R^{10}$, wherein each $C_{1-6}$-alkyl, $C_{2-6}$-alkenyl, 4- to 10-membered heterocyclyl or $C_{1-3}$-alkoxy is optionally substituted with one or more substituent(s) independently selected from the group consisting of $C_{1-3}$-alkyl, 5 to 10-membered heterocyclyl, $C_{1-6}$-alkoxy, halogen, cyano, hydroxy, $NR^{8'}R^{9'}$, C(═O)$OR^{10'}$ and C(═O)$NR^{11'}R^{12'}$, $R^8$ and $R^9$ are independently selected from the group consisting of hydrogen, $C_{1-6}$-alkyl, $C_{6-10}$-aryl and 5 to 10-membered heteroaryl, or $R^8$ and $R^9$ together with the N atom to which they are attached form a saturated or unsaturated heterocyclic ring having 3 to 12 ring atoms, wherein 1 ring atom is N and wherein 0, 1, 2, or 3 further ring atoms are selected from N, S and O;

wherein the $C_{1-6}$-alkyl, $C_{6-10}$-aryl or 5 to 10-membered heteroaryl or the heterocyclic ring formed by $R^8$ and $R^9$ together with the N atom to which they are attached is optionally substituted with one or more substituent(s) independently selected from the group consisting of $C_{1-6}$-alkyl, $C_{1-6}$-alkoxy, hydroxy and $NR^{8''}R^{9''}$;

$R^{10}$ is independently selected from hydrogen or $C_{1-3}$-alkyl, preferably from hydrogen, methyl or ethyl $R^{8'}$, $R^{9'}$, $R^{10'}$, $R^{11'}$ and $R^{12'}$ are independently selected from hydrogen or $C_{1-3}$-alkyl, preferably from hydrogen, methyl or ethyl, $R^{8''}$ and $R^{9''}$ are independently selected from hydrogen or $C_{1-3}$-alkyl, preferably from hydrogen, methyl or ethyl, and $R^{13}$ and $R^{14}$ together with the atoms to which they are attached form a 5 or 6-carbon atoms containing aromatic ring, wherein one or more of the ring-forming carbon atoms are optionally replaced by —NH—, —N═, ═N—, —O— or —S—, A1 is N or $CR^{15}$, wherein $R^{15}$ is independently hydrogen, $C_{1-3}$ alkyl or $C_{1-3}$ alkoxy, A2 is N or $CR^{16}$, wherein $R^{16}$ is independently hydrogen, $C_{1-3}$ alkyl or $C_{1-3}$ alkoxy, A3 is N or $CR^{17}$, wherein $R^{17}$ is independently hydrogen, $C_{1-3}$ alkyl or $C_{1-3}$ alkoxy, A4 is N or $CR^{18}$, wherein $R^{18}$ is independently hydrogen, $C_{1-3}$ alkyl or $C_{1-3}$ alkoxy, wherein none, one or two of A1, A2, A3 and A4 are N.

In an embodiment of the invention and/or embodiments thereof, $R^7$ is independently selected from the group consisting of methyl, ethyl, isopropyl, isopropenyl methoxy, ethoxy, propyl, isopropoxy, hydroxy, methyl sulfoxyl, methyl sulfonyl methylthio, amino, methylamino, ethylamino, (ethyl)(methyl)amino isopropylamino, dimethylamino, (isopropyl)(methyl)amino, hydroxyethylamino, (hydroxyethyl)(methyl)amino, methoxyethylamino, morpholin-4-yl, (methoxyethyl)(methyl)amino, pyrrolidin-1-yl, 3-hydroxypyrrolidin-1-yl 3-fluoroazetidinyl and 3,3-difluoroazetidinyl, and $R^{13}$ and $R^{14}$ together with the atoms to which they are attached form a 5 or 6-carbon atoms containing aromatic ring, wherein one or more of the ring-forming carbon atoms are optionally replaced by —NH—, —N═, ═N— or —S—, A1 is N or $CR^{15}$, wherein $R^{15}$ is independently hydrogen or $C_{1-3}$ alkoxy, A2 is N or $CR^{16}$, wherein $R^{16}$ is independently hydrogen or $C_{1-3}$ alkoxy, A3 is N or $CR^{17}$, wherein $R^{17}$ is independently hydrogen or $C_{1-3}$ alkoxy, preferably hydrogen, A4 is N or $CR^{18}$, wherein $R^{18}$ is independently hydrogen or $C_{1-3}$ alkoxy, preferably hydrogen, wherein none, one or two of A1, A2, A3 and A4 are N.

In an embodiment of the invention and/or embodiments thereof, the compounds are according to Formula (Ikx), (Ikxi), (Ikxii), (Ikxiii), (Ikxiv), (Ikxv), (Ikxvi), (Ikvii) or (Ikxviii)

Formula (Ikx)

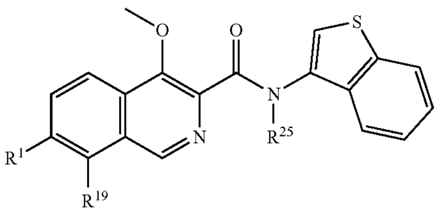

-continued

Formula (Ikxi)

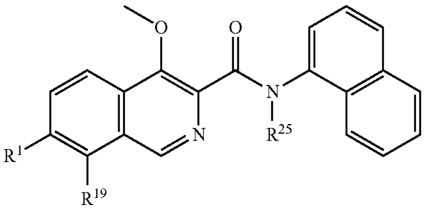

Formula (Ikxii)

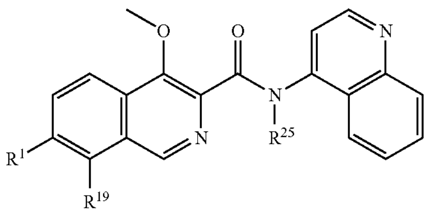

Formula (Ikiii)

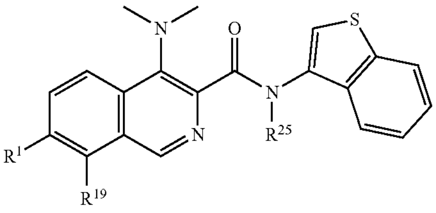

Formula (Ikxiv)

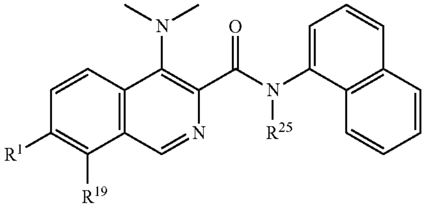

Formula (Ikxv)

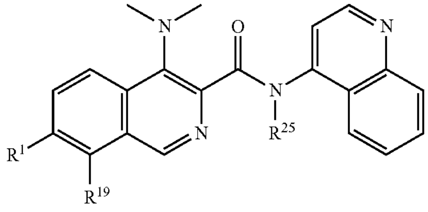

Formula (Ikxvi)

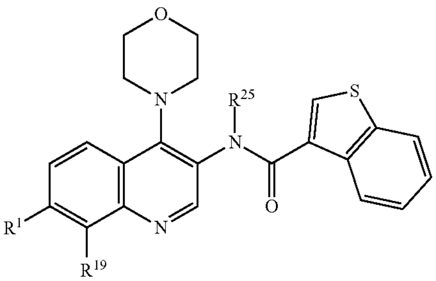

-continued

Formula (Ikxvii)

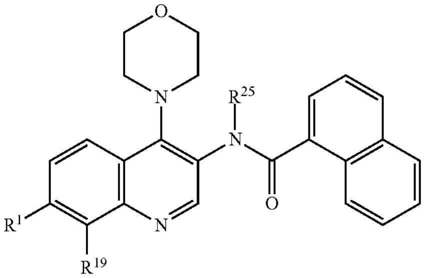

Formula (Ikxviii)

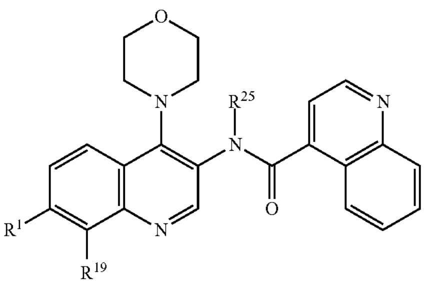

or a stereoisomer, physiologically acceptable salt, ester, solvate, polymorph, prodrug and mixtures thereof, wherein $R^1$, $R^9$ and $R^{25}$ are defined as in any of the embodiments described herein.

In an embodiment of the invention and/or embodiments thereof, the compounds are according to Formula (Ikx), preferably in form of the (S)-enantiomer. In an embodiment of the invention and/or embodiments thereof, the compounds are according to Formula (Ikxi), preferably in form of the (S)-enantiomer. In an embodiment of the invention and/or embodiments thereof, the compounds are according to Formula (Ikxii), preferably in form of the (S)-enantiomer. In an embodiment of the invention and/or embodiments thereof, the compounds are according to Formula (Ikxiii), preferably in form of the (S)-enantiomer. In an embodiment of the invention and/or embodiments thereof, the compounds are according to Formula (Ikxiv), preferably in form of the (S)-enantiomer. In an embodiment of the invention and/or embodiments thereof, the compounds are according to Formula (Ikxv), preferably in form of the (S)-enantiomer. In an embodiment of the invention and/or embodiments thereof, the compounds are according to Formula (Ikxvi), preferably in form of the (S)-enantiomer. In an embodiment of the invention and/or embodiments thereof, the compounds are according to Formula (Ikxvii), preferably in form of the (S)-enantiomer. In an embodiment of the invention and/or embodiments thereof, the compounds are according to Formula (Ikxviii), preferably in form of the (S)-enantiomer.

The invention provides a compound according to the invention and/or embodiments thereof, wherein $R^7$ and $R^{19}$ are defined as above.

In an embodiment of the invention and/or embodiments thereof, $R^7$ is independently selected from the group consisting of hydrogen, $C_{1-6}$-alkyl, $C_{2-6}$-alkenyl, $C_{3-10}$-cycloalkyl, 4 to 10-membered heterocyclyl, $C_{1-6}$-alkoxy, halogen, cyano, hydroxy, $NR^8R^9$, $C(=O)OR^{10}$, $SR^{10}$, $SOR^{10}$, $SO_2R^{10}$ and $C(=O)NR^{11}R^{12}$ wherein each $C_{1-6}$-alkyl, $C_{2-6}$-alkenyl, $C_{3-10}$-cycloalkyl, 4 to 10-membered heterocyclyl or $C_{1-6}$-alkoxy is optionally substituted with one or more substituent(s) independently selected from the group consisting of $C_{1-6}$-alkyl, $C_{3-10}$-cycloalkyl, 5 to 10-membered heterocyclyl, $C_{1-6}$-alkoxy, halogen, cyano, hydroxy, $NR^{8'}R^{9'}$, C(=O)$OR^{10'}$ and C(=O)$NR^{11'}R^{12'}$, $R^8$ and $R^9$ are independently selected from the group consisting of hydrogen, $C_{1-6}$-alkyl, $C_{3-10}$-cycloalkyl, $C_{6-10}$-aryl, 5 to 10-membered heterocyclyl and 5 to 10-membered heteroaryl, or $R^8$ and $R^9$ together with the N atom to which they are attached form a saturated or unsaturated heterocyclic ring having 3 to 12 ring atoms, wherein 1 ring atom is N and wherein 0, 1, 2, or 3 further ring atoms are selected from N, S and O;

wherein the $C_{1-6}$-alkyl, $C_{3-10}$-cycloalkyl, $C_{6-10}$-aryl, 5 to 10-membered heterocyclyl or 5 to 10-membered heteroaryl or the heterocyclic ring formed by $R^8$ and $R^9$ together with the N atom to which they are attached is optionally substituted with one or more substituent(s) independently selected from the group consisting of $C_{1-6}$-alkyl, $C_{1-6}$-alkoxy, halogen, cyano, hydroxy, $NR^{8''}R^{9''}$, C(=O)—$OR^{10''}$ and C(=O)$NR^{11''}R^{12''}$;

$R^{10}$, $R^{11}$ and $R^{12}$ are independently selected from hydrogen and $C_{1-6}$-alkyl, $R^{8'}$, $R^{9'}$, $R^{10'}$, $R^{11'}$ and $R^{12'}$ are independently selected from hydrogen and $C_{1-6}$-alkyl, $R^{8''}$, $R^{9''}$, $R^{10''}$, $R^{11''}$ and $R^{12''}$ are independently selected from hydrogen and $C_{1-6}$-alkyl, and $R^{19}$ is independently selected from the group consisting of $C_{6-10}$-aryl and 5 to 10-membered heteroaryl, wherein each $C_{6-10}$-aryl or 5 to 10-membered heteroaryl is optionally substituted with one or more substituent(s) independently selected from the group consisting of $C_{1-6}$-alkyl, $C_{3-10}$-cycloalkyl, $C_{1-6}$-alkoxy, 5 to 10-membered heterocyclyl, $C_{6-10}$-aryl, 5 to 10-membered heteroaryl, halogen, cyano, nitro, hydroxy, $NR^{20}R^{21}$, C(=O)$OR^{22}$ and C(=O)$NR^{23}R^{24}$, $R^{20}$ and $R^{21}$ are independently selected from the group consisting of hydrogen, $C_{1-6}$-alkyl, $C_{3-10}$-cycloalkyl and $C_{6-10}$-aryl or $R^{20}$ and $R^{21}$ together with the N atom to which they are attached form a saturated or unsaturated heterocyclic ring having 3 to 12 ring atoms, wherein 0, 1, 2, or 3 further ring atoms are selected from N, S and O;

wherein each $C_{1-6}$-alkyl, $C_{3-10}$-cycloalkyl or $C_{6-10}$-aryl or the heterocyclic ring formed by $R^{20}$ and $R^{21}$ together with the N atom to which they are attached is optionally substituted with one or more substituents independently selected from the group consisting of $C_{1-6}$-alkyl, $C_{3-10}$-cycloalkyl, $C_{1-6}$-alkoxy, 5 to 10-membered heterocyclyl, $C_{6-10}$-aryl, 5 to 10-membered heteroaryl, halogen, cyano, hydroxy, $NR^{20'}R^{21'}$, C(=O)$OR^{22'}$ and C(=O)$NR^{23'}R^{24'}$ $R^{22}$, $R^{23}$ and $R^{24}$ are independently selected from hydrogen and $C_{1-6}$-alkyl, $R^{20'}$, $R^{21'}$, $R^{22'}$, $R^{23'}$ and $R^{24'}$ are independently selected from hydrogen and $C_{1-6}$-alkyl.

In an embodiment of the invention and/or embodiments thereof, $R^7$ is independently selected from the group consisting of hydrogen, $C_{1-6}$-alkyl, $C_{2-6}$-alkenyl, 4- to 10-membered heterocyclyl, $C_{1-3}$-alkoxy, hydroxy, $NR^8R^9$, $SR^{10}$, $SOR^{10}$ and $SO_2R^{10}$, wherein each $C_{1-6}$-alkyl, $C_{2-6}$-alkenyl, 4- to 10-membered heterocyclyl or $C_{1-3}$-alkoxy is optionally substituted with one or more substituent(s) independently selected from the group consisting of $C_{1-3}$-alkyl, 5 to 10-membered heterocyclyl, $C_{1-6}$-alkoxy, halogen, cyano, hydroxy, $NR^{8'}R^{9'}$, C(=O)$OR^{10'}$ and C(=O)$NR^{11'}R^{12'}$, $R^8$ and $R^9$ are independently selected from the group consisting of hydrogen, $C_{1-6}$-alkyl, $C_{6-10}$-aryl and 5 to 10-membered heteroaryl, or $R^8$ and $R^9$ together with the N atom to which they are attached form a saturated or unsaturated heterocyclic ring having 3 to 12 ring atoms, wherein 1 ring atom is N and wherein 0, 1, 2, or 3 further ring atoms are selected from N, S and O;

wherein the $C_{1-6}$-alkyl, $C_{6-10}$-aryl or 5 to 10-membered heteroaryl or the heterocyclic ring formed by $R^8$ and $R^9$ together with the N atom to which they are attached is optionally substituted with one or more substituent(s) independently selected from the group consisting of $C_{1-6}$-alkyl, $C_{1-6}$-alkoxy, hydroxy and $NR^{8''}R^{9''}$;

$R^{10}$ is independently selected from hydrogen or $C_{1-3}$-alkyl, preferably from hydrogen, methyl or ethyl $R^{8'}$, $R^{9'}$, $R^{10'}$, $R^{11'}$ and $R^{12'}$ are independently selected from hydrogen or $C_{1-3}$-alkyl, preferably from hydrogen, methyl or ethyl, $R^{8''}$ and $R^{9''}$ are independently selected from hydrogen or $C_{1-3}$-alkyl, preferably from hydrogen, methyl or ethyl, and $R^{19}$ is independently selected from the group consisting of $C_{6-10}$-aryl and 5 to 10-membered heteroaryl wherein each $C_{6-10}$-aryl or 5 to 10-membered heteroaryl is optionally substituted with one or more substituent(s) independently selected from the group consisting of $C_{1-6}$-alkyl, $C_{1-6}$-alkoxy, halogen, cyano, nitro and hydroxy.

In an embodiment of the invention and/or embodiments thereof, $R^7$ is independently selected from the group consisting of methyl, ethyl, isopropyl, propyl, isopropenyl methoxy, ethoxy, isopropoxy, hydroxy, methyl sulfoxyl, methyl sulfonyl methylthio, amino, methylamino, ethylamino, (ethyl)(methyl)amino isopropylamino, dimethylamino, (isopropyl)(methyl)amino, hydroxyethylamino, (hydroxyethyl)(methyl)amino, methoxyethylamino, (methoxy-ethyl)(methyl) amino, morpholin-4-yl, pyrrolidin-1-yl, 3-hydroxy-pyrrolidin-1-yl 3-fluoroazetidinyl and 3,3-difluoro-azetidinyl, and $R^{19}$ is independently selected from the group consisting of 3-chlorophenyl, 2,3-dichlorophenyl, 3,5-dichlorophenyl, 3,5-difluorophenyl, 2,3,5-trifluorophenyl, 3,4,5-trifluorophenyl, 3-chloro-2-fluorophenyl, 5-chloro-3-fluorophenyl, 5-chloro-3-fluorophenyl, 3,5-dichloro-4-fluorophenyl, in particular 2,3,5-trifluorophenyl, 5-chloro-2-fluorophenyl, 2,3-dichlorophenyl and 3,5-dichlorophenyl.

In an embodiment of the invention and/or embodiments thereof, the compounds are according to Formula (Ili), (Ilii), (Iliii), (Iliv), (Ilv), (Ilvi), (Ilvii), (Ilviii) or (Ilix)

Formula (Ili)

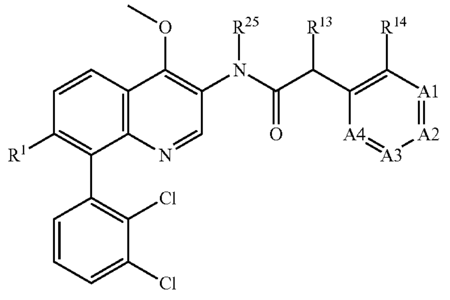

Formula (Ilii)

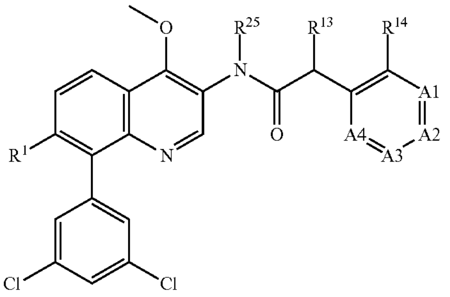

Formula (Iliii)

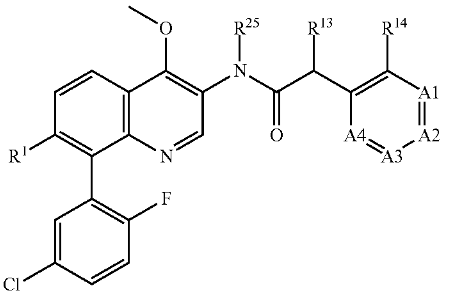

Formula (Iliv)

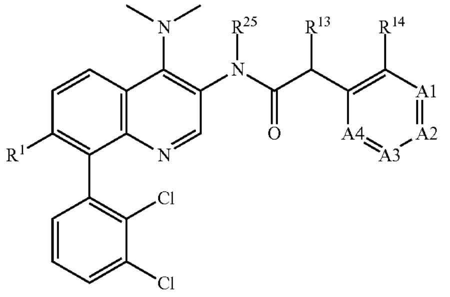

-continued

Formula (Ilv)

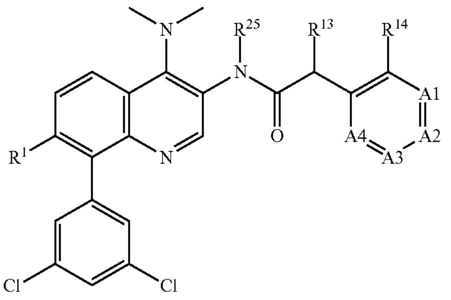

Formula (Ilvi)

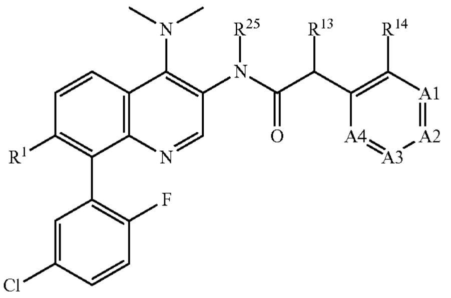

Formula (Ilvij)

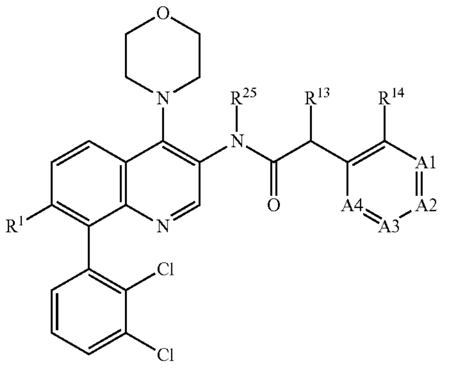

Formula (Ilviii)

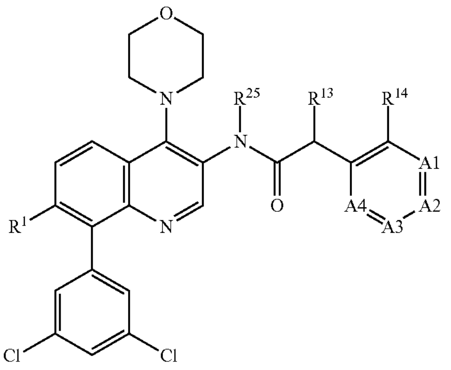

-continued

Formula (IIix)

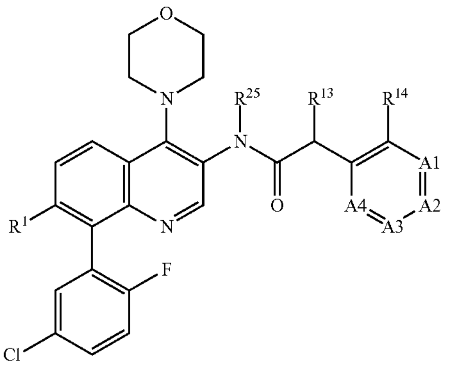

or a stereoisomer, physiologically acceptable salt, ester, solvate, polymorph, prodrug and mixtures thereof, wherein $R^1$, $R^{13}$, $R^{14}$, A1, A2, A3, A4 and $R^{25}$ are defined as in any of the embodiments described herein.

In an embodiment of the invention and/or embodiments thereof, the compounds are according to Formula (IIi), preferably in form of the (S)-enantiomer. In an embodiment of the invention and/or embodiments thereof, the compounds are according to Formula (IIii), preferably in form of the (S)-enantiomer. In an embodiment of the invention and/or embodiments thereof, the compounds are according to Formula (IIiii), preferably in form of the (S)-enantiomer. In an embodiment of the invention and/or embodiments thereof, the compounds are according to Formula (IIiv), preferably in form of the (S)-enantiomer. In an embodiment of the invention and/or embodiments thereof, the compounds are according to Formula (IIv), preferably in form of the (S)-enantiomer. In an embodiment of the invention and/or embodiments thereof, the compounds are according to Formula (IIvi), preferably in form of the (S)-enantiomer. In an embodiment of the invention and/or embodiments thereof, the compounds are according to Formula (IIvii), preferably in form of the (S)-enantiomer. In an embodiment of the invention and/or embodiments thereof, the compounds are according to Formula (IIviii), preferably in form of the (S)-enantiomer. In an embodiment of the invention and/or embodiments thereof, the compounds are according to Formula (IIix) preferably in form of the (S)-enantiomer.

The invention provides a compound according to the invention and/or embodiments thereof, wherein $R^7$ and $R^{25}$ are defined as above.

In an embodiment of the invention and/or embodiments thereof, $R^7$ is independently selected from the group consisting of
- hydrogen, $C_{1-6}$-alkyl, $C_{2-6}$-alkenyl, $C_{3-10}$-cycloalkyl, 4 to 10-membered heterocyclyl, $C_{1-6}$-alkoxy, halogen, cyano, hydroxy, $NR^8R^9$, $C(=O)OR^{10}$, $SR^{10}$, $SOR^{10}$, $SO_2R^{10}$ and $C(=O)NR^{11}R^{12}$,
- wherein each $C_{1-6}$-alkyl, $C_{2-6}$-alkenyl, $C_{3-10}$-cycloalkyl, 4 to 10-membered heterocyclyl or $C_{1-6}$-alkoxy is optionally substituted with one or more substituent(s) independently selected from the group consisting of
  - $C_{1-6}$-alkyl, $C_{3-10}$-cycloalkyl, 5 to 10-membered heterocyclyl, $C_{1-6}$-alkoxy, halogen, cyano, hydroxy, $NR^{8'}R^{9'}$, $C(=O)OR^{10'}$ and $C(=O)NR^{11'}R^{12'}$, $R^8$ and $R^9$ are independently selected from the group consisting of
- hydrogen, $C_{1-6}$-alkyl, $C_{3-10}$-cycloalkyl, $C_{6-10}$-aryl, 5 to 10-membered heterocyclyl and 5 to 10-membered heteroaryl, or $R^8$ and $R^9$ together with the N atom to which they are attached form a saturated or unsaturated heterocyclic ring having 3 to 12 ring atoms, wherein 1 ring atom is N and wherein 0, 1, 2, or 3 further ring atoms are selected from N, S and O;
- wherein the $C_{1-6}$-alkyl, $C_{3-10}$-cycloalkyl, $C_{6-10}$-aryl, 5 to 10-membered heterocyclyl or 5 to 10-membered heteroaryl or the heterocyclic ring formed by $R^8$ and $R^9$ together with the N atom to which they are attached is optionally substituted with one or more substituent(s) independently selected from the group consisting of
  - $C_{1-6}$-alkyl, $C_{1-6}$-alkoxy, halogen, cyano, hydroxy, $NR^{8''}R^{9''}$, $C(=O)—OR^{10''}$ and $C(=O)NR^{11''}R^{12''}$;

$R^{10}$, $R^{11}$ and $R^{12}$ are independently selected from hydrogen and $C_{1-6}$-alkyl, $R^{8'}$, $R^{9'}$, $R^{10'}$, $R^{11'}$ and $R^{12'}$ are independently selected from hydrogen and $C_{1-6}$-alkyl, $R^{8''}$, $R^{9''}$, $R^{10''}$, $R^{11''}$ and $R^{12''}$ are independently selected from hydrogen and $C_{1-6}$-alkyl, and $R^{25}$ is hydrogen or $C_{1-3}$-alkyl.

In an embodiment of the invention and/or embodiments thereof, $R^7$ is independently selected from the group consisting of
- methyl, ethyl, isopropyl, propyl, isopropenyl methoxy, ethoxy, isopropoxy, hydroxy, methyl sulfoxyl, methyl sulfonyl methylthio, amino, methylamino, ethylamino, (ethyl)(methyl)amino isopropylamino, dimethylamino, (isopropyl)(methyl)amino, hydroxyethylamino, (hydroxyethyl)(methyl)amino, methoxyethylamino, (methoxyethyl)(methyl)amino, morpholin-4-yl, pyrrolidin-1-yl, 3-hydroxy-pyrrolidin-1-yl 3-fluoroazetidinyl and 3,3-difluoroazetidinyl, and $R^{25}$ is hydrogen or methyl, preferably hydrogen.

In an embodiment of the invention and/or embodiments thereof, the compounds are according to Formula (Imi), (Imii), (Imiii), (Imiv), (Imv) or (Imiv)

Formula (Imi)

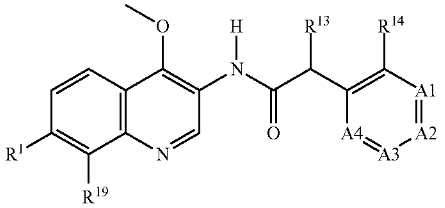

Formula (Imii)

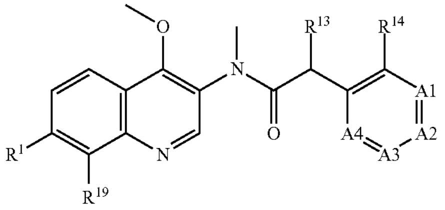

-continued

Formula (Imiii)

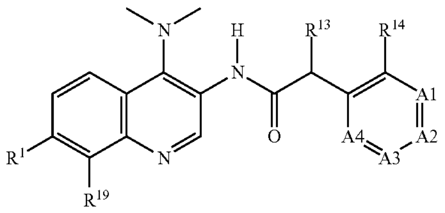

Formula (Imiv)

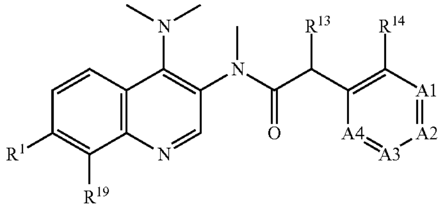

Formula (Imv)

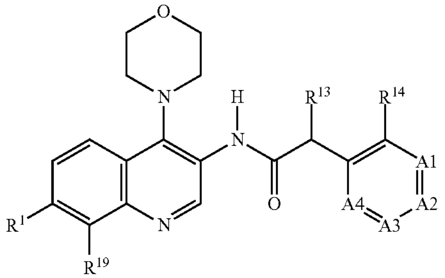

Formula (Imvi)

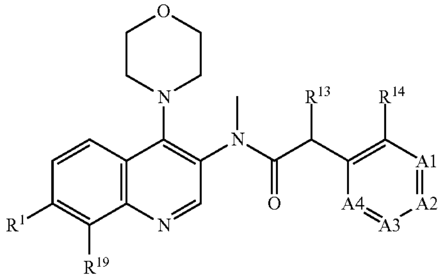

or a stereoisomer, physiologically acceptable salt, ester, solvate, polymorph, prodrug and mixtures thereof, wherein $R^1$, $R^{13}$ $R^{14}$, A1, A2, A3, A4 and $R^{19}$ are defined as in any of the embodiments described herein.

In an embodiment of the invention and/or embodiments thereof, the compounds are according to Formula (Imi), preferably in form of the (S)-enantiomer. In an embodiment of the invention and/or embodiments thereof, the compounds are according to Formula (Imii), preferably in form of the (S)-enantiomer. In an embodiment of the invention and/or embodiments thereof, the compounds are according to Formula (Imiii), preferably in form of the (S)-enantiomer. In an embodiment of the invention and/or embodiments thereof, the compounds are according to Formula (Imiv), preferably in form of the (S)-enantiomer. In an embodiment of the invention and/or embodiments thereof, the compounds are according to Formula (Imv), preferably in form of the (S)-enantiomer. In an embodiment of the invention and/or embodiments thereof, the compounds are according to Formula (Imvi), preferably in form of the (S)-enantiomer.

The invention provides a compound according to the invention and/or embodiments thereof, wherein $R^{13}$, $R^{14}$, A1, A2, A3 and A4 as well as $R^{19}$ are defined as above.

In one embodiment of the invention and/or embodiments thereof, $R^{13}$ and $R^{14}$ together with the atoms to which they are attached form a 5 or 6-carbon atoms containing non-aromatic ring, wherein the non-aromatic ring is optionally substituted with one or more $C_{1-3}$-alkyl or =O, and/or wherein one or more of the ring-forming carbon atoms are optionally replaced by —NH—, —O—, —S(O)—, —$S(O)_2$— or —S—, A1 is N or $CR^{15}$, wherein $R^{15}$ is independently hydrogen, halogen, $C_{1-3}$ alkyl, $C_{1-3}$ alkoxy, or $NR^{15'}R^{15''}$, wherein $R^{15'}$ and $R^{15''}$ are independently $C_{1-3}$-alkyl, A2 is N or $CR^{16}$, wherein $R^{16}$ is independently hydrogen, halogen, $C_{1-3}$ alkyl, $C_{1-3}$ alkoxy, or $NR^{16'}R^{16''}$, wherein $R^{16'}$ and $R^{16''}$ are independently $C_{1-3}$-alkyl, A3 is N or $CR^{17}$, wherein $R^{17}$ is independently hydrogen, halogen, $C_{1-3}$ alkyl, $C_{1-3}$ alkoxy, or $NR^{17'}R^{17''}$, wherein $R^{17'}$ and $R^{17''}$ are independently $C_{1-3}$-alkyl, A4 is N or $CR^{18}$, wherein $R^{18}$ is independently hydrogen, halogen, $C_{1-3}$ alkyl, $C_{1-3}$ alkoxy, or $NR^{18'}R^{18''}$, wherein $R^{18'}$ and $R^{18''}$ are independently $C_{1-3}$-alkyl and $R^{19}$ is independently selected from the group consisting of $C_{6-10}$-aryl and 5 to 10-membered heteroaryl, wherein each $C_{6-10}$-aryl or 5 to 10-membered heteroaryl is optionally substituted with one or more substituent(s) independently selected from the group consisting of $C_{1-6}$-alkyl, $C_{3-10}$-cycloalkyl, $C_{1-6}$-alkoxy, 5 to 10-membered heterocyclyl, $C_{6-10}$-aryl, 5 to 10-membered heteroaryl, halogen, cyano, nitro, hydroxy, $NR^{20}R^{21}$, C(=O)$OR^{22}$ and C(=O)$NR^{23}R^{24}$ $R^{20}$ and $R^{21}$ are independently selected from the group consisting of hydrogen, $C_{1-6}$-alkyl, $C_{3-10}$-cycloalkyl and $C_{6-10}$-aryl or $R^{20}$ and $R^{21}$ together with the N atom to which they are attached form a saturated or unsaturated heterocyclic ring having 3 to 12 ring atoms, wherein 0, 1, 2, or 3 further ring atoms are selected from N, S and O;

wherein each $C_{1-6}$-alkyl, $C_{3-10}$-cycloalkyl or $C_{6-10}$-aryl or the heterocyclic ring formed by $R^{20}$ and $R^{21}$ together with the N atom to which they are attached is optionally substituted with one or more substituents independently selected from the group consisting of $C_{1-6}$-alkyl, $C_{3-10}$-cycloalkyl, $C_{1-6}$-alkoxy, 5 to 10-membered heterocyclyl, $C_{6-10}$-aryl, 5 to 10-membered heteroaryl, halogen, cyano, hydroxy, $NR^{20'}R^{21'}$, C(=O)$OR^{22'}$ and C(=O)$NR^{23'}R^{24'}$ $R^{22}$, $R^{23}$ and $R^{24}$ are independently selected from hydrogen and $C_{1-6}$-alkyl, $R^{20'}$, $R^{21'}$, $R^{22'}$, $R^{23'}$ and $R^{24'}$ are independently selected from hydrogen and $C_{1-6}$-alkyl.

In one embodiment of the invention and/or embodiments thereof, $R^{13}$ and $R^{14}$ together with the atoms to which they are attached form a 5 or 6-carbon atoms containing non-aromatic ring, wherein one or more of the ring-forming carbon atoms are optionally replaced by —NH—, —O— or —S—, A1 is N or $CR^{15}$, wherein $R^{15}$ is independently hydrogen, $C_{1-3}$ alkyl or $C_{1-3}$ alkoxy, A2 is N or $CR^{16}$, wherein $R^{16}$ is independently hydrogen, $C_{1-3}$ alkyl or $C_{1-3}$ alkoxy, A3 is N or $CR^{17}$, wherein $R^{17}$ is independently hydrogen, $C_{1-3}$ alkyl or $C_{1-3}$ alkoxy, A4 is N or $CR^{18}$, wherein $R^{18}$ is independently hydrogen, $C_{1-3}$ alkyl or $C_{1-3}$ alkoxy, wherein none, one or two of A1, A2, A3 and A4 are N and $R^{19}$ is independently selected from the group consisting of $C_{6-10}$-aryl and 5 to 10-membered heteroaryl wherein each $C_{6-10}$-aryl or 5 to 10-membered heteroaryl is optionally substituted with one or more substituent(s) independently selected from the group consisting of $C_{1-6}$-alkyl, $C_{1-6}$-alkoxy, halogen, cyano, nitro and hydroxy.

In one embodiment of the invention and/or embodiments thereof, $R^{13}$ and $R^{14}$ together with the atoms to which they are attached form a 5 or 6-carbon atoms containing non-aromatic ring, wherein one or more of the ring-forming carbon atoms are optionally replaced by —NH— or —O—, A1 is N or $CR^{15}$, wherein $R^{15}$ is independently hydrogen or $C_{1-3}$ alkoxy, A2 is N or $CR^{16}$, wherein $R^{16}$ is independently hydrogen or $C_{1-3}$ alkoxy, A3 is N or $CR^{17}$, wherein $R^{17}$ is independently hydrogen or $C_{1-3}$ alkoxy, preferably hydrogen, A4 is N or $CR^{18}$, wherein $R^{18"}$ is independently hydrogen or $C_{1-3}$ alkoxy, preferably hydrogen, wherein none, one or two of A1, A2, A3 and A4 are N, and $R^{19}$ is independently selected from the group consisting of 3-chlorophenyl, 2,3-dichlorophenyl, 3,5-dichlorophenyl, 3,5-difluorophenyl, 2,3,5-trifluorophenyl, 3,4,5-trifluorophenyl, 3-chloro-2-fluorophenyl, 5-chloro-3-fluorophenyl, 5-chloro-3-fluorophenyl, 3,5-dichloro-4-fluorophenyl, in particular 2,3,5-trifluorophenyl, 5-chloro-2-fluorophenyl, 2,3-dichlorophenyl and 3,5-dichlorophenyl.

In an embodiment of the invention and/or embodiments thereof, the compounds are according to Formula (Ini), (Inii), (Iniii), (Iniv), (Inv), (Invi), (Invii), (Inviii) or (Inix)

Formula (Ini)

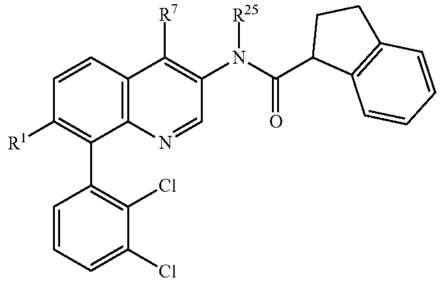

Formula (Inii)

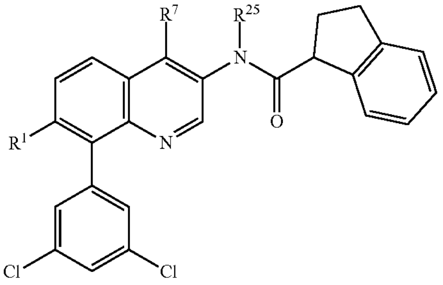

-continued

Formula (Iniii)

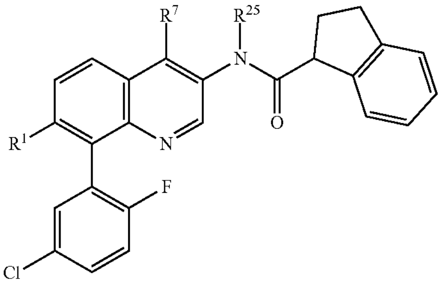

Formula (Iniv)

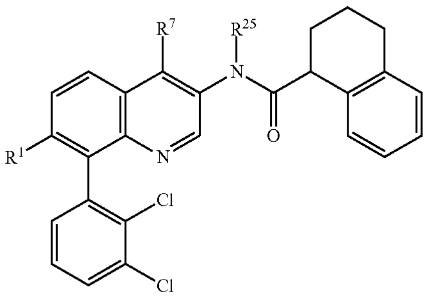

Formula (Inv)

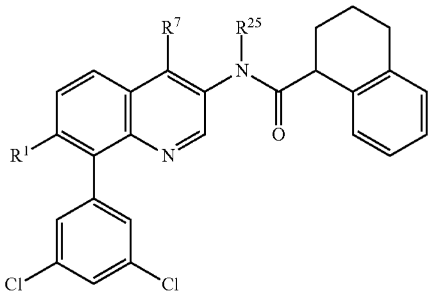

Formula (Invi)

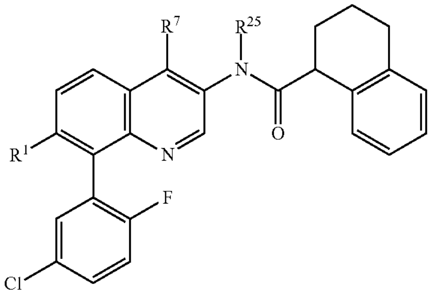

Formula (Invii)

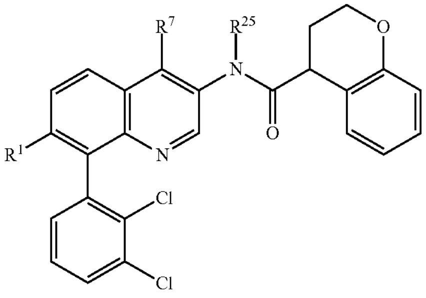

-continued

Formula (Inviii)

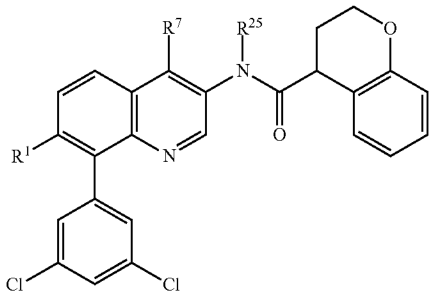

Formula (Inix)

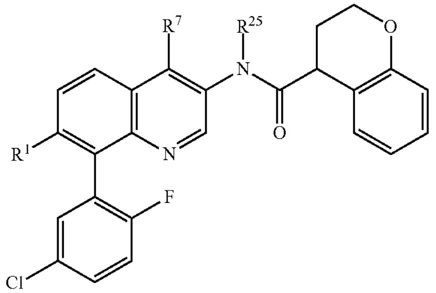

or a stereoisomer, physiologically acceptable salt, ester, solvate, polymorph, prodrug and mixtures thereof, wherein $R^1$, $R^7$ and $R^{25}$ are defined as in any of the embodiments described herein.

In an embodiment of the invention and/or embodiments thereof, the compounds are according to Formula (Ini), preferably in form of the (S)-enantiomer. In an embodiment of the invention and/or embodiments thereof, the compounds are according to Formula (Inii), preferably in form of the (S)-enantiomer. In an embodiment of the invention and/or embodiments thereof, the compounds are according to Formula (Iniii), preferably in form of the (S)-enantiomer. In an embodiment of the invention and/or embodiments thereof, the compounds are according to Formula (Iniv), preferably in form of the (S)-enantiomer. In an embodiment of the invention and/or embodiments thereof, the compounds are according to Formula (Inv), preferably in form of the (S)-enantiomer. In an embodiment of the invention and/or embodiments thereof, the compounds are according to Formula (Invi), preferably in form of the (S)-enantiomer. In an embodiment of the invention and/or embodiments thereof, the compounds are according to Formula (Invii), preferably in form of the (S)-enantiomer. In an embodiment of the invention and/or embodiments thereof, the compounds are according to Formula (Inviii), preferably in form of the (S)-enantiomer. In an embodiment of the invention and/or embodiments thereof, the compounds are according to Formula (Inix), preferably in form of the (S)-enantiomer.

In one embodiment of the invention and/or embodiments thereof, $R^{13}$ and $R^{14}$ together with the atoms to which they are attached form a 5 or 6-carbon atoms containing aromatic ring, wherein the aromatic ring is optionally substituted with one or more $C_{1-3}$-alkyl, and/or wherein one or more of the ring-forming carbon atoms are optionally replaced by —NH—, —N═, ═N—, —O— or —S—, A1 is N or $CR^{15}$, wherein $R^{15}$ is independently hydrogen, halogen $C_{1-3}$ alkyl, $C_{1-3}$ alkoxy or $NR^{15'}R^{15''}$, wherein $R^{15'}$ and $R^{15''}$ are independently $C_{1-3}$-alkyl, A2 is N or $CR^{16}$, wherein $R^{16}$ is independently hydrogen, halogen, $C_{1-3}$ alkyl, $C_{1-3}$ alkoxy or $NR^{16'}R^{16''}$, wherein $R^{16'}$ and $R^{16''}$ are independently $C_{1-3}$-alkyl, A3 is N or $CR^{17}$, wherein $R^{17}$ is independently hydrogen, halogen, $C_{1-3}$ alkyl, $C_{1-3}$ alkoxy or $NR^{15'}R^{15''}$, wherein $R^{15'}$ and $R^{15''}$ are independently $C_{1-3}$-alkyl, A4 is N or $CR^{18}$, wherein $R^{18}$ is independently hydrogen, halogen, $C_{1-3}$ alkyl, $C_{1-3}$ alkoxy or $NR^{15'}R^{15''}$, wherein $R^{15'}$ and $R^{15''}$ are independently $C_{1-3}$-alkyl, and $R^{19}$ is independently selected from the group consisting of $C_{6-10}$-aryl and 5 to 10-membered heteroaryl, wherein each $C_{6-10}$-aryl or 5 to 10-membered heteroaryl is optionally substituted with one or more substituent(s) independently selected from the group consisting of $C_{1-6}$-alkyl, $C_{3-10}$-cycloalkyl, $C_{1-6}$-alkoxy, 5 to 10-membered heterocyclyl, $C_{6-10}$-aryl, 5 to 10-membered heteroaryl, halogen, cyano, nitro, hydroxy, $NR^{20}R^{21}$, $C(═O)OR^{22}$ and $C(═O)NR^{23}R^{24}$ $R^{20}$ and $R^{21}$ are independently selected from the group consisting of hydrogen, $C_{1-6}$-alkyl, $C_{3-10}$-cycloalkyl and $C_{6-10}$-aryl or $R^{20}$ and $R^{21}$ together with the N atom to which they are attached form a saturated or unsaturated heterocyclic ring having 3 to 12 ring atoms, wherein 0, 1, 2, or 3 further ring atoms are selected from N, S and O;

wherein each $C_{1-6}$-alkyl, $C_{3-10}$-cycloalkyl or $C_{6-10}$-aryl or the heterocyclic ring formed by $R^{20}$ and $R^{21}$ together with the N atom to which they are attached is optionally substituted with one or more substituents independently selected from the group consisting of $C_{1-6}$-alkyl, $C_{3-10}$-cycloalkyl, $C_{1-6}$-alkoxy, 5 to 10-membered heterocyclyl, $C_{6-10}$-aryl, 5 to 10-membered heteroaryl, halogen, cyano, hydroxy, $NR^{20'}R^{21'}$, $C(═O)OR^{22'}$ and $C(═O)NR^{23'}R^{24'}$ $R^{22}$, $R^{23}$ and $R^{24}$ are independently selected from hydrogen and $C_{1-6}$-alkyl, $R^{20'}$, $R^{21'}$, $R^{22'}$, $R^{23'}$ and $R^{24'}$ are independently selected from hydrogen and $C_{1-6}$-alkyl.

Optionally, in an embodiment of the invention and/or embodiments thereof, $R^{13}$ and $R^{14}$ together with the atoms to which they are attached form a 5 or 6-carbon atoms containing aromatic ring, wherein one or more of the ring-forming carbon atoms are optionally replaced by —NH—, —N═, ═N—, —O— or —S—, A1 is N or $CR^{15}$, wherein $R^{15}$ is independently hydrogen, $C_{1-3}$ alkyl or $C_{1-3}$ alkoxy, A2 is N or $CR^{16}$, wherein $R^{16}$ is independently hydrogen, $C_{1-3}$ alkyl or $C_{1-3}$ alkoxy, A3 is N or $CR^{17}$, wherein $R^{17}$ is independently hydrogen, $C_{1-3}$ alkyl or $C_{1-3}$ alkoxy, A4 is N or $CR^{18}$, wherein $R^{18}$ is independently hydrogen, $C_{1-3}$ alkyl or $C_{1-3}$ alkoxy, wherein none, one or two of A1, A2, A3 and A4 are N. and $R^{19}$ is independently selected from the group consisting of $C_{6-10}$-aryl and 5 to 10-membered heteroaryl wherein each $C_{6-10}$-aryl or 5 to 10-membered heteroaryl is optionally substituted with one or more substituent(s) independently selected from the group consisting of $C_{1-6}$-alkyl, $C_{1-6}$-alkoxy, halogen, cyano, nitro and hydroxy.

In one embodiment of the invention and/or embodiments thereof, $R^{13}$ and $R^{14}$ together with the atoms to which they are attached form a 5 or 6-carbon atoms containing non-aromatic ring, wherein one or more of the ring-forming carbon atoms are optionally replaced by —NH— or —O—, $R^{13}$ and $R^{14}$ together with the atoms to which they are attached form a 5 or 6-carbon atoms containing aromatic ring, wherein one or more of the ring-forming carbon atoms are optionally replaced by —NH—, —N=, =N— or —S—, A1 is N or $CR^{15}$, wherein $R^{15}$ is independently hydrogen or $C_{1-3}$ alkoxy, A2 is N or $CR^{16}$, wherein $R^{16}$ is independently hydrogen or $C_{1-3}$ alkoxy, A3 is N or $CR^{17}$, wherein $R^{17}$ is independently hydrogen or $C_{1-3}$ alkoxy, preferably hydrogen, A4 is N or $CR^{18}$, wherein $R^{18}$ is independently hydrogen or $C_{1-3}$ alkoxy, preferably hydrogen, wherein none, one or two of A1, A2, A3 and A4 are N, and $R^{19}$ is independently selected from the group consisting of 3-chlorophenyl, 2,3-dichlorophenyl, 3,5-dichlorophenyl, 3,5-difluorophenyl, 2,3,5-trifluorophenyl, 3,4,5-trifluorophenyl, 3-chloro-2-fluorophenyl, 5-chloro-3-fluorophenyl, 5-chloro-3-fluorophenyl, 3,5-dichloro-4-fluorophenyl, in particular 2,3,5-trifluorophenyl, 5-chloro-2-fluorophenyl, 2,3-dichlorophenyl and 3,5-dichlorophenyl.

In an embodiment of the invention and/or embodiments thereof, the compounds are according to Formula (Inx), (Inxi), (Inxii), (Inxiii), (Inxiv), (Inxv), (Inxvi), (Inxvii) or (Inxviii)

Formula (Inx)

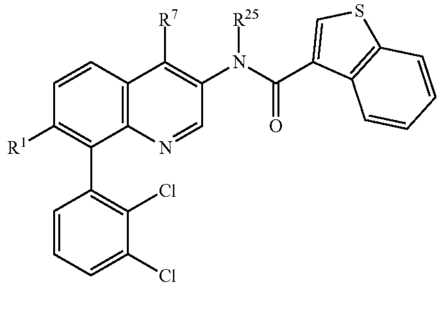

Formula (Inxi)

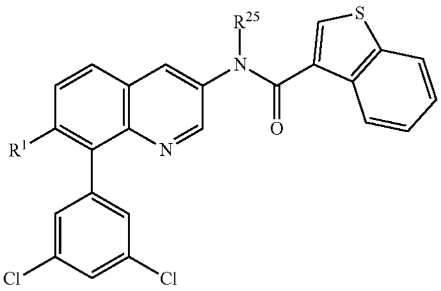

-continued

Formula (Inxii)

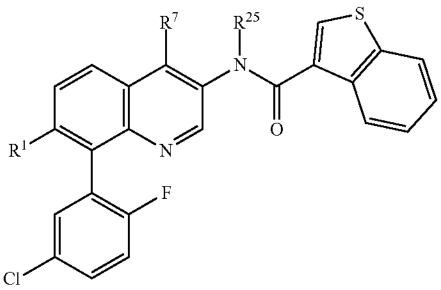

Formula (Inxiii)

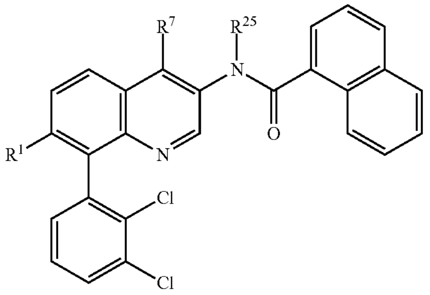

Formula (Inxiv)

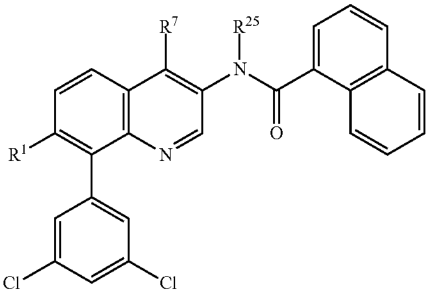

Formula (Inxv)

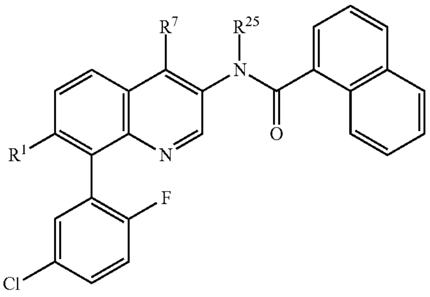

Formula (Inxvi)

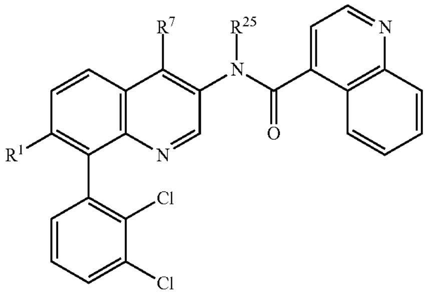

-continued

Formula (Inxvii)

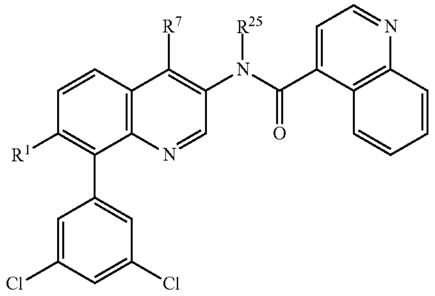

Formula (Inxviii)

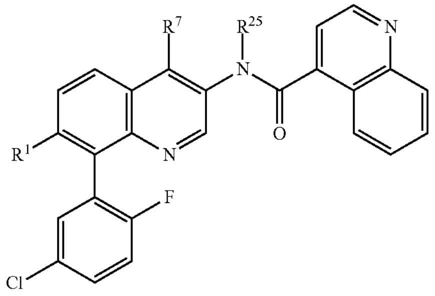

or a stereoisomer, physiologically acceptable salt, ester, solvate, polymorph, prodrug and mixtures thereof, wherein $R^1$, $R^7$ and $R^{25}$ are defined as in any of the embodiments described herein.

In an embodiment of the invention and/or embodiments thereof, the compounds are according to Formula (Inx), preferably in form of the (S)-enantiomer. In an embodiment of the invention and/or embodiments thereof, the compounds are according to Formula (Inxi), preferably in form of the (S)-enantiomer. In an embodiment of the invention and/or embodiments thereof, the compounds are according to Formula (Inxii), preferably in form of the (S)-enantiomer. In an embodiment of the invention and/or embodiments thereof, the compounds are according to Formula (Inxiii), preferably in form of the (S)-enantiomer. In an embodiment of the invention and/or embodiments thereof, the compounds are according to Formula (Inxiv), preferably in form of the (S)-enantiomer. In an embodiment of the invention and/or embodiments thereof, the compounds are according to Formula (Inxv), preferably in form of the (S)-enantiomer. In an embodiment of the invention and/or embodiments thereof, the compounds are according to Formula (Inxvi), preferably in form of the (S)-enantiomer. In an embodiment of the invention and/or embodiments thereof, the compounds are according to Formula (Inxvii), preferably in form of the (S)-enantiomer. In an embodiment of the invention and/or embodiments thereof, the compounds are according to Formula (Inxviii), preferably in form of the (S)-enantiomer.

The invention provides a compound according to the invention and/or embodiments thereof, wherein $R^{13}$, $R^{14}$, A1, A2, A3 and A4 as well as $R^{25}$ are defined as above.

In one embodiment of the invention and/or embodiments thereof, $R^{13}$ and $R^{14}$ together with the atoms to which they are attached form a 5 or 6-carbon atoms containing non-aromatic ring, wherein the non-aromatic ring is optionally substituted with one or more $C_{1-3}$-alkyl or =O, and/or wherein one or more of the ring-forming carbon atoms are optionally replaced by —NH—, —O—, —S(O)—, —S(O)$_2$— or —S—, A1 is N or $CR^{15}$, wherein $R^{15}$ is independently hydrogen, halogen, $C_{1-3}$ alkyl, $C_{1-3}$ alkoxy, or $NR^{15'}R^{15''}$, wherein $R^{15'}$ and $R^{15''}$ are independently $C_{1-3}$-alkyl, A2 is N or $CR^{16}$, wherein $R^{16}$ is independently hydrogen, halogen, $C_{1-3}$ alkyl, $C_{1-3}$ alkoxy, or $NR^{16'}R^{16''}$, wherein $R^{16'}$ and $R^{16''}$ are independently $C_{1-3}$-alkyl, A3 is N or $CR^{17}$, wherein $R^{17}$ is independently hydrogen, halogen, $C_{1-3}$ alkyl, $C_{1-3}$ alkoxy, or $NR^{17'}R^{17''}$, wherein $R^{17'}$ and $R^{17''}$ are independently $C_{1-3}$-alkyl, A4 is N or $CR^{18}$, wherein $R^{18}$ is independently hydrogen, halogen, $C_{1-3}$ alkyl, $C_{1-3}$ alkoxy, or $NR^{18'}R^{18''}$, wherein $R^{18'}$ and $R^{18''}$ are independently $C_{1-3}$-alkyl, and $R^{25}$ is hydrogen or $C_{1-3}$-alkyl.

In one embodiment of the invention and/or embodiments thereof, $R^{13}$ and $R^{14}$ together with the atoms to which they are attached form a 5 or 6-carbon atoms containing non-aromatic ring, wherein one or more of the ring-forming carbon atoms are optionally replaced by —NH— or —O—, A1 is N or $CR^{15}$, wherein $R^{15}$ is independently hydrogen or $C_{1-3}$ alkoxy, A2 is N or $CR^{16}$, wherein $R^{16}$ is independently hydrogen or $C_{1-3}$ alkoxy, A3 is N or $CR^{17}$, wherein $R^{17}$ is independently hydrogen or $C_{1-3}$ alkoxy, preferably hydrogen, A4 is N or $CR^{18}$, wherein $R^{18}$ is independently hydrogen or $C_{1-3}$ alkoxy, preferably hydrogen, wherein none, one or two of A1, A2, A3 and A4 are N, and $R^{25}$ is hydrogen or methyl, preferably hydrogen.

In an embodiment of the invention and/or embodiments thereof, the compounds are according to Formula (Ioi), (Ioii), (Ioiii), (Ioiv), (Iov) or (Iovi)

Formula (Ioi)

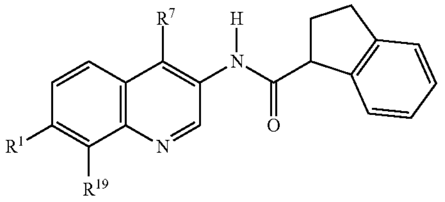

Formula (Ioii)

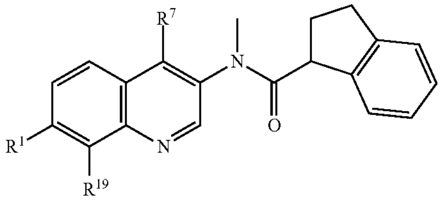

Formula (Ioiii)

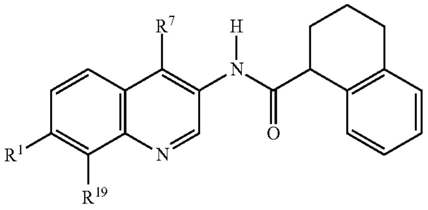

-continued

Formula (Ioiv)

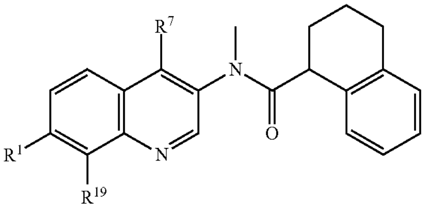

Formula (Iov)

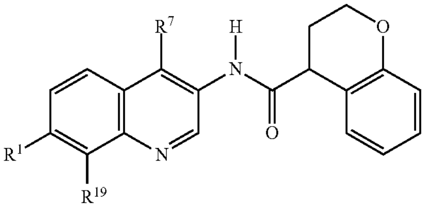

Formula (Iovi)

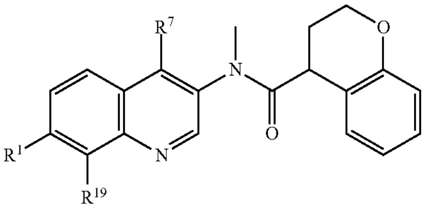

or a stereoisomer, physiologically acceptable salt, ester, solvate, polymorph, prodrug and mixtures thereof, wherein $R^1$, $R^7$ and $R^9$ are defined as in any of the embodiments described herein.

In an embodiment of the invention and/or embodiments thereof, the compounds are according to Formula (Ioi), preferably in form of the (S)-enantiomer. In an embodiment of the invention and/or embodiments thereof, the compounds are according to Formula (Ioii), preferably in form of the (S)-enantiomer. In an embodiment of the invention and/or embodiments thereof, the compounds are according to Formula (Ioiii), preferably in form of the (S)-enantiomer. In an embodiment of the invention and/or embodiments thereof, the compounds are according to Formula (Ioiv), preferably in form of the (S)-enantiomer. In an embodiment of the invention and/or embodiments thereof, the compounds are according to Formula (Iov), preferably in form of the (S)-enantiomer. In an embodiment of the invention and/or embodiments thereof, the compounds are according to Formula (Iovi), preferably in form of the (S)-enantiomer.

In one embodiment of the invention and/or embodiments thereof, $R^{13}$ and $R^{14}$ together with the atoms to which they are attached form a 5 or 6-carbon atoms containing aromatic ring, wherein the aromatic ring is optionally substituted with one or more $C_{1-3}$-alkyl, and/or wherein one or more of the ring-forming carbon atoms are optionally replaced by —NH—, —N=, =N—, —O— or —S—, A1 is N or $CR^{15}$, wherein $R^{15}$ is independently hydrogen, halogen $C_{1-3}$ alkyl, $C_{1-3}$ alkoxy or $NR^{15'}R^{15''}$, wherein $R^{15'}$ and $R^{15''}$ are independently $C_{1-3}$-alkyl, A2 is N or $CR^{16}$, wherein $R^{16}$ is independently hydrogen, halogen, $C_{1-3}$ alkyl, $C_{1-3}$ alkoxy or $NR^{16'}R^{16''}$, wherein $R^{16'}$ and $R^{16''}$ are independently $C_{1-3}$-alkyl, A3 is N or $CR^{17}$, wherein $R^{17}$ is independently hydrogen, halogen, $C_{1-3}$ alkyl, $C_{1-3}$ alkoxy or $NR^{15'}R^{15''}$, wherein $R^{15'}$ and $R^{15''}$ are independently $C_{1-3}$-alkyl, A4 is N or $CR^{18}$, wherein $R^{18}$ is independently hydrogen, halogen, $C_{1-3}$ alkyl, $C_{1-3}$ alkoxy or $NR^{15'}R^{15''}$, wherein $R^{15'}$ and $R^{15''}$ are independently $C_{1-3}$-alkyl, and $R^{25}$ is hydrogen or $C_{1-3}$-alkyl.

In one embodiment of the invention and/or embodiments thereof, $R^{13}$ and $R^{14}$ together with the atoms to which they are attached form a 5 or 6-carbon atoms containing aromatic ring, wherein one or more of the ring-forming carbon atoms are optionally replaced by —NH—, —N=, =N— or —S—, A1 is N or $CR^{15}$, wherein $R^{15}$ is independently hydrogen or $C_{1-3}$ alkoxy, A2 is N or $CR^{16}$, wherein $R^{16}$ is independently hydrogen or $C_{1-3}$ alkoxy, A3 is N or $CR^{17}$, wherein $R^{17}$ is independently hydrogen or $C_{1-3}$ alkoxy, preferably hydrogen, A4 is N or $CR^{18}$, wherein $R^{18}$ is independently hydrogen or $C_{1-3}$ alkoxy, preferably hydrogen, wherein none, one or two of A1, A2, A3 and A4 are N, and $R^{25}$ is hydrogen or methyl, preferably hydrogen.

In an embodiment of the invention and/or embodiments thereof, the compounds are according to Formula (Iovii), (Ioviii), (Ioix), (Iox), (Ioxi) or (Ioxii)

Formula (Iovii)

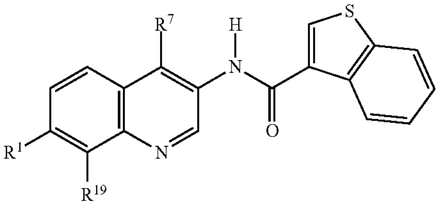

Formula (Ioviii)

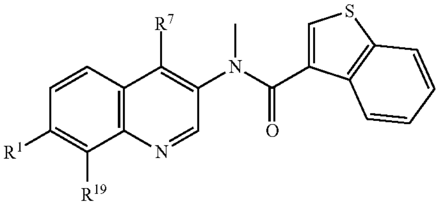

Formula (Ioix)

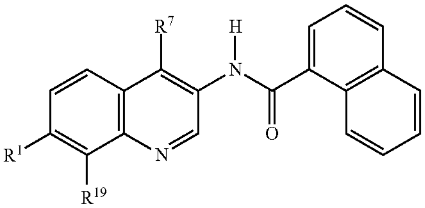

Formula (Iox)

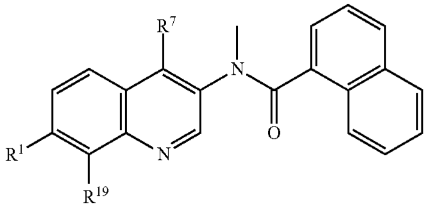

-continued

Formula (Ioxi)

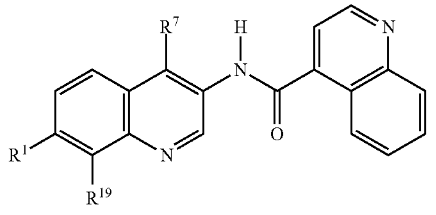

Formula (Ioxii)

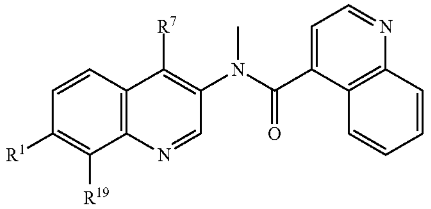

or a stereoisomer, physiologically acceptable salt, ester, solvate, polymorph, prodrug and mixtures thereof, wherein $R^1$, $R^7$ and $R^9$ are defined as in any of the embodiments described herein.

In an embodiment of the invention and/or embodiments thereof, the compounds are according to Formula (Iovii), preferably in form of the (S)-enantiomer. In an embodiment of the invention and/or embodiments thereof, the compounds are according to Formula (Ioviii), preferably in form of the (S)-enantiomer. In an embodiment of the invention and/or embodiments thereof, the compounds are according to Formula (Ioix), preferably in form of the (S)-enantiomer. In an embodiment of the invention and/or embodiments thereof, the compounds are according to Formula (lox), preferably in form of the (S)-enantiomer. In an embodiment of the invention and/or embodiments thereof, the compounds are according to Formula (Ioxi), preferably in form of the (S)-enantiomer. In an embodiment of the invention and/or embodiments thereof, the compounds are according to Formula (Ioxii), preferably in form of the (S)-enantiomer.

The invention provides a compound according to the invention and/or embodiments thereof, wherein $R^{19}$ and $R^{25}$ are defined as above.

In one embodiment of the invention and/or embodiments thereof, $R^{19}$ is independently selected from the group consisting of $C_{6-10}$-aryl and 5 to 10-membered heteroaryl, wherein each $C_{6-10}$-aryl or 5 to 10-membered heteroaryl is optionally substituted with one or more substituent(s) independently selected from the group consisting of $C_{1-6}$-alkyl, $C_{3-10}$-cycloalkyl, $C_{1-6}$-alkoxy, 5 to 10-membered heterocyclyl, $C_{6-10}$-aryl, 5 to 10-membered heteroaryl, halogen, cyano, nitro, hydroxy, $NR^{20}R^{21}$, $C(=O)OR^{22}$ and $C(=O)NR^{23}R^{24}$, $R^{20}$ and $R^{21}$ are independently selected from the group consisting of hydrogen, $C_{1-6}$-alkyl, $C_{3-10}$-cycloalkyl and $C_{6-10}$-aryl or $R^{20}$ and $R^{21}$ together with the N atom to which they are attached form a saturated or unsaturated heterocyclic ring having 3 to 12 ring atoms, wherein 0, 1, 2, or 3 further ring atoms are selected from N, S and O;

wherein each $C_{1-6}$-alkyl, $C_{3-10}$-cycloalkyl or $C_{6-10}$-aryl or the heterocyclic ring formed by $R^{20}$ and $R^{21}$ together with the N atom to which they are attached is optionally substituted with one or more substituents independently selected from the group consisting of $C_{1-6}$-alkyl, $C_{3-10}$-cycloalkyl, $C_{1-6}$-alkoxy, 5 to 10-membered heterocyclyl, $C_{6-10}$-aryl, 5 to 10-membered heteroaryl, halogen, cyano, hydroxy, $NR^{20'}R^{21'}$, $C(=O)OR^{22'}$ and $C(=O)NR^{23'}R^{24'}$ $R^{22}$, $R^{23}$ and $R^{24}$ are independently selected from hydrogen and $C_{1-6}$-alkyl, $R^{20'}$, $R^{21'}$, $R^{22'}$, $R^{23'}$ and $R^{24'}$ are independently selected from hydrogen and $C_{1-6}$-alkyl, and $R^{25}$ is hydrogen or $C_{1-3}$-alkyl.

In one embodiment of the invention and/or embodiments thereof, $R^{19}$ is independently selected from the group consisting of 3-chlorophenyl, 2,3-dichlorophenyl, 3,5-dichlorophenyl, 3,5-difluorophenyl, 2,3,5-trifluorophenyl, 3,4,5-trifluorophenyl, 3-chloro-2-fluorophenyl, 5-chloro-3-fluorophenyl, 5-chloro-3-fluorophenyl, 3,5-dichloro-4-fluorophenyl, in particular 2,3,5-trifluorophenyl, 5-chloro-2-fluorophenyl, 2,3-dichlorophenyl and 3,5-dichlorophenyl.

and $R^{25}$ is hydrogen or methyl, preferably hydrogen.

In an embodiment of the invention and/or embodiments thereof, the compounds are according to Formula (Ipi), (Ipii), (Ipiii), (Ipiv), (Ipv) or (Ipvi)

Formula (Ipi)

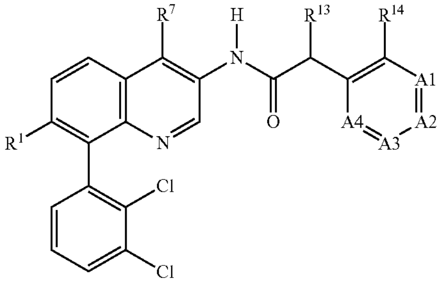

Formula (Ipii)

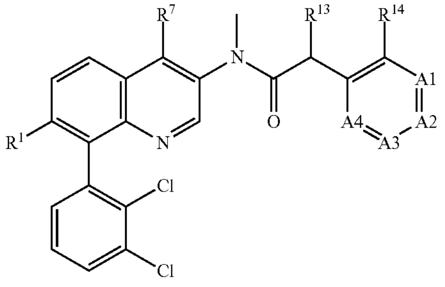

-continued

Formula (Ipiii)

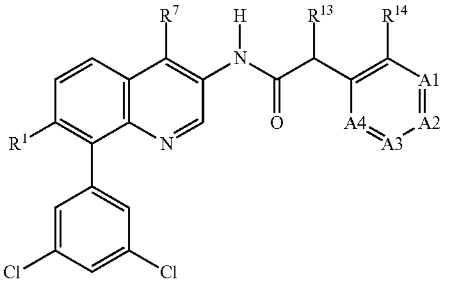

Formula (Ipiv)

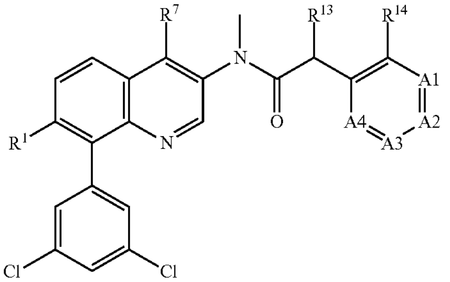

Formula (Ipv)

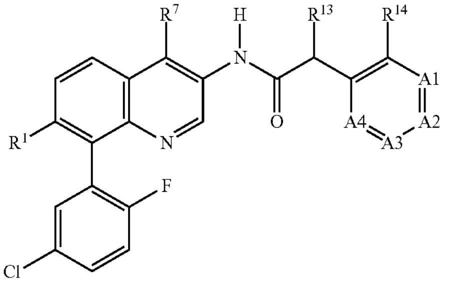

Formula (Ipvi)

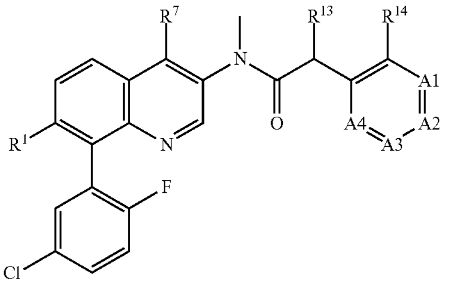

or a stereoisomer, physiologically acceptable salt, ester, solvate, polymorph, prodrug and mixtures thereof, wherein $R^1$, $R^7$ and $R^{13}$, $R^{14}$, A1, A2, A3 and A4 are defined as in any of the embodiments described herein.

In an embodiment of the invention and/or embodiments thereof, the compounds are according to Formula (Ipi), preferably in form of the (S)-enantiomer. In an embodiment of the invention and/or embodiments thereof, the compounds are according to Formula (Ipii), preferably in form of the (S)-enantiomer. In an embodiment of the invention and/or embodiments thereof, the compounds are according to Formula (Ipiii), preferably in form of the (S)-enantiomer. In an embodiment of the invention and/or embodiments thereof, the compounds are according to Formula (Ipiv), preferably in form of the (S)-enantiomer. In an embodiment of the invention and/or embodiments thereof, the compounds are according to Formula (Ipv), preferably in form of the (S)-enantiomer. In an embodiment of the invention and/or embodiments thereof, the compounds are according to Formula (Ipvi), preferably in form of the (S)-enantiomer.

The invention provides a compound according to the invention and/or embodiments thereof, wherein $R^1$, $R^7$ as well as $R^1$, $R^{14}$, A1, A2, A3 and A4 are defined as above.

Optionally, in an embodiment of the invention and/or embodiments thereof, $R^1$ is independently selected from the group consisting of hydrogen, $C_{1-6}$-alkyl, $C_{1-6}$-alkoxy and halogen, wherein $C_{1-6}$-alkyl and $C_{1-6}$-alkoxy is optionally substituted with one or more substituent(s) independently selected from the group consisting of $C_{1-6}$-alkyl, $C_{1-6}$-alkoxy, halogen, cyano, hydroxy and $NR^{2'}R^{3'}$, wherein $R^{2'}$ and $R^{3'}$ are independently selected from hydrogen and $C_{1-3}$-alkyl, more preferably from hydrogen and methyl, and $R^7$ is independently selected from the group consisting of hydrogen, $C_{1-6}$-alkyl, $C_{2-6}$-alkenyl, 4 to 10-membered heterocyclyl, $C_{1-3}$-alkoxy, hydroxy, $NR^8R^9$, $SR^{10}$, $SOR^{10}$ and $SO_2R^{10}$, wherein each $C_{1-6}$-alkyl, $C_{2-6}$-alkenyl, 4 to 10-membered heterocyclyl or $C_{1-3}$-alkoxy is optionally substituted with one or more substituent(s) independently selected from the group consisting of $C_{1-3}$-alkyl, 5 to 10-membered heterocyclyl, $C_{1-6}$-alkoxy, halogen, cyano, hydroxy, $NR^{8'}R^{9'}$, $C(=O)OR^{10'}$ and $C(=O)NR^{11'}R^{12'}$, $R^8$ and $R^9$ are independently selected from the group consisting of hydrogen, $C_{1-6}$-alkyl, $C_{6-10}$-aryl and 5 to 10-membered heteroaryl, or $R^8$ and $R^9$ together with the N atom to which they are attached form a saturated or unsaturated heterocyclic ring having 3 to 12 ring atoms, wherein 1 ring atom is N and wherein 0, 1, 2, or 3 further ring atoms are selected from N, S and O;

wherein the $C_{1-6}$-alkyl, $C_{6-10}$-aryl or 5 to 10-membered heteroaryl or the heterocyclic ring formed by $R^8$ and $R^9$ together with the N atom to which they are attached is optionally substituted with one or more substituent(s) independently selected from the group consisting of $C_{1-6}$-alkyl, $C_{1-6}$-alkoxy, hydroxy and $NR^{8''}R^{9''}$, $R^{10}$ is independently selected from hydrogen or $C_{1-3}$-alkyl, preferably from hydrogen, methyl or ethyl, $R^{8'}$, $R^{9'}$, $R^{10'}$, $R^{11'}$ and $R^{12'}$ are independently selected from hydrogen or $C_{1-3}$-alkyl, preferably from hydrogen, methyl or ethyl, $R^{8''}$ and $R^{9''}$ are independently selected from hydrogen or $C_{1-3}$-alkyl, preferably from hydrogen, methyl or ethyl, and $R^{13}$ and $R^{14}$ together with the atoms to which they are attached form a 5 or 6-carbon atoms containing non-aromatic ring, wherein the non-aromatic ring is optionally substituted with one or more $C_{1-3}$-alkyl or $=O$, and/or wherein one or more of the ring-forming carbon atoms are optionally replaced by —NH—, —O—, —S(O)—, —S(O)$_2$— or —S—, A1 is N or $CR^{15}$, wherein $R^{15}$ is independently hydrogen, halogen, $C_{1-3}$ alkyl, $C_{1-3}$ alkoxy, or $NR^{15'}R^{15''}$, wherein $R^{15'}$ and $R^{15''}$ are independently $C_{1-3}$-alkyl, A2 is N or $CR^{16}$, wherein $R^{16}$ is independently hydrogen, halogen, $C_{1-3}$ alkyl, $C_{1-3}$ alkoxy, or $NR^{16'}R^{16''}$, wherein $R^{16'}$ and $R^{16''}$ are independently $C_{1-3}$-alkyl, A3 is N or $CR^{17}$, wherein $R^{17}$ is independently hydrogen, halogen, $C_{1-3}$ alkyl, $C_{1-3}$ alkoxy, or $NR^{17'}R^{17''}$, wherein $R^{17'}$ and $R^{17''}$ are independently $C_{1-3}$-alkyl, A4 is N or $CR^{18}$, wherein $R^{18}$ is independently hydrogen, halogen, $C_{1-3}$ alkyl, $C_{1-3}$ alkoxy, or $NR^{18'}R^{18''}$, wherein $R^{18'}$ and $R^{18''}$ are independently $C_{1-3}$-alkyl.

In one embodiment of the invention and/or embodiments thereof, $R^1$ is independently selected from the group consisting of hydrogen, methyl, trifluoromethyl, ethyl, methoxy, ethoxy, fluoride and chloride, and $R^7$ is independently selected from the group consisting of methyl, ethyl, propyl, isopropyl, isopropenyl methoxy, ethoxy, isopropoxy, hydroxy, methyl sulfoxyl, methyl sulfonyl methylthio, amino, methylamino, ethylamino, (ethyl)(methyl)amino, isopropylamino, dimethylamino, (isopropyl)(methyl)amino, hydroxyethylamino, (hydroxyethyl)(methyl)amino, methoxyethylamino, morpholin-4-yl, pyrrolidin-1-yl, 3-hydroxy-pyrrolidin-1-yl 3-fluoroazetidinyl and 3,3-difluoroazetidinyl, and $R^{13}$ and $R^{14}$ together with the atoms to which they are attached form a 5 or 6-carbon atoms containing non-aromatic ring, wherein one or more of the ring-forming carbon atoms are optionally replaced by —NH— or —O—, A1 is N or $CR^{15}$, wherein $R^{15}$ is independently hydrogen or $C_{1-3}$ alkoxy, A2 is N or $CR^{16}$, wherein $R^{16}$ is independently hydrogen or $C_{1-3}$ alkoxy, A3 is N or $CR^{17}$, wherein $R^{17}$ is independently hydrogen or $C_{1-3}$ alkoxy, preferably hydrogen, A4 is N or $CR^{18}$, wherein $R^{18}$ is independently hydrogen or $C_{1-3}$ alkoxy, preferably hydrogen, wherein none, one or two of A1, A2, A3 and A4 are N.

In an embodiment of the invention and/or embodiments thereof, the compounds are according to Formula (Iqi), (Iqii), (Iqiii), (Iqiv), (Iqv) or (Iqvi)

Formula (Iqi)

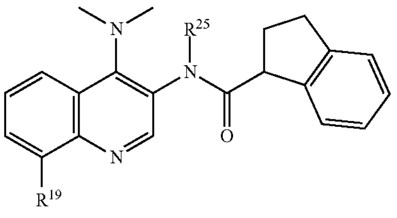

Fromula (Iqii)

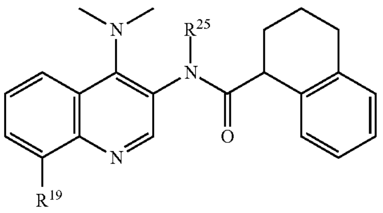

-continued

Formula (Iqiii)

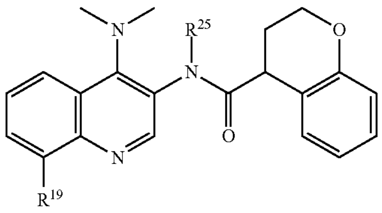

Formula (Iqiv)

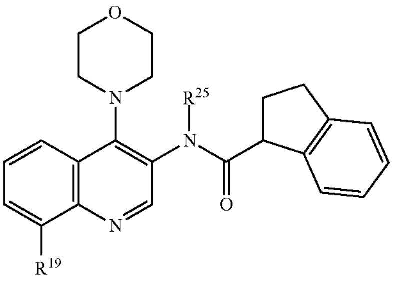

Formula (Iqv)

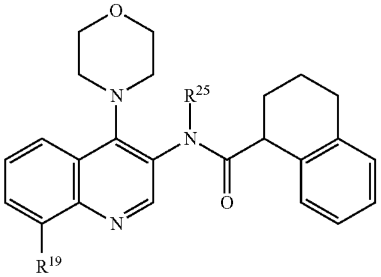

Formula (Iqvi)

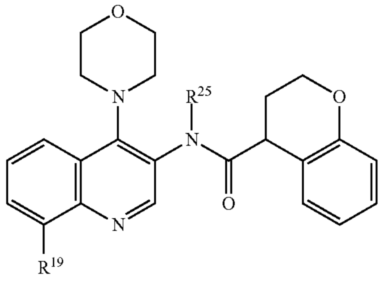

or a stereoisomer, physiologically acceptable salt, ester, solvate, polymorph, prodrug and mixtures thereof, wherein $R^{19}$ and $R^{25}$ are defined as in any of the embodiments described herein.

In an embodiment of the invention and/or embodiments thereof, the compounds are according to Formula (Iqi), preferably in form of the (S)-enantiomer. In an embodiment of the invention and/or embodiments thereof, the compounds are according to Formula (Iqii), preferably in form of the (S)-enantiomer. In an embodiment of the invention and/or embodiments thereof, the compounds are according to Formula (Iqiii), preferably in form of the (S)-enantiomer. In an embodiment of the invention and/or embodiments thereof, the compounds are according to Formula (Iqiv), preferably in form of the (S)-enantiomer. In an embodiment of the invention and/or embodiments thereof, the compounds are according to Formula (Iqv), preferably in form of the (S)-enantiomer. In an embodiment of the invention and/or embodiments thereof, the compounds are according to Formula (Iqvi), preferably in form of the (S)-enantiomer.

Optionally, in an embodiment of the invention and/or embodiments thereof, $R^1$ is independently selected from the group consisting of hydrogen, $C_{1-6}$-alkyl, $C_{1-6}$-alkoxy and halogen, wherein $C_{1-6}$-alkyl and $C_{1-6}$-alkoxy is optionally substituted with one or more substituent(s) independently selected from the group consisting of $C_{1-6}$-alkyl, $C_{1-6}$-alkoxy, halogen, cyano, hydroxy and $NR^{2'}R^{3'}$, wherein $R^{2'}$ and $R^{3'}$ are independently selected from hydrogen and $C_{1-3}$-alkyl, more preferably from hydrogen and methyl, and $R^7$ is independently selected from the group consisting of hydrogen, $C_{1-6}$-alkyl, $C_{2-6}$-alkenyl, 4 to 10-membered heterocyclyl, $C_{1-3}$-alkoxy, hydroxy, $NR^8R^9$, $SR^{10}$, $SOR^{10}$ and $SO_2R^{10}$, wherein each $C_{1-6}$-alkyl, $C_{2-6}$-alkenyl, 4 to 10-membered heterocyclyl or $C_{1-3}$-alkoxy is optionally substituted with one or more substituent(s) independently selected from the group consisting of $C_{1-3}$-alkyl, 5 to 10-membered heterocyclyl, $C_{1-6}$-alkoxy, halogen, cyano, hydroxy, $NR^{8'}R^{9'}$, $C(=O)OR^{10'}$ and $C(=O)NR^{11'}R^{12'}$, $R^8$ and $R^9$ are independently selected from the group consisting of hydrogen, $C_{1-6}$-alkyl, $C_{6-10}$-aryl and 5 to 10-membered heteroaryl, or $R^8$ and $R^9$ together with the N atom to which they are attached form a saturated or unsaturated heterocyclic ring having 3 to 12 ring atoms, wherein 1 ring atom is N and wherein 0, 1, 2, or 3 further ring atoms are selected from N, S and O;

wherein the $C_{1-6}$-alkyl, $C_{6-10}$-aryl or 5 to 10-membered heteroaryl or the heterocyclic ring formed by $R^8$ and $R^9$ together with the N atom to which they are attached is optionally substituted with one or more substituent(s) independently selected from the group consisting of $C_{1-6}$-alkyl, $C_{1-6}$-alkoxy, hydroxy and $NR^{8''}R^{9''}$, $R^{10}$ is independently selected from hydrogen or $C_{1-3}$-alkyl, preferably from hydrogen, methyl or ethyl, $R^{8'}$, $R^{9'}$, $R^{10'}$, $R^{11'}$ and $R^{12'}$ are independently selected from hydrogen or $C_{1-3}$-alkyl, preferably from hydrogen, methyl or ethyl, $R^{8''}$ and $R^{9''}$ are independently selected from hydrogen or $C_{1-3}$-alkyl, preferably from hydrogen, methyl or ethyl, and $R^{13}$ and $R^{14}$ together with the atoms to which they are attached form a 5 or 6-carbon atoms containing aromatic ring, wherein the aromatic ring is optionally substituted with one or more $C_{1-3}$-alkyl, and/or wherein one or more of the ring-forming carbon atoms are optionally replaced by —NH—, —N=, =N—, —O— or —S—, A1 is N or $CR^{15}$, wherein $R^{15}$ is independently hydrogen, halogen $C_{1-3}$ alkyl, $C_{1-3}$ alkoxy or $NR^{15'}R^{15''}$, wherein $R^{15'}$ and $R^{15''}$ are independently $C_{1-3}$-alkyl, A2 is N or $CR^{16}$, wherein $R^{16}$ is independently hydrogen, halogen, $C_{1-3}$ alkyl, $C_{1-3}$ alkoxy or $NR^{16'}R^{16''}$, wherein $R^{16'}$ and $R^{16''}$ are independently $C_{1-3}$-alkyl, A3 is N or $CR^{17}$, wherein $R^{17}$ is independently hydrogen, halogen, $C_{1-3}$ alkyl, $C_{1-3}$ alkoxy or $NR^{15'}R^{15''}$, wherein $R^{15'}$ and $R^{15''}$ are independently $C_{1-3}$-alkyl, A4 is N or $CR^{18}$, wherein $R^{18}$ is independently hydrogen, halogen, $C_{1-3}$ alkyl, $C_{1-3}$ alkoxy or $NR^{15'}R^{15''}$, wherein $R^{15'}$ and $R^{15''}$ are independently $C_{1-3}$-alkyl.

In one embodiment of the invention and/or embodiments thereof, $R^1$ is independently selected from the group consisting of hydrogen, methyl, trifluoromethyl, ethyl, methoxy, ethoxy, fluoride and chloride, and $R^7$ is independently selected from the group consisting of methyl, ethyl, propyl, isopropyl, isopropenyl methoxy, ethoxy, isopropoxy, hydroxy, methyl sulfoxyl, methyl sulfonyl methylthio, amino, methylamino, ethylamino, (ethyl)(methyl)amino, isopropylamino, dimethylamino, (isopropyl)(methyl)amino, hydroxyethylamino, (hydroxyethyl)(methyl)amino, methoxyethylamino, morpholin-4-yl, pyrrolidine-1-yl, 3-hydroxy-pyrrolidin-1-yl 3-fluoroazetidinyl and 3,3-difluoroazetidinyl, and $R^{13}$ and $R^{14}$ together with the atoms to which they are attached form a 5 or 6-carbon atoms containing aromatic ring, wherein one or more of the ring-forming carbon atoms are optionally replaced by —NH—, —N=, =N— or —S—, A1 is N or $CR^{15}$, wherein $R^{15}$ is independently hydrogen or $C_{1-3}$ alkoxy, A2 is N or $CR^{16}$, wherein $R^{16}$ is independently hydrogen or $C_{1-3}$ alkoxy, A3 is N or $CR^{17}$, wherein $R^{17}$ is independently hydrogen or $C_{1-3}$ alkoxy, preferably hydrogen, A4 is N or $CR^{18}$, wherein $R^{18}$ is independently hydrogen or $C_{1-3}$ alkoxy, preferably hydrogen, wherein none, one or two of A1, A2, A3 and A4 are N.

In an embodiment of the invention and/or embodiments thereof, the compounds are according to Formula (Iqvii), (Iqviii), (Iqix), (Iqx), (Iqxi) or (Iqxii)

Formula (Iqvii)

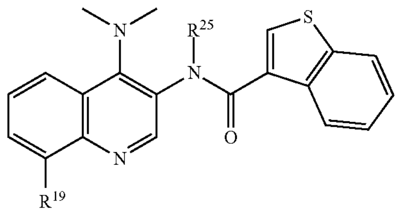

Fromula (Iqviii)

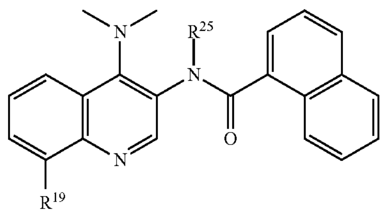

Formula (Iqix)

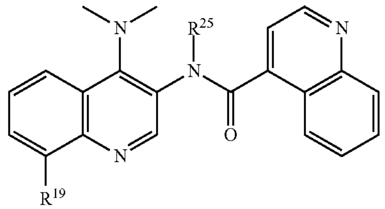

-continued

Formula (Iqx)

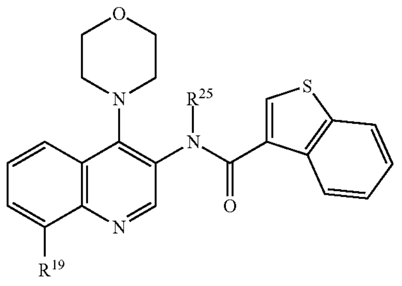

Formula (Iqv)

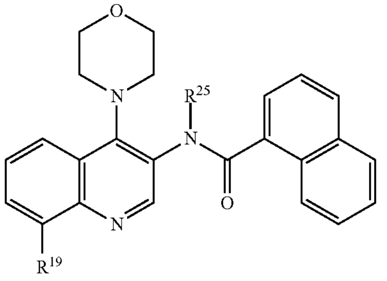

Formula (Iqxii)

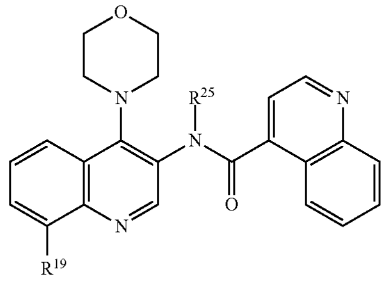

or a stereoisomer, physiologically acceptable salt, ester, solvate, polymorph, prodrug and mixtures thereof, wherein $R^{19}$ and $R^{25}$ are defined as in any of the embodiments described herein.

In an embodiment of the invention and/or embodiments thereof, the compounds are according to Formula (Iqvii), preferably in form of the (S)-enantiomer. In an embodiment of the invention and/or embodiments thereof, the compounds are according to Formula (Iqviii), preferably in form of the (S)-enantiomer. In an embodiment of the invention and/or embodiments thereof, the compounds are according to Formula (Iqix). preferably in form of the (S)-enantiomer. In an embodiment of the invention and/or embodiments thereof, the compounds are according to Formula (Iqx), preferably in form of the (S)-enantiomer. In an embodiment of the invention and/or embodiments thereof, the compounds are according to Formula (Iqxi), preferably in form of the (S)-enantiomer). In an embodiment of the invention and/or embodiments thereof, the compounds are according to Formula (Iqxii), preferably in form of the (S)-enantiomer.

The invention provides a compound according to the invention and/or embodiments thereof, wherein $R^1$, $R^7$ and $R^{19}$ are defined as above.

Optionally, in an embodiment of the invention and/or embodiments thereof, $R^1$ is independently selected from the group consisting of hydrogen, $C_{1-6}$-alkyl, $C_{1-6}$-alkoxy and halogen, wherein $C_{1-6}$-alkyl and $C_{1-6}$-alkoxy is optionally substituted with one or more substituent(s) independently selected from the group consisting of $C_{1-6}$-alkyl, $C_{1-6}$-alkoxy, halogen, cyano, hydroxy and $NR^{2'}R^{3'}$, wherein $R^{2'}$ and $R^{3'}$ are independently selected from hydrogen and $C_{1-3}$-alkyl, more preferably from hydrogen and methyl, and $R^7$ is independently selected from the group consisting of hydrogen, $C_{1-6}$-alkyl, $C_{2-6}$-alkenyl, 4- to 10-membered heterocyclyl, $C_{1-3}$-alkoxy, hydroxy, $NR^8R^9$, $SR^{10}$, $SOR^{10}$ and $SO_2R^{10}$, wherein each $C_{1-6}$-alkyl, $C_{2-6}$-alkenyl, 4- to 10-membered heterocyclyl or $C_{1-3}$-alkoxy is optionally substituted with one or more substituent(s) independently selected from the group consisting of $C_{1-3}$-alkyl, 5 to 10-membered heterocyclyl, $C_{1-6}$-alkoxy, halogen, cyano, hydroxy, $NR^{8'}R^{9'}$, $C(=O)OR^{10'}$ and $C(=O)NR^{11'}R^{12'}$, $R^8$ and $R^9$ are independently selected from the group consisting of hydrogen, $C_{1-6}$-alkyl, $C_{6-10}$-aryl and 5 to 10-membered heteroaryl, or $R^8$ and $R^9$ together with the N atom to which they are attached form a saturated or unsaturated heterocyclic ring having 3 to 12 ring atoms, wherein 1 ring atom is N and wherein 0, 1, 2, or 3 further ring atoms are selected from N, S and O;

wherein the $C_{1-6}$-alkyl, $C_{6-10}$-aryl or 5 to 10-membered heteroaryl or the heterocyclic ring formed by $R^8$ and $R^9$ together with the N atom to which they are attached is optionally substituted with one or more substituent(s) independently selected from the group consisting of $C_{1-6}$-alkyl, $C_{1-6}$-alkoxy, hydroxy and $NR^{8''}R^{9''}$;

$R^{10}$ is independently selected from hydrogen or $C_{1-3}$-alkyl, preferably from hydrogen, methyl or ethyl, $R^{8'}$, $R^{9'}$, $R^{10'}$, $R^{11'}$ and $R^{12'}$ are independently selected from hydrogen or $C_{1-3}$-alkyl, preferably from hydrogen, methyl or ethyl, $R^{8''}$ and $R^{9''}$ are independently selected from hydrogen or $C_{1-3}$-alkyl, preferably from hydrogen, methyl or ethyl, and $R^{19}$ is independently selected from the group consisting of $C_{6-10}$-aryl and 5 to 10-membered heteroaryl wherein each $C_{6-10}$-aryl or 5 to 10-membered heteroaryl is optionally substituted with one or more substituent(s) independently selected from the group consisting of $C_{1-6}$-alkyl, $C_{1-6}$-alkoxy, halogen, cyano, nitro and hydroxy.

In one embodiment of the invention and/or embodiments thereof, $R^1$ is independently selected from the group consisting of hydrogen, methyl, trifluoromethyl, ethyl, methoxy, ethoxy, fluoride and chloride, and $R^7$ is independently selected from the group consisting of methyl, ethyl, isopropyl, propyl, isopropenyl methoxy, ethoxy, isopropoxy, hydroxy, methyl sulfoxyl, methyl sulfonyl methylthio, amino, methylamino, ethylamino, (ethyl)(methyl)amino isopropylamino, dimethylamino, (isopropyl)(methyl)amino, hydroxyethylamino, (hydroxyethyl)(methyl)amino, methoxyethylamino, (methoxyethyl)(methyl)amino, morpholin-4-yl, pyrrolidine-1-yl, 3-hydroxy-pyrrolidin-1-yl 3-fluoroazetidinyl and 3,3-difluoroazetidinyl, and $R^{19}$ is selected from the group consisting of 3-chlorophenyl, 2,3-dichlorophenyl, 3,5-dichlorophenyl, 3,5-difluorophenyl, 2,3,5-trifluorophenyl, 3,4,5-trifluorophenyl, 3-chloro-2-fluorophenyl, 5-chloro-3-fluorophenyl, 5-chloro-3-fluorophenyl, 3,5-dichloro-4-fluorophenyl, in particular 2,3,5-trifluorophenyl, 5-chloro-2-fluorophenyl, 2,3-dichlorophenyl and 3,5-dichlorophenyl.

In an embodiment of the invention and/or embodiments thereof, the compounds are according to Formula (Iri), (Irii), (Iriii), (Iriv), (Irv) or (Irvi)

Formula (Iri)

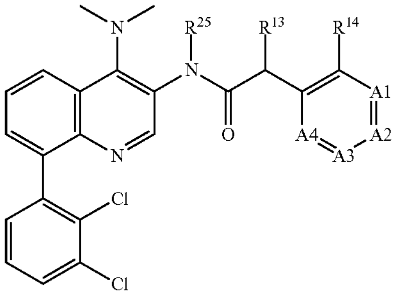

Formual (Irii)

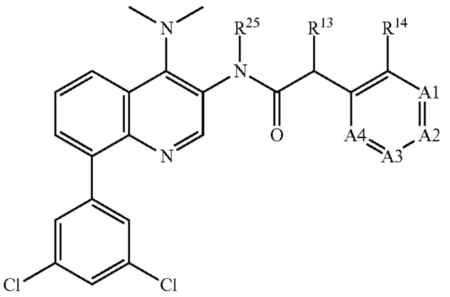

Formula (Iriii)

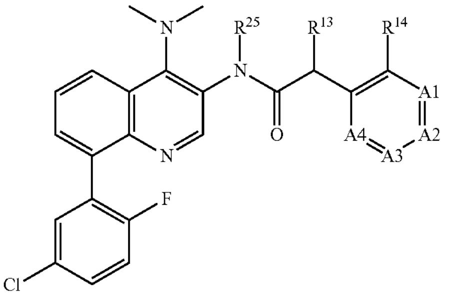

Formula (Iriv)

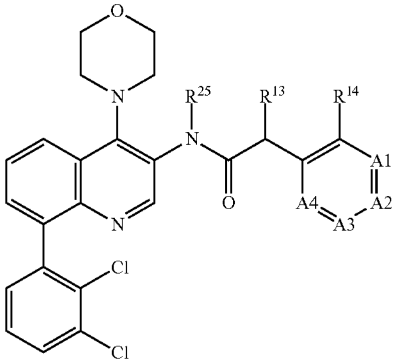

-continued

Formula (Irv)

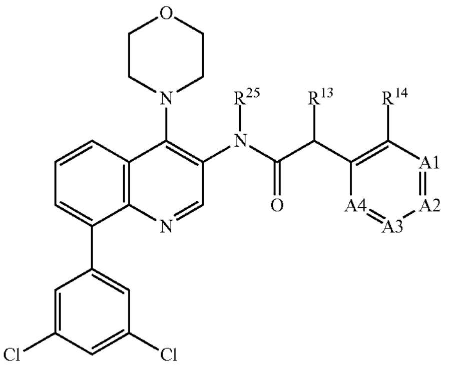

Formula (Irvi)

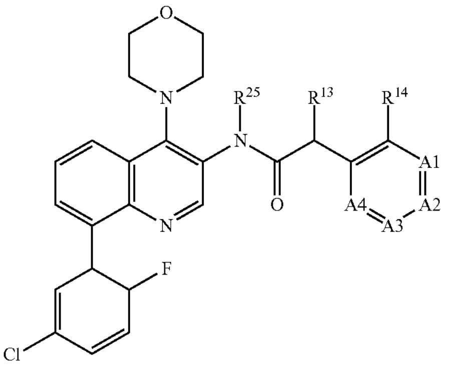

or a stereoisomer, physiologically acceptable salt, ester, solvate, polymorph, prodrug and mixtures thereof, wherein $R^3$, $R^{14}$, A1, A2, A3, A4 and $R^{25}$ are defined as in any of the embodiments described herein.

In an embodiment of the invention and/or embodiments thereof, the compounds are according to Formula (Iri), preferably in form of the (S)-enantiomer. In an embodiment of the invention and/or embodiments thereof, the compounds are according to Formula (Irii), preferably in form of the (S)-enantiomer. In an embodiment of the invention and/or embodiments thereof, the compounds are according to Formula (Iriii), preferably in form of the (S)-enantiomer. In an embodiment of the invention and/or embodiments thereof, the compounds are according to Formula (Iriv), preferably in form of the (S)-enantiomer. In an embodiment of the invention and/or embodiments thereof, the compounds are according to Formula (Irv), preferably in form of the (S)-enantiomer. In an embodiment of the invention and/or embodiments thereof, the compounds are according to Formula (Irvi), preferably in form of the (S)-enantiomer.

The invention provides a compound according to the invention and/or embodiments thereof, wherein $R^1$, $R^7$ and $R^{25}$ are defined as above.

Optionally, in an embodiment of the invention and/or embodiments thereof, $R^1$ is independently selected from the group consisting of hydrogen, $C_{1-6}$-alkyl, $C_{1-6}$-alkoxy and halogen, wherein $C_{1-6}$-alkyl and $C_{1-6}$-alkoxy is optionally substituted with one or more substituent(s) independently selected from the group consisting of $C_{1-6}$-alkyl, $C_{1-6}$-alkoxy, halogen, cyano, hydroxy and $NR^{2'}R^{3'}$, wherein $R^{2'}$ and $R^{3'}$ are independently selected from hydrogen and $C_{1-3}$-alkyl, more preferably from hydrogen and methyl, and $R^7$ is independently selected from the group consisting of hydrogen, $C_{1-6}$-alkyl, $C_{2-6}$-alkenyl, 4- to 10-membered heterocyclyl, $C_{1-3}$-alkoxy, hydroxy, $NR^8R^9$, $SR^{10}$, $SOR^{10}$ and $SO_2R^{10}$, wherein each $C_{1-6}$-alkyl, $C_{2-6}$-alkenyl, 4- to 10-membered heterocyclyl or $C_{1-3}$-alkoxy is optionally substituted with one or more substituent(s) independently selected from the group consisting of $C_{1-3}$-alkyl, 5 to 10-membered heterocyclyl, $C_{1-6}$-alkoxy, halogen, cyano, hydroxy, $NR^{8'}R^{9'}$, $C(=O)OR^{10'}$ and $C(=O)NR^{11'}R^{12'}$, $R^8$ and $R^9$ are independently selected from the group consisting of hydrogen, $C_{1-6}$-alkyl, $C_{6-10}$-aryl and 5 to 10-membered heteroaryl, or $R^8$ and $R^9$ together with the N atom to which they are attached form a saturated or unsaturated heterocyclic ring having 3 to 12 ring atoms, wherein 1 ring atom is N and wherein 0, 1, 2, or 3 further ring atoms are selected from N, S and O;

wherein the $C_{1-6}$-alkyl, $C_{6-10}$-aryl or 5 to 10-membered heteroaryl or the heterocyclic ring formed by $R^8$ and $R^9$ together with the N atom to which they are attached is optionally substituted with one or more substituent(s) independently selected from the group consisting of $C_{1-6}$-alkyl, $C_{1-6}$-alkoxy, hydroxy and $NR^{8''}R^{9''}$;

$R^{10}$ is independently selected from hydrogen or $C_{1-3}$-alkyl, preferably from hydrogen, methyl or ethyl, $R^{8'}$, $R^{9'}$, $R^{10'}$, $R^{11'}$ and $R^{12'}$ are independently selected from hydrogen or $C_{1-3}$-alkyl, preferably from hydrogen, methyl or ethyl, $R^{8''}$ and $R^{9''}$ are independently selected from hydrogen or $C_{1-3}$-alkyl, preferably from hydrogen, methyl or ethyl, and $R^{25}$ is hydrogen or $C_{1-3}$-alkyl.

Optionally, in an embodiment of the invention and/or embodiments thereof, $R^1$ is independently selected from the group consisting of hydrogen, methyl, trifluoromethyl, ethyl, methoxy, ethoxy, fluoride and chloride, and $R^7$ is independently selected from the group consisting of methyl, ethyl, isopropyl, propyl, isopropenyl methoxy, ethoxy, isopropoxy, hydroxy, methyl sulfoxyl, methyl sulfonyl methylthio, amino, methylamino, ethylamino, (ethyl)(methyl)amino isopropylamino, dimethylamino, (isopropyl)(methyl)amino, hydroxyethylamino, (hydroxyethyl)(methyl)amino, methoxyethylamino, (methoxyethyl)(methyl)amino, morpholin-4-yl, pyrrolidine-1-yl,3-hydroxy-pyrrolidin-1-yl 3-fluoroazetidinyl and 3,3-difluoroazetidinyl, and $R^{25}$ is hydrogen or methyl, preferably hydrogen.

In an embodiment of the invention and/or embodiments thereof, the compounds are according to Formula (Isi), (Isii), (Isiii) or (Isiv)

Formula (Isi)

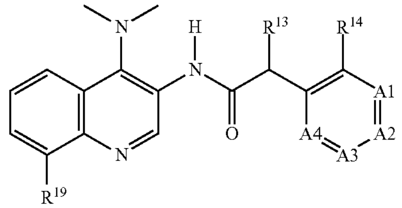

Formual (Isii)

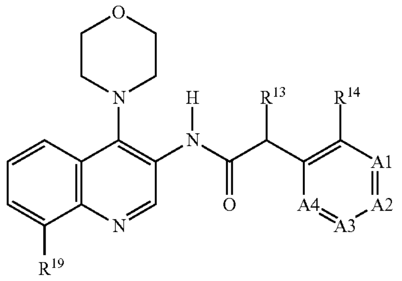

Formula (Isiii)

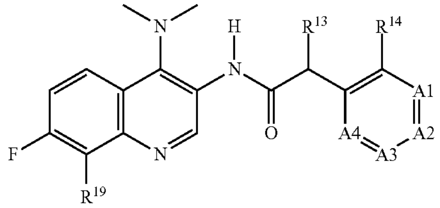

Formula (Isiv)

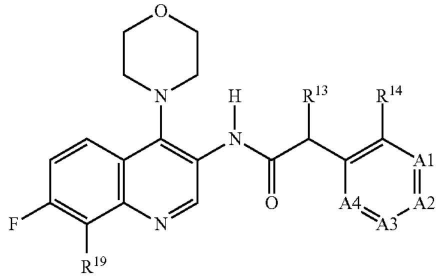

or a stereoisomer, physiologically acceptable salt, ester, solvate, polymorph, prodrug and mixtures thereof, wherein $R^{13}$, $R^{14}$, A1, A2, A3, A4 and $R^{29}$ are defined as in any of the embodiments described herein.

In an embodiment of the invention and/or embodiments thereof, the compounds are according to Formula (Isi), preferably in form of the (S)-enantiomer. In an embodiment of the invention and/or embodiments thereof, the compounds are according to Formula (Isii), preferably in form of the (S)-enantiomer. In an embodiment of the invention and/or embodiments thereof, the compounds are according to Formula (Isiii), preferably in form of the (S)-enantiomer. In an embodiment of the invention and/or embodiments thereof, the compounds are according to Formula (Isiv), preferably in form of the (S)-enantiomer.

The invention provides a compound according to the invention and/or embodiments thereof, wherein $R^1$, $R^{13}$, $R^{14}$, A1, A2, A3, A4 and $R^{19}$ are defined as above.

Optionally, in an embodiment of the invention and/or embodiments thereof, $R^1$ is independently selected from the group consisting of hydrogen, $C_{1-6}$-alkyl, $C_{1-6}$-alkoxy and halogen, wherein $C_{1-6}$-alkyl and $C_{1-6}$-alkoxy is optionally substituted with one or more substituent(s) independently selected from the group consisting of $C_{1-6}$-alkyl, $C_{1-6}$-alkoxy, halogen, cyano, hydroxy and $NR^{2'}R^{3'}$, wherein $R^{2'}$ and $R^{3'}$ are independently selected from hydrogen and $C_{1-3}$-alkyl, more preferably from hydrogen and methyl, and $R^{13}$ and $R^{14}$ together with the atoms to which they are attached form a 5 or 6-carbon atoms containing non-aromatic ring, wherein the non-aromatic ring is optionally substituted with one or more $C_{1-3}$-alkyl or =O, and/or wherein one or more of the ring-forming carbon atoms are optionally replaced by —NH—, —O—, —S(O)—, —$S(O)_2$— or —S—, A1 is N or $CR^{15}$, wherein $R^{15}$ is independently hydrogen, halogen, $C_{1-3}$ alkyl, $C_{1-3}$ alkoxy, or $NR^{15'}R^{15''}$, wherein $R^{15'}$ and $R^{15''}$ are independently $C_{1-3}$-alkyl, A2 is N or $CR^{16}$, wherein $R^{16}$ is independently hydrogen, halogen, $C_{1-3}$ alkyl, $C_{1-3}$ alkoxy, or $NR^{16'}R^{16''}$, wherein $R^{16'}$ and $R^{16''}$ are independently $C_{1-3}$-alkyl, A3 is N or $CR^{17}$, wherein $R^{17}$ is independently hydrogen, halogen, $C_{1-3}$ alkyl, $C_{1-3}$ alkoxy, or $NR^{17'}R^{17''}$, wherein $R^{17'}$ and $R^{17''}$ are independently $C_{1-3}$-alkyl, A4 is N or $CR^{18}$, wherein $R^{18}$ is independently hydrogen, halogen, $C_{1-3}$ alkyl, $C_{1-3}$ alkoxy, or $NR^{18'}R^{18''}$, wherein $R^{18'}$ and $R^{18''}$ are independently $C_{1-3}$-alkyl, and $R^{19}$ is independently selected from the group consisting of $C_{6-10}$-aryl and 5 to 10-membered heteroaryl wherein each $C_{6-10}$-aryl or 5 to 10-membered heteroaryl is optionally substituted with one or more substituent(s) independently selected from the group consisting of $C_{1-6}$-alkyl, $C_{1-6}$-alkoxy, halogen, cyano, nitro and hydroxy.

In one embodiment of the invention and/or embodiments thereof, $R^1$ is independently selected from the group consisting of hydrogen, methyl, trifluoromethyl, ethyl, methoxy, ethoxy, fluoride and chloride, and $R^{13}$ and $R^{14}$ together with the atoms to which they are attached form a 5 or 6-carbon atoms containing non-aromatic ring, wherein one or more of the ring-forming carbon atoms are optionally replaced by —NH— or —O—, A1 is N or $CR^{15}$, wherein $R^{15}$ is independently hydrogen or $C_{1-3}$ alkoxy, A2 is N or $CR^{16}$, wherein $R^{16}$ is independently hydrogen or $C_{1-3}$ alkoxy, A3 is N or $CR^{17}$, wherein $R^{17}$ is independently hydrogen or $C_{1-3}$ alkoxy, preferably hydrogen, A4 is N or $CR^{18}$, wherein $R^{18}$ is independently hydrogen or $C_{1-3}$ alkoxy, preferably hydrogen, wherein none, one or two of A1, A2, A3 and A4 are N, and $R^{19}$ is independently selected from the group consisting of 3-chlorophenyl, 2,3-dichlorophenyl, 3,5-dichlorophenyl, 3,5-difluorophenyl, 2,3,5-trifluorophenyl, 3,4,5-trifluorophenyl, 3-chloro-2-fluorophenyl, 5-chloro-3-fluorophenyl, 5-chloro-3-fluorophenyl, 3,5-dichloro-4-fluorophenyl, in particular 2,3,5-trifluorophenyl, 5-chloro-2-fluorophenyl, 2,3-dichlorophenyl and 3,5-dichlorophenyl.

In an embodiment of the invention and/or embodiments thereof, the compounds are according to Formula (Iti), (Itii), (Itiii), (Itiv), (Itv) or (Itvi)

Formula (Iti)

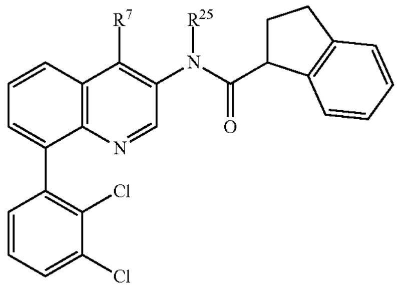

Formula (Itii)

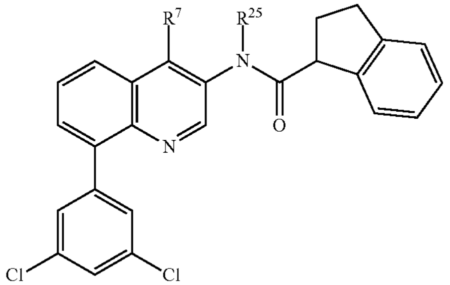

Formula (Itiii)

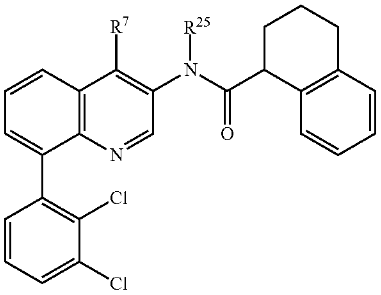

Formula (Itiv)

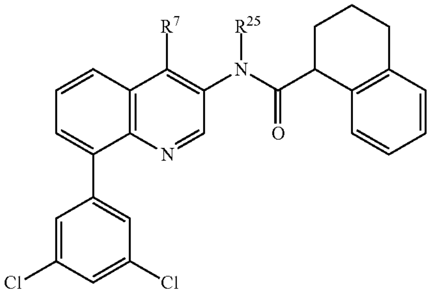

Formula (Itv)

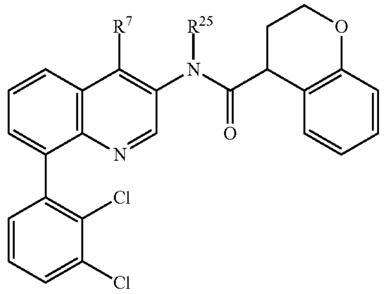

-continued

Formula (Itvi)

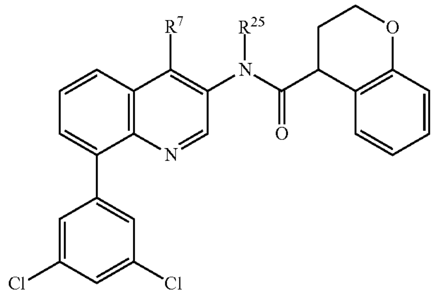

or a stereoisomer, physiologically acceptable salt, ester, solvate, polymorph, prodrug and mixtures thereof, wherein $R^7$ and $R^{25}$ are defined as in any of the embodiments described herein.

In an embodiment of the invention and/or embodiments thereof, the compounds are according to Formula (Iti), preferably in form of the (S)-enantiomer. In an embodiment of the invention and/or embodiments thereof, the compounds are according to Formula (Itii), preferably in form of the (S)-enantiomer. In an embodiment of the invention and/or embodiments thereof, the compounds are according to Formula (Itiii), preferably in form of the (S)-enantiomer. In an embodiment of the invention and/or embodiments thereof, the compounds are according to Formula (Itiv), preferably in form of the (S)-enantiomer. In an embodiment of the invention and/or embodiments thereof, the compounds are according to Formula (Itv), preferably in form of the (S)-enantiomer. In an embodiment of the invention and/or embodiments thereof, the compounds are according to Formula (Itvi), preferably in form of the (S)-enantiomer.

Optionally, in an embodiment of the invention and/or embodiments thereof, $R^1$ is independently selected from the group consisting of hydrogen, $C_{1-6}$-alkyl, $C_{1-6}$-alkoxy and halogen, wherein $C_{1-6}$-alkyl and $C_{1-6}$-alkoxy is optionally substituted with one or more substituent(s) independently selected from the group consisting of $C_{1-6}$-alkyl, $C_{1-6}$-alkoxy, halogen, cyano, hydroxy and $NR^{2'}R^{3'}$, wherein $R^{2'}$ and $R^{3'}$ are independently selected from hydrogen and $C_{1-3}$-alkyl, more preferably from hydrogen and methyl, and $R^{13}$ and $R^{14}$ together with the atoms to which they are attached form a 5 or 6-carbon atoms containing aromatic ring, wherein the aromatic ring is optionally substituted with one or more $C_{1-3}$-alkyl, and/or wherein one or more of the ring-forming carbon atoms are optionally replaced by —NH—, —N═, ═N—, —O— or —S—, A1 is N or $CR^{15}$, wherein $R^{15}$ is independently hydrogen, halogen $C_{1-3}$ alkyl, $C_{1-3}$ alkoxy or $NR^{15'}R^{15''}$, wherein $R^{15'}$ and $R^{15''}$ are independently $C_{1-3}$-alkyl, A2 is N or $CR^{16}$, wherein $R^{16}$ is independently hydrogen, halogen, $C_{1-3}$ alkyl, $C_{1-3}$ alkoxy or $NR^{16'}R^{16''}$, wherein $R^{16'}$ and $R^{16''}$ are independently $C_{1-3}$-alkyl, A3 is N or $CR^{17}$, wherein $R^{17}$ is independently hydrogen, halogen, $C_{1-3}$ alkyl, $C_{1-3}$ alkoxy or $NR^{15'}R^{15''}$, wherein $R^{15'}$ and $R^{15''}$ are independently $C_{1-3}$-alkyl, A4 is N or $CR^{18}$, wherein $R^{18}$ is independently hydrogen, halogen, $C_{1-3}$ alkyl, $C_{1-3}$ alkoxy or $NR^{15'}R^{15''}$, wherein $R^{15'}$ and $R^{15''}$ are independently $C_{1-3}$-alkyl, and $R^{19}$ is independently selected from the group consisting of $C_{6-10}$-aryl and 5 to 10-membered heteroaryl wherein each $C_{6-10}$-aryl or 5 to 10-membered heteroaryl is optionally substituted with one or more substituent(s) independently selected from the group consisting of $C_{1-6}$-alkyl, $C_{1-6}$-alkoxy, halogen, cyano, nitro and hydroxy.

In one embodiment of the invention and/or embodiments thereof, $R^1$ is independently selected from the group consisting of hydrogen, methyl, trifluoromethyl, ethyl, methoxy, ethoxy, fluoride and chloride, and $R^{13}$ and $R^{14}$ together with the atoms to which they are attached form a 5 or 6-carbon atoms containing aromatic ring, wherein one or more of the ring-forming carbon atoms are optionally replaced by —NH—, —N═, ═N— or —S—, A1 is N or $CR^{15}$, wherein $R^{15}$ is independently hydrogen or $C_{1-3}$ alkoxy, A2 is N or $CR^{16}$, wherein $R^{16}$ is independently hydrogen or $C_{1-3}$ alkoxy, A3 is N or $CR^{17}$, wherein $R^{17}$ is independently hydrogen or $C_{1-3}$ alkoxy, preferably hydrogen, A4 is N or $CR^{18}$, wherein $R^{18}$ is independently hydrogen or $C_{1-3}$ alkoxy, preferably hydrogen, wherein none, one or two of A1, A2, A3 and A4 are N, and $R^{19}$ is independently selected from the group consisting of 3-chlorophenyl, 2,3-dichlorophenyl, 3,5-dichlorophenyl, 3,5-difluorophenyl, 2,3,5-trifluorophenyl, 3,4,5-trifluorophenyl, 3-chloro-2-fluorophenyl, 5-chloro-3-fluorophenyl, 5-chloro-3-fluorophenyl, 3,5-dichloro-4-fluorophenyl, in particular 2,3,5-trifluorophenyl, 5-chloro-2-fluorophenyl, 2,3-dichlorophenyl and 3,5-dichlorophenyl.

In an embodiment of the invention and/or embodiments thereof, the compounds are according to Formula (Itvii), (Itviii), (Itix), (Itx), (Itxi) or (Itxii)

Formula (Itvii)

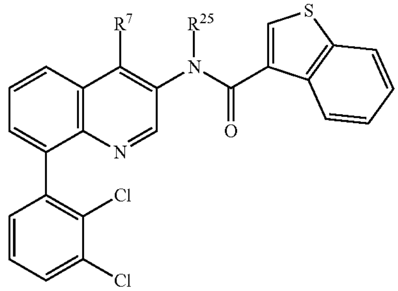

Formula (Itviii)

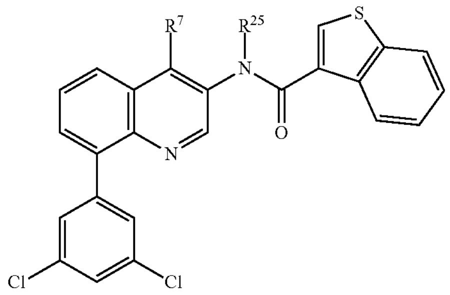

-continued

Formula (Itix)

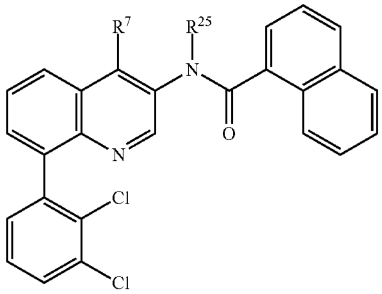

Formula (Itx)

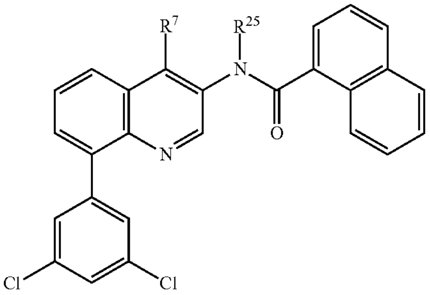

Formula (Itxi)

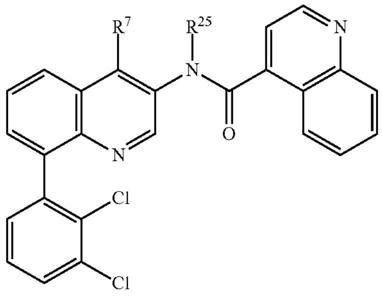

Formula (Itxii)

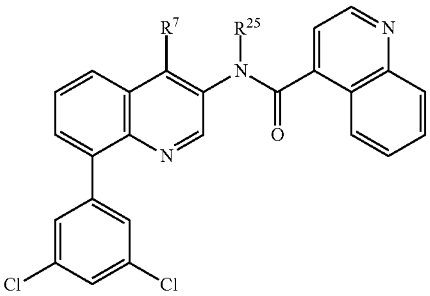

or a stereoisomer, physiologically acceptable salt, ester, solvate, polymorph, prodrug and mixtures thereof, wherein $R^7$ and $R^{25}$ are defined as in any of the embodiments described herein.

In an embodiment of the invention and/or embodiments thereof, the compounds are according to Formula (Itvii), preferably in form of the (S)-enantiomer. In an embodiment of the invention and/or embodiments thereof, the compounds are according to Formula (Itviii), preferably in form of the (S)-enantiomer. In an embodiment of the invention and/or embodiments thereof, the compounds are according to Formula (Itix), preferably in form of the (S)-enantiomer. In an embodiment of the invention and/or embodiments thereof, the compounds are according to Formula (Itx), preferably in form of the (S)-enantiomer. In an embodiment of the invention and/or embodiments thereof, the compounds are according to Formula (Itxi), preferably in form of the (S)-enantiomer. In an embodiment of the invention and/or embodiments thereof, the compounds are according to Formula (Itxii), preferably in form of the (S)-enantiomer.

The invention provides a compound according to the invention and/or embodiments thereof, wherein $R^1$, $R^{13}$, $R^{14}$, A1, A2, A3, A4 and $R^{25}$ are defined as above.

Optionally, in an embodiment of the invention and/or embodiments thereof, $R^1$ is independently selected from the group consisting of hydrogen, $C_{1-6}$-alkyl, $C_{1-6}$-alkoxy and halogen,
  wherein $C_{1-6}$-alkyl and $C_{1-6}$-alkoxy is optionally substituted with one or more substituent(s) independently selected from the group consisting of $C_{1-6}$-alkyl, $C_{1-6}$-alkoxy, halogen, cyano, hydroxy and $NR^{2'}R^{3'}$, wherein $R^{2'}$ and $R^{3'}$ are independently selected from hydrogen and $C_{1-3}$-alkyl, more preferably from hydrogen and methyl, and $R^{13}$ and $R^{14}$ together with the atoms to which they are attached form a 5 or 6-carbon atoms containing non-aromatic ring, wherein the non-aromatic ring is optionally substituted with one or more $C_{1-3}$-alkyl or =O, and/or wherein one or more of the ring-forming carbon atoms are optionally replaced by —NH—, —O—, —S(O)—, —S(O)$_2$— or —S—, A1 is N or $CR^{15}$, wherein $R^{15}$ is independently hydrogen, halogen, $C_{1-3}$ alkyl, $C_{1-3}$ alkoxy, or $NR^{15'}R^{15''}$, wherein $R^{15'}$ and $R^{15''}$ are independently $C_{1-3}$-alkyl, A2 is N or $CR^{16}$, wherein $R^{16}$ is independently hydrogen, halogen, $C_{1-3}$ alkyl, $C_{1-3}$ alkoxy, or $NR^{16'}R^{16''}$, wherein $R^{16'}$ and $R^{16''}$ are independently $C_{1-3}$-alkyl, A3 is N or $CR^{17}$, wherein $R^{17}$ is independently hydrogen, halogen, $C_{1-3}$ alkyl, $C_{1-3}$ alkoxy, or $NR^{17'}R^{17''}$, wherein $R^{17'}$ and $R^{17''}$ are independently $C_{1-3}$-alkyl, A4 is N or $CR^{18}$, wherein $R^{18}$ is independently hydrogen, halogen, $C_{1-3}$ alkyl, $C_{1-3}$ alkoxy, or $NR^{18'}R^{18''}$, wherein $R^{18'}$ and $R^{18''}$ are independently $C_{1-3}$-alkyl, and $R^{25}$ is hydrogen or $C_{1-3}$-alkyl.

In one embodiment of the invention and/or embodiments thereof, $R^1$ is independently selected from the group consisting of hydrogen, methyl, trifluoromethyl, ethyl, methoxy, ethoxy, fluoride and chloride, and $R^{13}$ and $R^{14}$ together with the atoms to which they are attached form a 5 or 6-carbon atoms containing non-aromatic ring, wherein one or more of the ring-forming carbon atoms are optionally replaced by —NH— or —O—, A1 is N or $CR^{15}$, wherein $R^{15}$ is independently hydrogen or $C_{1-3}$ alkoxy, A2 is N or $CR^{16}$, wherein $R^{16}$ is independently hydrogen or $C_{1-3}$ alkoxy, A3 is N or $CR^{17}$, wherein $R^{17}$ is independently hydrogen or $C_{1-3}$ alkoxy, preferably hydrogen, A4 is N or $CR^{18}$, wherein $R^{18}$ is independently hydrogen or $C_{1-3}$ alkoxy, preferably hydrogen, wherein none, one or two of A1, A2, A3 and A4 are N, and $R^{25}$ is hydrogen or methyl, preferably hydrogen.

In an embodiment of the invention and/or embodiments thereof, the compounds are according to Formula (Iui), (Iuii), (Iuiii), (Iuiv), (Iuv) or (Iuvi)

Formula (Iui)

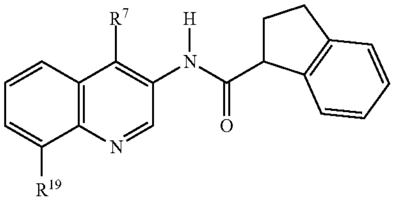

Formula (Iuii)

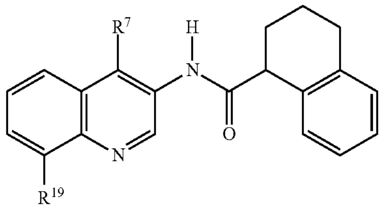

Formula (Iuiii)

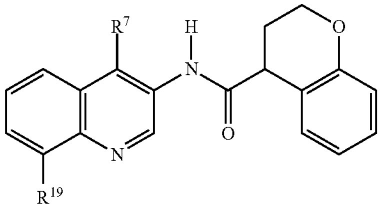

Formula (Iuiv)

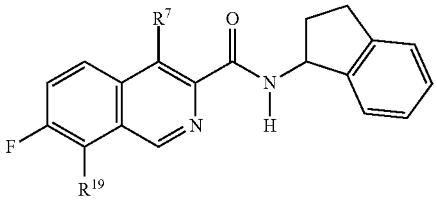

Formula (Iuv)

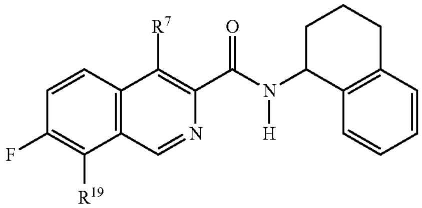

Formula (Iuvi)

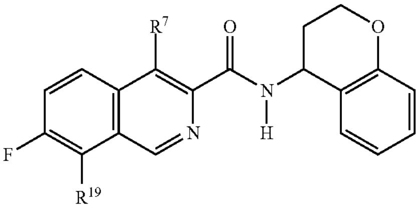

or a stereoisomer, physiologically acceptable salt, ester, solvate, polymorph, prodrug and mixtures thereof, wherein $R^7$ and $R^9$ are defined as in any of the embodiments described herein.

In an embodiment of the invention and/or embodiments thereof, the compounds are according to Formula (Iui), preferably in form of the (S)-enantiomer. In an embodiment of the invention and/or embodiments thereof, the compounds are according to Formula (Iuii), preferably in form of the (S)-enantiomer. In an embodiment of the invention and/or embodiments thereof, the compounds are according to Formula (Iuiii), preferably in form of the (S)-enantiomer. In an embodiment of the invention and/or embodiments thereof, the compounds are according to Formula (Iuiv), preferably in form of the (S)-enantiomer. In an embodiment of the invention and/or embodiments thereof, the compounds are according to Formula (Iuv), preferably in form of the (S)-enantiomer.

In an embodiment of the invention and/or embodiments thereof, the compounds are according to Formula (Iuvi), preferably in form of the (S)-enantiomer.

Optionally, in an embodiment of the invention and/or embodiments thereof, $R^1$ is independently selected from the group consisting of hydrogen, $C_{1-6}$-alkyl, $C_{1-6}$-alkoxy and halogen, wherein $C_{1-6}$-alkyl and $C_{1-6}$-alkoxy is optionally substituted with one or more substituent(s) independently selected from the group consisting of $C_{1-6}$-alkyl, $C_{1-6}$-alkoxy, halogen, cyano, hydroxy and $NR^{2'}R^{3'}$, wherein $R^{2'}$ and $R^{3'}$ are independently selected from hydrogen and $C_{1-3}$-alkyl, more preferably from hydrogen and methyl, and $R^{13}$ and $R^{14}$ together with the atoms to which they are attached form a 5 or 6-carbon atoms containing aromatic ring, wherein the aromatic ring is optionally substituted with one or more $C_{1-3}$-alkyl, and/or wherein one or more of the ring-forming carbon atoms are optionally replaced by —NH—, —N═, ═N—, —O— or —S—, A1 is N or $CR^{15}$, wherein $R^{15}$ is independently hydrogen, halogen $C_{1-3}$ alkyl, $C_{1-3}$ alkoxy or $NR^{15'}R^{15''}$, wherein $R^{15'}$ and $R^{15''}$ are independently $C_{1-3}$-alkyl, A2 is N or $CR^{16}$, wherein $R^{16}$ is independently hydrogen, halogen, $C_{1-3}$ alkyl, $C_{1-3}$ alkoxy or $NR^{16'}R^{16''}$, wherein $R^{16'}$ and $R^{16''}$ are independently $C_{1-3}$-alkyl, A3 is N or $CR^{17}$, wherein $R^{17}$ is independently hydrogen, halogen, $C_{1-3}$ alkyl, $C_{1-3}$ alkoxy or $NR^{15'}R^{15''}$, wherein $R^{15'}$ and $R^{15''}$ are independently $C_{1-3}$-alkyl, A4 is N or $CR^{18}$, wherein $R^{18}$ is independently hydrogen, halogen, $C_{1-3}$ alkyl, $C_{1-3}$ alkoxy or $NR^{15'}R^{15''}$, wherein $R^{15'}$ and $R^{15''}$ are independently $C_{1-3}$-alkyl, $R^{25}$ is hydrogen or $C_{1-3}$-alkyl.

In one embodiment of the invention and/or embodiments thereof, $R^1$ is independently selected from the group consisting of hydrogen, methyl, trifluoromethyl, ethyl, methoxy, ethoxy, fluoride and chloride, and $R^{13}$ and $R^{14}$ together with the atoms to which they are attached form a 5 or 6-carbon atoms containing aromatic ring, wherein one or more of the ring-forming carbon atoms are optionally replaced by —NH—, —N═, ═N— or —S—, A1 is N or $CR^{15}$, wherein $R^{15}$ is independently hydrogen or $C_{1-3}$ alkoxy, A2 is N or $CR^{16}$, wherein $R^{16}$ is independently hydrogen or $C_{1-3}$ alkoxy, A3 is N or $CR^{17}$, wherein $R^{17}$ is independently hydrogen or $C_{1-3}$ alkoxy, preferably hydrogen, A4 is N or $CR^{18}$, wherein $R^{18}$ is independently hydrogen or $C_{1-3}$ alkoxy, preferably hydrogen, wherein none, one or two of A1, A2, A3 and A4 are N, and $R^{25}$ is hydrogen or methyl, preferably hydrogen.

In an embodiment of the invention and/or embodiments thereof, the compounds are according to Formula (Iuvii), (Iuviii), (Iuix), (Iux), (Iuxi) or (Iuxii)

Formula (Iuvii)

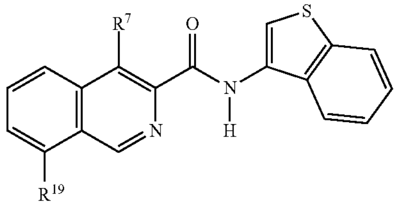

Formula (Iuviii)

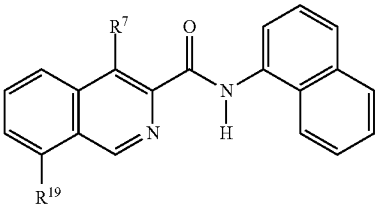

Formula (Iuix)

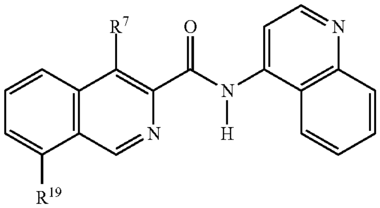

Formula (Iux)

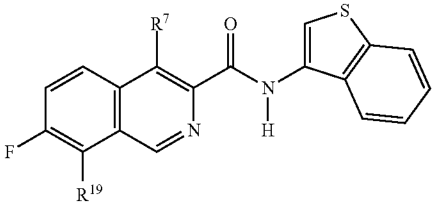

Formula (Iuxi)

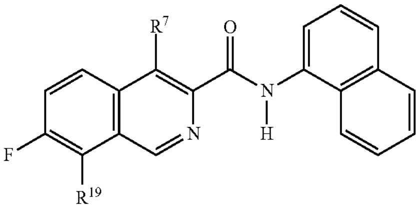

Formula (Iuvi)

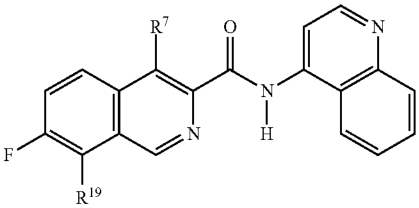

or a stereoisomer, physiologically acceptable salt, ester, solvate, polymorph, prodrug and mixtures thereof, wherein $R^7$ and $R^9$ are defined as in any of the embodiments described herein.

In an embodiment of the invention and/or embodiments thereof, the compounds are according to Formula (Iuvii), preferably in form of the (S)-enantiomer. In an embodiment of the invention and/or embodiments thereof, the compounds are according to Formula (Iuviii), preferably in form of the (S)-enantiomer. In an embodiment of the invention and/or embodiments thereof, the compounds are according to Formula (Iuix), preferably in form of the (S)-enantiomer. In an embodiment of the invention and/or embodiments thereof, the compounds are according to Formula (Iux), preferably in form of the (S)-enantiomer. In an embodiment of the invention and/or embodiments thereof, the compounds are according to Formula (Iuxi), preferably in form of the (S)-enantiomer. In an embodiment of the invention and/or embodiments thereof, the compounds are according to Formula (Iuxii), preferably in form of the (S)-enantiomer.

The invention provides a compound according to the invention and/or embodiments thereof, wherein $R^1$, $R^{19}$ and $R^{25}$ are defined as above.

Optionally, in an embodiment of the invention and/or embodiments thereof, $R^1$ is independently selected from the group consisting of hydrogen, $C_{1-6}$-alkyl, $C_{1-6}$-alkoxy and halogen, wherein $C_{1-6}$-alkyl and $C_{1-6}$-alkoxy is optionally substituted with one or more substituent(s) independently selected from the group consisting of $C_{1-6}$-alkyl, $C_{1-6}$-alkoxy, halogen, cyano, hydroxy and $NR^{2'}R^{3'}$, wherein $R^{2'}$ and $R^{3'}$ are independently selected from hydrogen and $C_{1-3}$-alkyl, more preferably from hydrogen and methyl, and $R^{19}$ is independently selected from the group consisting of $C_{6-10}$-aryl and 5 to 10-membered heteroaryl wherein each $C_{6-10}$-aryl or 5 to 10-membered heteroaryl is optionally substituted with one or more substituent(s) independently selected from the group consisting of $C_{1-6}$-alkyl, $C_{1-6}$-alkoxy, halogen, cyano, nitro and hydroxy, and $R^{25}$ is hydrogen or $C_{1-3}$-alkyl.

In one embodiment of the invention and/or embodiments thereof, $R^1$ is independently selected from the group consisting of hydrogen, methyl, trifluoromethyl, ethyl, methoxy, ethoxy, fluoride and chloride, and $R^{19}$ is independently selected from the group consisting of 3-chlorophenyl, 2,3-dichlorophenyl, 3,5-dichlorophenyl, 3,5-difluorophenyl, 2,3,5-trifluorophenyl, 3,4,5-trifluorophenyl, 3-chloro-2-fluorophenyl, 5-chloro-3-fluorophenyl, 5-chloro-3-fluorophenyl, 3,5-dichloro-4-fluorophenyl, in particular 2,3,5-trifluorophenyl, 5-chloro-2-fluorophenyl, 2,3-dichlorophenyl and 3,5-dichlorophenyl and $R^{25}$ is hydrogen or methyl, preferably hydrogen.

In an embodiment of the invention and/or embodiments thereof, the compounds are according to Formula (Ivi), (Ivii), (Iviii) or (Iviv)

Formula (Ivi)

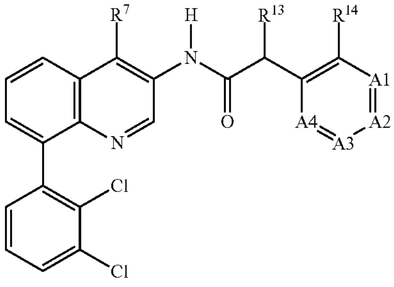

-continued

Formula (Ivii)

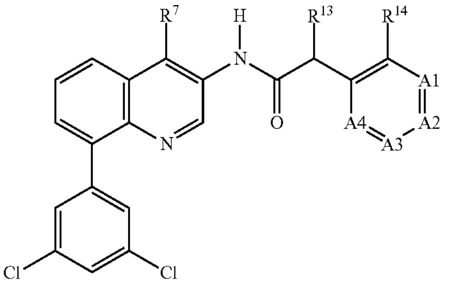

Formula (Iviii)

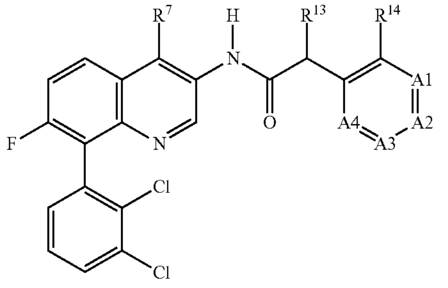

Formula (Iviv)

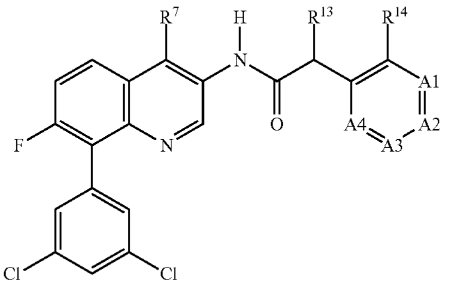

or a stereoisomer, physiologically acceptable salt, ester, solvate, polymorph, prodrug and mixtures thereof, wherein $R^7$ and R, $R^{14}$, A1, A2, A3 and A4 are defined as in any of the embodiments described herein.

In an embodiment of the invention and/or embodiments thereof, the compounds are according to Formula (Ivi), preferably in form of the (S)-enantiomer. In an embodiment of the invention and/or embodiments thereof, the compounds are according to Formula (Ivii), preferably in form of the (S)-enantiomer. In an embodiment of the invention and/or embodiments thereof, the compounds are according to Formula (Iviii), preferably in form of the (S)-enantiomer. In an embodiment of the invention and/or embodiments thereof, the compounds are according to Formula (Iviv), preferably in form of the (S)-enantiomer.

The invention provides a compound according to the invention and/or embodiments thereof, wherein $R^7$, R, $R^{14}$, A1, A2, A3, A4 and $R^{19}$ are defined as above.

Optionally, in an embodiment of the invention and/or embodiments thereof, $R^7$ is independently selected from the group consisting of hydrogen, $C_{1-6}$-alkyl, $C_{2-6}$-alkenyl, 4 to 10-membered heterocyclyl, $C_{1-3}$-alkoxy, hydroxy, $NR^8R^9$, $SR^{10}$, $SOR^{10}$ and $SO_2R^{10}$, wherein each $C_{1-6}$-alkyl, $C_{2-6}$-alkenyl, 4 to 10-membered heterocyclyl or $C_{1-3}$-alkoxy is optionally substituted with one or more substituent(s) independently selected from the group consisting of $C_{1-3}$-alkyl, 5 to 10-membered heterocyclyl, $C_{1-6}$-alkoxy, halogen, cyano, hydroxy, $NR^{8'}R^{9'}$, $C(=O)OR^{10'}$ and $C(=O)NR^{11'}R^{12'}$, $R^8$ and $R^9$ are independently selected from the group consisting of hydrogen, $C_{1-6}$-alkyl, $C_{6-10}$-aryl and 5 to 10-membered heteroaryl, or $R^8$ and $R^9$ together with the N atom to which they are attached form a saturated or unsaturated heterocyclic ring having 3 to 12 ring atoms, wherein 1 ring atom is N and wherein 0, 1, 2, or 3 further ring atoms are selected from N, S and O;

wherein the $C_{1-6}$-alkyl, $C_{6-10}$-aryl or 5 to 10-membered heteroaryl or the heterocyclic ring formed by $R^8$ and $R^9$ together with the N atom to which they are attached is optionally substituted with one or more substituent(s) independently selected from the group consisting of $C_{1-6}$-alkyl, $C_{1-6}$-alkoxy, hydroxy and $NR^{8''}R^{9''}$;

$R^{10}$ is independently selected from hydrogen or $C_{1-3}$-alkyl, preferably from hydrogen, methyl or ethyl, $R^{8'}$, $R^{9'}$, $R^{10'}$, $R^{11'}$ and $R^{12'}$ are independently selected from hydrogen or $C_{1-3}$-alkyl, preferably from hydrogen, methyl or ethyl, $R^{8''}$ and $R^{9''}$ are independently selected from hydrogen or $C_{1-3}$-alkyl, preferably from hydrogen, methyl or ethyl, and $R^{13}$ and $R^{14}$ together with the atoms to which they are attached form a 5 or 6-carbon atoms containing non-aromatic ring, wherein the non-aromatic ring is optionally substituted with one or more $C_{1-3}$-alkyl or =O, and/or wherein one or more of the ring-forming carbon atoms are optionally replaced by —NH—, —O—, —S(O)—, —S(O)$_2$— or —S—, A1 is N or $CR^{15}$, wherein $R^{15}$ is independently hydrogen, halogen, $C_{1-3}$ alkyl, $C_{1-3}$ alkoxy, or $NR^{15'}R^{15''}$, wherein $R^{15'}$ and $R^{15''}$ are independently $C_{1-3}$-alkyl, A2 is N or $CR^{16}$, wherein $R^{16}$ is independently hydrogen, halogen, $C_{1-3}$ alkyl, $C_{1-3}$ alkoxy, or $NR^{16'}R^{16''}$, wherein $R^{16'}$ and $R^{16''}$ are independently $C_{1-3}$-alkyl, A3 is N or $CR^{17}$, wherein $R^{17}$ is independently hydrogen, halogen, $C_{1-3}$ alkyl, $C_{1-3}$ alkoxy, or $NR^{17'}R^{17''}$, wherein $R^{17'}$ and $R^{17''}$ are independently $C_{1-3}$-alkyl, A4 is N or $CR^{18}$, wherein $R^{18}$ is independently hydrogen, halogen, $C_{1-3}$ alkyl, $C_{1-3}$ alkoxy, or $NR^{18'}R^{18''}$, wherein $R^{18'}$ and $R^{18''}$ are independently $C_{1-3}$-alkyl, and $R^{19}$ is independently selected from the group consisting of $C_{6-10}$-aryl and 5 to 10-membered heteroaryl wherein each $C_{6-10}$-aryl or 5 to 10-membered heteroaryl is optionally substituted with one or more substituent(s) independently selected from the group consisting of $C_{1-6}$-alkyl, $C_{1-6}$-alkoxy, halogen, cyano, nitro and hydroxy.

In one embodiment of the invention and/or embodiments thereof, $R^7$ is independently selected from the group consisting of methyl, ethyl, propyl, isopropyl, isopropenyl methoxy, ethoxy, isopropoxy, hydroxy, methyl sulfoxyl, methyl sulfonyl methylthio, amino, methylamino, ethylamino, (ethyl)(methyl)amino, isopropylamino, dimethylamino, (isopropyl)(methyl)amino, hydroxyethylamino, (hydroxyethyl)(methyl)amino, methoxyethylamino, (methoxyethyl)l(methyl) amino, morpholin-4-yl, pyrrolidin-1-yl, 3-hydroxy-pyrrolidin-1-yl 3-fluoroazetidinyl and 3,3-difluoro-azetidinyl, and $R^{13}$ and $R^{14}$ together with the atoms to which they are attached form a 5 or 6-carbon atoms containing non-aromatic ring, wherein one or more of the ring-forming carbon atoms are optionally replaced by —NH— or —O—, A1 is N or $CR^{15}$, wherein $R^{15}$ is independently hydrogen or $C_{1-3}$ alkoxy, A2 is N or $CR^{16}$, wherein $R^{16}$ is independently hydrogen or $C_{1-3}$ alkoxy, A3 is N or $CR^{17}$, wherein $R^{17}$ is independently hydrogen or $C_{1-3}$ alkoxy, preferably hydrogen, A4 is N or $CR^{18}$, wherein $R^{18}$ is independently hydrogen or $C_{1-3}$ alkoxy, preferably hydrogen, wherein none, one or two of A1, A2, A3 and A4 are N, and $R^{19}$ is independently selected from the group consisting of 3-chlorophenyl, 2,3-dichlorophenyl, 3,5-dichlorophenyl, 3,5-difluorophenyl, 2,3,5-trifluorophenyl, 3,4,5-trifluorophenyl, 3-chloro-2-fluorophenyl, 5-chloro-3-fluorophenyl, 5-chloro-3-fluorophenyl, 3,5-dichloro-4-fluorophenyl, in particular 2,3,5-trifluorophenyl, 5-chloro-2-fluorophenyl, 2,3-dichlorophenyl and 3,5-dichlorophenyl.

In an embodiment of the invention and/or embodiments thereof, the compounds are according to Formula (Iwi), (Iwii), (Iwiii), (Iwiv), (Iwv), (Iwvi), (Iwvii), (Iwviii), (Iwix), (Iwx), (Iwxi) or (Iwxii)

Formula (Iwi)

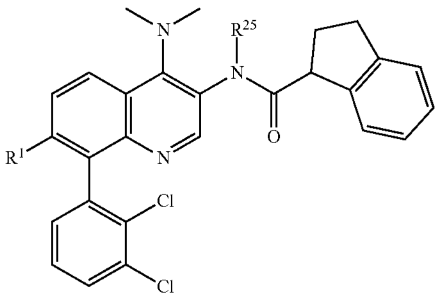

Formula (Iwii)

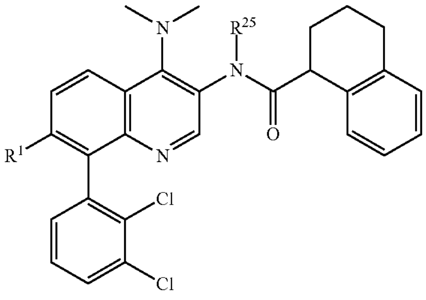

-continued

Formula (Iwiii)

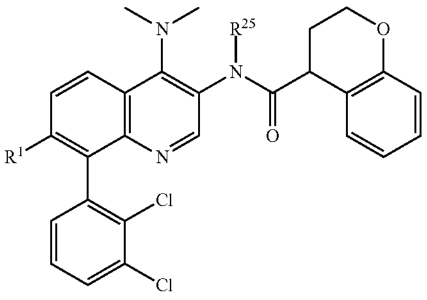

Formula (Iwiv)

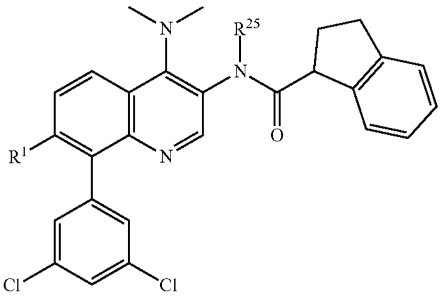

Formula (Iwv)

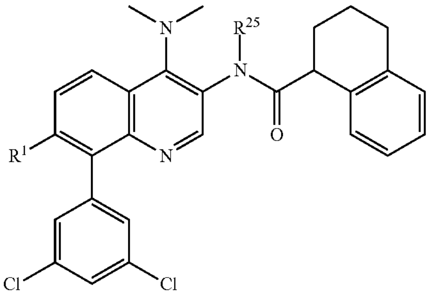

Formula (Iwvi)

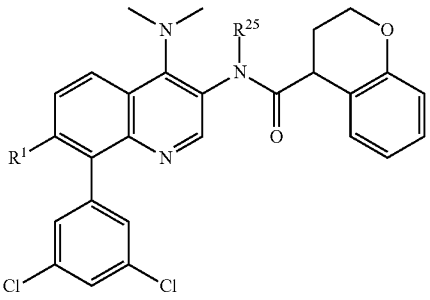

-continued

Formula (Iwvii)

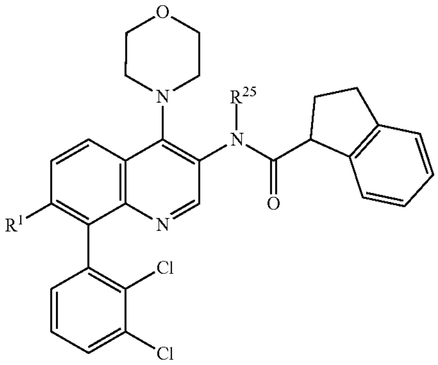

Formula (Iwviii)

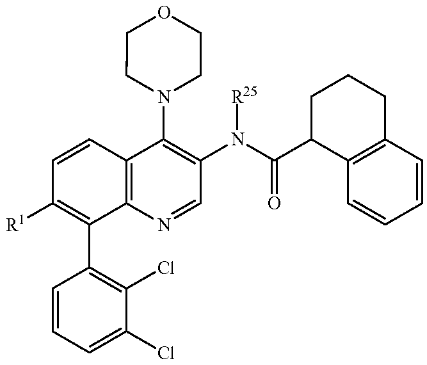

Formula (Iwix)

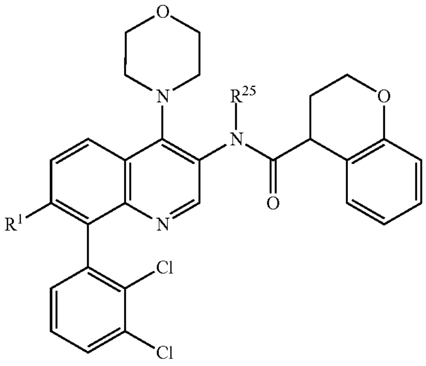

Formula (Iwx)

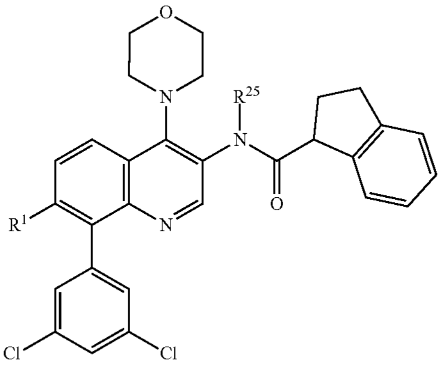

-continued

Formula (Iwxi)

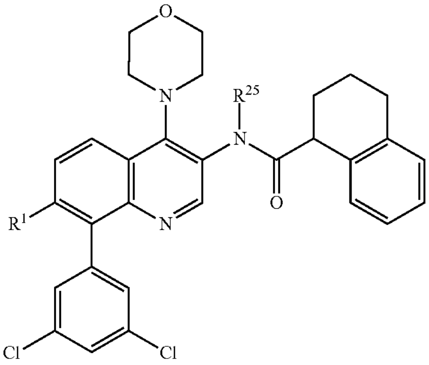

Formula (Iwxii)

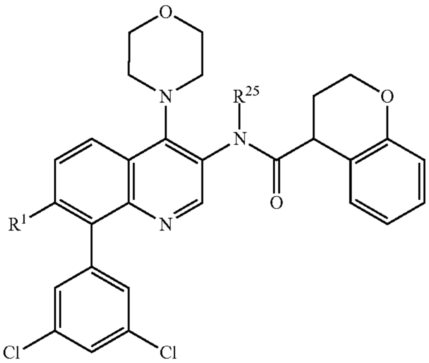

or a stereoisomer, physiologically acceptable salt, ester, solvate, polymorph, prodrug and mixtures thereof, wherein $R^1$ and $R^{25}$ are defined as in any of the embodiments described herein.

In an embodiment of the invention and/or embodiments thereof, the compounds are according to Formula (Iwi), preferably in form of the (S)-enantiomer. In an embodiment of the invention and/or embodiments thereof, the compounds are according to Formula (Iwii), preferably in form of the (S)-enantiomer. In an embodiment of the invention and/or embodiments thereof, the compounds are according to Formula (Iwiii), preferably in form of the (S)-enantiomer. In an embodiment of the invention and/or embodiments thereof, the compounds are according to Formula (Iwiv), preferably in form of the (S)-enantiomer. In an embodiment of the invention and/or embodiments thereof, the compounds are according to Formula (Iwv). preferably in form of the (S)-enantiomer. In an embodiment of the invention and/or embodiments thereof, the compounds are according to Formula (Iwvi), preferably in form of the (S)-enantiomer. In an embodiment of the invention and/or embodiments thereof, the compounds are according to Formula (Iwvii), preferably in form of the (S)-enantiomer. In an embodiment of the invention and/or embodiments thereof, the compounds are according to Formula (Iwviii), preferably in form of the (S)-enantiomer. In an embodiment of the invention and/or embodiments thereof, the compounds are according to Formula (Iwix), preferably in form of the (S)-enantiomer. In an embodiment of the invention and/or embodiments thereof, the compounds are according to Formula (Iwx), preferably in form of the (S)-enantiomer. In an embodiment of the invention and/or embodiments thereof, the compounds are according to Formula (Iwxi), preferably in form of the (S)-enantiomer. In an embodiment of the invention and/or embodiments thereof, the compounds are according to Formula (Iwxii), preferably in form of the (S)-enantiomer.

Optionally, in an embodiment of the invention and/or embodiments thereof, $R^7$ is independently selected from the group consisting of hydrogen, $C_{1-6}$-alkyl, $C_{2-6}$-alkenyl, 4 to 10-membered heterocyclyl, $C_{1-3}$-alkoxy, hydroxy, $NR^8R^9$, $SR^{10}$, $SOR^{10}$ and $SO_2R^{10}$, wherein each $C_{1-6}$-alkyl, $C_{2-6}$-alkenyl, 4 to 10-membered heterocyclyl or $C_{1-3}$-alkoxy is optionally substituted with one or more substituent(s) independently selected from the group consisting of $C_{1-3}$-alkyl, 5 to 10-membered heterocyclyl, $C_{1-6}$-alkoxy, halogen, cyano, hydroxy, $NR^{8'}R^{9'}$, $C(=O)OR^{10'}$ and $C(=O)NR^{11'}R^{12'}$, $R^8$ and $R^9$ are independently selected from the group consisting of hydrogen, $C_{1-6}$-alkyl, $C_{6-10}$-aryl and 5 to 10-membered heteroaryl, or $R^8$ and $R^9$ together with the N atom to which they are attached form a saturated or unsaturated heterocyclic ring having 3 to 12 ring atoms, wherein 1 ring atom is N and wherein 0, 1, 2, or 3 further ring atoms are selected from N, S and O;

wherein the $C_{1-6}$-alkyl, $C_{6-10}$-aryl or 5 to 10-membered heteroaryl or the heterocyclic ring formed by $R^8$ and $R^9$ together with the N atom to which they are attached is optionally substituted with one or more substituent(s) independently selected from the group consisting of $C_{1-6}$-alkyl, $C_{1-6}$-alkoxy, hydroxy and $NR^{8''}R^{9''}$;

$R^{10}$ is independently selected from hydrogen or $C_{1-3}$-alkyl, preferably from hydrogen, methyl or ethyl, $R^{8'}$, $R^{9'}$, $R^{10'}$, $R^{11'}$ and $R^{12'}$ are independently selected from hydrogen or $C_{1-3}$-alkyl, preferably from hydrogen, methyl or ethyl, $R^{8''}$ and $R^{9''}$ are independently selected from hydrogen or $C_{1-3}$-alkyl, preferably from hydrogen, methyl or ethyl, and $R^{13}$ and $R^{14}$ together with the atoms to which they are attached form a 5 or 6-carbon atoms containing aromatic ring, wherein the aromatic ring is optionally substituted with one or more $C_{1-3}$-alkyl, and/or wherein one or more of the ring-forming carbon atoms are optionally replaced by —NH—, —N═, ═N—, —O— or —S—, A1 is N or $CR^{15}$, wherein $R^{15}$ is independently hydrogen, halogen $C_{1-3}$ alkyl, $C_{1-3}$ alkoxy or $NR^{15'}R^{15''}$, wherein $R^{15'}$ and $R^{15''}$ are independently $C_{1-3}$-alkyl, A2 is N or $CR^{16}$, wherein $R^{16}$ is independently hydrogen, halogen, $C_{1-3}$ alkyl, $C_{1-3}$ alkoxy or $NR^{16'}R^{16''}$, wherein $R^{16'}$ and $R^{16''}$ are independently $C_{1-3}$-alkyl, A3 is N or $CR^{17}$, wherein $R^{17}$ is independently hydrogen, halogen, $C_{1-3}$ alkyl, $C_{1-3}$ alkoxy or $NR^{15'}R^{15''}$, wherein $R^{15'}$ and $R^{15''}$ are independently $C_{1-3}$-alkyl, A4 is N or $CR^{18}$, wherein $R^{18}$ is independently hydrogen, halogen, $C_{1-3}$ alkyl, $C_{1-3}$ alkoxy or $NR^{15'}R^{15''}$, wherein $R^{15'}$ and $R^{15''}$ are independently $C_{1-3}$-alkyl, and $R^{19}$ is independently selected from the group consisting of $C_{6-10}$-aryl and 5 to 10-membered heteroaryl wherein each $C_{6-10}$-aryl or 5 to 10-membered heteroaryl is optionally substituted with one or more substituent(s) independently selected from the group consisting of $C_{1-6}$-alkyl, $C_{1-6}$-alkoxy, halogen, cyano, nitro and hydroxy.

In one embodiment of the invention and/or embodiments thereof, $R^7$ is independently selected from the group consisting of methyl, ethyl, propyl, isopropyl, isopropenyl methoxy, ethoxy, isopropoxy, hydroxy, methyl sulfoxyl, methyl sulfonyl methylthio, amino, methylamino, ethylamino, (ethyl)(methyl)amino, isopropylamino, dimethylamino, (isopropyl)(methyl)amino, hydroxyethylamino, (hydroxyethyl)(methyl)amino, methoxyethylamino, (methoxyethyl)l(methyl) amino, morpholin-4-yl, pyrrolidine-1-yl, 3-hydroxy-pyrrolidin-1-yl 3-fluoroazetidinyl and 3,3-difluoro-azetidinyl, and $R^{13}$ and $R^{14}$ together with the atoms to which they are attached form a 5 or 6-carbon atoms containing aromatic ring, wherein one or more of the ring-forming carbon atoms are optionally replaced by —NH—, —N═, ═N— or —S—, A1 is N or $CR^{15}$, wherein $R^{15}$ is independently hydrogen or $C_{1-3}$ alkoxy, A2 is N or $CR^{16}$, wherein $R^{16}$ is independently hydrogen or $C_{1-3}$ alkoxy, A3 is N or $CR^{17}$, wherein $R^{17}$ is independently hydrogen or $C_{1-3}$ alkoxy, preferably hydrogen, A4 is N or $CR^{18}$, wherein $R^{18}$ is independently hydrogen or $C_{1-3}$ alkoxy, preferably hydrogen, wherein none, one or two of A1, A2, A3 and A4 are N, and $R^{19}$ is independently selected from the group consisting of 3-chlorophenyl, 2,3-dichlorophenyl, 3,5-dichlorophenyl, 3,5-difluorophenyl, 2,3,5-trifluorophenyl, 3,4,5-trifluorophenyl, 3-chloro-2-fluorophenyl, 5-chloro-3-fluorophenyl, 5-chloro-3-fluorophenyl, 3,5-dichloro-4-fluorophenyl, in particular 2,3,5-trifluorophenyl, 5-chloro-2-fluorophenyl, 2,3-dichlorophenyl and 3,5-dichlorophenyl.

In an embodiment of the invention and/or embodiments thereof, the compounds are according to Formula (Iwxiii), (Iwxiv), (Iwxv), (Iwxvi), (Iwxvii), (Iwxviii), (Iwxix), (Iwxx), (Iwxxi), (Iwxxii), (Iwxxiii) or (Iwxxiv)

Formula (Iwxiii)

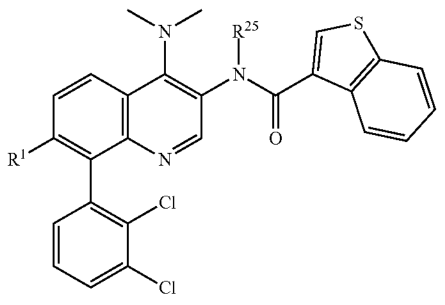

-continued
Formula (Iwxiv)
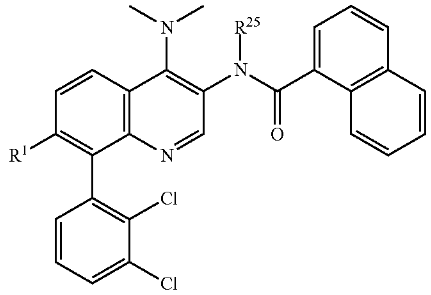
Formula (Iwxv)
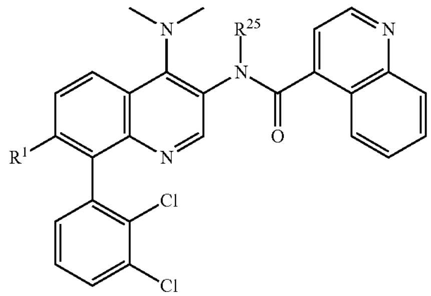
Formula (Iwxvi)
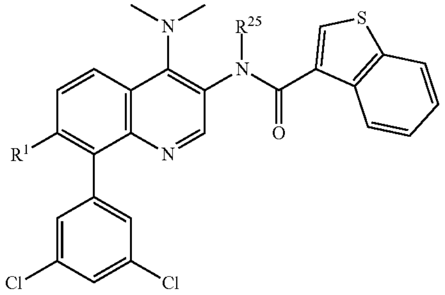
Formula (Iwxvii)
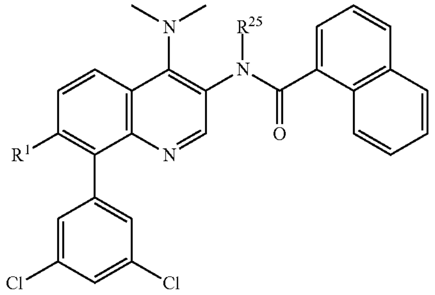
Formula (Iwxviii)
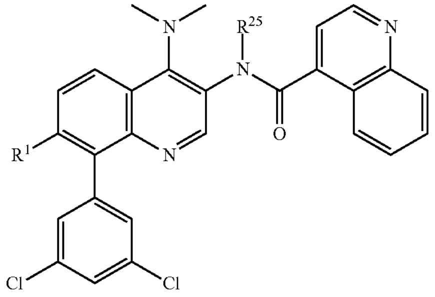
-continued
Formula (Iwxix)
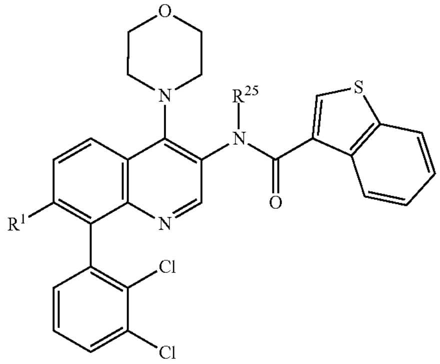
Formula (Iwxx)
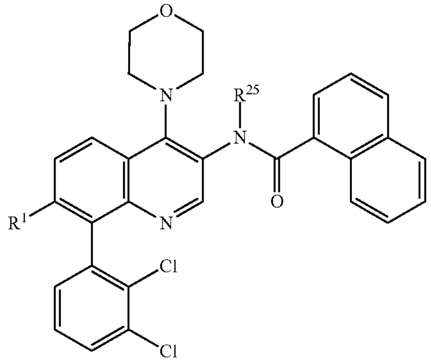
Formula (Iwxxi)
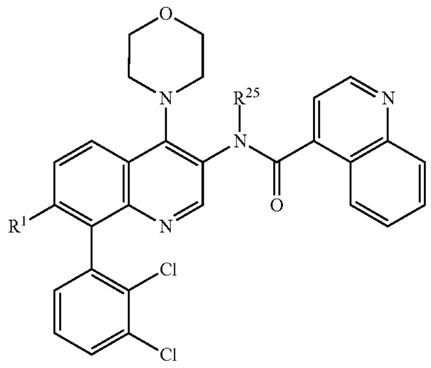
Formula (Iwxxii)
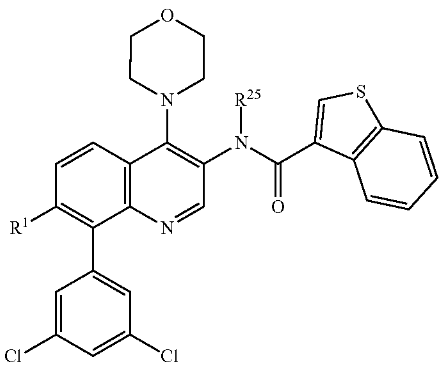

-continued

Formula (Iwxxiii)

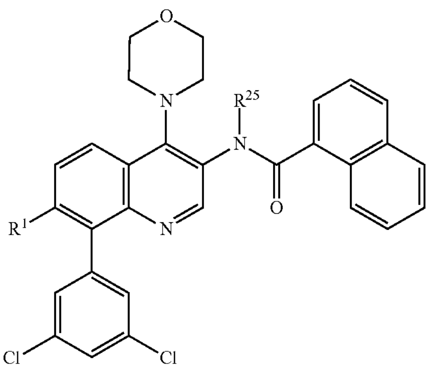

Formula (Iwxxiv)

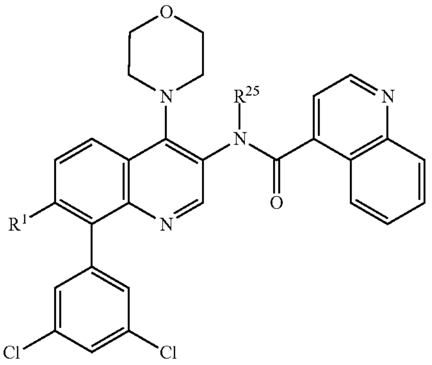

or a stereoisomer, physiologically acceptable salt, ester, solvate, polymorph, prodrug and mixtures thereof, wherein $R^1$ and $R^{25}$ are defined as in any of the embodiments described herein.

In an embodiment of the invention and/or embodiments thereof, the compounds are according to Formula (Iwxiii), preferably in form of the (S)-enantiomer. In an embodiment of the invention and/or embodiments thereof, the compounds are according to Formula (Iwxiv), preferably in form of the (S)-enantiomer. In an embodiment of the invention and/or embodiments thereof, the compounds are according to Formula (Iwxv), preferably in form of the (S)-enantiomer. In an embodiment of the invention and/or embodiments thereof, the compounds are according to Formula (Iwxvi), preferably in form of the (S)-enantiomer. In an embodiment of the invention and/or embodiments thereof, the compounds are according to Formula (Iwxvii), preferably in form of the (S)-enantiomer. In an embodiment of the invention and/or embodiments thereof, the compounds are according to Formula (Iwxviii), preferably in form of the (S)-enantiomer. In an embodiment of the invention and/or embodiments thereof, the compounds are according to Formula (Iwxix), preferably in form of the (S)-enantiomer. In an embodiment of the invention and/or embodiments thereof, the compounds are according to Formula (Iwxx), preferably in form of the (S)-enantiomer. In an embodiment of the invention and/or embodiments thereof, the compounds are according to Formula (Iwxxi), preferably in form of the (S)-enantiomer. In an embodiment of the invention and/or embodiments thereof, the compounds are according to Formula (Iwxxii), preferably in form of the (S)-enantiomer. In an embodiment of the invention and/or embodiments thereof, the compounds are according to Formula (Iwxxiii), preferably in form of the (S)-enantiomer. In an embodiment of the invention and/or embodiments thereof, the compounds are according to Formula (Iwxxiv), preferably in form of the (S)-enantiomer.

The invention provides a compound according to the invention and/or embodiments thereof, wherein $R^7$, $R^{13}$, $R^{14}$, A1, A2, A3, A4 and $R^{25}$ are defined as above.

Optionally, in an embodiment of the invention and/or embodiments thereof, $R^7$ is independently selected from the group consisting of hydrogen, $C_{1-6}$-alkyl, $C_{2-6}$-alkenyl, 4 to 10-membered heterocyclyl, $C_{1-3}$-alkoxy, hydroxy, $NR^8R^9$, $SR^{10}$, $SOR^{10}$ and $SO_2R^{10}$, wherein each $C_{1-6}$-alkyl, $C_{2-6}$-alkenyl, 4 to 10-membered heterocyclyl or $C_{1-3}$-alkoxy is optionally substituted with one or more substituent(s) independently selected from the group consisting of $C_{1-3}$-alkyl, 5 to 10-membered heterocyclyl, $C_{1-6}$-alkoxy, halogen, cyano, hydroxy, $NR^{8'}R^{9'}$, $C(=O)OR^{10'}$ and $C(=O)NR^{11'}R^{12'}$, $R^8$ and $R^9$ are independently selected from the group consisting of hydrogen, $C_{1-6}$-alkyl, $C_{6-10}$-aryl and 5 to 10-membered heteroaryl, or $R^8$ and $R^9$ together with the N atom to which they are attached form a saturated or unsaturated heterocyclic ring having 3 to 12 ring atoms, wherein 1 ring atom is N and wherein 0, 1, 2, or 3 further ring atoms are selected from N, S and O;

wherein the $C_{1-6}$-alkyl, $C_{6-10}$-aryl or 5 to 10-membered heteroaryl or the heterocyclic ring formed by $R^8$ and $R^9$ together with the N atom to which they are attached is optionally substituted with one or more substituent(s) independently selected from the group consisting of $C_{1-6}$-alkyl, $C_{1-6}$-alkoxy, hydroxy and $NR^{8''}R^{9''}$, $R^{10}$ is independently selected from hydrogen or $C_{1-3}$-alkyl, preferably from hydrogen, methyl or ethyl, $R^{8'}$, $R^{9'}$, $R^{10'}$, $R^{11'}$ and $R^{12'}$ are independently selected from hydrogen or $C_{1-3}$-alkyl, preferably from hydrogen, methyl or ethyl, $R^{8''}$ and $R^{9''}$ are independently selected from hydrogen or $C_{1-3}$-alkyl, preferably from hydrogen, methyl or ethyl, and $R^{13}$ and $R^{14}$ together with the atoms to which they are attached form a 5 or 6-carbon atoms containing non-aromatic ring, wherein the non-aromatic ring is optionally substituted with one or more $C_{1-3}$-alkyl or =O, and/or wherein one or more of the ring-forming carbon atoms are optionally replaced by —NH—, —O—, —S(O)—, —S(O)$_2$— or —S—, A1 is N or $CR^{15}$, wherein $R^{15}$ is independently hydrogen, halogen, $C_{1-3}$ alkyl, $C_{1-3}$ alkoxy, or $NR^{15'}R^{15''}$, wherein $R^{15'}$ and $R^{15''}$ are independently $C_{1-3}$-alkyl, A2 is N or $CR^{16}$, wherein $R^{16}$ is independently hydrogen, halogen, $C_{1-3}$ alkyl, $C_{1-3}$ alkoxy, or $NR^{16'}R^{16''}$, wherein $R^{16'}$ and $R^{16''}$ are independently $C_{1-3}$-alkyl, A3 is N or $CR^{17}$, wherein $R^{17}$ is independently hydrogen, halogen, $C_{1-3}$ alkyl, $C_{1-3}$ alkoxy, or $NR^{17'}R^{17''}$, wherein $R^{17'}$ and $R^{17''}$ are independently $C_{1-3}$-alkyl, A4 is N or $CR^{18}$, wherein $R^{18}$ is independently hydrogen, halogen, $C_{1-3}$ alkyl, $C_{1-3}$ alkoxy, or $NR^{18'}R^{18''}$, wherein $R^{18'}$ and $R^{18''}$ are independently $C_{1-3}$-alkyl, and $R^{25}$ is hydrogen or $C_{1-3}$-alkyl.

In one embodiment of the invention and/or embodiments thereof, $R^7$ is independently selected from the group consisting of methyl, ethyl, propyl, isopropyl, isopropenyl methoxy, ethoxy, isopropoxy, hydroxy, methyl sulfoxyl, methyl sulfonyl methylthio, amino, methylamino, ethylamino, (ethyl)(methyl)amino, isopropylamino, dimethylamino, (isopropyl)(methyl)amino, hydroxyethylamino, (hydroxyethyl)(methyl)amino, methoxyethylamino, (methoxyethyl)(methyl)amino, morpholin-4-yl, pyrrolidin-1-yl, 3-hydroxy-pyrrolidin-1-yl 3-fluoroazetidinyl and 3,3-difluoroazetidinyl, and $R^{13}$ and $R^{14}$ together with the atoms to which they are attached form a 5 or 6-carbon atoms containing non-aromatic ring, wherein one or more of the ring-forming carbon atoms are optionally replaced by —NH— or —O—, A1 is N or $CR^{15}$, wherein $R^{15}$ is independently hydrogen or $C_{1-3}$ alkoxy, A2 is N or $CR^{16}$, wherein $R^{16}$ is independently hydrogen or $C_{1-3}$ alkoxy, A3 is N or $CR^{17}$, wherein $R^{17}$ is independently hydrogen or $C_{1-3}$ alkoxy, preferably hydrogen, A4 is N or $CR^{18}$, wherein $R^{18}$ is independently hydrogen or $C_{1-3}$ alkoxy, preferably hydrogen, wherein none, one or two of A1, A2, A3 and A4 are N, $R^{25}$ is hydrogen or methyl, preferably hydrogen.

In an embodiment of the invention and/or embodiments thereof, the compounds are according to Formula (Ixi), (Ixii), (Ixiii), (Ixiv), (Ixv) or (Ixvi)

Formula (Ixi)

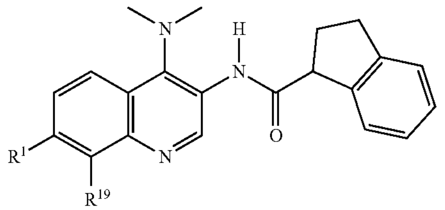

Formula (Ixii)

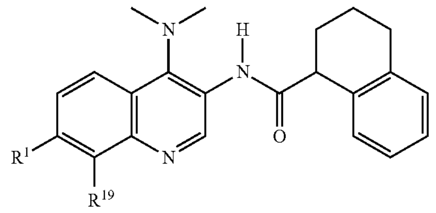

Formula (Ixiii)

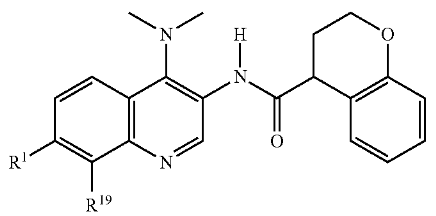

-continued

Formula (Ixiv)

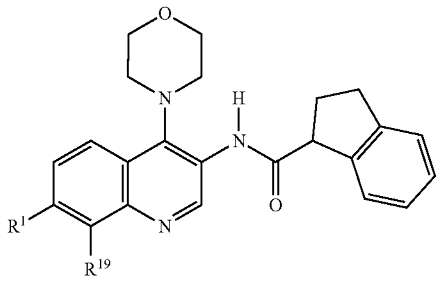

Formula (Ixv)

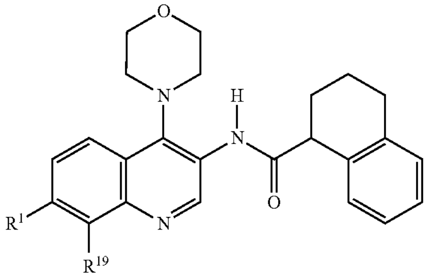

Formula (Ixvi)

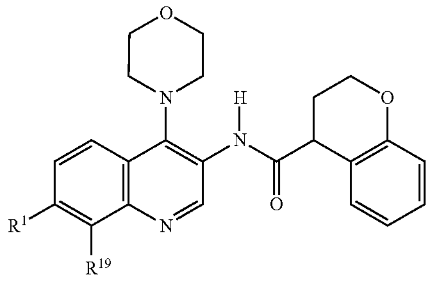

or a stereoisomer, physiologically acceptable salt, ester, solvate, polymorph, prodrug and mixtures thereof, wherein $R^1$ and $R^9$ are defined as in any of the embodiments described herein.

In an embodiment of the invention and/or embodiments thereof, the compounds are according to Formula (Ixi), preferably in form of the (S)-enantiomer. In an embodiment of the invention and/or embodiments thereof, the compounds are according to Formula (Ixii), preferably in form of the (S)-enantiomer. In an embodiment of the invention and/or embodiments thereof, the compounds are according to Formula (Ixiii), preferably in form of the (S)-enantiomer. In an embodiment of the invention and/or embodiments thereof, the compounds are according to Formula (Ixiv), preferably in form of the (S)-enantiomer. In an embodiment of the invention and/or embodiments thereof, the compounds are according to Formula (Ixv), preferably in form of the (S)-enantiomer.

In an embodiment of the invention and/or embodiments thereof, the compounds are according to Formula (Ixvi), preferably in form of the (S)-enantiomer.

Optionally, in an embodiment of the invention and/or embodiments thereof, $R^7$ is independently selected from the group consisting of hydrogen, $C_{1-6}$-alkyl, $C_{2-6}$-alkenyl, 4 to 10-membered heterocyclyl, $C_{1-3}$-alkoxy, hydroxy, $NR^8R^9$, $SR^{10}$, $SOR^{10}$ and $SO_2R^{10}$, wherein each $C_{1-6}$-alkyl, $C_{2-6}$-alkenyl, 4 to 10-membered heterocyclyl or $C_{1-3}$-alkoxy is optionally substituted with one or more substituent(s) independently selected from the group consisting of $C_{1-3}$-alkyl, 5 to 10-membered heterocyclyl, $C_{1-6}$-alkoxy, halogen, cyano, hydroxy, $NR^{8'}R^{9'}$, $C(=O)OR^{10'}$ and $C(=O)NR^{11'}R^{12'}$, $R^8$ and $R^9$ are independently selected from the group consisting of hydrogen, $C_{1-6}$-alkyl, $C_{6-10}$-aryl and 5 to 10-membered heteroaryl, or $R^8$ and $R^9$ together with the N atom to which they are attached form a saturated or unsaturated heterocyclic ring having 3 to 12 ring atoms, wherein 1 ring atom is N and wherein 0, 1, 2, or 3 further ring atoms are selected from N, S and O;

wherein the $C_{1-6}$-alkyl, $C_{6-10}$-aryl or 5 to 10-membered heteroaryl or the heterocyclic ring formed by $R^8$ and $R^9$ together with the N atom to which they are attached is optionally substituted with one or more substituent(s) independently selected from the group consisting of $C_{1-6}$-alkyl, $C_{1-6}$-alkoxy, hydroxy and $NR^{8''}R^{9''}$, $R^{10}$ is independently selected from hydrogen or $C_{1-3}$-alkyl, preferably from hydrogen, methyl or ethyl, $R^{8'}$, $R^{9'}$, $R^{10'}$, $R^{11'}$ and $R^{12'}$ are independently selected from hydrogen or $C_{1-3}$-alkyl, preferably from hydrogen, methyl or ethyl, $R^{8''}$ and $R^{9''}$ are independently selected from hydrogen or $C_{1-3}$-alkyl, preferably from hydrogen, methyl or ethyl, and $R^{13}$ and $R^{14}$ together with the atoms to which they are attached form a 5 or 6-carbon atoms containing aromatic ring, wherein the aromatic ring is optionally substituted with one or more $C_{1-3}$-alkyl, and/or wherein one or more of the ring-forming carbon atoms are optionally replaced by —NH—, —N=, =N—, —O— or —S—, A1 is N or $CR^{15}$, wherein $R^{15}$ is independently hydrogen, halogen $C_{1-3}$ alkyl, $C_{1-3}$ alkoxy or $NR^{15'}R^{15''}$, wherein $R^{15'}$ and $R^{15''}$ are independently $C_{1-3}$-alkyl, A2 is N or $CR^{16}$, wherein $R^{16}$ is independently hydrogen, halogen, $C_{1-3}$ alkyl, $C_{1-3}$ alkoxy or $NR^{16'}R^{16''}$, wherein $R^{16'}$ and $R^{16''}$ are independently $C_{1-3}$-alkyl, A3 is N or $CR^{17}$, wherein $R^{17}$ is independently hydrogen, halogen, $C_{1-3}$ alkyl, $C_{1-3}$ alkoxy or $NR^{15'}R^{15''}$, wherein $R^{15'}$ and $R^{15''}$ are independently $C_{1-3}$-alkyl, A4 is N or $CR^{18}$, wherein $R^{18}$ is independently hydrogen, halogen, $C_{1-3}$ alkyl, $C_{1-3}$ alkoxy or $NR^{15'}R^{15''}$, wherein $R^{15'}$ and $R^{15''}$ are independently $C_{1-3}$-alkyl, and $R^{25}$ is hydrogen or $C_{1-3}$-alkyl.

In one embodiment of the invention and/or embodiments thereof, $R^7$ is independently selected from the group consisting of methyl, ethyl, propyl, isopropyl, isopropenyl methoxy, ethoxy, isopropoxy, hydroxy, methyl sulfoxyl, methyl sulfonyl methylthio, amino, methylamino, ethylamino, (ethyl)(methyl)amino, isopropylamino, dimethylamino, (isopropyl)(methyl)amino, hydroxyethylamino, (hydroxyethyl)(methyl)amino, methoxyethylamino, (methoxyethyl)(methyl)amino, morpholin-4-yl, pyrrolidine-1-yl, 3-hydroxy-pyrrolidin-1-yl 3-fluoroazetidinyl and 3,3-difluoroazetidinyl, and $R^{13}$ and $R^{14}$ together with the atoms to which they are attached form a 5 or 6-carbon atoms containing aromatic ring, wherein one or more of the ring-forming carbon atoms are optionally replaced by —NH—, —N=, =N— or —S—, A1 is N or $CR^{15}$, wherein $R^{15}$ is independently hydrogen or $C_{1-3}$ alkoxy, A2 is N or $CR^{16}$, wherein $R^{16}$ is independently hydrogen or $C_{1-3}$ alkoxy, A3 is N or $CR^{17}$, wherein $R^{17}$ is independently hydrogen or $C_{1-3}$ alkoxy, preferably hydrogen, A4 is N or $CR^{18}$, wherein $R^{18}$ is independently hydrogen or $C_{1-3}$ alkoxy, preferably hydrogen, wherein none, one or two of A1, A2, A3 and A4 are N, and $R^{25}$ is hydrogen or methyl, preferably hydrogen.

In an embodiment of the invention and/or embodiments thereof, the compounds are according to Formula (Ixvii), (Ixviii), (Ixix), (Ixx), (Ixxi) or (Ixxii)

Formula (Ixvii)

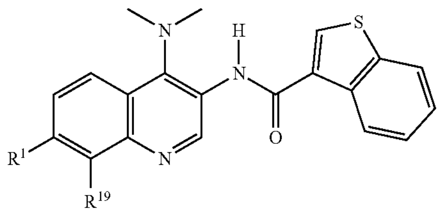

Formula (Ixviii)

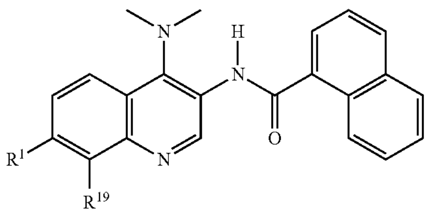

Formula (Ixix)

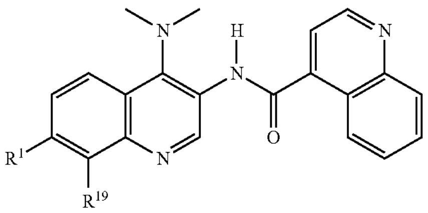

Formula (Ixx)

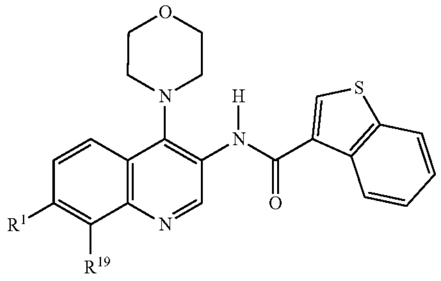

-continued

Formula (Ixxi)

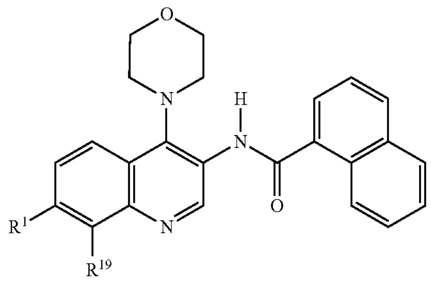

Formula (Ixxii)

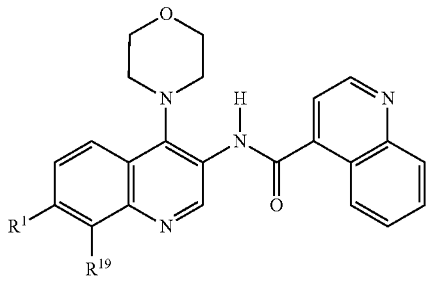

or a stereoisomer, physiologically acceptable salt, ester, solvate, polymorph, prodrug and mixtures thereof, wherein $R^1$ and $R^9$ are defined as in any of the embodiments described herein.

In an embodiment of the invention and/or embodiments thereof, the compounds are according to Formula (Ixvii), preferably in form of the (S)-enantiomer. In an embodiment of the invention and/or embodiments thereof, the compounds are according to Formula (Ixviii), preferably in form of the (S)-enantiomer. In an embodiment of the invention and/or embodiments thereof, the compounds are according to Formula (Ixix), preferably in form of the (S)-enantiomer. In an embodiment of the invention and/or embodiments thereof, the compounds are according to Formula (Ixx), preferably in form of the (S)-enantiomer. In an embodiment of the invention and/or embodiments thereof, the compounds are according to Formula (Ixxi), preferably in form of the (S)-enantiomer. In an embodiment of the invention and/or embodiments thereof, the compounds are according to Formula (Ixxii), preferably in form of the (S)-enantiomer.

The invention provides a compound according to the invention and/or embodiments thereof, wherein $R^7$, $R^{19}$ and $R^{25}$ are defined as above.

Optionally, in an embodiment of the invention and/or embodiments thereof, $R^7$ is independently selected from the group consisting of hydrogen, $C_{1-6}$-alkyl, $C_{2-6}$-alkenyl, 4 to 10-membered heterocyclyl, $C_{1-3}$-alkoxy, hydroxy, $NR^8R^9$, $SR^{10}$, $SOR^{10}$ and $SO_2R^{10}$, wherein each $C_{1-6}$-alkyl, $C_{2-6}$-alkenyl, 4 to 10-membered heterocyclyl or $C_{1-3}$-alkoxy is optionally substituted with one or more substituent(s) independently selected from the group consisting of $C_{1-3}$-alkyl, 5 to 10-membered heterocyclyl, $C_{1-6}$-alkoxy, halogen, cyano, hydroxy, $NR^{8'}R^{9'}$, $C(=O)OR^{10'}$ and $C(=O)NR^{11'}R^{12'}$, $R^8$ and $R^9$ are independently selected from the group consisting of hydrogen, $C_{1-6}$-alkyl, $C_{6-10}$-aryl and 5 to 10-membered heteroaryl, or $R^8$ and $R^9$ together with the N atom to which they are attached form a saturated or unsaturated heterocyclic ring having 3 to 12 ring atoms, wherein 1 ring atom is N and wherein 0, 1, 2, or 3 further ring atoms are selected from N, S and O;

wherein the $C_{1-6}$-alkyl, $C_{6-10}$-aryl or 5 to 10-membered heteroaryl or the heterocyclic ring formed by $R^8$ and $R^9$ together with the N atom to which they are attached is optionally substituted with one or more substituent(s) independently selected from the group consisting of $C_{1-6}$-alkyl, $C_{1-6}$-alkoxy, hydroxy and $NR^{8''}R^{9''}$;

$R^{10}$ is independently selected from hydrogen or $C_{1-3}$-alkyl, preferably from hydrogen, methyl or ethyl, $R^{8'}$, $R^{9'}$, $R^{10'}$, $R^{11'}$ and $R^{12'}$ are independently selected from hydrogen or $C_{1-3}$-alkyl, preferably from hydrogen, methyl or ethyl, $R^{8''}$ and $R^{9''}$ are independently selected from hydrogen or $C_{1-3}$-alkyl, preferably from hydrogen, methyl or ethyl, and $R^{19}$ is independently selected from the group consisting of $C_{6-10}$-aryl and 5 to 10-membered heteroaryl wherein each $C_{6-10}$-aryl or 5 to 10-membered heteroaryl is optionally substituted with one or more substituent(s) independently selected from the group consisting of $C_{1-6}$-alkyl, $C_{1-6}$-alkoxy, halogen, cyano, nitro and hydroxy, $R^{25}$ is hydrogen or $C_{1-3}$-alkyl.

In one embodiment of the invention and/or embodiments thereof, $R^7$ is independently selected from the group consisting of methyl, ethyl, propyl, isopropyl, isopropenyl methoxy, ethoxy, isopropoxy, hydroxy, methyl sulfoxyl, methyl sulfonyl methylthio, amino, methylamino, ethylamino, (ethyl)(methyl)amino isopropylamino, dimethylamino, (isopropyl)(methyl)amino, hydroxyethylamino, (hydroxyethyl)(methyl)amino, methoxyethylamino, (methoxyethyl)(methyl)amino, morpholin-4-yl, pyrrolidin-1-yl, 3-hydroxy-pyrrolidin-1-yl 3-fluoroazetidinyl and 3,3-difluoroazetidinyl, and $R^{19}$ is independently selected from the group consisting of 3-chlorophenyl, 2,3-dichlorophenyl, 3,5-dichlorophenyl, 3,5-difluorophenyl, 2,3,5-trifluorophenyl, 3,4,5-trifluorophenyl, 3-chloro-2-fluorophenyl, 5-chloro-3-fluorophenyl, 5-chloro-3-fluorophenyl, 3,5-dichloro-4-fluorophenyl, in particular 2,3,5-trifluorophenyl, 5-chloro-2-fluorophenyl, 2,3-dichlorophenyl and 3,5-dichlorophenyl, and $R^{25}$ is hydrogen or methyl, preferably hydrogen.

In an embodiment of the invention and/or embodiments thereof, the compounds are according to Formula (Iyi), (Iyii), (Iyiii) or (Iyiv)

Formula (Iyi)

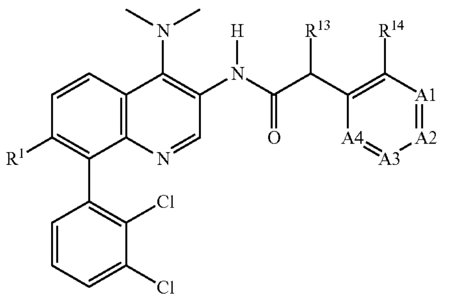

Formula (Iyii)

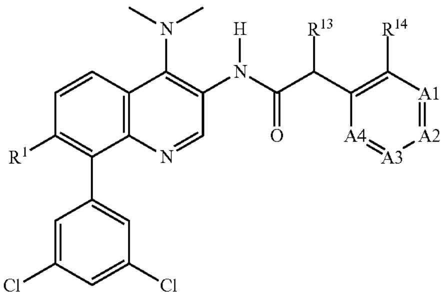

Formula (Iyiii)

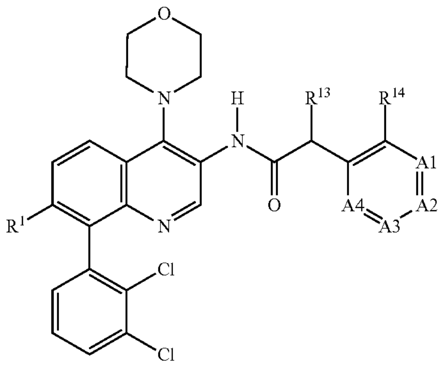

Formula (Iyiv)

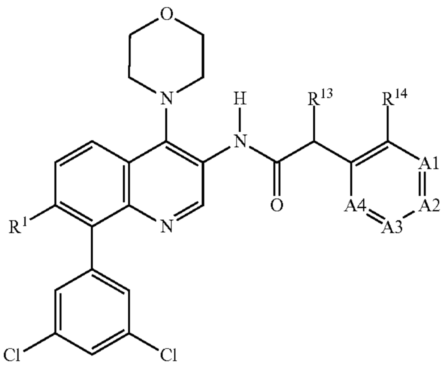

or a stereoisomer, physiologically acceptable salt, ester, solvate, polymorph, prodrug and mixtures thereof, wherein $R^1$, $R^{13}$, $R^{14}$, A1, A2, A3 and A4 are defined as in any of the embodiments described herein.

In an embodiment of the invention and/or embodiments thereof, the compounds are according to Formula (Iyi), preferably in form of the (S)-enantiomer. In an embodiment of the invention and/or embodiments thereof, the compounds are according to Formula (Iyii), preferably in form of the (S)-enantiomer. In an embodiment of the invention and/or embodiments thereof, the compounds are according to Formula (Iyiii), preferably in form of the (S)-enantiomer. In an embodiment of the invention and/or embodiments thereof, the compounds are according to Formula (Iyiv), preferably in form of the (S)-enantiomer.

The invention provides a compound according to the invention and/or embodiments thereof, wherein $R^{13}$, $R^{14}$, A1, A2, A3, A4, $R^{19}$ and $R^{25}$ are defined as above.

Optionally, in an embodiment of the invention and/or embodiments thereof, $R^{13}$ and $R^{14}$ together with the atoms to which they are attached form a 5 or 6-carbon atoms containing non-aromatic ring, wherein the non-aromatic ring is optionally substituted with one or more $C_{1-3}$-alkyl or =O, and/or wherein one or more of the ring-forming carbon atoms are optionally replaced by —NH—, —O—, —S(O)—, —$S(O)_2$— or —S—, A1 is N or $CR^{15}$, wherein $R^{15}$ is independently hydrogen, halogen, $C_{1-3}$ alkyl, $C_{1-3}$ alkoxy, or $NR^{15'}R^{15''}$, wherein $R^{15'}$ and $R^{15''}$ are independently $C_{1-3}$-alkyl, A2 is N or $CR^{16}$, wherein $R^{16}$ is independently hydrogen, halogen, $C_{1-3}$ alkyl, $C_{1-3}$ alkoxy, or $NR^{16'}R^{16''}$, wherein $R^{16'}$ and $R^{16''}$ are independently $C_{1-3}$-alkyl, A3 is N or $CR^{17}$, wherein $R^{17}$ is independently hydrogen, halogen, $C_{1-3}$ alkyl, $C_{1-3}$ alkoxy, or $NR^{17'}R^{17''}$, wherein $R^{17'}$ and $R^{17''}$ are independently $C_{1-3}$-alkyl, A4 is N or $CR^{18}$, wherein $R^{18}$ is independently hydrogen, halogen, $C_{1-3}$ alkyl, $C_{1-3}$ alkoxy, or $NR^{18'}R^{18''}$, wherein $R^{18'}$ and $R^{18''}$ are independently $C_{1-3}$-alkyl, and $R^{19}$ is independently selected from the group consisting of $C_{6-10}$-aryl and 5 to 10-membered heteroaryl wherein each $C_{6-10}$-aryl or 5 to 10-membered heteroaryl is optionally substituted with one or more substituent(s) independently selected from the group consisting of $C_{1-6}$-alkyl, $C_{1-6}$-alkoxy, halogen, cyano, nitro and hydroxy, and $R^{25}$ is hydrogen or $C_{1-3}$-alkyl.

In one embodiment of the invention and/or embodiments thereof, $R^{13}$ and $R^{14}$ together with the atoms to which they are attached form a 5 or 6-carbon atoms containing non-aromatic ring, wherein one or more of the ring-forming carbon atoms are optionally replaced by —NH— or —O—, A1 is N or $CR^{15}$, wherein $R^{15}$ is independently hydrogen or $C_{1-3}$ alkoxy, A2 is N or $CR^{16}$, wherein $R^{16}$ is independently hydrogen or $C_{1-3}$ alkoxy, A3 is N or $CR^{17}$, wherein $R^{17}$ is independently hydrogen or $C_{1-3}$ alkoxy, preferably hydrogen, A4 is N or $CR^{18}$, wherein $R^{18}$ is independently hydrogen or $C_{1-3}$ alkoxy, preferably hydrogen, wherein none, one or two of A1, A2, A3 and A4 are N, and $R^{19}$ is independently selected from the group consisting of 3-chlorophenyl, 2,3-dichlorophenyl, 3,5-dichlorophenyl, 3,5-difluorophenyl, 2,3,5-trifluorophenyl, 3,4,5-trifluorophenyl, 3-chloro-2-fluorophenyl, 5-chloro-3-fluorophenyl, 5-chloro-3-fluorophenyl, 3,5-dichloro-4-fluorophenyl, in particular 2,3,5-trifluorophenyl, 5-chloro-2-fluorophenyl, 2,3-dichlorophenyl and 3,5-dichlorophenyl, and $R^{25}$ is hydrogen or methyl, preferably hydrogen.

In an embodiment of the invention and/or embodiments thereof, the compounds are according to Formula (Izi), (Izii), (Iziii), (Iziv), (Izv) or (Izvi)

Formula (Izi)

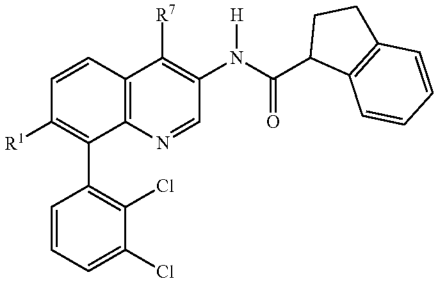

Formula (Izii)

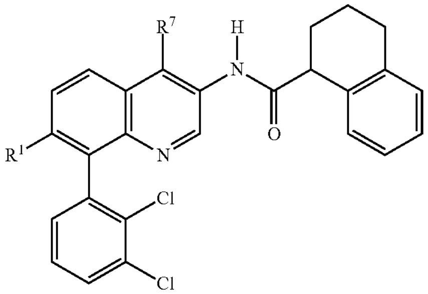

Formula (Iziii)

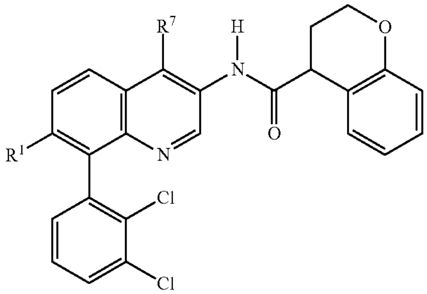

Formula (Iziv)

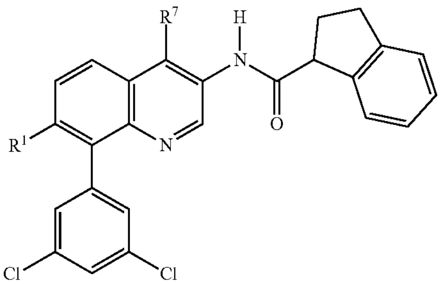

Formula (Izv)

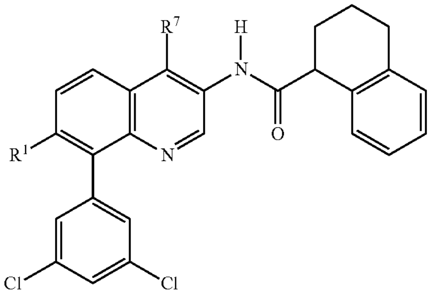

-continued

Formula (Izvi)

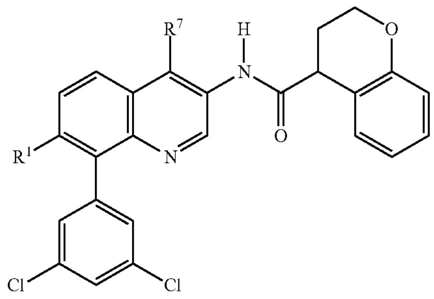

or a stereoisomer, physiologically acceptable salt, ester, solvate, polymorph, prodrug and mixtures thereof, wherein $R^1$ and $R^7$ are defined as in any of the embodiments described herein.

In an embodiment of the invention and/or embodiments thereof, the compounds are according to Formula (Izi), preferably in form of the (S)-enantiomer. In an embodiment of the invention and/or embodiments thereof, the compounds are according to Formula (Izii), preferably in form of the (S)-enantiomer. In an embodiment of the invention and/or embodiments thereof, the compounds are according to Formula (Iziii), preferably in form of the (S)-enantiomer. In an embodiment of the invention and/or embodiments thereof, the compounds are according to Formula (Iziv), preferably in form of the (S)-enantiomer. In an embodiment of the invention and/or embodiments thereof, the compounds are according to Formula (Izv), preferably in form of the (S)-enantiomer. In an embodiment of the invention and/or embodiments thereof, the compounds are according to Formula (Izvi), preferably in form of the (S)-enantiomer.

Optionally, in an embodiment of the invention and/or embodiments thereof, $R^{13}$ and $R^{14}$ together with the atoms to which they are attached form a 5 or 6-carbon atoms containing aromatic ring, wherein the aromatic ring is optionally substituted with one or more $C_{1-3}$-alkyl, and/or wherein one or more of the ring-forming carbon atoms are optionally replaced by —NH—, —N═, ═N—, —O— or —S—, A1 is N or $CR^{15}$, wherein $R^{15}$ is independently hydrogen, halogen $C_{1-3}$ alkyl, $C_{1-3}$ alkoxy or $NR^{15'}R^{15''}$, wherein $R^{15'}$ and $R^{15''}$ are independently $C_{1-3}$-alkyl, A2 is N or $CR^{16}$, wherein $R^{16}$ is independently hydrogen, halogen, $C_{1-3}$ alkyl, $C_{1-3}$ alkoxy or $NR^{16'}R^{16''}$, wherein $R^{16'}$ and $R^{16''}$ are independently $C_{1-3}$-alkyl, A3 is N or $CR^{17}$, wherein $R^{17}$ is independently hydrogen, halogen, $C_{1-3}$ alkyl, $C_{1-3}$ alkoxy or $NR^{15'}R^{15''}$, wherein $R^{15'}$ and $R^{15''}$ are independently $C_{1-3}$-alkyl, A4 is N or $CR^{18}$, wherein $R^{18}$ is independently hydrogen, halogen, $C_{1-3}$ alkyl, $C_{1-3}$ alkoxy or $NR^{15'}R^{15''}$, wherein $R^{15'}$ and $R^{15''}$ are independently $C_{1-3}$-alkyl, and $R^{19}$ is independently selected from the group consisting of $C_{6-10}$-aryl and 5 to 10-membered heteroaryl wherein each $C_{6-10}$-aryl or 5 to 10-membered heteroaryl is optionally substituted with one or more substituent(s) independently selected from the group consisting of $C_{1-6}$-alkyl, $C_{1-6}$-alkoxy, halogen, cyano, nitro and hydroxy, and $R^{25}$ is hydrogen or $C_{1-3}$-alkyl.

Optionally, in an embodiment of the invention and/or embodiments thereof, $R^{13}$ and $R^{14}$ together with the atoms to which they are attached form a 5 or 6-carbon atoms containing aromatic ring, wherein one or more of the ring-forming carbon atoms are optionally replaced by —NH—, —N═, ═N— or —S—, A1 is N or $CR^{15}$, wherein $R^{15}$ is independently hydrogen or $C_{1-3}$ alkoxy, A2 is N or $CR^{16}$, wherein $R^{16}$ is independently hydrogen or $C_{1-3}$ alkoxy, A3 is N or $CR^{17}$, wherein $R^{17}$ is independently hydrogen or $C_{1-3}$ alkoxy, preferably hydrogen, A4 is N or $CR^{18}$, wherein $R^{18}$ is independently hydrogen or $C_{1-3}$ alkoxy, preferably hydrogen, wherein none, one or two of A1, A2, A3 and A4 are N, and $R^{19}$ is independently selected from the group consisting of 3-chlorophenyl, 2,3-dichlorophenyl, 3,5-dichlorophenyl, 3,5-difluorophenyl, 2,3,5-trifluorophenyl, 3,4,5-trifluorophenyl, 3-chloro-2-fluorophenyl, 5-chloro-3-fluorophenyl, 5-chloro-3-fluorophenyl, 3,5-dichloro-4-fluorophenyl, in particular 2,3,5-trifluorophenyl, 5-chloro-2-fluorophenyl, 2,3-dichlorophenyl and 3,5-dichlorophenyl, and $R^{25}$ is hydrogen or methyl, preferably hydrogen.

In an embodiment of the invention and/or embodiments thereof, the compounds are according to Formula (Izvii), (Izviii), (Izix), (Izx), (Izxi) or (Izxii)

Formula (Izvii)

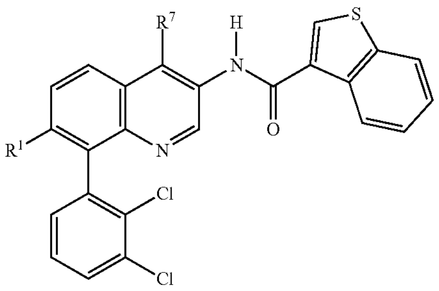

Formula (Izviii)

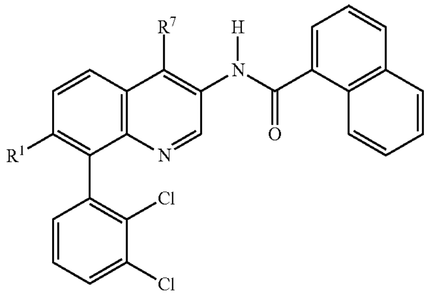

-continued

Formula (Izix)

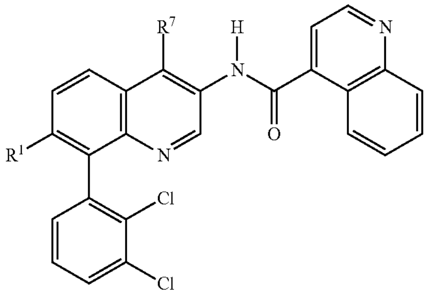

Formula (Izx)

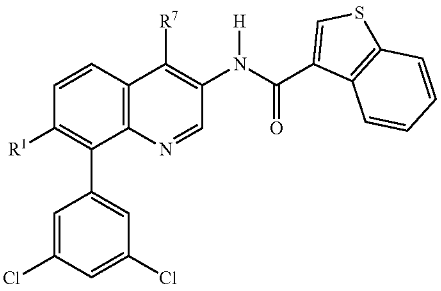

Formula (Izxi)

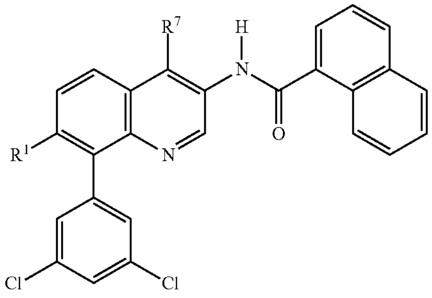

Formula (Izxii)

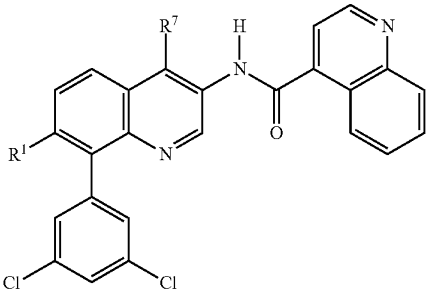

or a stereoisomer, physiologically acceptable salt, ester, solvate, polymorph, prodrug and mixtures thereof, wherein $R^1$ and $R^7$ are defined as in any of the embodiments described herein.

In an embodiment of the invention and/or embodiments thereof, the compounds are according to Formula (Izvii), preferably in form of the (S)-enantiomer. In an embodiment of the invention and/or embodiments thereof, the compounds are according to Formula (Izviii), preferably in form of the (S)-enantiomer. In an embodiment of the invention and/or embodiments thereof, the compounds are according to Formula (Izix), preferably in form of the (S)-enantiomer. In an embodiment of the invention and/or embodiments thereof, the compounds are according to Formula (Izx), preferably in form of the (S)-enantiomer. In an embodiment of the invention and/or embodiments thereof, the compounds are according to Formula (Izxi), preferably in form of the (S)-enantiomer. In an embodiment of the invention and/or embodiments thereof, the compounds are according to Formula (Izxii), preferably in form of the (S)-enantiomer.

The compound according to invention can be considered as an "active" agent, which in this context is regarded as a substance that will inhibit the growth of helminths such as *Dirofilaria*, in particular *Dirofilaria immitis*. The term "inhibiting the growth" indicates that the rate of increase in the numbers of a population of a helminth is reduced. Thus, the term includes situations in which the helminth population increases but at a reduced rate, as well as situations where the growth of the population is stopped, as well as situations where the numbers of the helminth in the population are reduced or the population is even eliminated.

Further, the present invention provides a process for preparing the compound according to Formula (I) comprising the step of reacting a compound of Formula (A)

Formula (A)

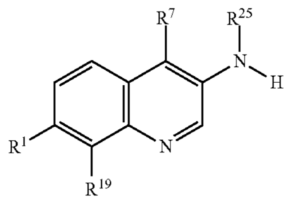

with a compound of Formula (B)

Formula (B)

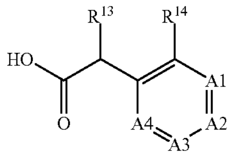

wherein $R^1$ is independently selected from the group consisting of hydrogen, $C_{1-6}$-alkyl, $C_{2-6}$-alkenyl, $C_{2-6}$-alkynyl, $C_{3-10}$-cycloalkyl, 5- to 10-membered heterocyclyl, $C_{6-10}$ aryl, 5- to 10-membered heteroaryl, $C_{1-6}$-alkoxy, $C_{1-6}$-alkylmercapto, halogen, cyano, nitro, hydroxy, mercapto, $NR^2R^3$, COOH, $C(=O)OR^4$, $SR^4$, $SOR^4$, $SO_2R^4$, $SO_2NR^5R^6$ and $C(=O)NR^5R^6$, wherein each $C_{1-6}$-alkyl, $C_{2-6}$-alkenyl, $C_{2-6}$-alkynyl, $C_{3-10}$-cycloalkyl, 5- to 10-membered heterocyclyl, $C_{6-10}$ aryl, 5- to 10-membered heteroaryl, $C_{1-6}$-alkoxy or $C_{1-6}$-alkylmercapto, is optionally substituted with one or more substituent(s) independently selected from the group consisting of $C_{1-6}$-alkyl, $C_{2-6}$-alkenyl, $C_{2-6}$-alkynyl, $C_{3-10}$-cycloalkyl, 5- to 10-membered heterocyclyl, $C_{6-10}$-aryl, 5- to 10-membered heteroaryl, $C_{1-6}$-alkoxy, $C_{1-6}$-alkylmercapto, halogen, cyano, nitro, hydroxy, mercapto, $NR^{2'}R^{3'}$, $C(=O)OR^{4'}$, $SR^{4'}$, $SOR^{4'}$, $SO_2R^{4'}$, $SO_2NR^{5'}R^{6'}$ and $C(=O)NR^{5'}R^{6'}$, $R^2$ and $R^3$ are independently selected from the group consisting of hydrogen, $C_{1-6}$-alkyl, $C_{2-6}$-alkenyl, $C_{2-6}$-alkynyl, $C_{3-10}$-cycloalkyl, 5- to 10-membered heterocyclyl, $C_{6-10}$-aryl, 5- to 10-membered heteroaryl, $C_{1-6}$-alkoxy-$C_{1-6}$-alkyl, $C_{1-6}$-alkyl substituted with $C_{3-10}$-cycloalkyl, $C_{1-6}$-alkyl substituted with 5- to 10-membered heterocyclyl, $C_{1-6}$-alkyl substituted with $C_{6-10}$-aryl and $C_{1-6}$-alkyl substituted with 5- to 10-membered heteroaryl, or $R^2$ and $R^3$ together with the N atom to which they are attached form a saturated or unsaturated heterocyclic ring having 3 to 12 ring atoms, wherein 0, 1, 2, or 3 further ring atoms are selected from N, S and O, wherein each $C_{1-6}$-alkyl, $C_{2-6}$-alkenyl, $C_{2-6}$-alkynyl, $C_{3-10}$-cycloalkyl, 5- to 10-membered heterocyclyl, $C_{6-10}$-aryl, 5- to 10-membered heteroaryl, $C_{1-6}$-alkoxy-$C_1$-6-alkyl, $C_{1-6}$-alkyl substituted with $C_{3-10}$-cycloalkyl, $C_{1-6}$-alkyl substituted with 5- to 10-membered heterocyclyl, $C_{1-6}$-alkyl substituted with $C_{6-10}$-aryl or $C_{1-6}$-alkyl substituted with 5- to 10-membered heteroaryl or the heterocyclic ring formed by $R^2$ and $R^3$ together with the N atom to which they are attached is optionally substituted with one or more substituent(s) independently selected from the group consisting of $C_{1-6}$-alkyl, $C_{2-6}$-alkenyl, $C_{2-6}$-alkynyl, $C_{3-10}$-cycloalkyl, 5- to 10-membered heterocyclyl, $C_{6-10}$-aryl, 5- to 10-membered heteroaryl, $C_{1-6}$-alkoxy, carbonyl, halogen, cyano, hydroxy, mercapto, $NR^{2''}R^{3''}$, $C(=O)OR^{4''}$, $SR^{4''}$, $SOR^4$, $SO_2R^{4''}$, $SO_2NR^{5''}R^{6''}$ and $C(=O)NR^{5''}R^{6''}$;

$R^4$, $R^5$ and $R^6$ are independently selected from hydrogen and $C_{1-6}$-alkyl, $R^{2'}$, $R^{3'}$, $R^{4'}$, $R^{5'}$ and $R^{6'}$ are independently selected from hydrogen and $C_{1-6}$-alkyl, $R^{2''}$, $R^{3''}$, $R^{4''}$, $R^{5''}$ and $R^{6''}$ are independently selected from hydrogen and $C_{1-6}$-alkyl, $R^7$ is independently selected from the group consisting of hydrogen, $C_{1-6}$-alkyl, $C_{2-6}$-alkenyl, $C_{2-6}$-alkynyl, $C_{3-10}$-cycloalkyl, 4- to 10-membered heterocyclyl, $C_{6-10}$ aryl, 5- to 10-membered heteroaryl, $C_{1-6}$-alkoxy, $C_{1-6}$-alkylmercapto, halogen, cyano, nitro, hydroxy, mercapto, $NR^8R^9$, COOH, $C(=O)OR^{10}$, $SR^{10}$, $SOR^{10}$, $SO_2R^{10}$, $SO_2NR^{11}R^{12}$ and $C(=O)NR^{11}R^{12}$ wherein each $C_{1-6}$-alkyl, $C_{2-6}$-alkenyl, $C_{2-6}$-alkynyl, $C_{3-10}$-cycloalkyl, 4- to 10-membered heterocyclyl, $C_{6-10}$ aryl, 5- to 10-membered heteroaryl, $C_{1-6}$-alkoxy or $C_{1-6}$-alkylmercapto, is optionally substituted with one or more substituent(s) independently selected from the group consisting of $C_{1-6}$-alkyl, $C_{2-6}$-alkenyl, $C_{2-6}$-alkynyl, $C_{3-10}$-cycloalkyl, 5- to 10-membered heterocyclyl, $C_{6-10}$-aryl, 5- to 10-membered heteroaryl, $C_{1-6}$-alkoxy, $C_{1-6}$-alkylmercapto, halogen, cyano, nitro, hydroxy, mercapto, $NR^{8'}R^{9'}$, $C(=O)OR^{10'}$, $SR^{10'}$, $SOR^{10'}$, $SO_2R^{10'}$, $SO_2NR^{11'}R^{12'}$ and $C(=O)NR^{11'}R^{12'}$, $R^8$ and $R^9$ are independently selected from the group consisting of hydrogen, $C_{1-6}$-alkyl, $C_{2-6}$-alkenyl, $C_{2-6}$-alkynyl, $C_{3-10}$-cycloalkyl, 5- to 10-membered heterocyclyl, $C_{6-10}$-aryl, 5- to 10-membered heteroaryl, $C_{1-6}$-alkoxy-$C_{1-6}$-alkyl, $C_{1-6}$-alkyl substituted with $C_{3-10}$-cycloalkyl, $C_{1-6}$-alkyl substituted with 5- to 10-membered heterocyclyl, $C_{1-6}$-alkyl substituted with $C_{6-10}$-aryl, $C_{1-6}$-alkyl substituted with 5- to 10-membered heteroaryl, or $R^8$ and $R^9$ together with the N atom to which they are attached form a saturated or unsaturated heterocyclic ring having 3 to 12 ring atoms, wherein 0, 1, 2, or 3 further ring atoms are selected from N, S and O, wherein each $C_{1-6}$-alkyl, $C_{2-6}$-alkenyl, $C_{2-6}$-alkynyl, $C_{3-10}$-cycloalkyl, 5- to 10-membered heterocyclyl, $C_{6-10}$-aryl, 5- to 10-membered heteroaryl, $C_{1-6}$-alkoxy-$C_1$-6-alkyl, $C_{1-6}$-alkyl substituted with $C_{3-10}$-cycloalkyl, $C_{1-6}$-alkyl substituted with 5- to 10-membered heterocyclyl, $C_{1-6}$-alkyl substituted with $C_{6-10}$-aryl or $C_{1-6}$-alkyl substituted with 5- to 10-membered heteroaryl or the heterocyclic ring formed by $R^8$ and $R^9$ together with the N atom to which they are attached is optionally substituted with one or more substituent(s) independently selected from the group consisting of $C_{1-6}$-alkyl, $C_{2-6}$-alkenyl, $C_{2-6}$-alkynyl, $C_{3-10}$-cycloalkyl, 5- to 10-membered heterocyclyl, $C_{6-10}$-aryl, 5- to 10-membered heteroaryl, $C_{1-6}$-alkoxy, carbonyl, halogen, cyano, hydroxy, mercapto, $NR^{8''}R^{9''}$, $C(=O)OR^{10''}$, $SR^{10''}$, $SOR^{10''}$, $SO_2R^{10''}$, $SO_2NR^{11''}R^{12''}$ and $C(=O)NR^{11''}R^{12''}$;

$R^{10}$, $R^{11}$ and $R^{12}$ are independently selected from hydrogen and $C_{1-6}$-alkyl, $R^{8'}$, $R^{9'}$, $R^{10'}$, $R^{11'}$ and $R^{12'}$ are independently selected from hydrogen and $C_{1-6}$-alkyl, $R^{8''}$, $R^{9}$, $R^{10}$, $R^{11''}$ and $R^{12''}$ are independently selected from hydrogen and $C_{1-6}$-alkyl, $R^{13}$ is hydrogen or $C_{1-3}$ alkyl, $R^{14}$ is hydrogen, $C_{1-3}$ alkyl, $C_{1-3}$ alkoxy, $NR^{14'}R^{14''}$, wherein $R^{14'}$ and $R^{14''}$ are independently $C_{1-3}$-alkyl or $R^{13}$ and $R^{14}$ together with the atoms to which they are attached form a 5 or 6-carbon atoms containing non-aromatic ring, wherein the 5 or 6-carbon atoms containing ring is optionally substituted with one or more $C_{1-3}$-alkyl or $=O$, and/or wherein one or more of the ring forming carbon atoms are optionally replaced by —NH—, —N=, =N—, —O—, —S(O)—, —$S(O)_2$— or —S—, or $R^{13}$ and $R^{14}$ together with the atoms to which they are attached form a 5 or 6-carbon atoms containing aromatic ring, wherein the 5 or 6-carbon atoms containing ring is optionally substituted with one or more $C_{1-3}$-alkyl, and/or wherein one or more of the ring forming carbon atoms are optionally replaced by —NH—, —N=, =N—, —O— or —S—, A1 is N or $CR^{15}$, wherein $R^{15}$ is independently hydrogen, halogen, $C_{1-3}$ alkyl, $C_{1-3}$ alkoxy, or $NR^{15'}R^{15''}$, wherein $R^{15'}$ and $R^{15''}$ are independently $C_{1-3}$-alkyl, A2 is N or $CR^{16}$, wherein $R^{16}$ is independently hydrogen, halogen, $C_{1-3}$ alkyl, $C_{1-3}$ alkoxy, or $NR^{16'}R^{16''}$, wherein $R^{16'}$ and $R^{16''}$ are independently $C_{1-3}$-alkyl, A3 is N or $CR^{17}$, wherein $R^{17}$ is independently hydrogen, halogen, $C_{1-3}$ alkyl, $C_{1-3}$ alkoxy, or $NR^{17'}R^{17''}$, wherein $R^{17'}$ and $R^{17''}$ are independently $C_{1-3}$-alkyl, A4 is N or $CR^{18}$, wherein $R^{18}$ is independently hydrogen, halogen $C_{1-3}$ alkyl, $C_{1-3}$ alkoxy, or $NR^{18'}R^{18''}$, wherein $R^{18'}$ and $R^{18''}$ are independently $C_{1-3}$-alkyl, $R^{19}$ is independently selected from the group consisting of $C_{6-10}$-aryl and 5- to 10-membered heteroaryl, wherein each $C_{6-10}$-aryl or 5- to 10-membered heteroaryl is optionally substituted with one or more substituent(s) independently selected from the group consisting of $C_{1-6}$-alkyl, $C_{2-6}$-alkenyl, $C_{3-10}$-cycloalkyl, 5- to 10-membered heterocyclyl, $C_{6-10}$-aryl, 5- to 10-membered heteroaryl, $C_{1-6}$-alkoxy, $C_{1-6}$-alkylmercapto, halogen, cyano, nitro, hydroxy, mercapto, $NR^{20}R^{21}$, $C(=O)OR^{22}$, $SR^{22}$, $SOR^{22}$, $SO_2R^{22}$, $SO_2NR^{23}R^{24}$ and $C(=O)NR^{23}R^{24}$ $R^{20}$ and $R^{21}$ are independently selected from the group consisting of hydrogen, $C_{1-6}$-alkyl, $C_{3-10}$-cycloalkyl, $C_{6-10}$-aryl, 5- to 10-membered heteroaryl, $C_{1-6}$-alkoxy-$C_{1-6}$-alkyl, $C_1$-$C_6$-alkyl substituted with $C_{6-10}$-aryl, $C_{1-6}$-alkyl substituted with 5- to 10-membered heteroaryl, or $R^{20}$ and $R^{21}$ together with the N atom to which they are attached form a saturated or unsaturated heterocyclic ring having 3 to 12 ring atoms, wherein 0, 1, 2, or 3 further ring atoms are selected from N, S and O;

wherein each $C_{1-6}$-alkyl, $C_{2-6}$-alkenyl, $C_{3-10}$-cycloalkyl, 5- to 10-membered heterocyclyl, $C_{6-10}$-aryl, 5- to 10-membered heteroaryl, $C_{1-6}$-alkoxy or $C_{1-6}$-alkylmercapto or the heterocyclic ring formed by $R^{20}$ and $R^{21}$ together with the N atom to which they are attached is optionally substituted with one or more substituents independently selected from the group consisting of $C_{1-6}$-alkyl, $C_{2-6}$-alkenyl, $C_{2-6}$-alkynyl, $C_{3-10}$-cycloalkyl, 5- to 10-membered heterocyclyl, $C_{6-10}$-aryl, 5- to 10-membered heteroaryl, $C_{1-6}$-alkoxy, carbonyl, halogen, cyano, hydroxy, mercapto, $NR^{20'}R^{21'}$, $C(=O)OR^{22'}$ $SR^{22'}$, $SOR^{22'}$, $SO_2R^{22'}$, $SO_2NR^{23'}R^{24'}$, and $C(=O)NR^{23'}R^{24'}$ $R^{22}$, $R^{23}$ and $R^{24}$ are independently selected from hydrogen and $C_{1-6}$-alkyl, $R^{20'}$, $R^{21'}$, $R^{22'}$, $R^{23'}$ and $R^{24'}$ are independently selected from hydrogen and $C_{1-6}$-alkyl, $R^{25}$ is independently selected from hydrogen and $C_{1-6}$-alkyl, to obtain the compound according to Formula (I).

In an embodiment of the invention and/or embodiments thereof, as far as $R^1$, $R^7$, $R^{13}$, $R^{14}$, A1, A2, A3, A4, $R^{19}$ and $R^{25}$ are concerned, the same applies as described above with regard to the compound according to the invention.

The compounds of Formula (A) and Formula (B) are either commercially or synthetically available.

In an embodiment of the invention and/or embodiments thereof, the amine of Formula (A) and the carboxylic acid according to Formula (B) can be submitted to form the corresponding amide group in an organic solvent in the presence of a coupling agent.

A coupling agent can be regarded as a substance generally facilitating the formation of an ester or an amide. The coupling agent reacts with a carboxy group by forming a reactive intermediate which is subsequently further reacted with an alcohol or an amine to form the final product, i.e. an ester or an amide.

Examples of coupling agents include, but are not limited to, carbodiimides such as N,N'-dicyclohexylcarbodiimide (DCC), diisopropylcarbodiimide (DIC), 1-etyhl-3-(3-dimethylaminopropyl) carbodiimide (EDC), 1-etyhl-3-(3-dimethylaminopropyl) carbodiimide hydrochloride (EDCxHCl) and N-Cyclohexyl-N'-(2-morpholinoethyl)carbodiimid-methyl-p-toluolsulfonat (CMC), Phosphonium salts such as Benzotriazol-1-yl-oxytripyrrolidino-phosphoniumhexafluorophosphat (PyBOP), aminium salts such as 3-[bis(dimethyl-amino)methyliumyl]-3H-benzotriazol-1-oxid-hexafluorphosphat (HBTU) and carbonyldiimidazole (CDI).

In an embodiment of the invention and/or embodiments thereof, the coupling agent is selected from N,N'-dicyclohexylcarbodiimide (DCC), diisopropylcarbodiimide (DIC), 1-etyhl-3-(3-dimethylaminopropyl) carbodiimide (EDC), 1-etyhl-3-(3-dimethylaminopropyl) carbodiimide hydrochloride (EDCxHCl) and carbonyldiimidazole (CDI). More preferably the coupling agent is 1-etyhl-3-(3-dimethylaminopropyl) carbodiimide hydrochloride.

Organic solvents are known to the skilled person.

A suitable organic solvent for the process according to the present invention can for example be acetonitrile, dioxane, tetrahydrofuran (THF) and dimethylformamide (DMF), dimethyl sulfoxide (DMSO), preferably dimethylformamide (DMF).

In an embodiment of the invention and/or embodiments thereof, the process can be carried out in the presence of an auxiliary alkaline compound. Suitable alkaline compounds include, but are not limited to, pyridines such as 4-(dimethylamino) pyridine (DMAP), amidines such 1,8-diazabicyclo [5.4.0]undec-7-ene (DBU) and amines such as triethylamine and diisopropylethylamine (DIPEA), preferably 4-(dimethylamino) pyridine (DMAP).

In an embodiment of the invention and/or embodiments thereof, the process can be carried out at a temperature of 5° to 120° C., preferably at 20 to 100° C.

In an alternative embodiment of the invention and/or embodiments thereof, the carboxylic acid according to Formula (B) can be reacted with thionyl chloride or oxalyl chloride, preferably oxalyl chloride, to form the corresponding acid chloride. Subsequently the corresponding acid chloride can be submitted to a reaction with the amine according to Formula (A) to obtain the compound of Formula (I).

In an alternative embodiment of the invention and/or embodiments thereof, the alternative process can be carried out in an organic solvent and/or in the presence of an auxiliary alkaline compound.

A suitable organic solvent can for example be acetonitrile, toluene, dioxane, tetrahydrofuran, chloroform or dichloromethane.

As far as the auxiliary alkaline compound is concerned, the same applies as described above, preferred are pyridine, DMAP, triethylamine and diisopropylethylamine Further, the invention provides a veterinary composition comprising the compound according to the invention and one or more physiologically acceptable excipient(s).

Veterinary compositions of the present invention and/or embodiments thereof comprise a therapeutically effective amount of a compound of the present invention and/or embodiments thereof formulated together with one or more physiologically acceptable excipient(s).

Physiologically acceptable excipients are known in the art. For example, they are described in "Gennaro, Remington: The Science and Practice of Pharmacy" ($20^{th}$ Edition, 2000). All such physiologically acceptable excipients must be substantially pharmaceutically or veterinary pure and non-toxic in the amounts employed and must be compatible with the active ingredients.

In one preferred embodiment of the invention and/or embodiments thereof the one or more physiologically acceptable excipient(s) is selected from carriers, binders, antioxidants, buffers, sugar components, surfactants, lubricants, stabilizers, flow agents, disintegration agents and preservatives and mixtures thereof.

As used herein, the term "carrier" means a non-toxic, inert, solid, semi-solid or liquid filler or diluent carrying/encapsulating material of any type. Some examples of materials that can serve as physiologically acceptable carriers are, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil, safflower oil, sesame oil, olive oil, corn oil and soybean oil; esters such as ethyl oleate and ethyl laurate; agar.

A binder is a substance which is capable of making other substances stick together. The binder is a component that, in case binder is a polymer, preferably has a melting temperature or a glass transition temperature ($T_g$) in the range of 25 to 100° C., preferably 35 to 85° C., in particular 40 to 70° C. The glass transition temperature is the temperature at which a polymer becomes brittle as it cools down and soft as it heats up. This means that hydrophilic polymers become soft at temperatures above the glass transition temperature ($T_g$) and become plastically deformable without breaking. The glass transition temperature or melting point are determined via methods known by the skilled person.

In one preferred embodiment of the invention and/or embodiments thereof the binder is selected from polyethylene glycol, polypropylene glycol, polyethylene glycol-polypropylene glycol copolymer, microcrystalline wax, glycerol monostearate, hydrogenated castor oil, polyethylene glycol glycerol hydroxystearate, polysaccharides, polyvinylpyrrolidone, polyvinyl alcohol, poly(meth)acrylates, polyvinylpyrrolidone-polyacetate copolymer and mixtures thereof.

Antioxidants are substances that are used to inhibit oxidation. Antioxidants suitable to be comprised in the present soft chewable veterinary dosage form include, but are not limited to, ascorbic acid, glutathione, tocopherol and its esters, tert-butylhydroquinone (TBHQ), butyl hydroxy anisole (BHA also referred to as 2-tert-butyl-4-hydroxy anisole, 3-tert-butyl-4-hydroxy anisole or a mixture thereof) and butyl hydroxy toluene (BHT also referred as 2,6-di tert-butyl 4-methyl phenol). It is preferred that the antioxidant is present in the conglomerate. In one preferred embodiment of the invention and/or embodiments thereof antioxidants comprised in the veterinary dosage form may be in the range of 0.001 to 1.00 weight %.

Buffers are substances to maintain/adjust the pH value of a product. Non-limiting examples of buffers are hydrogen carbonate salts, dihydrogen phosphate salts, hydrogen phosphate salts.

Sugar components are used to sweeten the taste of a product. They comprise natural sugars (carbohydrates) as well as sugar substitutes. In one preferred embodiment of the invention and/or embodiments thereof buffers comprised in the veterinary dosage form may be in the range of 1 to 10 weight %.

Surfactants can be regarded as substances lowering the interfacial tension between two phases. Common surfactants are alkylsulfates (for example sodium lauryl sulfate), alkyl trimethyl ammonium salts, alcohol ethoxylates and the like. In one preferred embodiment of the invention and/or embodiments thereof surfactants comprised in the veterinary dosage form may be in the range of 0.1 to 10.0 weight %.

Lubricants generally can be regarded as substances which are suitable to reduce friction, such as static friction, sliding friction and rolling friction. The lubricant is preferably a stearate or fatty acid, more preferably an earth alkali metal stearate, such as magnesium stearate. In one preferred embodiment of the invention and/or embodiments thereof lubricants comprised in the veterinary dosage form may be in the range of 0.1 to 10.0 weight %.

A stabiliser is a physiologically acceptable excipient which helps to preserve the product. Examples include, but are not limited to, alginates, carrageen, gelatine, pectin and natural gums. In one preferred embodiment of the invention and/or embodiments thereof surfactants comprised in the veterinary dosage form may be in the range of 0.01 to 3.0 weight %.

Flow agents, also referred to as glidants, can be used to improve the flowability. Traditionally, talc was used as glidant but is nowadays nearly fully replaced by colloidal silica. In one preferred embodiment of the invention and/or embodiments thereof flow agents comprised in the veterinary dosage form may be in the range of 1 to 3 weight %.

Disintegration agents, also referred to as disintegrants, are compounds which enhance the ability of the dosage form, preferably the ability of the tablet, when in contact with a liquid, preferably water, to break into smaller fragments. Non-limiting examples of disintegration agents include sodium carboxymethyl starch, sodium starch glycolate, cross-linked polyvinyl pyrrolidone, sodium carboxymethyl glycolate, preferably sodium starch glycolate. In one preferred embodiment of the invention and/or embodiments thereof surfactants comprised in the veterinary dosage form may be in the range of 1.0 to 7.0 weight %.

Preservatives are substances that can be added to prevent decomposition by microbial growth or by undesirable chemical changes. Non-limiting examples include lactic acid, benzoic acid benzoates and hydroxybenzoates. In one preferred embodiment of the invention and/or embodiments thereof surfactants comprised in the veterinary dosage form may be in the range of 0.01 to 1.0 weight %.

The compounds according to this invention may be administered in various dosage forms. The term "dosage form" means that the compounds according to this invention are formulated into a product suitable for administering to the animal via the envisaged dosage route. Such dosage forms are sometimes referred to herein as Formulations or pharmaceutical compositions.

The pharmaceutical compositions of this invention and/or embodiments thereof can be administered to animals orally, rectally, intravaginally, parenterally, topically, buccally or nasally.

In one preferred embodiment of the invention and/or embodiments thereof dosage forms useful for oral administration can be liquid or solid dosage forms.

Liquid dosage forms of the compounds are generally solutions, suspensions or emulsions. A solution is a mixture of two or more components that form a single phase that is homogeneous down to the molecular level. A suspension consists of insoluble solid particles dispersed in a liquid medium, with the solid particles accounting for about 0.5% to about 30% of the suspension. The liquid may be aqueous, oily or both. An emulsion is a heterogeneous dispersion of one immiscible liquid in another; it relies on an emulsifying agent for stability. A dry powder (or granule) for reconstitution is mixed and reconstituted with a diluent (e.g. water) as a solution, or as a suspension immediately prior to injection. The principal advantage of this dosage form is that it overcomes the problem of instability in solution or suspension.

Liquid dosage forms for oral administration include pharmaceutically acceptable emulsions, micro-emulsions, solutions, suspensions, syrups, drench, in-feed or drinking water Formulations and elixirs. A drench is a liquid oral Formulation that is administered directly into the mouth/throat of an animal, especially a dog, by means of a "drench gun" or syringe or another suitable device. When the composition is administered in the animal recipient's drinking water or as a drench, it may be convenient to use a solution or suspension Formulation. This Formulation can, for example, be a concentrated suspension that is mixed with water or a dry preparation that is mixed and suspended in the water. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular cottonseed, groundnut, corn, germ, olive castor, and sesame oils), glycerol, tetrahydrofurfuryl alcohol, polyethylene glycols and fatty acid esters of sorbitane and mixtures thereof. Besides inert diluents, the oral compositions can also include adjuvants such as wetting agents, emulsifying and suspending agents, sweetening, flavouring and perfuming agents.

Solid dosage forms for oral administration include capsules, tablets, dragées, pills, powders and granules, chewable treats, premixes and medicated blocks. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid; b) binders such as, for example, carboxymethyl-cellulose, alginates, gelatin, polyvinyl pyrrolidinone, sucrose, and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as, for example, acetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

The active compounds can also be in micro-encapsulated form with one or more excipients as noted above. The solid dosage forms of tablets, dragées, capsules, pills and granules can be prepared with coatings and shells such as enteric coatings and other coatings well known in the pharmaceutical formulating art such as enteric coatings, release-controlling coatings and other coatings. In such solid dosage forms the active compound may be admixed with at least one inert diluent such as sucrose, lactose or starch. Such dosage forms may also comprise, as is normal practice, additional substances other than inert diluents, e.g. tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient (s) only, or preferentially, in a certain part of the intestinal tract, optionally, in a delayed manner. Examples of embedding compositions include polymeric substances and waxes.

Solid compositions of a similar type may also be employed as fillers in soft and hard gelatine capsules using such excipients as lactose or milk sugar as well as high molecular weight polyethylene glycols and the like.

Solid oral formulations are either administered directly to an animal (tablet, capsule) or mixed with the feed or via medicated feed blocks.

When the oral formulation is administered via a non-human animal's feed, it may, for example, be fed as a discrete feed or as a chewable treat. Alternatively (or additionally), it may for example be intimately dispersed in the animal recipient's regular feed, used as a top dressing or in the form of solid pellets, paste or liquid that is added to the finished feed. When the oral Formulation is administered as a feed additive, it may be convenient to prepare a "premix" in which the oral Formulation is dispersed in a small amount of a liquid or solid carrier. This "premix" is, in turn, dispersed in the animal's regular feed using for example a conventional mixer.

In one preferred embodiment of the invention and/or embodiments thereof dosage forms useful for rectal and vaginal administration can be regarded as semi solid dosage forms.

Compositions for rectal or vaginal administration can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

In one preferred embodiment of the invention and/or embodiments thereof the dosage forms are useful for parenteral administrations. One dosage route (administration route) is the parenteral, especially injection administration (e.g. subcutaneous injection, intravenous injection, intramuscular injection etc.). Parenteral Formulations and delivery systems for non-oral routes comprise liquids (e.g. solutions, suspensions, emulsions and dry powders for reconstitution), semi-solids and solids (e.g. implants). The majority of implants that are used in veterinary medicine are compressed tablets or dispersed matrix systems in which the drug is uniformly dispersed within a nondegradable polymer or alternatively extrusion products. In one embodiment the compounds of the current invention are administered subcutaneously.

Injectable formulations, for example sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil can be employed including synthetic mono-or diglycerides. In addition, fatty acids such as oleic acid are used in the preparation of injectables.

The injectable formulations can be sterilized, for example by filtration through a bacterial-retaining filter, or by incorporating sterilizing agents in the form of sterile solid compositions that can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends on its rate of dissolution that, in turn, may depend on crystal size and crystalline form. Alternatively, delayed absorption of a parenterally administered drug form may be accomplished by dissolving or suspending the drug in an oil vehicle. Injectable depot forms are made by forming microencapsulation matrices of the drug in biodegradable polymers such as polylactide-polyglycolide. Depending on the ratio of drug to polymer and the nature of the particular polymer employed, the rate of drug release can be controlled. Examples of other biodegradable polymers include poly(orthoesters) and poly(anhydrides). Depot injectable Formulations may also be prepared by entrapping the drug in liposomes or microemulsions that are compatible with body tissues.

In one preferred embodiment of the invention and/or embodiments thereof dosage forms useful for topical administration (also referred to as transdermal administration) of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic Formulations, ear drops and the like are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide or mixtures thereof.

Compounds of the invention may also be formulated for use as topical powders and sprays that can contain, in addition to the compounds of this invention, excipients such as lactose, talc, silicic acid, aluminium hydroxide, calcium silicates and polyamide powder or mixtures of these substances.

Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin.

The rate can be controlled by either providing a rate controlling membrane or by dispersing the compound in a polymer matrix or gel.

In one preferred embodiment of the invention and/or embodiments thereof dosage forms useful for buccal administration of a compound of this invention include orally disintegrating tablets (ODT), films, sublingual drops, lozenges, effervescent buccal tablets, toothpaste and mouthwash.

In one preferred embodiment of the invention and/or embodiments thereof dosage forms useful for nasal administration of a compound of this invention include liquid aerosols or inhalable dry powders. Liquid aerosol Formulations may be nebulized predominantly into particle sizes that can be delivered to the terminal and respiratory bronchioles.

Liquid aerosol and inhalable dry powder Formulations are preferably delivered throughout the endobronchial tree to the terminal bronchioles and eventually to the parenchymal tissue.

Aerosolized formulations of the invention may be delivered using an aerosol forming device, such as a jet, vibrating porous plate or ultrasonic nebulizer, preferably selected to allow the formation of aerosol particles having a mass medium average diameter predominantly between 1 to 5 pm.

Further, the formulation preferably has a balanced osmolarity ionic strength and chloride concentration and the smallest aerosolizable volume able to deliver an effective dose of the compounds of the invention to the site of the infection. Additionally, the aerosolized formulation preferably does not impair negatively the functionality of the airways and does not cause undesirable side effects.

Aerosolization devices suitable for administration of aerosol Formulations of the invention include for example jet, vibrating porous plate, ultrasonic nebulizers and energized dry powder inhalers that are able to nebulize the Formulation of the invention into aerosol particle size predominantly in the size range of 1-5 pm. Predominantly in this application means that at least 70% but preferably more than 90% of all generated aerosol particles are in the 1 to 5 pm range. A jet nebulizer works by air pressure to break a liquid solution into aerosol droplets. Vibrating porous plate nebulizers work by using a sonic vacuum produced by a rapidly vibrating porous plate to extrude a solvent droplet through a porous plate. An ultrasonic nebulizer works by a piezoelectric crystal that shears a liquid into small aerosol droplets.

The concentration of the compounds according to this invention in the applied dosage form may vary widely depending on for example the dosage route. In general, the concentration of the present compound or embodiments thereof in the Formulation according to the present invention or embodiments thereof is from 1 to 70% by weight, based on the total weight of the Formulation. In some embodiments the concentration is from 1 to 50% by weight, or from 10 to 50% by weight. In other embodiments, the concentration is from 35 to 65% by weight, from 40 to 60% by weight, from 45 to 55% by weight, or about 50% by weight.

Preferred concentrations of the compound according to the present invention or embodiments thereof dissolved in drinking water are from 0.01 to 0.05% weight by volume, particularly 0.01 to 0.025%, and in-feed from 100 to 400 ppm (g/metric ton), particularly 100 to 200 ppm.

In a preferred embodiment of the invention or embodiments thereof the veterinary compositions of the present invention and/or embodiments thereof comprise a therapeutically effective amount of a compound of the present invention and/or embodiments thereof as the single active agent.

In a preferred embodiment of the invention or embodiments thereof the veterinary compositions of the present invention and/or embodiments thereof comprise a therapeutically effective amount of a compound of the present invention and/or embodiments thereof in combination with one or more other known active agents. These one or more other known active agent(s) may be of a similar spectrum as the present compound to synergistically enhance treatment of the infections covered by the spectrum of the present compound. Alternatively, these one or more other known active agent(s) may be of a different spectrum as the present compound, when multiple organisms are suspected in which another agent of a different spectrum may be required in addition to the present compound. The treatment can involve administering a composition having the present compound and one or more further known active agent(s) or administration of the inventive compounds followed by or preceded by administration of one or more additional active agent.

Further aspects regarding the Formulation of drugs and various excipients are found in for example Gennaro, A. R., et al., eds., Remington: The Science and Practice of Pharmacy (Lippincott Williams & Wilkins, $20^{th}$ Ed., 2000). Moreover, methods of Formulation are well known in the art and are disclosed for example in Remington: The Science and Practice of Pharmacy, Mack Publishing Company, Easton, Pa., $19^{th}$ Edition (1995).

As indicated above, the compound according to invention can be considered as an "active" agent, which is regarded as a substance that will inhibit the growth of helminths such as *Dirofilaria*, in particular *Dirofilaria immitis*. The term "inhibiting the growth" indicates that the rate of increase in the numbers of a population of a helminth is reduced.

In a preferred embodiment the compounds according to this invention are used to treat a helminth infection, such as an infection caused by one or more helminths selected from the group consisting of a) cestodes: e.g. *Anaplocephala* spp.; *Dipylidium* spp.; *Diphyllobothrium* spp.; *Echinococcus* spp.; *Moniezia* spp.; *Taenia* spp.; *b*) trematodes e.g. *Dicrocoelium* spp.; *Fasciola* spp.; *Paramphistomum* spp.; *Schistosoma* spp.; or *c*) nematodes, e.g. *Acanthocheilonema* spp.; *Ancylostoma* spp.; *Anecator* spp.; *Ascaridia* spp.; *Ascaris* spp.; *Brugia* spp.; *Bunostomum* spp.; *Capillaria* spp.; *Chabertia* spp.; *Cooperia* spp.; *Cyathostomum* spp.; *Cylicocyclus* spp.; *Cylicodontophorus* spp.; *Cylicostephanus* spp.; *Craterostomum* spp.; *Dictyocaulus* spp.; *Dipetalonema* spp; *Dirofilaria* spp.; *Dracunculus* spp.; *Enterobius* spp.; *Filaroides* spp.; *Habronema* spp.; *Haemonchus* spp.; *Heterakis* spp.; *Hyostrongylus* spp.; *Metastrongylus* spp.; *Meullerius* spp. *Necator* spp.; *Nematodirus* spp.; *Nippostrongylus* spp.; *Oesophagostomum* spp.; *Onchocerca* spp.; *Oncocercidae* spp; *Ostertagia* spp.; *Oxyuris* spp.; *Parascaris* spp.; *Stephanurus* spp.; *Strongylus* spp.; *Syngamus* spp.; *Toxocara* spp.; *Strongyloides* spp.; *Teladorsagia* spp.; *Toxascaris* spp.; *Trichinella* spp.; *Trichuris* spp.; *Trichostrongylus* spp.; *Triodontophorous* spp.; *Uncinaria* spp., *and/or Wuchereria* spp.; preferably nematodes; in particular *Dirofilaria* spp.; *Haemonchus* spp.; *Ascaridia* spp; *Strongylus* spp; especially *Dirofilaria immitis.*

It is understood that the term "treating" or "treatment" used herein includes prophylactic, metaphylactic and therapeutic treatment or curative treatment. Prophylactic or metaphylactic treatment, i.e. deworming, is commonly used to prevent helminth infection so to control parasitic infections in animals. In addition, helminths can infect humans and therefore pose a threat to human health as well. Prophylactic treatments comprise treatments which are done at regular intervals such as 1-6 times per year, or 2-4 times per year or 1-4 per month, or even continuous such as via the drinking water. Metaphylactic treatment comprise treatment of all animal e.g. in the same area, when a number of animals is diagnosed to prevent the spread of the parasite to the other animals. Metaphylactic and prophylactic treatment may also occur seasonal, e.g. when the vector is especially active.

In therapeutic or curative treatment the compounds are administered after clinical diagnosis. In this method, there is reduced expenses for anthelmintics, possibility of selection for resistance is significantly reduced if only some animals are treated and this will ensure the presence of a susceptible parasite population within the herd or flock, but its disadvantage is that, it requires regular monitoring which increases labour input.

The present invention provides the compounds according to the invention or the veterinary composition according to the present invention for use as a medicament. In a preferred embodiment the compounds according to the invention or the veterinary composition according to the present invention are suitable for use as a medicament for the treatment of helminth infection such as filariasis and in particular heartworm disease.

The compounds according to the present invention or the veterinary composition according to the present invention are used to make a medicament. In a preferred embodiment the compounds according to the present invention or the veterinary composition according to the present invention are used to make a medicament for the treatment of helminth infection such as filariasis and in particular heartworm disease.

Further, the invention provides the use of the compound according to the present invention or the veterinary composition according to the present invention for the manufacture of a medicament.

Further, the invention provides the use of the compounds of the present invention or the veterinary composition according to the present invention for the manufacture of a medicament for the treatment of helminth infection such as filariasis and in particular heartworm disease. Preferably, the compounds of the present invention or the veterinary composition according to the present invention are used for the manufacture of a medicament for the treatment of helminth infection such as filariasis and in particular heartworm disease.

Moreover, the present invention provides the compounds according to the present invention or the composition of the present invention for use in the treatment of disorders/diseases caused by helminths, preferably by one or more helminths selected from the group consisting of a) cestodes: *e.g. Anaplocephala* spp.; *Dipylidium* spp.; *Diphyllobothrium* spp.; *Echinococcus* spp.; *Moniezia* spp.; *Taenia* spp.; *b*) trematodes e.g. *Dicrocoelium* spp.; *Fasciola* spp.; *Paramphistomum* spp.; *Schistosoma* spp.; or *c*) nematodes, e.g. *Acanthocheilonema* spp.; *Ancylostoma* spp.; *Anecator* spp.; *Ascaridia* spp.; *Ascaris* spp.; *Brugia* spp.; *Bunostomum* spp.; *Capillaria* spp.; *Chabertia* spp.; *Cooperia* spp.; *Cyathostomum* spp.; *Cylicocyclus* spp.; *Cylicodontophorus* spp.; *Cylicostephanus* spp.; *Craterostomum* spp.; *Dictyocaulus* spp.; *Dipetalonema* spp; *Dirofilaria* spp.; *Dracunculus* spp.; *Enterobius* spp.; *Filaroides* spp.; *Habronema* spp.; *Haemonchus* spp.; *Heterakis* spp.; *Hyostrongylus* spp.; *Metastrongylus* spp.; *Meullerius* spp. *Necator* spp.; *Nematodirus* spp.; *Nippostrongylus* spp.; *Oesophagostomum* spp.; *Onchocerca* spp.; *Oncocercidae* spp; *Ostertagia* spp.; *Oxyuris* spp.; *Parascaris* spp.; *Stephanurus* spp.; *Strongylus* spp.; *Syngamus* spp.; *Toxocara* spp.; *Strongyloides* spp.; *Teladorsagia* spp.; *Toxascaris* spp.; *Trichinella* spp.; *Trichuris* spp.; *Trichostrongylus* spp.; *Triodontophorous* spp.; *Uncinaria* spp., *and/or Wuchereria* spp.; more preferably nematodes, in particular *Dirofilaria* spp.; *Haemonchus* spp.; *Ascaridia* spp; *Strongylus* spp and *Oesophagostomun dentatum*, especially *Dirofilaria immitis.*

In a preferred embodiment of the invention or embodiments thereof, the compounds according to the present invention or the composition of the present invention are for use in the treatment of helminth infection such as filariasis and in particular heartworm disease. In a preferred embodiment of the invention or embodiments thereof, the compounds according to the present invention or the composition of the present invention are for use in the treatment of disorders/diseases caused by helminths, wherein the helminths are *Dirofilaria* spp., more in particular *Dirofilaria repens* or *Dirofilaria immitis.*

In a preferred embodiment of the invention or embodiments thereof, the compounds according to the present invention or the composition of the present invention are for use in the treatment of haemonchosis. In a preferred embodiment of the invention or embodiments thereof, the compounds according to the present invention or the composition of the present invention are for use in the treatment of disorders/diseases caused by helminths, wherein the helminths are *Haemonchus* spp. and in particular *Haemonchus placei* and *Haemonchus contortus.*

In a preferred embodiment of the invention or embodiments thereof, the compounds according to the present invention or the composition of the present invention are for use in the treatment of ascaridiasis. In a preferred embodiment of the invention or embodiments thereof, the compounds according to the present invention or the composition of the present invention are for use in the treatment of disorders/diseases caused by helminths, wherein the helminths are *Ascaridia galli.*

In a preferred embodiment of the invention or embodiments thereof, the compounds according to the present invention or the composition of the present invention are for use in the treatment of oesophagostomiasis. In a preferred embodiment of the invention or embodiments thereof, the compounds according to the present invention or the composition of the present invention are for use in the treatment of disorders/diseases caused by helminths, wherein the helminths are *Oesophagostomum* spp. and in particular *Oesophagostomum venulosum* and *Oesophagostomum dentalum.*

In a preferred embodiment of the invention or embodiments thereof, the compounds according to the present invention or the composition of the present invention are for use in the treatment of *Trichostrongylus* infection. In a preferred embodiment of the invention or embodiments thereof, the compounds according to the present invention or the composition of the present invention are for use in the treatment of disorders/diseases caused by helminths, wherein the helminths are *Trichostrongylus* spp. and in particular *Trichostrongylus axei* and *Trichostrongylus colubriformis.*

In a preferred embodiment of the invention or embodiments thereof, the compounds according to the present invention or the composition of the present invention are for use in the treatment of Ostertagiosis. In a preferred embodiment of the invention or embodiments thereof, the compounds according to the present invention or the composition of the present invention are for use in the treatment of disorders/diseases caused by helminths, wherein the helminths are *Ostertagia* spp. and in particular *Ostertagia ostertagi.*

In a preferred embodiment of the invention or embodiments thereof, the compounds according to the present invention or the composition of the present invention are for use in the treatment of *Cooperia* infection. In a preferred embodiment of the invention or embodiments thereof, the compounds according to the present invention or the composition of the present invention are for use in the treatment of disorders/diseases caused by helminths, wherein the helminths are *Cooperia* spp. and in particular *Cooperia oncophora.*

In a preferred embodiment of the invention or embodiments thereof, the compounds according to the present invention or the composition of the present invention are for use in the treatment of Nematodiriasis. In a preferred embodiment of the invention or embodiments thereof, the compounds according to the present invention or the composition of the present invention are for use in the treatment of disorders/diseases caused by helminths, wherein the helminths are *Nematodirus* spp. and in particular *Nematodirus helvetianus, Nematodirus spathiger.*

It is contemplated that the compounds according to this invention and compounds corresponding to the use according to the invention may be used to treat animals, including humans and non-human animals, especially non-human mammals. Such non-human mammals include, for example, livestock mammals (e.g., swine, livestock ruminants like bovines, sheep, goats, etc.), laboratory mammals (e.g., mice, rats, jirds, etc.), companion mammals (e.g., dogs, cats, equines, etc.), and wild and zoo mammals (e.g., buffalo, deer, etc.). It is contemplated that the compounds also are suitable to treat non-mammals, such as poultry (e.g., turkeys, chickens, ducks, etc.) and fish (e.g., salmon, trout, koi, etc.).

In the following the use of the compounds as disclosed and covered by the general structures disclosed in this application for use in the treatment of helminth infection such as filariasis and in particular heartworm disease, especially if associated with *Dirofilaria*, in particular *Dirofilaria immitis*, is sometimes referred to as "use according to the invention".

It has been shown by the inventors that the compounds of the current invention as disclosed and defined earlier are especially suitable for the treatment of helminth infection such as filariasis and in particular heartworm disease, especially in dogs.

The compounds according to the present invention or the veterinary composition according to present invention are administered to treat or prevent disorders/diseases caused by one or more helminths selected from the group consisting of a) cestodes: e.g. *Acanthocheilonema* spp.; *Anaplocephala* spp.; *Dipylidium* spp.; *Diphyllobothrium* spp.; *Echinococcus* spp.; *Moniezia* spp.; *Taenia* spp.; *b*) trematodes e.g. *Dicrocoelium* spp.; *Fasciola* spp.; *Paramphistomum* spp.; *Schistosoma* spp.; or *c*) nematodes, e.g. *Ancylostoma* spp.; *Anecator* spp.; *Ascaridia* spp.; *Ascaris* spp.; *Brugia* spp.; *Bunostomum* spp.; *Capillaria* spp.; *Chabertia* spp.; *Cooperia* spp.; *Cyathostomum* spp.; *Cylicocyclus* spp.; *Cylicodontophorus* spp.; *Cylicostephanus* spp.; *Craterostomum* spp.; *Dictyocaulus* spp.; *Dipetalonema* spp; *Dirofilaria* spp.; *Dracunculus* spp.; *Enterobius* spp.; *Filaroides* spp.; *Habronema* spp.; *Haemonchus* spp.; *Heterakis* spp.; *Hyostrongylus* spp.; *Metastrongylus* spp.; *Meullerius* spp. *Necator* spp.; *Nematodirus* spp.; *Nippostrongylus* spp.; *Oesophagostomum* spp.; *Onchocerca* spp.; *Oncocercidae* spp; *Ostertagia* spp.; *Oxyuris* spp.; *Parascaris* spp.; *Stephanurus* spp.; *Strongylus* spp.; *Syngamus* spp.; *Toxocara* spp.; *Strongyloides* spp.; *Teladorsagia* spp.; *Toxascaris* spp.; *Trichinella* spp.; *Trichuris* spp.; *Trichostrongylus* spp.; *Triodontophorous* spp.; *Uncinaria* spp., *and/or Wuchereria* spp.; more preferably nematodes, in particular *Dirofilaria* spp.; *Haemonchus* spp.; *Ascaridia* spp; *Strongylus* spp and *Oesophagostomun dentatum*, especially *Dirofilaria immitis*.

In particular, the compounds according to the present invention or the veterinary composition according to present invention are administered to treat or prevent disorders/diseases caused by one or more helminths selected from the group consisting of a) Cestodes such as *Monezia expansa*; b) Trematodes such as *Fasciola hepatica, Fascioloides magna, Dicrocoelium dentriticum, Paramphistomum cervi*; and c) nematodes: *Ostertagia ostertagi, Cooperia oncophora, Cooperia punctata, Trichostrongylus axei, Haemonchus placei, Haemonchus contortus, Nematodirus helvetianus, Nematodirus spathiger, Trichostrongylus colubriformis, Trichostrongylus circumcincta, Oesophagostomum venulosum, Chabertia ovina, Dictyocaulus viviparous, Dictyocaulus filaria, Dirofilaria immitis, Dirofilaria repens.*

More preferably, compounds according to the present invention or the veterinary composition according to present invention are administered to treat or prevent infection with helminths such as filariasis and in particular heartworm disease.

The term "treatment" as used herein refers to reversing, alleviating, inhibiting the progress of a disease, disorder or condition. In case of the helminth infection such as filariasis and in particular heartworm disease, this means that the clinical symptoms (reduced function of lung, heart, liver and/or kidney) are alleviated.

Thus, the invention provides a method of treating a disease caused by helminths such as nematodes which comprises administering to an animal, in particular a dog, a therapeutically effective amount of a compound according to the present invention or the composition according to the present invention. In other words, the invention provides a method of treating helminth infection such as filariasis and in particular heartworm disease comprising administering a therapeutically effective amount of a compound according to the invention or the composition according to the present invention to a mammal, in particular a dog, in need thereof.

The invention is also directed to a method for treating an animal with diseases caused by a nematode comprising administering to the subject in need thereof an effective amount of a compound according to the present invention or a composition according to the present invention and/or embodiments thereof, wherein the nematode is at least one selected from the group of *Dirofilaria*, in particular *Dirofilaria immitis*. Suitably the subject is a mammal, in particular a dog or a cat, especially a dog.

The invention is also directed to a method for treating a mammal, preferably a dog, suffering from a disease caused by a helminth, in particular a nematode, comprising administering to the subject in need thereof an effective amount of a compound according the present invention or the composition according to the present invention and/or embodiments thereof, wherein the nematode is at least one selected from the group of *Dirofilaria*, in particular *Dirofilaria immitis.*

In a preferred embodiment the compounds according to this invention are used to treat a disease caused by helminths such as nematodes in an animal, wherein the nematode is at least one of helminths such as *Dirofilaria*, in particular *Dirofilaria immitis*, comprising administering an effective amount of a compound according to the invention to the animal in need thereof.

According to the treatment by the compounds of the present invention and/or embodiments thereof, diseases caused by helminths, in particular nematodes, especially *Dirofilaria*, more especially *Dirofilaria immitis*, are treated or prevented in a mammal, in particular a dog, by administering to the animal a therapeutically effective amount of a compound of the invention in such amounts and for such time as is necessary to achieve the desired result.

A "therapeutically effective amount" of a compound of the invention and/or embodiments thereof means a sufficient amount of the compound according to the present invention or the composition according to the present invention for treating helminth infection such as filariasis and in particular heartworm disease, at a reasonable benefit/risk ratio applicable to any medical treatment. It will be understood, however, that the total daily usage of a compound according to the invention and a composition according to present invention will be decided by the attending physician or veterinary doctor within the scope of sound medical judgment. The specific therapeutically effective dose level for any particular animal will depend on a variety of factors including the disorder being treated and the severity of the disorder; the activity of the specific compound employed; the specific composition employed; the age, body weight, general health, sex and diet of the animal; the time of administration, route of administration, and rate of excretion of the specific compound employed; the duration of the treatment; drugs used in combination or coincidental with the specific compound employed; and like factors well known in the medical arts.

When the compound according to this invention is administered orally or parenterally by subcutaneous injection, the total dose is preferably greater than about 0.001 mg/kg (i.e. 0.001 milligram of compound according to this invention per kilogram body weight of the treated animal). In some such embodiments, the total dose is from about 0.001 to about 200 mg/kg, from about 0.01 to about 20 mg/kg, from about 0.1 to about 10 mg/kg or from about 1 to about 20 mg/kg. The same dose range may be suitable for other dosage routes. The desired dose, however, may be less in some instances where the compound according to this invention is administered intravenously.

The dose used to control diseases caused by *Dirofilaria immitis* might vary with the compound, the severity of the disease and the age, weight, and condition of the animal, in particular the dog. The total dose required for several days' protection will generally, however, be in the range of from about 0.1 to about 200 mg/kg bodyweight, and preferably will be in the range of from about 1 to about 100 mg/kg. Protection for up to about seven days can be provided by a single injection; the length of protection will depend on the dose given. The total dose can also be divided into smaller doses given at intervals, such as once daily for two to seven days. Obviously, other suitable dosage regimens can be constructed.

Especially preferred is the use of the compounds according to the present invention or the composition according to the present invention in dogs. The compounds according to the present invention or the composition according to the present invention can be used in animals of different weight, including animals of a weight higher than 35 kg.

Other exemplary animals that can be treated with the compounds according to the present invention or the composition according to the present invention are smaller pets such as cats. In one embodiment the compounds according to the present invention or the composition according to the present invention are used to treat diseases such as severe lung disease, heart failure and damage to other inner organs caused by *Dirofilaria*, more especially *Dirofilaria immitis*.

In one embodiment, the animal that is treated is a dog and the disease that is treated is helminth infection such as filariasis and in particular heartworm disease.

In a preferred embodiment of the invention or embodiments thereof a single administration of a composition according to this invention is sufficient to treat a disease caused by nematode, in particular *Dirofilaria immitis*, or at least to diminish the clinical symptoms in the diseased animal. This can be called "one shot" administration. Although the administration of such a "one shot" single dose is very suitable, it is contemplated that multiple doses can be used, e.g. two administrations 12-24 hours apart or alternatively two administrations 48-72 hours apart.

Protection is preferably for at least 7 days, more preferably for at least 10 days, more preferably for at least 2 weeks, more preferably for at least 3 weeks, more preferably for at least 4 weeks. The protection is for 1, 2, 3, 4, 5, 6, 7, 8, 9, 10, 11, 12, 13, 14, 15, 16, 17, 18, 19, 20 weeks or more. Preferably the protection is for at least 1, 2, 3, 4, 5, 6, 7, 8, 9, 10, 11, or 12 months or more.

Factors affecting the preferred dosage may include for example the disease to be treated, the type (e.g. species and breed), age, size, sex, diet, activity and condition of the of the diseased animal, the dosage route, pharmacological considerations such as the activity, efficacy, pharmacokinetic, and toxicology profiles of the particular compound according to the present invention and the composition administered and whether the compound according to the present invention is administered as part of a combination of active ingredients. Thus, the preferred amount of the compound according to this invention can vary and can therefore deviate from the typical dosages set forth above. Determining such dosage adjustments is generally within the skill of those in the art. The effective dosage will vary; for example, for prophylactic treatment relatively low doses would be administered over an extended time. The Formulation type selected for a dosage form in any instance will depend on the particular purpose envisaged and the physical, chemical and biological properties of the compound according to this invention.

The veterinary compositions, the uses as medicament and uses in the treatment of diseases caused by helminths, in particular nematodes, especially *Dirofilaria immitis*, and methods according to the present invention encompass methods wherein a compound according to this invention is the sole active ingredient administered to the recipient animal. It is contemplated, however, that the veterinary compositions, the uses as medicament and uses in the treatment of diseases caused by helminths such as nematodes, in particular *Dirofilaria immitis*, and methods according to the present invention also encompass combination therapies wherein a compound is administered in combination with one or more other pharmaceutically acceptable active ingredients. The other active ingredient(s) may be, for example, one or more other compounds according to this invention. Alternatively (or additionally), the other active ingredient(s) may be one or more pharmaceutically acceptable compounds that are not compounds according to this invention. The other active ingredient(s) may target the same and/or different diseases or conditions.

Contemplated active ingredient(s) that may be administered in combination with the compounds according to the present invention include, for example, antibacterials, anti-inflammatories, pharmaceutically acceptable anthelmintics, insecticides and acaricides, insect growth regulators, hormones, immunostimulants, dermatological preparations (e.g. antiseptics and disinfectants) and immunobiologicals (e.g. vaccines and antisera) for disease prevention.

Particular combinations comprise a) one or more compounds according to this invention with b) one or more pharmaceutically acceptable active compounds which differ in structure from component a). The active compounds b) are preferably anthelmintic compounds, more preferably selected from the group consisting of avermectins (e.g., ivermectin, selamectin, doramectin, abamectin, emamectin and eprinomectin); milbemycins (moxidectin and milbemycin oxime); pro-benzimidazoles (e.g., febantel, netobimin, and thiophanate); benzimidazole derivatives, such as a thiazole benzimidazole derivative (e.g., thiabendazole and cambendazole) or a carbamate benzimidazole derivatives (e.g., fenbendazole, albendazole (oxide), mebendazole, oxfendazole, parbendazole, oxibendazole, flubendazole, and triclabendazole); an imidazothiazole (e.g., levamisole and tetramisole); a tetrahydropyrimidine (morantel and pyrantel), organophosphates (e.g., trichlorphon, haloxon, dichlorvos, and naphthalophos); salicylanilides (e.g., closantel, oxyclozanide, rafoxanide, and niclosamide); nitrophenolic compounds (e.g., nitroxynil and nitroscanate); benzenedisulphonamides (e.g., clorsulon); pyrazineisoquinolines (e.g., praziquantel and epsiprantel); heterocyclic compounds (e.g., piperazine, diethylcarbamazine, dichlorophen, and phenothiazine); arsenicals (e.g., thiacetarsamide, melorsamine, and arsenamide); cyclooctadepsipeptides (e.g., emodepside, PF1022A); paraherquamides (e.g., derquantel, paraherquanide); and amino-acetonitrile compounds (e.g. monepantel, AAD 1566); tribendimidine (amidine compound); amidine compounds (e.g., amidantel and tribendimidin), including all pharmaceutically acceptable forms, such as salts, solvates or N-oxides.

The compounds as described in this specification can be combined with pharmaceutically acceptable insecticides or acaricides. Such pharmaceutically acceptable insecticides and acaricides include, for example, acetamiprid, acetoprole, amitraz, amidoflumet, avermectin, azadirachtin, bifenthrin, bifenazate, broflanilide, buprofezin, bistrifluron, chlorfenapyr, chlorfluazuron, chlorantraniliprole, chlorpyrifos, chromafenozide, clothianidin, cyantraniliprole, cyflumetofen, 13-cyfluthrin, cyhalothrin, Acyhalothrin, cymiazole cypermethrin, cyromazine, deltamethrin, demiditraz, diafenthiuron, diazinon, diflubenzuron, dimefluthrin, dinotefuran, emamectin, esfenvalerate, ethiprole, fenoxycarb, fenpropathrin, fenvalerate, fipronil, flonicamid, flubendiamide, flucythrinate, tau-fluvalinate, flufenoxuron, halofenozide, hexaflumuron, imidacloprid, indoxacarb, lufenuron, metaflumizone, methoprene, metofluthrin, methoxyfenozide, nitenpyram, novaluron, noviflumuron, permethrin, phosmet, profluthrin, protrifenbute, pymetrozine, pyrafluprole, pyrethrin, pyridalyl, pyrifluquinazon, pyriprole, pyriproxyfen, rotenone, ryanodine, sisapronil, spinetoram, spinosad, spirodiclofen, spiromesifen, spirotetramat, sulfoxaflor, tebufenozide, tebufenpyrad, teflubenzuron, tefluthrin, tetrachlorvinphos, tetramethylfluthrin, thiacloprid, thiamethoxam, tigolaner, tolfenpyrad, tralomethrin, and triflumuron. General references discussing antiparasitic agents, such as insecticides and acaricides, include, for example, The Pesticide Manual, 18th Edition, J. A. Turner, Ed., British Crop Protection Council Publications, U.K. (2018).

The compounds as described in this specification can be combined with pharmaceutically acceptable insect growth regulators. Such pharmaceutically acceptable insect growth regulators include, for example, methoprene, pyriproxyfen, tetrahydroazadirachtin, chlorfluazuron, cyromazine, diflubenzuron, fluazuron, flucycloxuron, flufenoxuron, hexaflumuron, lufenuron, ifenuron, tebufenozide, and triflumuron. These compounds tend to provide both initial and sustained treatment of parasite infections at all stages of insect development, including eggs, on the animal subject, as well as within the environment of the animal subject.

The compounds as described in this specification can be combined with pharmaceutically acceptable anti-protozoals. Such pharmaceutically acceptable anti-protozoals include, for example, triazintriones like, for example, toltrazuril and ponazuril and triazindiones such as clazuril, diclazuril and letrazuril. In some contemplated embodiments, the compounds are administered with dihydroazole compounds, such as, for example, compounds discussed in WO 2010/75591.

In some contemplated embodiments, the compounds of the present invention are administered with anthelminic proteins, such as, for example *Bacillus thuringensiscrystal* proteins e.g. described in WO 2010/053517.

In some contemplated embodiments, the compounds are administered with pyridylmethylamine derivatives, such as, for example, pyridylmethylamine derivatives discussed in EP0539588 WO 2007/115643.

In some contemplated embodiments, the compounds is administered with nodulisporic acids and derivatives thereof, such as, for example, compounds discussed in U.S. Pat. Nos. 5,399,582; 5,945,317; 5,962,499; 5,834,260; 6,221,894; or U.S. Pat. No. 5,595,991; or WO 96/29073.

In some contemplated embodiments, the compounds are administered with isoxazoline compounds (e.g., sarolaner, fluralaner, lotilaner, afoxolaner, fluxametamide, isocycloseram) Other antiparasitic compounds contemplated to be useful in combination therapies with the compounds include, for example, imidazo[1,2-b] pyridazine compounds discussed in US 2005/0182059; 1-(4-Mono and dihalomethylsulphonylphenyl)-2-acylamino-3-fluoropropanol compounds discussed U.S. Pat. No. 7,361,689; trifluoromethanesulfonanilide oxime ether compounds discussed in U.S. Pat. No. 7,312,248; n-[(phenyloxy)phenyl]-1,1,1-trifluoromethanesulfonamide and n-[(phenylsulfanyl)phenyl]-1,1,1-trifluoromethanesulfonamide compounds discussed in US 2006/0281695; and 2-phenyl-3-(1H-pyrrol-2-yl)acrylonitrile compounds discussed in US 2006/0128779; azole compounds discussed in WO 2017/192385, WO 2019/170626, WO 2019/197468, WO 2019/201835, WO 2019/206799, WO 2019/215198, WO 2020/053364, WO 2020/053365, WO 2020/070049, WO 2020/079198, WO 2020/094363, WO 2020/169445, WO 2020/193341, WO 2020/201079, WO 2020/201398, WO 2020/208036, WO 2020/212235, and WO 2020/219871.

Features of the invention have been described in embodiments in the present application; however, for brevity not all combinations of the features are literally described. Combinations of features as described above are, however, expressly considered to be part of the invention.

Experimental Part

Analytics—HPLC Methods

Method 1

Chromatographic System:

Column: Xbridge BEH C18 Waters, 2.1×50 mm, 2.5μ

Oven: 40° C.

Eluents: Solvent A: water/$HCO_2H$ (0.05%); Solvent B: acetonitrile/$HCO_2H$ (0.05%)

Flow: 0.8 ml/min

Gradient:

| Time [min] | Solvent A [%] | Solvent B [%] |
|---|---|---|
| 0.0 | 98 | 2 |
| 1.2 | 0 | 100 |
| 1.7 | 0 | 100 |
| 2.2 | 98 | 2 |

Run time: 2.2 min+0.5 min equilibration time

Method—2

Chromatographic System:

Column: Xbridge BEH C18 Waters, 2.1×50 mm, 2.5μ

Oven: 40° C.

Eluents: Solvent A: water/$NH_3$ (0.1%); Solvent B: acetonitrile

Flow: 0.8 ml/min

Gradient:

| Time [min] | Solvent A [%] | Solvent B [%] |
|---|---|---|
| 0.0 | 98 | 2 |
| 1.2 | 0 | 100 |
| 1.7 | 0 | 100 |
| 1.8 | 98 | 2 |

Run time: 2.2 min+0.5 min equilibration time

Method—3

Chromatographic System:

Column: Xbridge BEH Phenyl Waters, 2.1×50 mm, 2.5μ

Oven: 40° C.

Eluents: Solvent A: water/$HCO_2H$ (0.05%); Solvent B: acetonitrile/$HCO_2H$ (0.05%)

Flow: 0.8 ml/min

Gradient:

| Time [min] | Solvent A [%] | Solvent B [%] |
|---|---|---|
| 0.0 | 98 | 2 |
| 1.2 | 0 | 100 |
| 1.7 | 0 | 100 |
| 1.8 | 98 | 2 |

Run time: 2.2 min+0.5 min equilibration time

Method—4

Chromatographic System:

Column: Poroshell HPH-C18, 3×50 mm, 2.7 μm

Oven: 40° C.

Eluents: Solvent A: water/$NH_4CO_3$ (5 mM); Solvent B: acetonitrile

Flow: 1.2 ml/min

Gradient:

| Time [min] | Solvent A [%] | Solvent B [%] |
|---|---|---|
| 0.0 | 50 | 50 |
| 3.5 | 5 | 95 |
| 4.8 | 5 | 95 |
| 4.9 | 50 | 50 |

Run time: 4.9 min+0.3 min equilibration time

Method—5

Chromatographic System:

Column: Poroshell HPH-C18, 3×50 mm, 2.7 μm

Oven: 40° C.

Eluents: Solvent A: water/$NH_4CO_3$ (5 mM); Solvent B: acetonitrile

Flow: 1.2 ml/min

Gradient:

| Time [min] | Solvent A [%] | Solvent B [%] |
|---|---|---|
| 0.0 | 50 | 50 |
| 2.1 | 5 | 95 |
| 2.7 | 5 | 95 |
| 2.75 | 50 | 50 |

Run time: 2.75 min+0.25 min equilibration time

Method—6

Chromatographic System:

Column: Poroshell HPH-C18, 3×50 mm, 2.7 μm

Oven: 40° C.

Eluents: Solvent A: water/$NH_4CO_3$ (5 mM); Solvent B: acetonitrile

Flow: 1.2 ml/min

Gradient:

| Time [min] | Solvent A [%] | Solvent B [%] |
|---|---|---|
| 0.0 | 90 | 10 |
| 2.0 | 5 | 95 |
| 2.7 | 5 | 95 |
| 2.75 | 90 | 10 |

Run time: 2.75 min+0.25 min equilibration time

Method—7

Chromatographic System:

Column: Shim-pack XR-ODS, 3×50 mm, 2.2 μm

Oven: 40° C.

Eluents: Solvent A: water/TFA (0.05%); Solvent B: acetonitrile/TFA (0.05%)

Flow: 1.2 ml/min

Gradient:

| Time [min] | Solvent A [%] | Solvent B [%] |
|---|---|---|
| 0.0 | 50 | 50 |
| 3.2 | 0 | 100 |
| 4.8 | 0 | 100 |
| 4.9 | 50 | 50 |

Run time: 4.9 min+0.3 min equilibration time

Method—8

Chromatographic System:

Column: Shim-pack XR-ODS, 3×50 mm, 2.2 μm

Oven: 40° C.

Eluents: Solvent A: water/TFA (0.05%); Solvent B: acetonitrile/TFA (0.05%)

Flow: 1.2 ml/min

Gradient:

| Time [min] | Solvent A [%] | Solvent B [%] |
|---|---|---|
| 0.0 | 60 | 40 |
| 3.2 | 0 | 100 |
| 4.8 | 0 | 100 |
| 4.9 | 95 | 5 |

Run time: 4.9 min+0.3 min equilibration time

Method—9

Chromatographic System:

Column: Shim-pack XR-ODS, 3×50 mm, 2.2 μm

Oven: 40° C.

Eluents: Solvent A: water/TFA (0.05%); Solvent B: acetonitrile/TFA (0.05%)

Flow: 1.2 ml/min

Gradient:

| Time [min] | Solvent A [%] | Solvent B [%] |
|---|---|---|
| 0.0 | 95 | 5 |
| 2.0 | 0 | 100 |
| 2.7 | 0 | 100 |
| 2.75 | 95 | 5 |

Run time: 2.75 min+0.25 min equilibration time

Method—10

Chromatographic System:

Column: Kinetex, EVO C18 100 A, 3×50 mm, 2.7 μm

Oven: 40° C.

Eluents: Solvent A: water/$NH_4CO_3$ (5 mM); Solvent B: acetonitrile

Flow: 1.2 ml/min

Gradient:

| Time [min] | Solvent A [%] | Solvent B [%] |
|---|---|---|
| 0.0 | 70 | 30 |
| 3 | 30 | 70 |
| 4 | 5 | 95 |
| 4.8 | 5 | 95 |
| 4.9 | 90 | 10 |

Run time: 4.9 min+0.3 min equilibration time

Method—11

Chromatographic System:

Column: Kinetex, EVO C18 100 A, 3×50 mm, 2.7 μm

Oven: 40° C.

Eluents: Solvent A: water/$NH_4CO_3$ (5 mM); Solvent B: acetonitrile

Flow: 1.2 ml/min

Gradient:

-continued

| Time [min] | Solvent A [%] | Solvent B [%] |
|---|---|---|
| 0.0 | 90 | 10 |
| 2.0 | 5 | 95 |
| 2.7 | 5 | 95 |
| 2.75 | 90 | 10 |

Run time: 2.75 min+0.25 min equilibration time

Method—12

Chromatographic System:

Column: Kinetex, XB C18, 3×50 mm, 2.6 μm

Oven: 40° C.

Eluents: Solvent A: water/TFA (0.05%); Solvent B: acetonitrile/TFA (0.05%)

Flow: 1.2 ml/min

Gradient:

| Time [min] | Solvent A [%] | Solvent B [%] |
|---|---|---|
| 0.0 | 95 | 5 |
| 2 | 0 | 100 |
| 2.7 | 0 | 100 |
| 2.75 | 95 | 5 |

Run time: 2.75 min+0.25 min equilibration time

Method—13

Chromatographic System:

Column: Halo C18, 3×30 mm, 2 μm

Oven: 40° C.

Eluents: Solvent A: water/TFA (0.05%); Solvent B: acetonitrile/TFA (0.05%)

Flow: 1.5 ml/min

Gradient:

| Time [min] | Solvent A [%] | Solvent B [%] |
|---|---|---|
| 0.0 | 95 | 5 |
| 2.5 | 5 | 95 |
| 2.8 | 5 | 95 |
| 2.81 | 95 | 5 |

Run time: 2.81 min+0.19 min equilibration time

General Synthetic Procedures

The compounds of Formula (I) can be synthesized as shown in Scheme 1 below:

Scheme 1

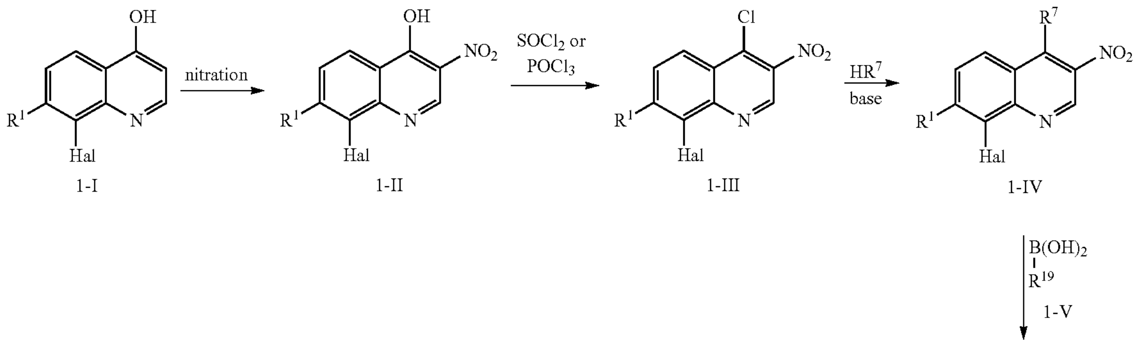

1-I 1-II 1-III 1-IV

1-V

-continued

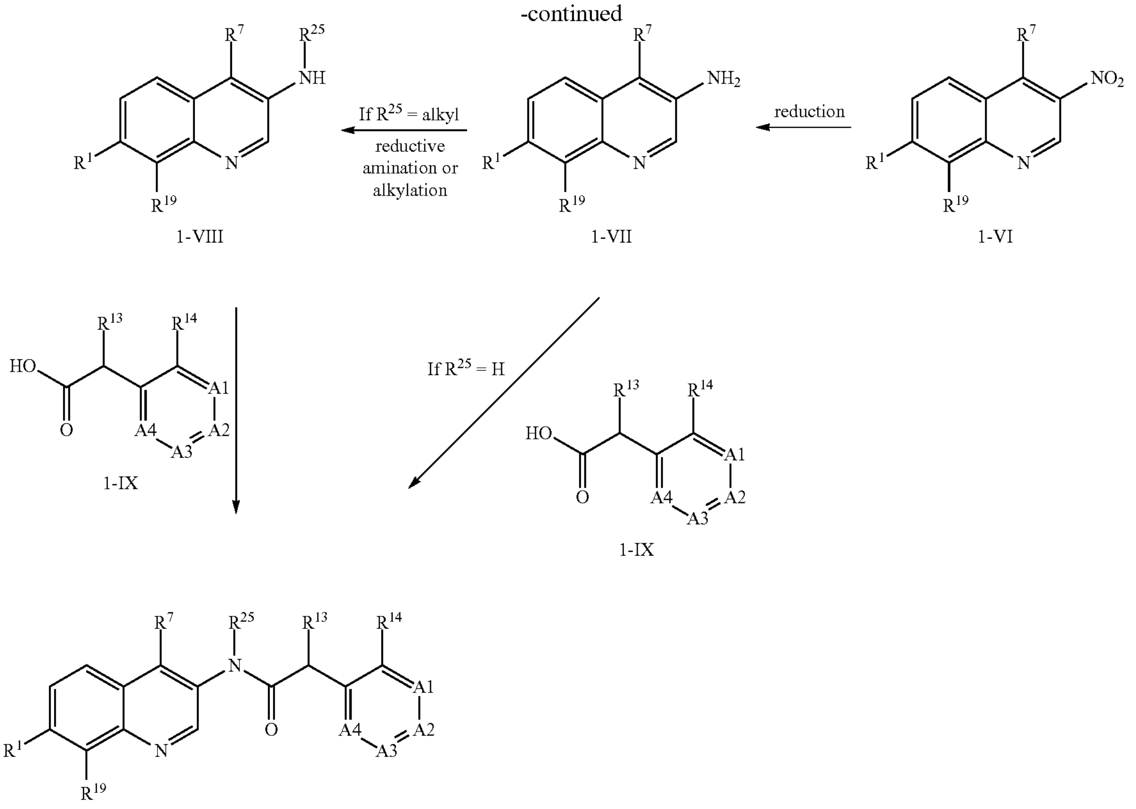

1-VIII 1-VII 1-VI

1-IX 1-IX

1-X

A quinoline compound 1-I is nitrated to obtain the 3-nitro derivative 1-IT. Quinolines are commercially available or can be synthesized as described in, for example, Volume E7a part 1 of *Methods of Organic Chemistry* (*Houben-Weyl*), $4^{th}$ edition, Stuttgart-New York 1991. Nitration can be performed by heating with nitric acid in a suitable solvent like an organic, high-boiling acid as described in Journal of Medicinal Chemistry, 48(10), 3481-3491, 2005. Chlorination by heating with thionyl chloride or phosphoryl chloride gives the 4-chloro compound 1-III. Nucleophilic displacement of chloro by a nucleophile HR in presence of base gives 1-IV. Nucleophiles like amines can be introduced in the presence of an amine base like triethylamine or EDIPA, alcohols can be introduced with a stronger base like sodium alkoxide. Suzuki coupling with an aryl or hetaryl boronic acid 1-V gives 1-VI as described in Tetrahedron 58(48), 9633-9695, 2002. Reduction of the nitro group can be achieved by hydrogenation using a catalyst like platinum on charcoal. In case that the amide nitrogen in Formula (I) is alkylated, the alkyl group can be introduced by reductive alkylation of the amino compound 1-VII with an aldehyde and a reducing agent as described in Eur. J. Med. Chem 127, 2017, 509-520 or by alkylation with an alkylhalide as described in Bioorg. Med. Chem. Lett. 2006, 16(13), 3484-3488 to give the alkylated amino compound 1-VIII. Acylation of 1-VII or 1-VIII with a carboxylic acid 1-IX gives the amide 1-X under conditions as described in, for example volume E22a of *Methods of Organic Chemistry* (*Houben-Weyl*), *Synthesis of Peptides and Peptidomimetics*, 4th edition, Georg Thieme Verlag, Stuttgart—New York, 2002.

Alternatively, compounds of Formula I, for example where $R^7$ is an alkyl or alkenyl group, can be synthesized as shown in scheme 2.

Scheme 2

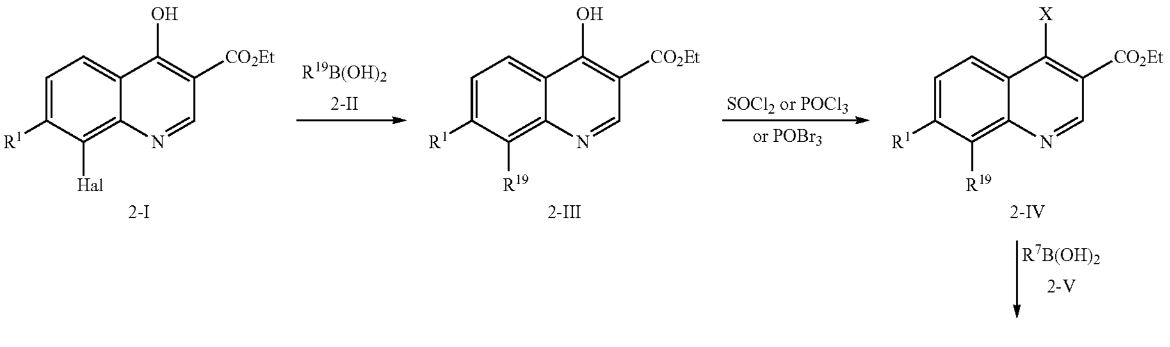

2-I 2-III 2-IV

-continued

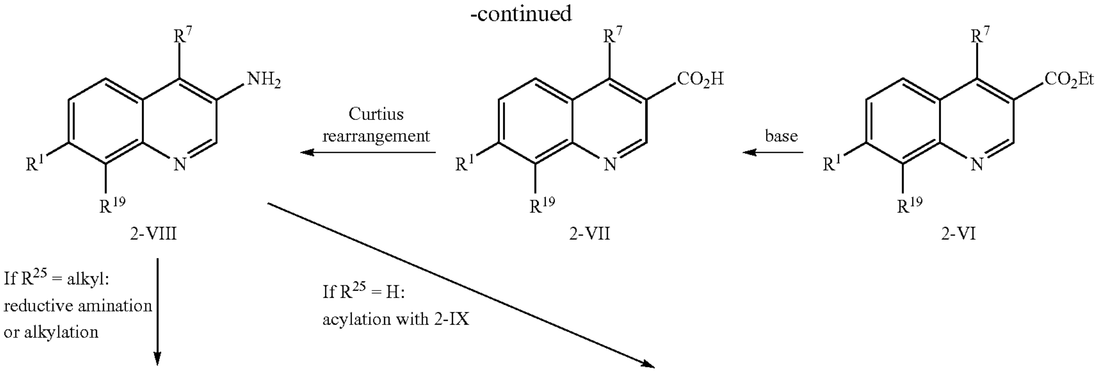

2-VIII 2-VII 2-VI

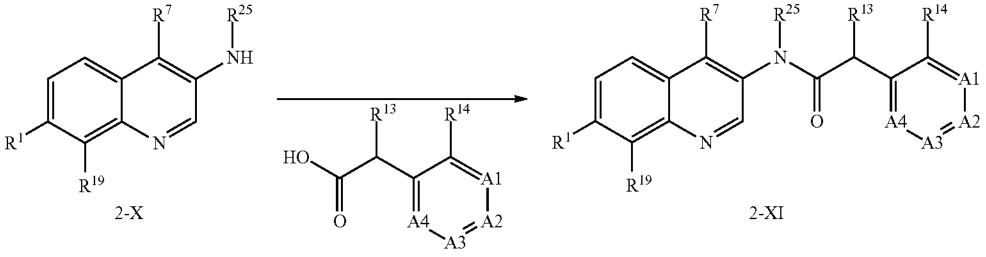

2-X 2-IX 2-XI

A quinoline carboxylic ester 2-I is coupled with a boronic acid 2-II to form the biaryl compound 2-III. As an alternative to the free boronic acid 2-II an analogous boronic ester might be used, for example a pinacolo ester. Quinoline esters 2-I are known or can be synthesized as described in, for example, WO2018/087036. Halogenation of 2-III with sulfonyl chloride or phosphoryl chloride gives the 4-chloroquinoline ester 2-IV (the analogous 4-bromide can be obtained by employing phosphoryl bromide). The halogen can be substituted with an alkyl boronic acid 2-V to give the 4-alkylquinoline 2-VI as described in ChemMedChem, 2014, 9(4), 719-723. Base hydrolysis leads to the carboxylic acid 2-VII that can be subjected to a Curtius rearrangement to give the amino compound 2-VIII as described in, for example, Eur. J. Med. Chem. 2017, 127, 509-520 or in Synthesis, 1983, 38-40. In case that the amide nitrogen in Formula (I) is alkylated, the alkylgroup can be introduced by reductive alkylation of the amino compound 2-VIII with an aldehyde and a reducing agent as described in Eur. J. Med. Chem 127, 2017, 509-520 or by alkylation with an alkylhalide as described in Bioorg. Med. Chem. Lett. 2006, 16(13), 3484-3488 to give the alkylated amino compound 2-X. Acylation of 2-VIII or 2-X with a carboxylic acid 2-IX gives the amide 2-X under conditions as described in, for example volume E22a of *Methods of Organic Chemistry* (*Houben-Weyl*), *Synthesis of Peptides and Peptidomimetics*, $4^{th}$ edition, Georg Thieme Verlag, Stuttgart—New York, 2002.

Synthetic Procedures—Specific Compounds

Synthesis of N-(8-(2,3-dichlorophenyl)-4-morpholinoquinolin-3-yl)chromane-4-carboxamide (example 83)

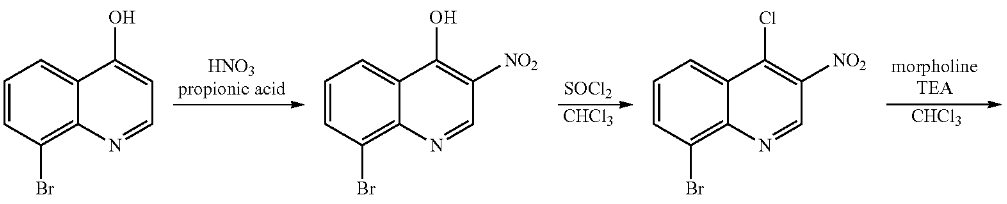

-continued

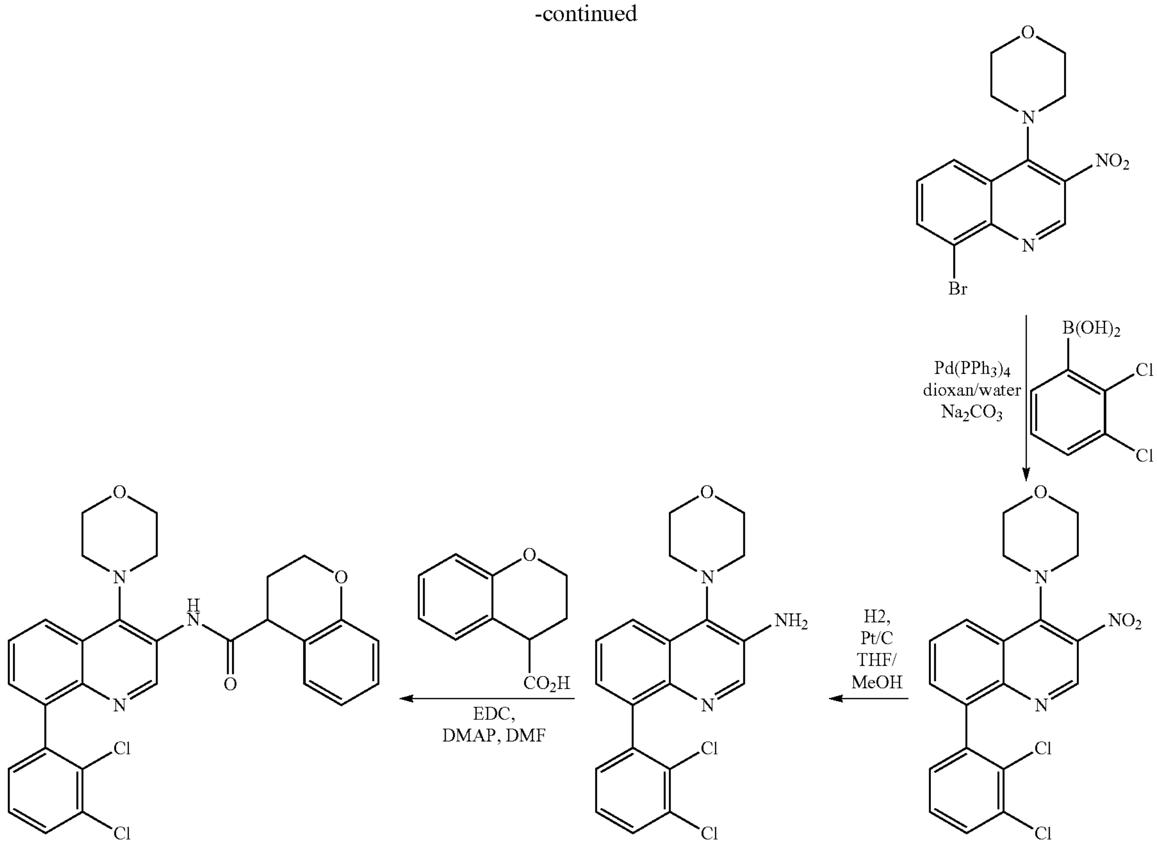

1. 8-Bromo-3-nitroquinolin-4-ol

8-Bromoquinolin-4-ol (1 g, 4.46 mmol) was added to propionic acid (10 ml) and the mixture was heated to 125° C. At this temperature nitric acid (0.675 ml, 9.82 mmol) was added dropwise and the heating was continued for 2.5 h. The mixture was cooled to ambient temperature, diluted with ethanol and the precipitate was isolated by filtration. It was washed with water and ethanol, dried overnight at reduced pressure at 50° C. to yield 502 mg of a solid (42% yield).

2. 8-Bromo-4-chloro-3-nitroquinoline

8-Bromo-3-nitroquinolin-4-ol (502 mg, 1.866 mmol) was added to chloroform (10 ml). DMF (0.159 ml, 2.052 mmol) was added followed by dropwise addition of thionyl chloride (0.150 ml, 2.052 mmol). After the addition was complete, the mixture was stirred at reflux for 2.5 h, cooled to ambient temperature and used directly in the next step.

3. 4-(8-Bromo-3-nitroquinolin-4-yl)morpholine

The mixture of step 2. was cooled to −15° C., TEA (0.390 ml, 2.80 mmol) and morpholine (0.247 ml, 2.84 mmol) were added with stirring. After 2 minutes the cooling bath was removed and the mixture was stirred at reflux for 45 minutes. The mixture was cooled to ambient temperature, the solvent evaporated under reduced pressure, the residue was taken up in water and the precipitate was isolated by filtration, washed with water and dried over the weekend under reduced pressure at 50° C. to yield 595 mg of a solid (94% yield, 2 steps). MS (ESI) 340.0 $[M+H]^+$.

4. 4-(8-(2,3-dichlorophenyl)-3-nitroquinolin-4-yl)morpholine 4-(8-Bromo-3-nitroquinolin-4-yl)morpholine (595 mg, 1.760 mmol), (2,3-dichlorophenyl)boronic acid (436 mg, 2.287 mmol) and $Pd(Ph_3P)_4$ (122 mg, 0.106 mmol) were placed in a flask, evaporated and back-filled three times with argon. Dioxane (14 ml) and sodium carbonate (559 mg, 5.28 mmol) dissolved in water (4 ml) were added and the mixture was purged with argon. The mixture was stirred at 100° C. for 90 min, concentrated under reduced pressure and the residue was purified by chromatography (silica, n-pentan/EtOAc) yielding 734 mg of a solid (98% yield).

5. 8-(2,3-Dichlorophenyl)-4-morpholinoquinolin-3-amine

To 4-(8-(2,3-Dichlorophenyl)-3-nitroquinolin-4-yl)morpholine (734 mg, 1.725 mmol) was added MeOH (10 ml) and THE (10.00 ml) followed by platinum on carbon (67.3 mg, 0.017 mmol). The flask was closed with a septum, and the slurry was stirred under an atmosphere of hydrogen for three hours. The mixture was filtered through a pad of celite, the solid was washed sequentially with MeOH, MeOH/DCM and THF. The combined filtrates were concentrated under reduced pressure and the residue was purified by chromatography (silica, DCM/EtOAc) to yield 282 mg of a solid (44% yield).

6. N-(8-(2,3-Dichlorophenyl)-4-morpholinoquinolin-3-yl)chromane-4-carboxamide 8-(2,3-Dichlorophenyl)-4-morpholinoquinolin-3-amine (60 mg, 0.16 mmol), chromane-4-carboxylic acid (29 mg, 0.16 mmol), EDC (46 mg, 0.24 mmol) and DMAP (10 mg, 0.08 mmol) were placed in a vial, DMF (1 ml) was added and the mixture stirred at ambient temperature overnight. The mixture was diluted with a mixture of acetonitrile and water (1:1) and purified by preparative HPLC (Waters XBridge, eluting with a gradient of acetonitrile containing 10% THF and water containing 0.1% formic acid) yielding 30 mg of a solid (34% yield). MS (ESI) m/z: 532.1 $[M+H]^+$.

Synthesis of N-(8-(2,3-dichlorophenyl)-4-ethoxy-quinolin-3-yl)-2,3-dihydro-1H-indene-1-carboxamide (example 57)

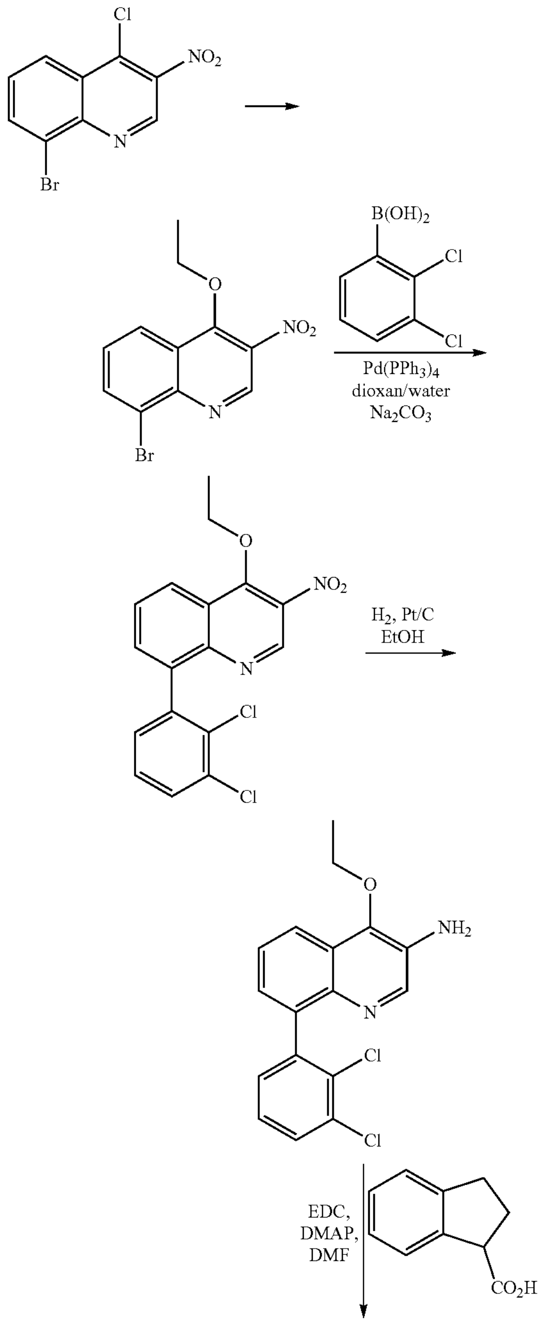

-continued

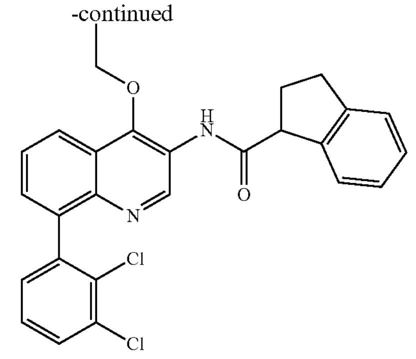

1. 8-Bromo-4-ethoxy-3-nitroquinoline

8-Bromo-4-chloro-3-nitroquinoline (500 mg, 1.739 mmol) was suspended in EtOH (4 ml), sodium ethoxide (237 mg, 3.48 mmol) was added, and the mixture was stirred at ambient temperature for 30 min. The mixture was diluted with water and a clear solution was obtained. The mixture was extracted with dichloromethane, the extract was dried with sodium sulfate, filtered, concentrated under reduced pressure and used directly in the next step.

2. 8-(2,3-Dichlorophenyl)-4-ethoxy-3-nitroquinoline

The residue of step 1. was combined with (2,3-dichloro-phenyl)boronic acid (431 mg, 2.261 mmol), $Pd(Ph_3P)_4$ (121 mg, 0.104 mmol) and sodium carbonate (553 mg, 5.22 mmol) in a flask under argon. A mixture of dioxane (15 ml) and degassed water (5 ml) was added and the resulting reaction mixture was stirred at 100° C. for 75 min. The mixture was diluted with water and extracted with ethyl acetate (3×), the combined extracts were dried with sodium sulfate, filtered and concentrated under reduced pressure. The residue was purified by column chromatography (silica, elution with a gradient of n-pentan/EtOAc) to yield 497 mg of a solid (77% yield). MS (ESI) m/z: 363.0 $[M+H]^+$.

3. 8-(2,3-Dichlorophenyl)-4-ethoxyquinolin-3-amine 8-(2,3-Dichlorophenyl)-4-ethoxy-3-nitroquinoline (497 mg, 1.368 mmol) was suspended in ethanol (5 ml), platinum on carbon (5%, 53.4 mg, 0.014 mmol) was added, the mixture was purged with hydrogen and stirred under an atmosphere of hydrogen overnight. The suspension was filtered through a pad of celite, the filter cake was washed with ethanol and the combined filtrates were concentrated under reduced pressure to yield 417 mg of a solid (87% yield). MS (ESI) m/z: 333.0 $[M+H]^+$.

4. N-(8-(2,3-dichlorophenyl)-4-ethoxyquinolin-3-yl)-2,3-dihydro-1H-indene-1-carboxamide 8-(2,3-Dichlorophenyl)-4-ethoxyquinolin-3-amine (40 mg, 0.120 mmol), 2,3-dihydro-1H-indene-1-carboxylic acid (20 mg, 0.120 mmol), EDC (34.5 mg, 0.180 mmol) and DMAP (7.33 mg, 0.060 mmol) were placed in a vial, DMF (1 ml) was added and the mixture stirred at ambient temperature overnight. The mixture was purified by preparative HPLC (Waters XBridge $C_{18}$, eluting with acetonitrile/water containing 0.1% formic acid) to yield 19.5 mg of a solid (34% yield). MS (ESI) m/z: 477.1 $[M+H]^+$.

Synthesis of N-(8-(3,5-dichlorophenyl)-4-isopropoxyquinolin-3-yl)-1,2,3,4-tetrahydro-naphthalene-1-carboxamide (example 76)

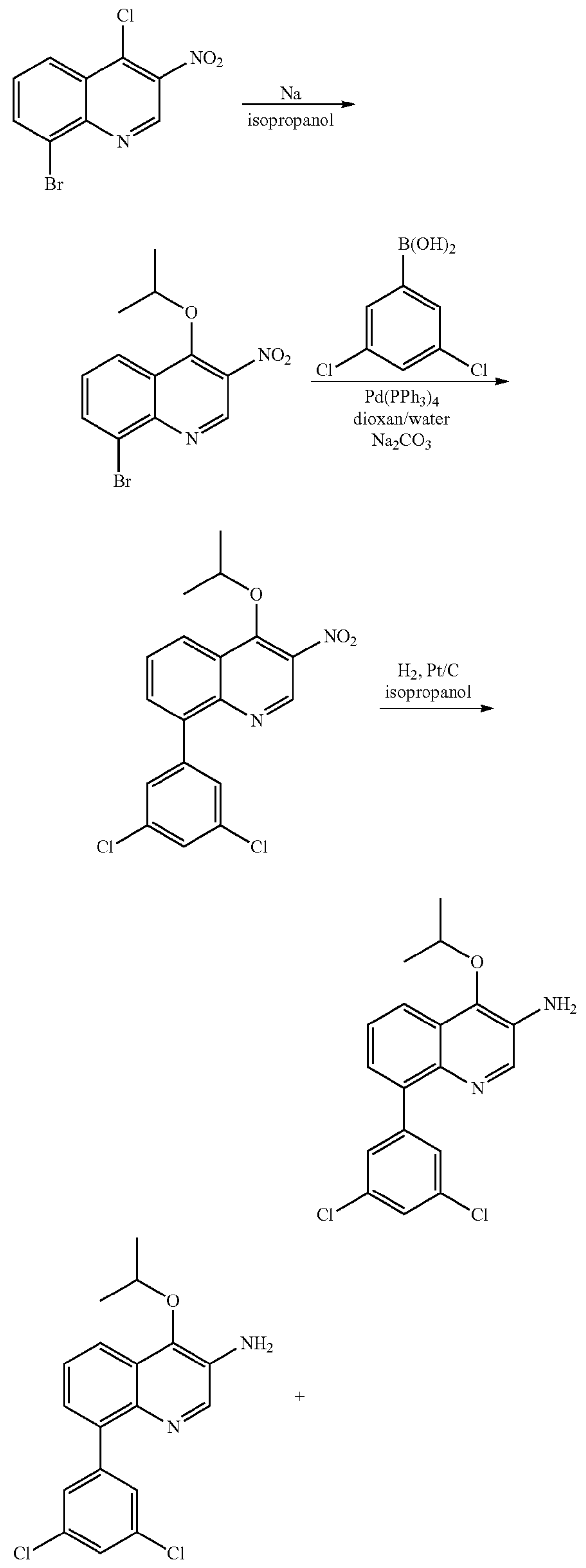

-continued

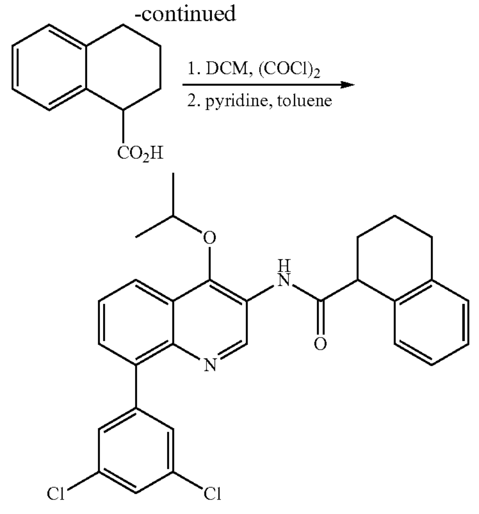

1. 8-Bromo-4-isopropoxy-3-nitroquinoline

Isopropanol (15 ml) was placed in a flask, sodium (78 mg, 3.4 mmol) was added and the mixture was stirred at ambient temperature for 2 hours. Then 8-bromo-4-chloro-3-nitroquinoline (520 mg, 1.7 mmol) was added and the mixture was stirred at ambient temperature overnight. The mixture was filtered, the filtrate was concentrated under reduced pressure. The residue was dissolved in dichloromethane, the solution was washed with water, dried over sodium sulfate and concentrated under reduced pressure to give a solid (579 mg, 96% yield).

2. 8-(3,5-Dichlorophenyl)-4-isopropoxy-3-nitroquinoline

8-Bromo-4-isopropoxy-3-nitroquinoline (529 mg, 1.7 mmol), (3,5-dichlorophenyl)boronic acid (422 mg, 2.21 mmol), $Pd(Ph_3P)_4$ (118 mg, 0.1 mmol) and sodium carbonate (541 mg, 5.1 mmol) were combined in a flask under argon. A mixture of dioxane (15 ml) and degassed water (5 ml) was added and the resulting reaction mixture was stirred at 100° C. for one hour. The mixture was cooled, diluted with ethyl acetate and brine, the phases were separated. The organic phase was washed with brine, concentrated under reduced pressure and the resulting residue was purified by column chromatography (silica, elution with a gradient of n-pentan/EtOAc) to yield 621 mg of a solid (97% yield).

3. 8-(3,5-Dichlorophenyl)-4-isopropoxyquinolin-3-amine 8-(3,5-Dichlorophenyl)-4-isopropoxy-3-nitroquinoline (621 mg, 1.65 mmol) was suspended in isopropanol (10 ml), platinum on carbon (5%, 64 mg, 0.016 mmol) was added, the mixture was purged with hydrogen and stirred under an atmosphere of hydrogen overnight. Additional platinum on carbon (5%, 25 mg, 0.006 mmol, suspended in 1 ml isopropanol) was added and stirring under hydrogen atmosphere was continued overnight. Addition of catalyst and stirring overnight was repeated, afterwards the suspension was filtered through a pad of celite, the filter cake was washed with isopropanol and the combined filtrates were concentrated under reduced pressure and the resulting residue was purified by flash chromatography (silica, n-pentane/ethyl acetate) to yield 354 mg of a solid (62% yield). MS (ESI) m/z: 347.0 $[M+H]^+$.

4. N-(8-(3,5-dichlorophenyl)-4-isopropoxyquinolin-3-yl)-1,2,3,4-tetrahydronaphthalene-1-carboxamide 1,2,3,4-tetrahydronaphthalene-1-carboxylic acid (16 mg, 0.09 mmol) was dissolved in DCM (1 ml containing a trace of DMF). Oxalyl chloride (8.7 µl, 1 mmol) was added and the mixture was stirred at ambient temperature until gas evolution ceased. This solution was added to a mixture of 8-(3,5-dichlorophenyl)-4-isopropoxyquinolin-3-amine (31 mg, 0.09 mmol) in toluene (2 ml) and pyridine (15 µl, 0.18 mmol) and stirred at 100° C. for 3 hours. The resulting mixture was concentrated under reduced pressure and purified by preparative HPLC (Waters XBridge $C_{18}$, eluting with acetonitrile/water containing 0.1% formic acid) to yield 12 mg of a solid (26% yield). MS (ESI) m/z: 505.1 $[M+H]^+$.

Table A: Examples

Table A below provides the structure for each of the exemplified compounds (No) of Formula (I), wherein in all exemplified compounds $R^{17}$ and $R^{18}$ are hydrogen. R/S denotes the absolute stereochemistry at the carbon bearing $R^{13}$, blank meaning that the racemate is present.

TABLE A

Formula (I)

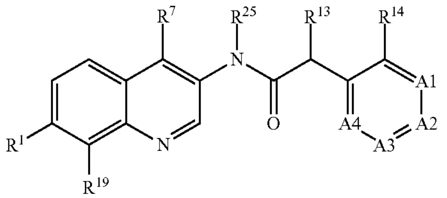

| No | R/S | $R^1$ | $R^7$ | $R^{13}$ | $R^{14}$ | A1 | A2 | A3 | A4 | $R^{19}$ | $R^{25}$ |
|---|---|---|---|---|---|---|---|---|---|---|---|
| 1 | | H | dimethylamino | H | H | CH | CH | CH | CH | 2,3-dichlorophenyl | H |
| 2 | | H | methoxy | H | H | CH | CH | CH | CH | 2,3-dichlorophenyl | H |
| 3 | | H | dimethylamino | H | H | CH | CH | CH | CH | 3,5-dichlorophenyl | H |
| 4 | | H | methoxy | H | H | CH | CH | CH | CH | 3,5-dichlorophenyl | H |
| 5 | | H | morpholin-4-yl | H | H | CH | CH | CH | CH | 3,5-dichlorophenyl | H |
| 6 | | H | ethoxy | H | H | CH | CH | CH | CH | 3,5-dichlorophenyl | H |
| 7 | | H | morpholin-4-yl | $—CH_2—CH_2—O—$ | | CH | CH | CH | CH | 3,5-dichlorophenyl | H |
| 8 | | H | morpholin-4-yl | $—CH_2—CH_2—CH_2—$ | | CH | CH | CH | CH | 3,5-dichlorophenyl | H |
| 9 | | H | morpholin-4-yl | CH3 | H | CH | CH | CH | CH | 3,5-dichlorophenyl | H |
| 10 | | H | dimethylamino | CH3 | H | CH | CH | CH | CH | 2,3-dichlorophenyl | H |
| 11 | | H | methoxy | CH3 | H | CH | CH | CH | CH | 2,3-dichlorophenyl | H |
| 12 | | H | dimethylamino | $—CH_2—CH_2—O—$ | | CH | CH | CH | CH | 2,3-dichlorophenyl | H |
| 13 | | H | dimethylamino | $—CH_2—CH_2—CH_2—$ | | CH | CH | CH | CH | 2,3-dichlorophenyl | H |
| 14 | | H | methoxy | $—CH_2—CH_2—CH_2—$ | | CH | CH | CH | CH | 2,3-dichlorophenyl | H |
| 15 | | H | methoxy | $—CH_2—CH_2—O—$ | | CH | CH | CH | CH | 2,3-dichlorophenyl | H |
| 16 | | H | methoxy | $—CH_2—CH_2—$ | | CH | CH | CH | CH | 2,3-dichlorophenyl | H |
| 17 | | H | pyrrolidin-1-yl | $—CH_2—CH_2—O—$ | | CH | CH | CH | CH | 2,3-dichlorophenyl | H |
| 18 | | H | pyrrolidin-1-yl | $—CH_2—CH_2—$ | | CH | CH | CH | CH | 2,3-dichlorophenyl | H |
| 19 | | H | morpholin-4-yl | $—CH_2—CH_2—CH_2—$ | | CH | CH | CH | CH | 2,3-dichlorophenyl | H |
| 20 | | H | morpholin-4-yl | $—CH_2—CH_2—$ | | CH | CH | CH | CH | 2,3-dichlorophenyl | H |
| 21 | | H | morpholin-4-yl | CH3 | H | CH | CH | CH | CH | 2,3-dichlorophenyl | H |
| 22 | | H | morpholin-4-yl | H | H | CH | CH | CH | CH | 2,3-dichlorophenyl | H |
| 23 | | H | dimethylamino | $—CH_2—CH_2—$ | | CH | CH | CH | CH | 2,3-dichlorophenyl | H |
| 24 | | H | dimethylamino | CH3 | H | CH | CH | CH | CH | 2,3-dichlorophenyl | H |
| 25 | | H | dimethylamino | H | H | CH | CCI | CH | CH | 2,3-dichlorophenyl | H |
| 26 | | H | dimethylamino | H | H | CH | $C—CH_3$ | CH | CH | 2,3-dichlorophenyl | H |
| 27 | | H | dimethylamino | H | H | CH | $C—OCH_3$ | CH | CH | 2,3-dichlorophenyl | H |
| 28 | | H | dimethylamino | CH3 | H | C—Cl | CH | CH | CH | 2,3-dichlorophenyl | H |
| 29 | | H | dimethylamino | CH3 | H | $C—OCH_3$ | CH | CH | CH | 2,3-dichlorophenyl | H |
| 30 | | H | dimethylamino | $—CH_2—C(=O)—$ | | CH | CH | CH | CH | 2,3-dichlorophenyl | H |
| 31 | | H | dimethylamino | =CH—CH=CH— | | CH | CH | CH | CH | 2,3-dichlorophenyl | H |
| 32 | | H | isopropoxy | $—CH_2—CH_2—O—$ | | CH | CH | CH | CH | 2,3-dichlorophenyl | H |
| 33 | | H | dimethylamino | $—CH_2—CH_2—CH_2—$ | | CH | CH | CH | CH | 2,3-dichlorophenyl | H |
| 34 | | H | dimethylamino | H | H | CH | CH | CH | CH | 2,3-dichlorophenyl | H |
| 35 | | H | dimethylamino | H | H | $C—CH_3$ | CH | CH | CH | 2,3-dichlorophenyl | H |
| 36 | | H | dimethylamino | H | H | $C—OCH_3$ | CH | CH | CH | 2,3-dichlorophenyl | H |
| 37 | | H | 3-hydroxy-pyrrolidin-1-yl | $—CH_2—CH_2—O—$ | | CH | CH | CH | CH | 2,3-dichlorophenyl | H |
| 38 | | H | dimethylamino | $—CH_2—CH_2—O—$ | | CH | CH | CH | CH | 3,5-difluorophenyl | H |
| 39 | | H | dimethylamino | $—CH_2—CH_2—O—$ | | CH | CH | CH | CH | 3,4,5-trifluorophenyl | H |
| 40 | | H | dimethylamino | $—CH_2—CH_2—O—$ | | CH | CH | CH | CH | 3-chlorophenyl | H |
| 41 | | H | dimethylamino | $—CH_2—CH_2—O—$ | | CH | CH | CH | CH | 5-chloro-3-fluorophenyl | H |
| 42 | | H | dimethylamino | $—CH_2—CH_2—O—$ | | CH | CH | CH | CH | 3-chloro-2-fluorophenyl | H |
| 43 | | H | dimethylamino | $—CH_2—CH_2—O—$ | | CH | CH | CH | CH | 5-chloro-2-fluorophenyl | H |
| 44 | | H | dimethylamino | CH3 | H | $C—CH_3$ | CH | CH | CH | 2,3-dichlorophenyl | H |
| 45 | | H | 3-hydroxy-pyrrolidin-1-yl | $—CH_2—CH_2—$ | | CH | CH | CH | CH | 2,3-dichlorophenyl | H |

TABLE A-continued

Formula (I)

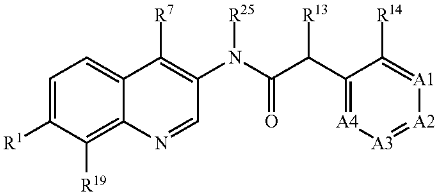

| No | R/S | $R^1$ | $R^7$ | $R^{13}$ | $R^{14}$ | A1 | A2 | A3 | A4 | $R^{19}$ | $R^{25}$ |
|---|---|---|---|---|---|---|---|---|---|---|---|
| 46 | | H | dimethylamino | $—CH_2—CH_2—O—$ | | CH | CH | CH | CH | 3,5-dichloro-4-fluorophenyl | H |
| 47 | | H | dimethylamino | $—CH_2—CH_2—O—$ | | CH | CH | CH | CH | 2,3,5-trifluorophenyl | H |
| 48 | | H | dimethylamino | H | H | CH | $CN(CH_3)_2$ | CH | CH | 2,3-dichlorophenyl | H |
| 49 | | H | dimethylamino | H | H | $CN(CH_3)_2$ | CH | CH | CH | 2,3-dichlorophenyl | H |
| 50 | | H | dimethylamino | CH3 | H | $CN(CH_3)_2$ | CH | CH | CH | 2,3-dichlorophenyl | H |
| 51 | | H | morpholin-4-yl | $—CH_2—CH_2—O—$ | | CH | CH | CH | CH | 2,3-dichlorophenyl | H |
| 52 | | H | morpholin-4-yl | =CH—CH=CH— | | CH | CH | CH | CH | 2,3-dichlorophenyl | H |
| 53 | S | H | morpholin-4-yl | $—CH_2—CH_2—CH_2—$ | | CH | CH | CH | CH | 2,3-dichlorophenyl | H |
| 54 | S | H | ethoxy | $—CH_2—CH_2—CH_2—$ | | CH | CH | CH | CH | 2,3-dichlorophenyl | H |
| 55 | | H | ethoxy | $—CH_2—CH_2—CH_2—$ | | CH | CH | CH | CH | 2,3-dichlorophenyl | H |
| 56 | | H | ethoxy | $—CH_2—CH_2—O—$ | | CH | CH | CH | CH | 2,3-dichlorophenyl | H |
| 57 | | H | ethoxy | $—CH_2—CH_2—$ | | CH | CH | CH | CH | 2,3-dichlorophenyl | H |
| 58 | | H | ethoxy | =CH—CH=CH— | | CH | CH | CH | CH | 2,3-dichlorophenyl | H |
| 59 | | H | isopropoxy | $—CH_2—CH_2—CH_2—$ | | CH | CH | CH | CH | 2,3-dichlorophenyl | H |
| 60 | | H | isopropoxy | $—CH_2—CH_2—$ | | CH | CH | CH | CH | 2,3-dichlorophenyl | H |
| 61 | | H | isopropoxy | =CH—CH=CH— | | CH | CH | CH | CH | 2,3-dichlorophenyl | H |
| 62 | | H | methoxy | =CH—CH=CH— | | CH | CH | CH | CH | 2,3-dichlorophenyl | H |
| 63 | | H | hydroxy | $—CH_2—CH_2—CH_2—$ | | CH | CH | CH | CH | 3,5-dichlorophenyl | H |
| 64 | | H | hydroxy | $—CH_2—CH_2—O—$ | | CH | CH | CH | CH | 3,5-dichlorophenyl | H |
| 65 | | H | hydroxy | $—CH_2—CH_2—$ | | CH | CH | CH | CH | 3,5-dichlorophenyl | H |
| 66 | | H | hydroxy | =CH—CH=CH— | | CH | CH | CH | CH | 3,5-dichlorophenyl | H |
| 67 | | H | dimethylamino | $—CH_2—CH_2—O—$ | | CH | CH | CH | CH | 3,5-dichlorophenyl | H |
| 68 | | H | dimethylamino | $—CH_2—CH_2—CH_2—$ | | CH | CH | CH | CH | 3,5-dichlorophenyl | H |
| 69 | | H | methoxy | $—CH_2—CH_2—CH_2—$ | | CH | CH | CH | CH | 3,5-dichlorophenyl | H |
| 70 | | H | methoxy | $—CH_2—CH_2—O—$ | | CH | CH | CH | CH | 3,5-dichlorophenyl | H |
| 71 | | H | methoxy | $—CH_2—CH_2—$ | | CH | CH | CH | CH | 3,5-dichlorophenyl | H |
| 72 | | H | methoxy | =CH—CH=CH— | | CH | CH | CH | CH | 3,5-dichlorophenyl | H |
| 73 | | H | dimethylamino | $—CH_2—CH_2—$ | | CH | CH | CH | CH | 3,5-dichlorophenyl | H |
| 74 | | H | morpholin-4-yl | =CH—CH=CH— | | CH | CH | CH | CH | 3,5-dichlorophenyl | H |
| 75 | | H | ethoxy | $—CH_2—CH_2—CH_2—$ | | CH | CH | CH | CH | 3,5-dichlorophenyl | H |
| 76 | | H | isopropoxy | $—CH_2—CH_2—CH_2—$ | | CH | CH | CH | CH | 3,5-dichlorophenyl | H |
| 77 | | H | ethoxy | $—CH_2—CH_2—O—$ | | CH | CH | CH | CH | 3,5-dichlorophenyl | H |
| 78 | | H | isopropoxy | $—CH_2—CH_2—O—$ | | CH | CH | CH | CH | 3,5-dichlorophenyl | H |
| 79 | | H | ethoxy | $—CH_2—CH_2—$ | | CH | CH | CH | CH | 3,5-dichlorophenyl | H |
| 80 | | H | isopropoxy | $—CH_2—CH_2—$ | | CH | CH | CH | CH | 3,5-dichlorophenyl | H |
| 81 | | H | isopropoxy | =CH—CH=CH— | | CH | CH | CH | CH | 3,5-dichlorophenyl | H |
| 82 | | H | morpholin-4-yl | $—CH_2—CH_2—$ | | CH | CH | CH | CH | 3,5-dichlorophenyl | H |
| 83 | S | H | dimethylamino | $—CH_2—CH_2—$ | | CH | CH | CH | CH | 3,5-dichlorophenyl | H |
| 84 | | H | amino | $—CH_2—CH_2—O—$ | | CH | CH | CH | CH | 2,3-dichlorophenyl | H |
| 85 | | H | methylamino | $—CH_2—CH_2—O—$ | | CH | CH | CH | CH | 2,3-dichlorophenyl | H |
| 86 | | H | ethylamino | $—CH_2—CH_2—O—$ | | CH | CH | CH | CH | 2,3-dichlorophenyl | H |
| 87 | | H | isopropylamino | $—CH_2—CH_2—O—$ | | CH | CH | CH | CH | 2,3-dichlorophenyl | H |
| 88 | | H | N(Me)(Et) | $—CH_2—CH_2—O—$ | | CH | CH | CH | CH | 2,3-dichlorophenyl | H |
| 89 | | H | N-isopropyl-N-methylamino | $—CH_2—CH_2—O—$ | | CH | CH | CH | CH | 2,3-dichlorophenyl | H |
| 90 | | H | NCH2CH2OH | $—CH_2—CH_2—O—$ | | CH | CH | CH | CH | 2,3-dichlorophenyl | H |
| 91 | | H | NHCH2CH2OCH3 | $—CH_2—CH_2—O—$ | | CH | CH | CH | CH | 2,3-dichlorophenyl | H |
| 92 | | H | N(CH2CH2OH)(CH3) | $—CH_2—CH_2—O—$ | | CH | CH | CH | CH | 2,3-dichlorophenyl | H |
| 93 | | H | N(CH3)(CH2CH2OCH3) | $—CH_2—CH_2—O—$ | | CH | CH | CH | CH | 2,3-dichlorophenyl | H |
| 94 | | H | amino | $—CH_2—CH_2—CH_2—$ | | CH | CH | CH | CH | 2,3-dichlorophenyl | H |
| 95 | | H | methylamino | $—CH_2—CH_2—CH_2—$ | | CH | CH | CH | CH | 2,3-dichlorophenyl | H |
| 96 | | H | ethylamino | $—CH_2—CH_2—CH_2—$ | | CH | CH | CH | CH | 2,3-dichlorophenyl | H |
| 97 | | H | isopropylamino | $—CH_2—CH_2—CH_2—$ | | CH | CH | CH | CH | 2,3-dichlorophenyl | H |
| 98 | | H | N(Me)(Et) | $—CH_2—CH_2—CH_2—$ | | CH | CH | CH | CH | 2,3-dichlorophenyl | H |
| 99 | | H | N-isopropyl-N-methylamino | $—CH_2—CH_2—CH_2—$ | | CH | CH | CH | CH | 2,3-dichlorophenyl | H |
| 100 | | H | NCH2CH2OH | $—CH_2—CH_2—CH_2—$ | | CH | CH | CH | CH | 2,3-dichlorophenyl | H |
| 101 | | H | NHCH2CH2OCH3 | $—CH_2—CH_2—CH_2—$ | | CH | CH | CH | CH | 2,3-dichlorophenyl | H |
| 102 | | H | N(CH2CH2OH)(CH3) | $—CH_2—CH_2—CH_2—$ | | CH | CH | CH | CH | 2,3-dichlorophenyl | H |
| 103 | | H | N(CH3)(CH2CH2OCH3) | $—CH_2—CH_2—CH_2—$ | | CH | CH | CH | CH | 2,3-dichlorophenyl | H |
| 104 | | H | ethyl | =CH—CH=N— | | CH | CH | CH | CH | 2,3-dichlorophenyl | H |
| 105 | | H | ethyl | $—CH_2—CH_2—O—$ | | CH | CH | CH | CH | 2,3-dichlorophenyl | H |
| 106 | | H | methyl | =CH—CH=N— | | CH | CH | CH | CH | 2,3-dichlorophenyl | H |
| 107 | | H | ethyl | =CH—CH=CH— | | CH | CH | CH | CH | 2,3-dichlorophenyl | H |
| 108 | | H | ethyl | $—CH_2—CH_2—CH_2—$ | | CH | CH | CH | CH | 2,3-dichlorophenyl | H |
| 109 | | H | isopropyl | $—CH_2—CH_2—CH_2—$ | | CH | CH | CH | CH | 2,3-dichlorophenyl | H |

TABLE A-continued

Formula (I)

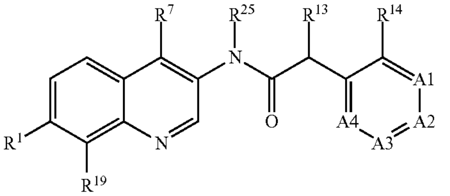

| No | R/S | $R^1$ | $R^7$ | $R^{13}$ $R^{14}$ | A1 | A2 | A3 | A4 | $R^{19}$ | $R^{25}$ |
|---|---|---|---|---|---|---|---|---|---|---|
| 110 | | H | ethyl | =CH—CH=CH— | CH | CH | CH | CH | 2,3-dichlorophenyl | H |
| 111 | | H | hydroxy | —CH$_2$—CH$_2$— | CH | CH | CH | CH | 2,3-dichlorophenyl | H |
| 112 | | H | hydroxy | —CH$_2$—CH$_2$—O— | CH | CH | CH | CH | 2,3-dichlorophenyl | H |
| 113 | | F | methoxy | —CH$_2$—CH$_2$—CH$_2$— | CH | CH | CH | CH | 3,5-dichlorophenyl | H |
| 114 | | F | ethoxy | —CH$_2$—CH$_2$—CH$_2$— | CH | CH | CH | CH | 3,5-dichlorophenyl | H |
| 115 | | F | dimethylamino | —CH$_2$—CH$_2$—CH$_2$— | CH | CH | CH | CH | 3,5-dichlorophenyl | H |
| 116 | | F | morpholin-4-yl | —CH$_2$—CH$_2$—CH$_2$— | CH | CH | CH | CH | 3,5-dichlorophenyl | H |
| 117 | | F | isopropoxy | —CH$_2$—CH$_2$—CH$_2$— | CH | CH | CH | CH | 3,5-dichlorophenyl | H |
| 118 | | F | methoxy | —CH$_2$—CH$_2$—CH$_2$— | CH | CH | CH | CH | 2,3-dichlorophenyl | H |
| 119 | | F | ethoxy | —CH$_2$—CH$_2$—CH$_2$— | CH | CH | CH | CH | 2,3-dichlorophenyl | H |
| 120 | | F | dimethylamino | —CH$_2$—CH$_2$—CH$_2$— | CH | CH | CH | CH | 2,3-dichlorophenyl | H |
| 121 | | F | morpholin-4-yl | —CH$_2$—CH$_2$—CH$_2$— | CH | CH | CH | CH | 2,3-dichlorophenyl | H |
| 122 | | F | isopropoxy | —CH$_2$—CH$_2$—CH$_2$— | CH | CH | CH | CH | 2,3-dichlorophenyl | H |
| 123 | | F | methoxy | —CH$_2$—CH$_2$—O— | CH | CH | CH | CH | 3,5-dichlorophenyl | H |
| 124 | | F | ethoxy | —CH$_2$—CH$_2$—O— | CH | CH | CH | CH | 3,5-dichlorophenyl | H |
| 125 | | F | dimethylamino | —CH$_2$—CH$_2$—O— | CH | CH | CH | CH | 3,5-dichlorophenyl | H |
| 126 | | F | morpholin-4-yl | —CH$_2$—CH$_2$—O— | CH | CH | CH | CH | 3,5-dichlorophenyl | H |
| 127 | | F | isopropoxy | —CH$_2$—CH$_2$—O— | CH | CH | CH | CH | 3,5-dichlorophenyl | H |
| 128 | | F | methoxy | —CH$_2$—CH$_2$—O— | CH | CH | CH | CH | 2,3-dichlorophenyl | H |
| 129 | | F | ethoxy | —CH$_2$—CH$_2$—O— | CH | CH | CH | CH | 2,3-dichlorophenyl | H |
| 130 | | F | dimethylamino | —CH$_2$—CH$_2$—O— | CH | CH | CH | CH | 2,3-dichlorophenyl | H |
| 131 | | F | morpholin-4-yl | —CH$_2$—CH$_2$—O— | CH | CH | CH | CH | 2,3-dichlorophenyl | H |
| 132 | | F | isopropoxy | —CH$_2$—CH$_2$—O— | CH | CH | CH | CH | 2,3-dichlorophenyl | H |
| 133 | | F | methoxy | —CH$_2$—CH$_2$— | CH | CH | CH | CH | 3,5-dichlorophenyl | H |
| 134 | | F | ethoxy | —CH$_2$—CH$_2$— | CH | CH | CH | CH | 3,5-dichlorophenyl | H |
| 135 | | F | dimethylamino | —CH$_2$—CH$_2$— | CH | CH | CH | CH | 3,5-dichlorophenyl | H |
| 136 | | F | morpholin-4-yl | —CH$_2$—CH$_2$— | CH | CH | CH | CH | 3,5-dichlorophenyl | H |
| 137 | | F | isopropoxy | —CH$_2$—CH$_2$— | CH | CH | CH | CH | 3,5-dichlorophenyl | H |
| 138 | | F | methoxy | —CH$_2$—CH$_2$— | CH | CH | CH | CH | 2,3-dichlorophenyl | H |
| 139 | | F | ethoxy | —CH$_2$—CH$_2$— | CH | CH | CH | CH | 2,3-dichlorophenyl | H |
| 140 | | F | dimethylamino | —CH$_2$—CH$_2$— | CH | CH | CH | CH | 2,3-dichlorophenyl | H |
| 141 | | F | morpholin-4-yl | —CH$_2$—CH$_2$— | CH | CH | CH | CH | 2,3-dichlorophenyl | H |
| 142 | | F | isopropoxy | —CH$_2$—CH$_2$— | CH | CH | CH | CH | 2,3-dichlorophenyl | H |
| 143 | | F | methoxy | =CH—CH=CH— | CH | CH | CH | CH | 3,5-dichlorophenyl | H |
| 144 | | F | ethoxy | =CH—CH=CH— | CH | CH | CH | CH | 3,5-dichlorophenyl | H |
| 145 | | F | dimethylamino | =CH—CH=CH— | CH | CH | CH | CH | 3,5-dichlorophenyl | H |
| 146 | | F | morpholin-4-yl | =CH—CH=CH— | CH | CH | CH | CH | 3,5-dichlorophenyl | H |
| 147 | | F | isopropoxy | =CH—CH=CH— | CH | CH | CH | CH | 3,5-dichlorophenyl | H |
| 148 | | F | methoxy | =CH—CH=CH— | CH | CH | CH | CH | 2,3-dichlorophenyl | H |
| 149 | | F | ethoxy | =CH—CH=CH— | CH | CH | CH | CH | 2,3-dichlorophenyl | H |
| 150 | | F | dimethylamino | =CH—CH=CH— | CH | CH | CH | CH | 2,3-dichlorophenyl | H |
| 151 | | F | morpholin-4-yl | =CH—CH=CH— | CH | CH | CH | CH | 2,3-dichlorophenyl | H |
| 152 | | F | isopropoxy | =CH—CH=CH— | CH | CH | CH | CH | 2,3-dichlorophenyl | H |
| 153 | | H | dimethylamino | =CH—CH=CH— | CH | CH | CH | CH | 3,5-dichlorophenyl | H |
| 154 | S | H | ethoxy | —CH$_2$—CH$_2$—CH$_2$— | CH | CH | CH | CH | 3,5-dichlorophenyl | H |
| 155 | S | H | methoxy | —CH$_2$—CH$_2$—CH$_2$— | CH | CH | CH | CH | 3,5-dichlorophenyl | H |
| 156 | S | H | dimethylamino | —CH$_2$—CH$_2$—CH$_2$— | CH | CH | CH | CH | 3,5-dichlorophenyl | H |
| 157 | | H | morpholin-4-yl | —CH$_2$—CH$_2$—O— | CH | CH | CH | CH | 3,5-dichlorophenyl | $CH_3$ |
| 158 | | H | morpholin-4-yl | —CH$_2$—CH$_2$—O— | CH | CH | CH | CH | 2,3-dichlorophenyl | $CH_3$ |
| 159 | | H | morpholin-4-yl | —CH$_2$—CH$_2$—O— | CH | CH | CH | CH | 2,3-dichlorophenyl | $CH_2CH_3$ |
| 160 | | H | dimethylamino | —CH$_2$—CH$_2$—O— | CH | CH | CH | CH | 2,3-dichlorophenyl | $CH_3$ |
| 161 | | H | dimethylamino | —CH$_2$—CH$_2$—O— | CH | CH | CH | CH | 2,3-dichlorophenyl | $CH_2CH_3$ |
| 162 | | H | dimethylamino | —CH$_2$—CH$_2$—O— | CH | CH | CH | CH | 3,5-dichlorophenyl | $CH_2CH_3$ |
| 163 | | H | morpholin-4-yl | —CH$_2$—CH$_2$—O— | CH | CH | CH | CH | 3,5-dichlorophenyl | $CH_2CH_3$ |
| 164 | | $CH_3$ | methoxy | —CH$_2$—CH$_2$—O— | CH | CH | CH | CH | 2,3-dichlorophenyl | H |
| 165 | | Cl | methoxy | —CH$_2$—CH$_2$—O— | CH | CH | CH | CH | 2,3-dichlorophenyl | H |
| 166 | | Cl | dimethylamino | —CH$_2$—CH$_2$—O— | CH | CH | CH | CH | 2,3-dichlorophenyl | H |
| 167 | | Cl | morpholin-4-yl | —CH$_2$—CH$_2$—O— | CH | CH | CH | CH | 2,3-dichlorophenyl | H |
| 168 | | $CH_3$ | dimethylamino | —CH$_2$—CH$_2$—O— | CH | CH | CH | CH | 2,3-dichlorophenyl | H |
| 169 | | $CH_3$ | morpholin-4-yl | —CH$_2$—CH$_2$—O— | CH | CH | CH | CH | 2,3-dichlorophenyl | H |
| 170 | | Cl | morpholin-4-yl | —CH$_2$—CH$_2$—O— | CH | CH | CH | CH | 3,5-dichlorophenyl | H |
| 171 | | Cl | dimethylamino | —CH$_2$—CH$_2$—O— | CH | CH | CH | CH | 3,5-dichlorophenyl | H |
| 172 | | Cl | methoxy | —CH$_2$—CH$_2$—O— | CH | CH | CH | CH | 3,5-dichlorophenyl | H |
| 173 | | $CH_3$ | methoxy | —CH$_2$—CH$_2$—O— | CH | CH | CH | CH | 3,5-dichlorophenyl | H |
| 174 | | $CH_3$ | morpholin-4-yl | —CH$_2$—CH$_2$—O— | CH | CH | CH | CH | 3,5-dichlorophenyl | H |
| 175 | | $CH_3$ | dimethylamino | —CH$_2$—CH$_2$—O— | CH | CH | CH | CH | 3,5-dichlorophenyl | H |
| 176 | S | $CH_3$ | methoxy | —CH$_2$—CH$_2$— | CH | CH | CH | CH | 2,3-dichlorophenyl | H |

TABLE A-continued

Formula (I)

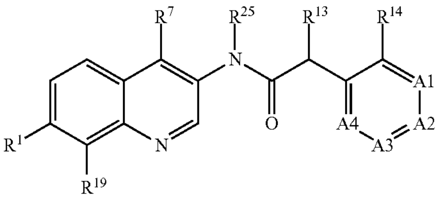

| No | R/S | $R^1$ | $R^7$ | $R^{13}$ $R^{14}$ | A1 | A2 | A3 | A4 | $R^{19}$ | $R^{25}$ |
|---|---|---|---|---|---|---|---|---|---|---|
| 177 | S | Cl | methoxy | $—CH_2—CH_2—$ | CH | CH | CH | CH | 2,3-dichlorophenyl | H |
| 178 | S | $CH_3$ | morpholin-4-yl | $—CH_2—CH_2—$ | CH | CH | CH | CH | 2,3-dichlorophenyl | H |
| 179 | S | Cl | morpholin-4-yl | $—CH_2—CH_2—$ | CH | CH | CH | CH | 3,5-dichlorophenyl | H |
| 180 | S | Cl | dimethylamino | $—CH_2—CH_2—$ | CH | CH | CH | CH | 3,5-dichlorophenyl | H |
| 181 | S | $CH_3$ | morpholin-4-yl | $—CH_2—CH_2—$ | CH | CH | CH | CH | 3,5-dichlorophenyl | H |
| 182 | S | $CH_3$ | dimethylamino | $—CH_2—CH_2—$ | CH | CH | CH | CH | 3,5-dichlorophenyl | H |
| 183 | S | $CH_3$ | methoxy | $—CH_2—CH_2—CH_2—$ | CH | CH | CH | CH | 2,3-dichlorophenyl | H |
| 184 | S | $CH_3$ | dimethylamino | $—CH_2—CH_2—CH_2—$ | CH | CH | CH | CH | 2,3-dichlorophenyl | H |
| 185 | S | Cl | morpholin-4-yl | $—CH_2—CH_2—CH_2—$ | CH | CH | CH | CH | 3,5-dichlorophenyl | H |
| 186 | S | Cl | dimethylamino | $—CH_2—CH_2—CH_2—$ | CH | CH | CH | CH | 3,5-dichlorophenyl | H |
| 187 | | H | n-propyl | $=CH—CH=CH—$ | CH | CH | CH | CH | 2,3-dichlorophenyl | H |
| 188 | | H | n-propyl | $—CH_2—CH_2—$ | CH | CH | CH | CH | 2,3-dichlorophenyl | H |
| 189 | | H | isopropenyl | $=CH—CH=CH—$ | CH | CH | CH | CH | 2,3-dichlorophenyl | H |
| 190 | | H | methyl | $=CH—CH=CH—$ | CH | CH | CH | CH | 2,3-dichlorophenyl | H |
| 191 | | H | ethyl | $—CH_2—CH_2—CH_2—$ | CH | CH | CH | CH | 3,5-dichlorophenyl | H |
| 192 | | H | methyl | $—CH_2—CH_2—CH_2—$ | CH | CH | CH | CH | 3,5-dichlorophenyl | H |
| 193 | | H | isopropenyl | $—CH_2—CH_2—CH_2—$ | CH | CH | CH | CH | 3,5-dichlorophenyl | H |
| 194 | | H | methyl | $—CH_2—CH_2—O—$ | CH | CH | CH | CH | 3,5-dichlorophenyl | H |
| 195 | | H | ethyl | $—CH_2—CH_2—O—$ | CH | CH | CH | CH | 3,5-dichlorophenyl | H |
| 196 | | H | isopropenyl | $—CH_2—CH_2—O—$ | CH | CH | CH | CH | 3,5-dichlorophenyl | H |
| 197 | S | H | ethyl | $—CH_2—CH_2—CH_2—$ | CH | CH | CH | CH | 3,5-dichlorophenyl | H |
| 198 | | H | methyl | $=CH—CH=CH—$ | CH | CH | CH | CH | 3,5-dichlorophenyl | H |
| 199 | | H | ethyl | $=CH—CH=CH—$ | CH | CH | CH | CH | 3,5-dichlorophenyl | H |
| 200 | | H | isopropenyl | $=CH—CH=CH—$ | CH | CH | CH | CH | 3,5-dichlorophenyl | H |
| 201 | | H | isopropenyl | $—CH_2—CH_2—$ | CH | CH | CH | CH | 2,3-dichlorophenyl | H |
| 202 | | H | isopropenyl | $—CH_2—CH_2—CH_2—$ | CH | CH | CH | CH | 2,3-dichlorophenyl | H |
| 203 | | H | methyl | $—CH_2—CH_2—O—$ | CH | CH | CH | CH | 2,3-dichlorophenyl | H |
| 204 | S | H | ethyl | $—CH_2—CH_2—CH_2—$ | CH | CH | CH | CH | 2,3-dichlorophenyl | H |
| 205 | | $OCH_3$ | morpholin-4-yl | $—CH_2—CH_2—O—$ | CH | CH | CH | CH | 3,5-dichlorophenyl | H |
| 206 | | $OCH_3$ | dimethylamino | $—CH_2—CH_2—O—$ | CH | CH | CH | CH | 2,3-dichlorophenyl | H |
| 207 | | $OCH_3$ | dimethylamino | $—CH_2—CH_2—O—$ | CH | CH | CH | CH | 3,5-dichlorophenyl | H |
| 208 | | $OCH_3$ | morpholin-4-yl | $—CH_2—CH_2—O—$ | CH | CH | CH | CH | 2,3-dichlorophenyl | H |
| 209 | | $CF_3$ | morpholin-4-yl | $—CH_2—CH_2—O—$ | CH | CH | CH | CH | 2,3-dichlorophenyl | H |
| 210 | | $CF_3$ | morpholin-4-yl | $—CH_2—CH_2—O—$ | CH | CH | CH | CH | 3,5-dichlorophenyl | H |
| 211 | | $CF_3$ | dimethylamino | $—CH_2—CH_2—O—$ | CH | CH | CH | CH | 2,3-dichlorophenyl | H |
| 212 | | $CF_3$ | dimethylamino | $—CH_2—CH_2—O—$ | CH | CH | CH | CH | 3,5-dichlorophenyl | H |
| 213 | | H | methylthio $_3$ | $—CH_2—CH_2—O—$ | CH | CH | CH | CH | 2,3-dichlorophenyl | H |
| 214 | | H | methylsulfonyl 3 | $—CH_2—CH_2—O—$ | CH | CH | CH | CH | 2,3-dichlorophenyl | H |
| 215 | | H | methylsulfoxyl 3 | $—CH_2—CH_2—O—$ | CH | CH | CH | CH | 2,3-dichlorophenyl | H |
| 216 | | H | methylthio | $—CH_2—CH_2—CH_2—$ | CH | CH | CH | CH | 2,3-dichlorophenyl | H |
| 217 | | H | methylsulfonyl 3 | $—CH_2—CH_2—CH_2—$ | CH | CH | CH | CH | 2,3-dichlorophenyl | H |
| 218 | | H | methylsulfoxyl | $—CH_2—CH_2—CH_2—$ | CH | CH | CH | CH | 2,3-dichlorophenyl | H |
| 219 | | $OCH_3$ | morpholin-4-yl | $=CH—CH=CH—$ | CH | CH | CH | CH | 3,5-dichlorophenyl | H |
| 220 | | $OCH_3$ | morpholin-4-yl | $=CH—CH=CH—$ | CH | CH | CH | CH | 2,3-dichlorophenyl | H |
| 221 | | $OCH_3$ | dimethylamino | $=CH—CH=CH—$ | CH | CH | CH | CH | 2,3-dichlorophenyl | H |
| 222 | | $CF_3$ | morpholin-4-yl | $=CH—CH=CH—$ | CH | CH | CH | CH | 2,3-dichlorophenyl | H |
| 223 | | $CF_3$ | morpholin-4-yl | $=CH—CH=CH—$ | CH | CH | CH | CH | 3,5-dichlorophenyl | H |
| 224 | | $CF_3$ | dimethylamino | $=CH—CH=CH—$ | CH | CH | CH | CH | 2,3-dichlorophenyl | H |
| 225 | | $CF_3$ | dimethylamino | $=CH—CH=CH—$ | CH | CH | CH | CH | 3,5-dichlorophenyl | H |
| 226 | | $CF_3$ | dimethylamino | $=CH—CH=CH—$ | N | CH | CH | CH | 3,5-dichlorophenyl | H |
| 227 | | $OCH_3$ | dimethylamino | $=CH—CH=CH—$ | N | CH | CH | CH | 3,5-dichlorophenyl | H |
| 228 | | $OCH_3$ | morpholin-4-yl | $=CH—CH=CH—$ | N | CH | CH | CH | 2,3-dichlorophenyl | H |
| 229 | | $OCH_3$ | morpholin-4-yl | $=CH—CH=CH—$ | N | CH | CH | CH | 3,5-dichlorophenyl | H |
| 230 | | $CH_3$ | dimethylamino | $=CH—CH=CH—$ | CH | CH | CH | CH | 3,5-dichlorophenyl | H |
| 231 | | $CH_3$ | dimethylamino | $=CH—CH=CH—$ | CH | CH | CH | CH | 2,3-dichlorophenyl | H |
| 232 | | $CH_3$ | morpholin-4-yl | $=CH—CH=CH—$ | CH | CH | CH | CH | 2,3-dichlorophenyl | H |
| 233 | | $CH_3$ | methoxy | $=CH—CH=CH—$ | CH | CH | CH | CH | 2,3-dichlorophenyl | H |
| 234 | | $CH_3$ | morpholin-4-yl | $=CH—CH=CH—$ | CH | CH | CH | CH | 3,5-dichlorophenyl | H |
| 235 | | Cl | dimethylamino | $=CH—CH=CH—$ | CH | CH | CH | CH | 3,5-dichlorophenyl | H |
| 236 | | Cl | morpholin-4-yl | $=CH—CH=CH—$ | CH | CH | CH | CH | 3,5-dichlorophenyl | H |
| 237 | | Cl | dimethylamino | $=CH—CH=CH—$ | CH | CH | CH | CH | 2,3-dichlorophenyl | H |
| 238 | S | F | dimethylamino | $—CH_2—CH_2—$ | CH | CH | CH | CH | 2,3-dichlorophenyl | H |
| 239 | S | F | dimethylamino | $—CH_2—CH_2—CH_2—$ | CH | CH | CH | CH | 2,3-dichlorophenyl | H |
| 240 | S | F | morpholin-4-yl | $—CH_2—CH_2—O—$ | CH | CH | CH | CH | 3,5-dichlorophenyl | H |
| 241 | S | F | morpholin-4-yl | $—CH_2—CH_2—O—$ | CH | CH | CH | CH | 2,3-dichlorophenyl | H |
| 242 | | F | morpholin-4-yl | $=CH—CH=CH—$ | CH | N | CH | CH | 2,3-dichlorophenyl | H |
| 243 | | F | morpholin-4-yl | $=CH—CH=CH—$ | N | CH | CH | CH | 2,3-dichlorophenyl | H |

TABLE A-continued

Formula (I)

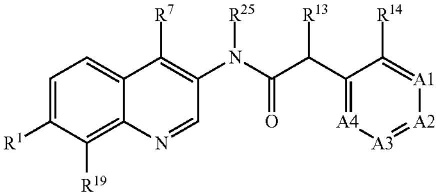

| No | R/S | $R^1$ | $R^7$ | $R^{13}$ $R^{14}$ | A1 | A2 | A3 | A4 | $R^{19}$ | $R^{25}$ |
|---|---|---|---|---|---|---|---|---|---|---|
| 244 | | F | dimethylamino | =CH—CH=CH— | N | CH | CH | CH | 3,5-dichlorophenyl | H |
| 245 | | F | morpholin-4-yl | =CH—CH=CH— | N | CH | CH | CH | 3,5-dichlorophenyl | H |
| 246 | | $CH_3$ | morpholin-4-yl | =CH—CH=CH— | N | CH | CH | CH | 3,5-dichlorophenyl | H |
| 247 | | Cl | dimethylamino | =CH—CH=CH— | N | CH | CH | CH | 3,5-dichlorophenyl | H |
| 248 | | Cl | morpholin-4-yl | =CH—CH=CH— | N | CH | CH | CH | 3,5-dichlorophenyl | H |
| 249 | | F | dimethylamino | =CH—CH=CH— | CH | CH | CH | CH | 2,3,5-trifluorophenyl | H |
| 250 | | F | morpholin-4-yl | =C(—OEt)—CH=CH— | CH | CH | CH | CH | 2,3-dichlorophenyl | H |
| 251 | | F | morpholin-4-yl | =C(—OEt)—CH=CH— | CH | CH | CH | CH | 3,5-dichlorophenyl | H |
| 252 | | F | morpholin-4-yl | =CH—CH=C(—Et)— | CH | CH | CH | CH | 2,3-dichlorophenyl | H |
| 253 | | F | morpholin-4-yl | =CH—CH=C(—Et)— | CH | CH | CH | CH | 3,5-dichlorophenyl | H |
| 254 | | F | morpholin-4-yl | =CH—CH=CF— | CH | CH | CH | CH | 2,3-dichlorophenyl | H |
| 255 | | F | morpholin-4-yl | =CH—CH=CF— | CH | CH | CH | CH | 3,5-dichlorophenyl | H |
| 256 | | F | morpholin-4-yl | =CH—CH=CH— | CH | CH | CH | N | 2,3-dichlorophenyl | H |
| 257 | | F | morpholin-4-yl | =CH—CH=CH— | CH | CH | CH | N | 3,5-dichlorophenyl | H |
| 258 | | F | morpholin-4-yl | =CH—CH=CH— | N | CH | CH | N | 2,3-dichlorophenyl | H |
| 259 | | F | morpholin-4-yl | =CH—CH=CH— | N | CH | CH | N | 3,5-dichlorophenyl | H |
| 260 | | F | dimethylamino | =CH—CH=CH— | N | CH | CH | CH | 2,3-dichlorophenyl | H |
| 261 | | F | dimethylamino | =CH—CH=CH— | CH | N | CH | CH | 2,3-dichlorophenyl | H |
| 262 | | F | dimethylamino | =CH—CH=CH— | CH | N | CH | CH | 3,5-dichlorophenyl | H |
| 263 | | H | methylthio | —$CH_2$—$CH_2$—O— | CH | CH | CH | CH | 2,3-dichlorophenyl | H |
| 264 | | H | methylsulfoxyl | —$CH_2$—$CH_2$—O— | CH | CH | CH | CH | 2,3-dichlorophenyl | H |
| 265 | | H | methylsulfonyl | —$CH_2$—$CH_2$—O— | CH | CH | CH | CH | 2,3-dichlorophenyl | H |
| 266 | | H | methylthio | —$CH_2$—$CH_2$—$CH_2$— | CH | CH | CH | CH | 2,3-dichlorophenyl | H |
| 267 | | H | methylsulfoxyl | —$CH_2$—$CH_2$—$CH_2$— | CH | CH | CH | CH | 2,3-dichlorophenyl | H |
| 268 | | H | methylsulfonyl | —$CH_2$—$CH_2$—$CH_2$— | CH | CH | CH | CH | 2,3-dichlorophenyl | H |
| 269 | | H | methyl | —$CH_2$—$CH_2$—$CH_2$— | CH | CH | CH | CH | 2,3-dichlorophenyl | H |
| 270 | | H | isopropyl | —$CH_2$—$CH_2$—O— | CH | CH | CH | CH | 2,3-dichlorophenyl | H |
| 271 | | H | isopropenyl | —$CH_2$—$CH_2$—O— | CH | CH | CH | CH | 2,3-dichlorophenyl | H |
| 272 | | H | methyl | —$CH_2$—$CH_2$— | CH | CH | CH | CH | 2,3-dichlorophenyl | H |
| 273 | | H | isopropyl | —$CH_2$—$CH_2$— | CH | CH | CH | CH | 2,3-dichlorophenyl | H |
| 274 | | H | isopropyl | =CH—CH=CH— | CH | CH | CH | CH | 2,3-dichlorophenyl | H |
| 275 | | H | isopropyl | —$CH_2$—$CH_2$—$CH_2$— | CH | CH | CH | CH | 3,5-dichlorophenyl | H |
| 276 | | H | isopropyl | —$CH_2$—$CH_2$—O— | CH | CH | CH | CH | 3,5-dichlorophenyl | H |
| 277 | | H | methyl | —$CH_2$—$CH_2$— | CH | CH | CH | CH | 3,5-dichlorophenyl | H |
| 278 | | H | ethyl | —$CH_2$—$CH_2$— | CH | CH | CH | CH | 3,5-dichlorophenyl | H |
| 279 | | H | isopropyl | —$CH_2$—$CH_2$— | CH | CH | CH | CH | 3,5-dichlorophenyl | H |
| 280 | | H | isopropenyl | —$CH_2$—$CH_2$— | CH | CH | CH | CH | 3,5-dichlorophenyl | H |
| 281 | | H | isopropyl | =CH—CH=CH— | CH | CH | CH | CH | 3,5-dichlorophenyl | H |
| 282 | | H | dimethylamino | =CH—CH=N— | CH | CH | CH | CH | 3,5-dichlorophenyl | H |
| 283 | | H | morpholin-4-yl | =CH—CH=N— | CH | CH | CH | CH | 3,5-dichlorophenyl | H |
| 284 | | H | dimethylamino | =CH—S— | CH | CH | CH | CH | 3,5-dichlorophenyl | H |
| 285 | | H | morpholin-4-yl | =CH—S— | CH | CH | CH | CH | 3,5-dichlorophenyl | H |
| 286 | | H | dimethylamino | =CH—O— | CH | CH | CH | CH | 3,5-dichlorophenyl | H |
| 287 | | H | morpholin-4-yl | =CH—O— | CH | CH | CH | CH | 3,5-dichlorophenyl | H |
| 288 | | H | dimethylamino | =CH—NH— | CH | CH | CH | CH | 3,5-dichlorophenyl | H |
| 289 | | H | morpholin-4-yl | =CH—NH— | CH | CH | CH | CH | 3,5-dichlorophenyl | H |
| 290 | | H | dimethylamino | =CH—N($CH_3$)— | CH | CH | CH | CH | 3,5-dichlorophenyl | H |
| 291 | | H | morpholin-4-yl | =CH—N($CH_3$)— | CH | CH | CH | CH | 3,5-dichlorophenyl | H |
| 292 | | H | dimethylamino | =CH—N=CH— | CH | CH | CH | CH | 3,5-dichlorophenyl | H |
| 293 | | H | morpholin-4-yl | =CH—N=CH— | CH | CH | CH | CH | 3,5-dichlorophenyl | H |
| 294 | | H | dimethylamino | —$CH_2$—S— | CH | CH | CH | CH | 3,5-dichlorophenyl | H |
| 295 | | H | morpholin-4-yl | —$CH_2$—S— | CH | CH | CH | CH | 3,5-dichlorophenyl | H |
| 296 | | H | dimethylamino | —$CH_2$—O— | CH | CH | CH | CH | 3,5-dichlorophenyl | H |
| 297 | | H | morpholin-4-yl | —$CH_2$—O— | CH | CH | CH | CH | 3,5-dichlorophenyl | H |
| 298 | | H | dimethylamino | —$CH_2$—NH— | CH | CH | CH | CH | 3,5-dichlorophenyl | H |
| 299 | | H | morpholin-4-yl | —$CH_2$—NH— | CH | CH | CH | CH | 3,5-dichlorophenyl | H |
| 300 | | H | dimethylamino | —$CH_2$—N($CH_3$)— | CH | CH | CH | CH | 3,5-dichlorophenyl | H |
| 301 | | H | morpholin-4-yl | —$CH_2$—N($CH_3$)— | CH | CH | CH | CH | 3,5-dichlorophenyl | H |
| 302 | | H | dimethylamino | =CH—CH=N— | CH | CH | CH | CH | 2,3-dichlorophenyl | H |
| 303 | | H | morpholin-4-yl | =CH—CH=N— | CH | CH | CH | CH | 2,3-dichlorophenyl | H |
| 304 | | H | dimethylamino | =CH—S— | CH | CH | CH | CH | 2,3-dichlorophenyl | H |
| 305 | | H | morpholin-4-yl | =CH—S— | CH | CH | CH | CH | 2,3-dichlorophenyl | H |
| 306 | | H | dimethylamino | =CH—O— | CH | CH | CH | CH | 2,3-dichlorophenyl | H |
| 307 | | H | morpholin-4-yl | =CH—O— | CH | CH | CH | CH | 2,3-dichlorophenyl | H |
| 308 | | H | dimethylamino | =CH—NH— | CH | CH | CH | CH | 2,3-dichlorophenyl | H |
| 309 | | H | morpholin-4-yl | =CH—NH— | CH | CH | CH | CH | 2,3-dichlorophenyl | H |
| 310 | | H | dimethylamino | =CH—N($CH_3$)— | CH | CH | CH | CH | 2,3-dichlorophenyl | H |

TABLE A-continued

Formula (I)

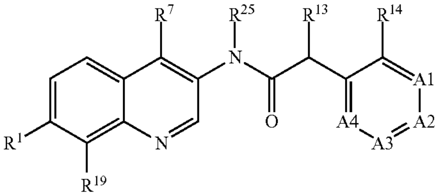

| No | R/S | $R^1$ | $R^7$ | $R^{13}$ $R^{14}$ | A1 | A2 | A3 | A4 | $R^{19}$ | $R^{25}$ |
|---|---|---|---|---|---|---|---|---|---|---|
| 311 | | H | morpholin-4-yl | =CH—N($CH_3$)— | CH | CH | CH | CH | 2,3-dichlorophenyl | H |
| 312 | | H | dimethylamino | =CH—N=CH— | CH | CH | CH | CH | 2,3-dichlorophenyl | H |
| 313 | | H | morpholin-4-yl | =CH—N=CH— | CH | CH | CH | CH | 2,3-dichlorophenyl | H |
| 314 | | H | dimethylamino | —$CH_2$—S— | CH | CH | CH | CH | 2,3-dichlorophenyl | H |
| 315 | | H | morpholin-4-yl | —$CH_2$—S— | CH | CH | CH | CH | 2,3-dichlorophenyl | H |
| 316 | | H | dimethylamino | —$CH_2$—O— | CH | CH | CH | CH | 2,3-dichlorophenyl | H |
| 317 | | H | morpholin-4-yl | —$CH_2$—O— | CH | CH | CH | CH | 2,3-dichlorophenyl | H |
| 318 | | H | dimethylamino | —$CH_2$—NH— | CH | CH | CH | CH | 2,3-dichlorophenyl | H |
| 319 | | H | morpholin-4-yl | —$CH_2$—NH— | CH | CH | CH | CH | 2,3-dichlorophenyl | H |
| 320 | | H | dimethylamino | —$CH_2$—N($CH_3$)— | CH | CH | CH | CH | 2,3-dichlorophenyl | H |
| 321 | | H | morpholin-4-yl | —$CH_2$—N($CH_3$)— | CH | CH | CH | CH | 2,3-dichlorophenyl | H |
| 322 | | H | dimethylamino | —$CH_2$—$CH_2$—O— | CH | CH | CH | CH | 2,6-dichloropyridin-4-yl | H |
| 323 | | H | dimethylamino | —$CH_2$—$CH_2$—O— | CH | CH | CH | CH | 2,6-difluoropyridin-4-yl | H |
| 324 | | H | dimethylamino | —$CH_2$—$CH_2$—O— | CH | CH | CH | CH | 2,5-dichloropyridin-4-yl | H |
| 325 | | H | dimethylamino | —$CH_2$—$CH_2$—O— | CH | CH | CH | CH | 5-chloro-2-thienyl | H |
| 326 | | H | dimethylamino | —$CH_2$—$CH_2$—O— | CH | CH | CH | CH | 5-chloro-3-thienyl | H |
| 327 | | H | dimethylamino | —$CH_2$—$CH_2$—O— | CH | CH | CH | CH | quinolin-8-yl | H |
| 328 | | H | morpholin-4-yl | —$CH_2$—$CH_2$—O— | CH | CH | CH | CH | 2,6-dichloropyridin-4-yl | H |
| 329 | | H | morpholin-4-yl | —$CH_2$—$CH_2$—O— | CH | CH | CH | CH | 2,6-difluoropyridin-4-yl | H |
| 330 | | H | morpholin-4-yl | —$CH_2$—$CH_2$—O— | CH | CH | CH | CH | 2,5-dichloropyridin-4-yl | H |
| 331 | | H | morpholin-4-yl | —$CH_2$—$CH_2$—O— | CH | CH | CH | CH | 5-chloro-2-thienyl | H |
| 332 | | H | morpholin-4-yl | —$CH_2$—$CH_2$—O— | CH | CH | CH | CH | 5-chloro-3-thienyl | H |
| 333 | | H | morpholin-4-yl | —$CH_2$—$CH_2$—O— | CH | CH | CH | CH | quinolin-8-yl | H |
| 334 | | H | morpholin-4-yl | —$CH_2$—$CH_2$—O— | CH | CH | CH | CH | quinolin-4-yl | H |
| 335 | | H | morpholin-4-yl | —$CH_2$—$CH_2$—O— | CH | CH | CH | CH | pyridin-2-yl | H |
| 336 | | H | morpholin-4-yl | —$CH_2$—$CH_2$—O— | CH | CH | CH | CH | pyridin-3-yl | H |
| 337 | | H | morpholin-4-yl | —$CH_2$—$CH_2$—O— | CH | CH | CH | CH | pyrimidin-4-yl | H |
| 338 | | H | morpholin-4-yl | —$CH_2$—$CH_2$—O— | CH | CH | CH | CH | pyridin-4-yl | H |
| 339 | | H | dimethylamino | —$CH_2$—$CH_2$—O— | CH | CH | CH | CH | quinolin-8-yl | H |
| 340 | | H | dimethylamino | —$CH_2$—$CH_2$—O— | CH | CH | CH | CH | quinolin-4-yl | H |
| 341 | | H | dimethylamino | —$CH_2$—$CH_2$—O— | CH | CH | CH | CH | pyridin-2-yl | H |
| 342 | | H | dimethylamino | —$CH_2$—$CH_2$—O— | CH | CH | CH | CH | pyridin-3-yl | H |
| 343 | | H | dimethylamino | —$CH_2$—$CH_2$—O— | CH | CH | CH | CH | pyrimidin-4-yl | H |
| 344 | | H | dimethylamino | —$CH_2$—$CH_2$—O— | CH | CH | CH | CH | pyridin-4-yl | H |
| 345 | | H | morpholin-4-yl | —$CH_2$—$CH_2$—O— | CH | CH | CH | CH | 2,3,5-trifluorophenyl | H |
| 346 | | H | morpholin-4-yl | —$CH_2$—$CH_2$—$CH_2$— | CH | CH | CH | CH | 2,3,5-trifluorophenyl | H |
| 347 | | H | morpholin-4-yl | —$CH_2$—$CH_2$— | CH | CH | CH | CH | 2,3,5-trifluorophenyl | H |
| 348 | | H | dimethylamino | —$CH_2$—$CH_2$—O— | CH | CH | CH | CH | 2,3,5-trifluorophenyl | H |
| 349 | | H | dimethylamino | —$CH_2$—$CH_2$—$CH_2$— | CH | CH | CH | CH | 2,3,5-trifluorophenyl | H |
| 350 | | H | dimethylamino | —$CH_2$—$CH_2$— | CH | CH | CH | CH | 2,3,5-trifluorophenyl | H |
| 351 | | H | methoxy | —$CH_2$—$CH_2$—O— | CH | CH | CH | CH | 2,3,5-trifluorophenyl | H |
| 352 | | H | methoxy | —$CH_2$—$CH_2$—$CH_2$— | CH | CH | CH | CH | 2,3,5-trifluorophenyl | H |
| 353 | | H | methoxy | —$CH_2$—$CH_2$— | CH | CH | CH | CH | 2,3,5-trifluorophenyl | H |
| 354 | | H | morpholin-4-yl | —$CH_2$—$CH_2$—O— | CH | CH | CH | CH | 5-chloro-2-fluorophenyl | H |
| 355 | | H | morpholin-4-yl | —$CH_2$—$CH_2$—$CH_2$— | CH | CH | CH | CH | 5-chloro-2-fluorophenyl | H |
| 356 | | H | morpholin-4-yl | —$CH_2$—$CH_2$— | CH | CH | CH | CH | 5-chloro-2-fluorophenyl | H |
| 357 | | H | dimethylamino | —$CH_2$—$CH_2$—O— | CH | CH | CH | CH | 5-chloro-2-fluorophenyl | H |
| 358 | | H | dimethylamino | —$CH_2$—$CH_2$—$CH_2$— | CH | CH | CH | CH | 5-chloro-2-fluorophenyl | H |
| 359 | | H | dimethylamino | —$CH_2$—$CH_2$— | CH | CH | CH | CH | 5-chloro-2-fluorophenyl | H |
| 360 | | H | methoxy | —$CH_2$—$CH_2$—O— | CH | CH | CH | CH | 5-chloro-2-fluorophenyl | H |
| 361 | | H | methoxy | —$CH_2$—$CH_2$—$CH_2$— | CH | CH | CH | CH | 5-chloro-2-fluorophenyl | H |
| 362 | | H | methoxy | —$CH_2$—$CH_2$— | CH | CH | CH | CH | 5-chloro-2-fluorophenyl | H |
| 363 | | $OCH_3$ | dimethylamino | —$CH_2$—$CH_2$—O— | CH | CH | CH | CH | 2,3-dichlorophenyl | H |
| 364 | | $OCH_3$ | dimethylamino | —$CH_2$—$CH_2$—O— | CH | CH | CH | CH | 3,5-dichlorophenyl | H |
| 365 | | $OCH_3$ | morpholin-4-yl | —$CH_2$—$CH_2$—O— | CH | CH | CH | CH | 2,3-dichlorophenyl | H |
| 366 | | $OCH_3$ | morpholin-4-yl | —$CH_2$—$CH_2$—O— | CH | CH | CH | CH | 3,5-dichlorophenyl | H |
| 367 | | Cl | morpholin-4-yl | —$CH_2$—$CH_2$—O— | CH | CH | CH | CH | 2,3-dichlorophenyl | H |
| 368 | | Cl | morpholin-4-yl | —$CH_2$—$CH_2$—O— | CH | CH | CH | CH | 3,5-dichlorophenyl | H |
| 369 | | $OCH_3$ | dimethylamino | —$CH_2$—$CH_2$—O— | CH | CH | CH | CH | 2,3-dichlorophenyl | H |
| 370 | | $OCH_3$ | dimethylamino | —$CH_2$—$CH_2$—O— | CH | CH | CH | CH | 3,5-dichlorophenyl | H |
| 371 | | $OCH_3$ | morpholin-4-yl | —$CH_2$—$CH_2$—O— | CH | CH | CH | CH | 2,3-dichlorophenyl | H |
| 372 | | $OCH_3$ | morpholin-4-yl | —$CH_2$—$CH_2$—O— | CH | CH | CH | CH | 3,5-dichlorophenyl | H |
| 373 | | Cl | dimethylamino | —$CH_2$—$CH_2$—O— | CH | CH | CH | CH | 2,3-dichlorophenyl | H |
| 374 | | Cl | dimethylamino | —$CH_2$—$CH_2$—O— | CH | CH | CH | CH | 3,5-dichlorophenyl | H |
| 375 | | Cl | morpholin-4-yl | —$CH_2$—$CH_2$—O— | CH | CH | CH | CH | 2,3-dichlorophenyl | H |
| 376 | | Cl | morpholin-4-yl | —$CH_2$—$CH_2$—O— | CH | CH | CH | CH | 3,5-dichlorophenyl | H |
| 377 | | $CH_3$ | dimethylamino | —$CH_2$—$CH_2$—O— | CH | CH | CH | CH | 2,3-dichlorophenyl | H |

TABLE A-continued

Formula (I)

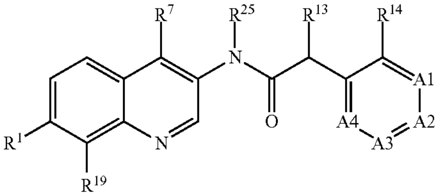

| No | R/S | $R^1$ | $R^7$ | $R^{13}$ | $R^{14}$ | A1 | A2 | A3 | A4 | $R^{19}$ | $R^{25}$ |
|---|---|---|---|---|---|---|---|---|---|---|---|
| 378 | | $CH_3$ | dimethylamino | $—CH_2—CH_2—O—$ | | CH | CH | CH | CH | 3,5-dichlorophenyl | H |
| 379 | | $CH_3$ | morpholin-4-yl | $—CH_2—CH_2—O—$ | | CH | CH | CH | CH | 2,3-dichlorophenyl | H |
| 380 | | $CH_3$ | morpholin-4-yl | $—CH_2—CH_2—O—$ | | CH | CH | CH | CH | 3,5-dichlorophenyl | H |
| 381 | | H | dimethylamino | $—CH_2—CH_2—O—$ | | CH | CH | CH | CH | 2,3-dichlorophenyl | H |
| 382 | | H | dimethylamino | $—CH_2—CH_2—O—$ | | CH | CH | CH | CH | 3,5-dichlorophenyl | H |
| 383 | | H | morpholin-4-yl | $—CH_2—CH_2—O—$ | | CH | CH | CH | CH | 2,3-dichlorophenyl | H |
| 384 | | H | morpholin-4-yl | $—CH_2—CH_2—O—$ | | CH | CH | CH | CH | 3,5-dichlorophenyl | H |
| 385 | | H | dimethylamino | $—CH_2—CH_2—O—$ | | CH | CH | CH | CH | 2,3-dichlorophenyl | H |
| 386 | | H | dimethylamino | $—CH_2—CH_2—O—$ | | CH | CH | CH | CH | 3,5-dichlorophenyl | H |
| 387 | | H | morpholin-4-yl | $—CH_2—CH_2—O—$ | | CH | CH | CH | CH | 2,3-dichlorophenyl | H |
| 388 | | H | morpholin-4-yl | $—CH_2—CH_2—O—$ | | CH | CH | CH | CH | 3,5-dichlorophenyl | H |
| 389 | | H | 3-fluoro-azetidin-1-yl | $—CH_2—CH_2—O—$ | | CH | CH | CH | CH | 3,5-dichlorophenyl | H |
| 390 | | F | 3-fluoro-azetidin-1-yl | $—CH_2—CH_2—O—$ | | CH | CH | CH | CH | 3,5-dichlorophenyl | H |
| 391 | | H | 3-fluoro-azetidin-1-yl | $—CH_2—CH_2—O—$ | | CH | CH | CH | CH | 2,3-dichlorophenyl | H |
| 392 | | F | 3-fluoro-azetidin-1-yl | $—CH_2—CH_2—O—$ | | CH | CH | CH | CH | 2,3-dichlorophenyl | H |
| 393 | | F | 3,3-difluoroazetin-1-yl | =CH—CH=CH— | | CH | CH | CH | CH | 2,3-dichlorophenyl | H |
| 394 | | F | 3,3-difluoroazetin-1-yl | =CH—CH=CH— | | CH | CH | CH | CH | 3,5-dichlorophenyl | H |
| 395 | | F | 3,3-difluoroazetin-1-yl | =CH—CH=CH— | | CH | CH | CH | CH | 2,3,5-trifluorophenyl | H |
| 396 | | F | 3-fluoroazetin-1-yl | =CH—CH=CH— | | CH | CH | CH | CH | 2,3-dichlorophenyl | H |
| 397 | | F | 3-fluoroazetin-1-yl | =CH—CH=CH— | | CH | CH | CH | CH | 3,5-dichlorophenyl | H |
| 398 | | F | 3-fluoroazetin-1-yl | =CH—CH=CH— | | CH | CH | CH | CH | 2,3,5-trifluorophenyl | H |
| 399 | | F | morpholin-4-yl | =CH—CH=CH— | | CH | CH | CH | CH | 2,3,5-trifluorophenyl | H |

Table B: Analytical Data

Table B shows the calculated molecular weight (MW) (gram/mol), the observed MS signal (m/z), the HPLC retention time (Rt) in minutes, and the HPLC-method as described in above ("Analytics: HPLC-Methods") used for analysis.

TABLE B

| No | HPLC Method | HPLC Rt | mass signal | MW |
|---|---|---|---|---|
| 1 | 1 | 1.031 | 450.1 | 450.4 |
| 2 | 1 | 1.238 | 437.0 | 437.3 |
| 3 | 1 | 1.181 | 450.1 | 450.4 |
| 4 | 1 | 1.352 | 437.0 | 437.3 |
| 5 | 1 | 1.187 | 492.1 | 492.4 |
| 6 | 2 | 1.338 | 451.0 | 451.3 |
| 7 | 2 | 1.332 | 534.1 | 534.4 |
| 8 | 2 | 1.386 | 532.0 | 532.5 |
| 9 | 2 | 1.336 | 506.1 | 506.4 |
| 10 | 2 | 1.292 | 464.1 | 464.4 |
| 11 | 2 | 1.240 | 451.1 | 451.3 |
| 12 | 2 | 1.300 | 492.0 | 492.4 |
| 13 | 2 | 1.375 | 490.1 | 490.4 |
| 14 | 2 | 1.304 | 477.1 | 477.4 |
| 15 | 2 | 1.239 | 479.0 | 479.4 |
| 16 | 2 | 1.261 | 463.0 | 463.4 |
| 17 | 2 | 1.376 | 518.1 | 518.4 |
| 18 | 2 | 1.410 | 502.1 | 502.4 |
| 19 | 2 | 1.290 | 532.1 | 532.5 |
| 20 | 1 | 1.222 | 518.1 | 518.4 |
| 21 | 2 | 1.234 | 506.1 | 506.4 |
| 22 | 2 | 1.188 | 492.1 | 492.4 |
| 23 | 2 | 1.330 | 476.0 | 476.4 |
| 24 | 2 | 1.314 | 464.1 | 464.4 |
| 25 | 2 | 1.298 | 484.0 | 484.8 |
| 26 | 2 | 1.306 | 464.1 | 464.4 |
| 27 | 2 | 1.250 | 480.1 | 480.4 |
| 28 | 2 | 1.346 | 498.0 | 498.8 |
| 29 | 2 | 1.308 | 494.1 | 494.4 |

TABLE B-continued

| No | HPLC Method | HPLC Rt | mass signal | MW |
|---|---|---|---|---|
| 30 | 2 | 1.192 | 490.0 | 490.4 |
| 31 | 2 | 1.317 | 486.0 | 486.4 |
| 32 | 2 | 1.329 | 507.1 | 507.4 |
| 33 | 2 | 1.377 | 490.1 | 490.4 |
| 34 | 2 | 1.300 | 484.0 | 484.8 |
| 35 | 2 | 1.307 | 464.1 | 464.4 |
| 36 | 2 | 1.256 | 480.1 | 480.4 |
| 37 | 2 | 1.200 | 534.0 | 534.4 |
| 38 | 2 | 1.304 | 460.1 | 459.5 |
| 39 | 2 | 1.315 | 478.1 | 477.5 |
| 40 | 2 | 1.327 | 458.1 | 458.0 |
| 41 | 2 | 1.362 | 476.1 | 475.9 |
| 42 | 1 | 1.163 | 476.1 | 475.9 |
| 43 | 1 | 1.172 | 476.1 | 475.9 |
| 44 | 2 | 1.362 | 478.1 | 478.4 |
| 45 | 2 | 1.229 | 518.1 | 518.4 |
| 46 | 2 | 1.523 | 510.1 | 510.4 |
| 47 | 2 | 1.259 | 478.1 | 477.5 |
| 48 | 2 | 1.369 | 493.1 | 493.4 |
| 49 | 2 | 1.382 | 493.1 | 493.4 |
| 50 | 2 | 1.516 | 507.1 | 507.5 |
| 51 | 1 | 1.205 | 534.1 | 534.4 |
| 52 | 1 | 1.253 | 528.1 | 528.4 |
| 53 | 1 | 1.259 | 532.2 | 532.5 |
| 54 | 1 | 1.358 | 491.0 | 491.4 |
| 55 | 1 | 1.362 | 491.1 | 491.4 |
| 56 | 1 | 1.294 | 493.0 | 493.4 |
| 57 | 1 | 1.310 | 477.0 | 477.4 |
| 58 | 1 | 1.310 | 487.0 | 487.4 |
| 59 | 1 | 1.395 | 505.0 | 505.4 |
| 60 | 1 | 1.341 | 491.1 | 491.4 |
| 61 | 1 | 1.347 | 501.0 | 501.4 |
| 62 | 1 | 1.274 | 473.0 | 473.4 |
| 63 | 1 | 1.300 | 463.0 | 463.4 |
| 64 | 1 | 1.227 | 465.0 | 465.3 |
| 65 | 1 | 1.255 | 449.0 | 449.3 |
| 66 | 1 | 1.287 | 459.0 | 459.3 |

TABLE B-continued

| No | HPLC Method | HPLC Rt | mass signal | MW |
|---|---|---|---|---|
| 67 | 1 | 1.291 | 492.1 | 492.4 |
| 68 | 1 | 1.386 | 490.1 | 490.4 |
| 69 | 1 | 1.436 | 477.0 | 477.4 |
| 70 | 1 | 1.349 | 479.0 | 479.4 |
| 71 | 1 | 1.374 | 463.0 | 463.4 |
| 72 | 1 | 1.297 | 473.0 | 473.4 |
| 73 | 1 | 1.286 | 476.1 | 476.4 |
| 74 | 1 | 1.340 | 528.1 | 528.4 |
| 75 | 1 | 1.458 | 491.1 | 491.4 |
| 76 | 1 | 1.486 | 505.1 | 505.4 |
| 77 | 1 | 1.394 | 493.1 | 493.4 |
| 78 | 1 | 1.425 | 507.0 | 507.4 |
| 79 | 1 | 1.410 | 477.1 | 477.4 |
| 80 | 1 | 1.437 | 491.1 | 491.4 |
| 81 | 1 | 1.431 | 501.0 | 501.4 |
| 82 | 1 | 1.253 | 518.1 | 518.4 |
| 83 | 1 | 1.327 | 476.1 | 476.4 |
| 84 | 10 | 2.192 | 464.2 | 464.3 |
| 85 | 12 | 1.417 | 478.2 | 478.4 |
| 86 | 9 | 1.462 | 492.2 | 492.4 |
| 87 | 13 | 1.357 | 506.1 | 506.4 |
| 88 | 9 | 1.601 | 506.1 | 506.4 |
| 89 | 5 | 1.932 | 520.2 | 520.4 |
| 90 | 10 | 2.101 | 508.2 | 508.4 |
| 91 | 11 | 1.834 | 522.2 | 522.4 |
| 92 | 6 | 1.913 | 522.2 | 522.4 |
| 93 | 6 | 2.104 | 536.3 | 536.4 |
| 94 | 10 | 2.468 | 462.2 | 462.4 |
| 95 | 9 | 1.460 | 478.1 | 476.4 |
| 96 | 9 | 1.514 | 490.2 | 490.4 |
| 97 | 13 | 1.440 | 504.2 | 504.5 |
| 98 | 13 | 1.859 | 504.1 | 504.5 |
| 99 | 4 | 2.920 | 518.2 | 518.5 |
| 100 | 6 | 1.667 | 506.2 | 506.4 |
| 101 | 9 | 1.525 | 520.2 | 520.4 |
| 102 | 5 | 1.362 | 520.2 | 520.4 |
| 103 | 5 | 1.789 | 534.3 | 534.5 |
| 104 | 1 | 1.209 | 472.0 | 472.4 |
| 105 | 1 | 1.287 | 477.1 | 477.4 |
| 106 | 1 | 1.182 | 458.0 | 458.3 |
| 107 | 1 | 1.298 | 461.1 | 461.4 |
| 108 | 1 | 1.333 | 475.1 | 475.4 |
| 109 | 1 | 1.374 | 489.1 | 489.4 |
| 110 | 1 | 1.308 | 471.1 | 471.4 |
| 111 | 1 | 1.209 | 449.0 | 449.3 |
| 112 | 1 | 1.180 | 465.0 | 465.3 |
| 113 | 1 | 1.403 | 495.0 | 495.4 |
| 114 | 1 | 1.444 | 509.1 | 509.4 |
| 115 | 1 | 1.396 | 508.1 | 508.4 |
| 116 | 1 | 1.377 | 550.1 | 550.5 |
| 117 | 1 | 1.460 | 523.0 | 523.4 |
| 118 | 1 | 1.300 | 495.0 | 495.4 |
| 119 | 1 | 1.345 | 509.1 | 509.4 |
| 120 | 1 | 1.275 | 508.0 | 508.4 |
| 121 | 1 | 1.275 | 550.0 | 550.5 |
| 122 | 1 | 1.375 | 523.1 | 523.4 |
| 123 | 1 | 1.331 | 497.0 | 497.3 |
| 124 | 1 | 1.384 | 511.0 | 511.4 |
| 125 | 1 | 1.306 | 510.1 | 510.4 |
| 126 | 1 | 1.312 | 552.1 | 552.4 |
| 127 | 1 | 1.404 | 525.1 | 525.4 |
| 128 | 1 | 1.235 | 497.0 | 497.3 |
| 129 | 1 | 1.281 | 511.0 | 511.4 |
| 130 | 1 | 1.175 | 510.1 | 510.4 |
| 131 | 1 | 1.210 | 552.0 | 552.4 |
| 132 | 1 | 1.313 | 525.1 | 525.4 |
| 133 | 1 | 1.367 | 481.0 | 481.3 |
| 134 | 1 | 1.395 | 495.0 | 495.4 |
| 135 | 1 | 1.307 | 494.1 | 494.4 |
| 136 | 1 | 1.324 | 536.0 | 536.4 |
| 137 | 1 | 1.415 | 509.1 | 509.4 |
| 138 | 1 | 1.261 | 481.0 | 481.3 |
| 139 | 1 | 1.307 | 495.0 | 495.4 |
| 140 | 1 | 1.178 | 494.0 | 494.4 |
| 141 | 1 | 1.222 | 536.1 | 536.4 |
| 142 | 1 | 1.328 | 509.1 | 509.4 |
| 143 | 1 | 1.362 | 491.0 | 491.3 |
| 144 | 1 | 1.395 | 505.0 | 505.4 |

TABLE B-continued

| No | HPLC Method | HPLC Rt | mass signal | MW |
|---|---|---|---|---|
| 145 | 1 | 1.310 | 504.0 | 504.4 |
| 146 | 1 | 1.333 | 546.0 | 546.4 |
| 147 | 1 | 1.412 | 519.0 | 519.4 |
| 148 | 1 | 1.265 | 491.0 | 491.3 |
| 149 | 1 | 1.271 | 505.0 | 505.4 |
| 150 | 1 | 1.187 | 504.0 | 504.4 |
| 151 | 1 | 1.231 | 546.1 | 546.4 |
| 152 | 1 | 1.336 | 519.0 | 519.4 |
| 153 | 1 | 1.252 | 486.1 | 486.4 |
| 154 | 1 | 1.456 | 491.0 | 491.4 |
| 155 | 1 | 1.428 | 477.1 | 477.4 |
| 156 | 1 | 1.384 | 490.1 | 490.4 |
| 157 | 1 | 1.379 | 548.1 | 548.5 |
| 158 | 1 | 1.261 | 548.1 | 548.5 |
| 159 | 1 | 1.311 | 562.1 | 562.5 |
| 160 | 1 | 1.231 | 506.1 | 506.4 |
| 161 | 1 | 1.287 | 520.1 | 520.4 |
| 162 | 2 | 1.429 | 520.1 | 520.4 |
| 163 | 1 | 1.420 | 562.1 | 562.5 |
| 164 | 1 | 1.297 | 493.1 | 493.4 |
| 165 | 1 | 1.340 | 513.0 | 513.8 |
| 166 | 1 | 1.395 | 526.0 | 526.8 |
| 167 | 1 | 1.322 | 568.0 | 568.9 |
| 168 | 1 | 1.222 | 506.1 | 506.4 |
| 169 | 1 | 1.301 | 548.1 | 548.5 |
| 170 | 1 | 1.443 | 568.0 | 568.9 |
| 171 | 3 | 1.520 | 526.1 | 526.8 |
| 172 | 1 | 1.410 | 513.0 | 513.8 |
| 173 | 1 | 1.377 | 493.1 | 493.4 |
| 174 | 1 | 1.328 | 548.1 | 548.5 |
| 175 | 1 | 1.253 | 506.1 | 506.4 |
| 176 | 1 | 1.303 | 477.1 | 477.4 |
| 177 | 1 | 1.351 | 497.0 | 497.8 |
| 178 | 1 | 1.259 | 532.1 | 532.5 |
| 179 | 1 | 1.421 | 552.0 | 552.9 |
| 180 | 1 | 1.409 | 510.0 | 510.8 |
| 181 | 1 | 1.328 | 532.1 | 532.5 |
| 182 | 3 | 1.156 | 490.1 | 490.4 |
| 183 | 1 | 1.354 | 491.1 | 491.4 |
| 184 | 3 | 1.228 | 504.1 | 504.5 |
| 185 | 3 | 1.346 | 566.1 | 566.9 |
| 186 | 3 | 1.396 | 524.0 | 524.9 |
| 187 | 3 | 1.295 | 485.1 | 485.4 |
| 188 | 1 | 1.339 | 475.1 | 475.4 |
| 189 | 3 | 1.306 | 483.0 | 483.4 |
| 190 | 1 | 1.279 | 457.0 | 457.4 |
| 191 | 3 | 1.325 | 475.1 | 475.4 |
| 192 | 3 | 1.297 | 461.1 | 461.4 |
| 193 | 3 | 1.395 | 487.1 | 487.4 |
| 194 | 3 | 1.261 | 463.0 | 463.4 |
| 195 | 3 | 1.285 | 477.1 | 477.4 |
| 196 | 3 | 1.345 | 489.1 | 489.4 |
| 197 | 3 | 1.323 | 475.0 | 475.4 |
| 198 | 3 | 1.289 | 457.0 | 457.4 |
| 199 | 3 | 1.312 | 471.0 | 471.4 |
| 200 | 1 | 1.460 | 482.9 | 483.4 |
| 201 | 3 | 1.287 | 473.1 | 473.4 |
| 202 | 3 | 1.332 | 487.1 | 487.4 |
| 203 | 3 | 1.194 | 463.0 | 463.4 |
| 204 | 3 | 1.262 | 475.0 | 475.4 |
| 205 | 2 | 1.278 | 564.0 | 564.5 |
| 206 | 2 | 1.255 | 522.1 | 522.4 |
| 207 | 2 | 1.341 | 522.1 | 522.4 |
| 208 | 2 | 1.216 | 564.1 | 564.5 |
| 209 | 2 | 1.300 | 602.0 | 602.4 |
| 210 | 2 | 1.392 | 602.0 | 602.4 |
| 211 | 2 | 1.351 | 560.0 | 560.4 |
| 212 | 2 | 1.445 | 560.1 | 560.4 |
| 213 | 4 | 2.215 | 495.1 | 495.4 |
| 214 | 4 | 1.438 | 511.2 | 511.4 |
| 215 | 7 | 1.846 | 527.1 | 527.4 |
| 216 | 4 | 2.666 | 493.2 | 493.4 |
| 217 | 8 | 2.384 | 509.1 | 509.4 |
| 218 | 8 | 2.544 | 525.1 | 525.4 |
| 219 | 1 | 1.119 | 558.1 | 558.5 |
| 220 | 1 | 1.042 | 558.1 | 558.5 |
| 221 | 1 | 0.966 | 516.1 | 516.4 |
| 222 | 1 | 1.336 | 596.1 | 596.4 |

TABLE B-continued

| No | HPLC Method | HPLC Rt | mass signal | MW |
|---|---|---|---|---|
| 223 | 1 | 1.397 | 596.0 | 596.4 |
| 224 | 1 | 1.360 | 554.0 | 554.4 |
| 225 | 1 | 1.425 | 554.0 | 554.4 |
| 226 | 1 | 1.317 | 555.0 | 555.4 |
| 227 | 1 | 0.889 | 517.0 | 517.4 |
| 228 | 1 | 0.901 | 559.0 | 559.4 |
| 229 | 1 | 0.987 | 559.0 | 559.4 |
| 230 | 1 | 1.182 | 500.0 | 500.4 |
| 231 | 1 | 1.127 | 500.0 | 500.4 |
| 232 | 1 | 1.210 | 542.0 | 542.5 |
| 233 | 1 | 1.307 | 487.0 | 487.4 |
| 234 | 1 | 1.294 | 542.1 | 542.5 |
| 235 | 1 | 1.412 | 520.0 | 520.8 |
| 236 | 1 | 1.392 | 562.0 | 562.9 |
| 237 | 1 | 1.307 | 520.0 | 520.8 |
| 238 | 1 | 1.205 | 510.0 | 494.4 |
| 239 | 1 | 1.199 | 494.0 | 508.4 |
| 240 | 1 | 1.380 | 552.0 | 552.4 |
| 241 | 1 | 1.271 | 552.0 | 552.4 |
| 242 | 1 | 0.990 | 547.0 | 547.4 |
| 243 | 1 | 1.073 | 547.1 | 547.4 |
| 244 | 1 | 1.010 | 505.1 | 505.4 |
| 245 | 1 | 1.185 | 547.0 | 547.4 |
| 246 | 1 | 1.179 | 543.0 | 543.4 |
| 247 | 1 | 1.292 | 521.0 | 521.8 |
| 248 | 1 | 1.291 | 563.0 | 563.9 |
| 249 | 1 | 1.220 | 490.1 | 489.5 |
| 250 | 1 | 1.265 | 590.0 | 590.5 |
| 251 | 1 | 1.363 | 590.1 | 590.5 |
| 252 | 1 | 1.297 | 574.1 | 574.5 |
| 253 | 1 | 1.387 | 574.1 | 574.5 |
| 254 | 1 | 1.251 | 564.0 | 564.4 |
| 255 | 1 | 1.345 | 564.1 | 564.4 |
| 256 | 1 | 1.261 | 547.0 | 474.4 |
| 257 | 1 | 1.380 | 547.0 | 474.4 |
| 258 | 1 | 1.192 | 548.0 | 548.4 |
| 259 | 1 | 1.319 | 548.1 | 548.4 |
| 260 | 1 | 1.022 | 505.0 | 505.4 |
| 261 | 1 | 0.950 | 505.0 | 505.4 |
| 262 | 1 | 1.073 | 505.0 | 505.4 |

Biological Examples

In Vitro Assay: *Ascaridia galli* and *Oesophagostumum Dentatum*

*Ascaridia galli* (intestinal roundworm of chicken), larval stage 3 ("L3"); and *Oesophagostumum dentatum* (nodular worm of swine), larval stages 3 and 4 (respectively "L3" and "L4") where suspended in a nutrient medium and distributed to 96 well plates with 20 larvae per well. The wells were spiked DMSO solutions of the compounds with declining concentration. The anthelmintic effects were determined by microscopic examination and defined by the minimum effective concentration ("MEC"), which is the concentration by which at least one of the larvae shows mortality, a change in motility or a change in progression of development.

The following compounds an MEC of 50 μM or less against *Ascaridia galli* L3:

1, 2, 3, 4, 5, 6, 7, 8, 9, 10, 11, 12, 13, 14, 15, 16, 17, 18, 19, 20, 21, 22, 23, 24, 28, 29, 30, 31, 32, 33, 34, 37, 38, 39, 40, 41, 42, 43, 44, 45, 46, 47, 50, 51, 52, 53, 54, 54, 55, 56, 57, 58, 59, 60, 61, 62, 66, 67, 68, 69, 70, 71, 73, 74, 75, 76, 77, 79, 83, 84, 86, 87, 88, 89, 90, 91, 93, 94, 95, 96, 97, 98, 99, 100, 101, 102, 103, 104, 105, 107, 108, 109, 110, 113, 115, 116, 118, 119, 120, 121, 122, 123, 124, 125, 126, 127, 128, 129, 130, 131, 132, 133, 135, 136, 138, 139, 140, 141, 142, 143, 144, 145, 146, 148, 149, 150, 151, 152, 153, 154, 155, 156, 157, 159, 160, 162, 164, 165, 166, 167, 168, 169, 170, 171, 172, 173, 174, 175, 176, 177, 178, 179, 180, 181, 182, 183, 184, 185, 186, 187, 189, 190, 192, 193, 194, 195, 196, 197, 198, 199, 200, 201, 202, 203, 204, 205, 206, 207, 208, 209, 210, 211, 212

The following compounds showed an MEC of 10 μM or less against *Ascaridia galli* L3:

5, 7, 8, 9, 11, 13, 19, 20, 22, 23, 31, 33, 42, 43, 47, 51, 52, 53, 54, 54, 55, 57, 58, 59, 61, 62, 68, 74, 87, 91, 93, 94, 97, 98, 100, 101, 103, 105, 108, 109, 110, 118, 119, 120, 121, 125, 126, 128, 129, 130, 131, 135, 139, 140, 141, 144, 145, 146, 148, 149, 150, 151, 152, 153, 156, 166, 167, 168, 169, 170, 171, 174, 178, 179, 181, 183, 184, 185, 186, 187, 189, 190, 192, 202, 203, 204, 205, 206, 207, 208, 209, 211

The following compounds an MEC of 50 μM or less against *Oesophagostumum dentatum* L3:

1, 2, 3, 4, 5, 6, 7, 8, 9, 10, 12, 13, 14, 15, 16, 17, 19, 20, 21, 22, 23, 24, 25, 26, 27, 30, 31, 32, 33, 34, 35, 36, 37, 38, 39, 40, 41, 42, 43, 44, 45, 46, 47, 48, 49, 51, 52, 53, 54, 54, 55, 56, 57, 58, 59, 62, 66, 67, 68, 69, 70, 71, 72, 73, 74, 75, 77, 79, 81, 82, 83, 84, 85, 86, 88, 90, 91, 92, 93, 94, 95, 96, 98, 99, 100, 101, 102, 103, 105, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 153, 154, 155, 156, 158, 160, 161, 162, 164, 165, 166, 167, 168, 169, 170, 171, 172, 173, 174, 175, 176, 177, 178, 179, 180, 181, 182, 183, 184, 185, 186, 187, 189, 190, 191, 193, 194, 195, 196, 197, 199, 200, 201, 202, 203, 204, 205, 206, 207, 208, 209, 211, 212

The following compounds showed an MEC of 10 μM or less against *Oesophagostumum dentatum* L3:

2, 5, 7, 8, 9, 12, 13, 14, 15, 16, 17, 19, 20, 21, 22, 23, 30, 31, 33, 36, 37, 38, 39, 40, 41, 42, 43, 44, 45, 46, 47, 49, 51, 52, 53, 54, 55, 58, 59, 62, 66, 67, 68, 69, 70, 71, 72, 73, 74, 82, 83, 84, 86, 88, 91, 92, 93, 94, 95, 96, 98, 100, 101, 102, 103, 105, 107, 108, 109, 110, 111, 113, 115, 116, 117, 118, 119, 120, 121, 123, 124, 125, 126, 128, 129, 130, 131, 133, 134, 135, 136, 138, 139, 140, 141, 143, 144, 145, 146, 148, 149, 150, 151, 153, 154, 155, 156, 164, 166, 167, 168, 169, 170, 171, 172, 173, 174, 175, 176, 178, 179, 180, 181, 182, 183, 184, 185, 186, 187, 189, 190, 194, 195, 197, 199, 200, 203, 204, 205, 206, 207, 208

The following compounds an MEC of 50 μM or less against *Oesophagostumum dentatum* L4:

1, 2, 3, 4, 5, 6, 7, 8, 9, 10, 12, 13, 14, 15, 16, 18, 19, 20, 21, 22, 23, 24, 25, 26, 27, 28, 29, 30, 31, 33, 34, 35, 36, 37, 38, 39, 40, 41, 42, 43, 45, 46, 47, 48, 49, 51, 52, 53, 54, 54, 55, 56, 57, 58, 62, 67, 68, 69, 70, 71, 72, 73, 74, 75, 77, 79, 82, 83, 84, 86, 88, 90, 91, 92, 93, 94, 95, 96, 98, 99, 100, 101, 102, 103, 105, 107, 108, 109, 110, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 153, 154, 155, 156, 158, 160, 163, 164, 165, 166, 167, 168, 169, 170, 171, 172, 173, 174, 175, 176, 177, 178, 179, 180, 181, 182, 183, 184, 185, 186, 187, 189, 190, 191, 192, 193, 194, 195, 196, 197, 199, 200, 201, 202, 203, 204, 205, 206, 207, 208, 209, 211, 212

The following compounds showed an MEC of 10 μM or less against *Oesophagostumum dentatum* L4:

1, 2, 3, 5, 6, 7, 8, 9, 12, 13, 14, 15, 16, 19, 20, 21, 22, 23, 24, 25, 26, 31, 33, 34, 35, 36, 38, 39, 40, 41, 42, 43, 46, 47, 51, 52, 53, 54, 54, 55, 56, 57, 58, 62, 67, 68, 69, 70, 71, 72, 73, 74, 75, 77, 79, 82, 83, 84, 86, 88, 90, 91, 93, 94, 95, 96, 98, 99, 100, 101, 102, 103, 105, 107, 108, 109, 110, 113, 114, 115, 116, 117, 118, 119, 120, 121, 122, 123, 124, 125, 126, 127, 128, 129, 130, 131, 132, 133, 134, 135, 136, 138, 139, 140, 141, 142, 143, 144, 145, 146, 147, 148, 149, 150, 151, 153, 154, 155, 156, 164, 165, 166, 167, 168, 169, 170, 171, 172, 173, 174, 175, 176, 177, 178, 179, 180, 181, 182, 183, 184, 185, 186, 187, 189, 190, 191, 193, 194, 195, 196, 197, 199, 200, 201, 202, 203, 204, 205, 206, 207, 208, 209, 211

In Vitro Assay: *Haemonchus contortus*

Solutions of compounds with declining concentrations in DMSO were prepared, diluted with nutrient medium and distributed to 96 well microtiterplates. Exsheathed L3 larvae of *Haemonchus contortus* were incubated for 20 min at 37° C. in a water bath, separated by centrifugation and added to the wells with 300 Larvae/well. After incubation for 7 days motility was assessed by automated microscopy. Ivermectin was used as positive control, DMSO as negative control and $ED_{50}$ values were calculated which represent the concentration for an individual compound that reduces motility by 50% with respect to the positive control.

The following compounds showed an $ED_{50}$ value below 50 μM agaist *Haemonchus contortus:*

1, 2, 4, 5, 7, 8, 9, 12, 14, 15, 19, 20, 21, 22, 23, 24, 30, 31, 33, 38, 40, 41, 42, 43, 46, 47, 51, 52, 53, 54, 54, 55, 56, 57, 58, 62, 67, 68, 69, 70, 71, 73, 74, 75, 77, 79, 82, 83, 84, 86, 94, 95, 96, 100, 101, 108, 110, 115, 116, 118, 120, 121, 123, 124, 125, 126, 128, 129, 130, 131, 138, 140, 141, 145, 146, 148, 149, 150, 151, 155, 156

The following compounds showed an $ED_{50}$ value below 10 μM agaist *Haemonchus contortus:*

1, 2, 5, 7, 9, 12, 14, 15, 19, 20, 21, 22, 30, 38, 41, 43, 47, 51, 52, 53, 54, 55, 56, 57, 58, 62, 67, 68, 69, 70, 71, 73, 74, 75, 77, 82, 83, 84, 94, 95, 96, 100, 101, 115, 118, 120, 121, 123, 124, 125, 126, 128, 129, 130, 131, 140, 141, 146, 148, 149, 150, 151, 155

In Vitro Assay: *Dirofilaria immitis* L1

Approximately 500 *D. immitis* microfilaria were added to a microtiter plate containing a nutrient medium and the test compound in DMSO at varying concentrations. After incubation for 3 days, activity was evaluated as reduction in motility as compared to DMSO as negative control. Compounds were tested in duplicates. Based on the concentration response curves $EC_{50}$ values were calculated.

The following compounds showed an $EC_{50}$ value below 10 μM: 1, 3, 5, 6, 7, 8, 9, 10, 11, 12, 13, 14, 15, 16, 19, 20, 21, 22, 23, 24, 25, 26, 28, 29, 30, 31, 33, 36, 38, 39, 40, 41, 42, 43, 45, 46, 47, 51, 52, 53, 54, 54, 55, 56, 57, 58, 62, 63, 65, 67, 68, 69, 70, 71, 72, 73, 74, 75, 77, 79, 82, 83, 84, 85, 86, 88, 90, 91, 92, 93, 94, 95, 96, 98, 99, 100, 101, 102, 103, 105, 107, 108, 109, 110, 113, 114, 115, 116, 117, 118, 119, 120, 121, 123, 124, 125, 126, 128, 129, 130, 131, 133, 134, 135, 136, 138, 139, 140, 141, 143, 144, 145, 146, 148, 149, 150, 151, 153, 154, 155, 156

The following compounds showed an $EC_{50}$ value below 1 μM: 1, 3, 5, 6, 7, 8, 9, 10, 12, 13, 14, 15, 16, 19, 20, 21, 22, 23, 24, 25, 26, 30, 31, 33, 36, 38, 39, 40, 41, 42, 43, 45, 46, 47, 51, 52, 53, 54, 54, 55, 56, 57, 58, 62, 65, 67, 68, 69, 70, 71, 72, 73, 74, 75, 77, 79, 82, 83, 84, 85, 86, 88, 90, 91, 92, 93, 94, 95, 96, 98, 99, 100, 101, 102, 103, 105, 107, 108, 109, 110, 113, 114, 115, 116, 117, 118, 119, 120, 121, 123, 124, 125, 126, 128, 129, 130, 131, 133, 134, 135, 136, 138, 139, 140, 141, 143, 144, 145, 146, 148, 149, 150, 151, 153, 154, 155, 156

The following compounds showed an $EC_{50}$ value below 0.1 μM: 5, 7, 8, 9, 12, 13, 14, 15, 16, 19, 20, 21, 22, 23, 31, 33, 38, 39, 40, 41, 42, 43, 45, 46, 47, 51, 52, 53, 54, 54, 55, 56, 57, 58, 62, 65, 67, 68, 69, 70, 71, 72, 73, 74, 75, 77, 79, 82, 83, 84, 86, 88, 90, 91, 92, 93, 94, 95, 96, 98, 99, 100, 101, 102, 103, 105, 107, 108, 109, 110, 113, 114, 115, 116, 117, 118, 119, 120, 121, 123, 124, 125, 126, 128, 129, 130, 131, 133, 134, 135, 136, 138, 139, 140, 141, 143, 144, 145, 146, 148, 149, 150, 151, 153, 154, 155, 156

In Vitro Assay: *Dirofilaria immitis* L4

10 larvae L4 of *D. immitis* were added to a microtiter plate containing a nutrient medium and the test compound in DMSO at varying concentrations. After incubation for 3 days, activity was evaluated as reduction in motility as compared to DMSO as negative control. Compounds were tested in duplicates. Based on the concentration response curves $EC_{50}$ values were calculated.

The following compounds showed an $EC_{50}$ value below 1 μM: 1, 3, 5, 7, 8, 12, 14, 19, 20, 31, 43, 55, 69, 74, 82

The following compounds showed an $EC_{50}$ value below 0.1 μM: 1, 5, 7, 8, 12, 14, 19, 20, 31, 43, 55, 69, 74, 82

In Vitro Assay: *Acanthocheilonema viteae* L1

Approximately 500 *A. viteae* microfilaria were added to a microtiter plate containing a nutrient medium and the test compound in DMSO at varying concentrations. After incubation for 3 days, activity was evaluated as reduction in motility as compared to DMSO as negative control. Compounds were tested in duplicates. Based on the concentration response curves $EC_{50}$ values were calculated.

The following compounds showed an $EC_{50}$ value below 10 μM: 5, 7, 8, 19, 20, 43, 51, 52, 53, 53, 54, 54, 84, 85, 86, 87, 88, 90, 91, 92, 93, 94, 95, 96, 98, 100, 101, 102, 103, 108, 109, 110, 113, 114, 115, 116, 117, 118, 119, 120, 121, 123, 124, 125, 126, 127, 128, 129, 130, 131, 132, 133, 134, 135, 136, 138, 139, 140, 141, 143, 144, 145, 146, 147, 148, 149, 150, 151, 153, 154, 155, 156, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 189, 190, 191, 192, 193, 194, 195, 196, 197, 198, 199, 200, 201, 202, 203, 204, 205,206, 207, 208, 209, 210, 211, 212

The following compounds showed an $EC_{50}$ value below 1 μM: 5, 7, 8, 19, 20, 43, 51, 52, 53, 53, 54, 54, 84, 85, 86, 88, 90, 91, 92, 93, 94, 95, 96, 100, 101, 102, 103, 108, 109, 110, 113, 114, 115, 116, 117, 118, 119, 120, 121, 123, 124, 125, 126, 128, 129, 130, 131, 133, 134, 135, 136, 138, 139, 140, 141, 143, 144, 145, 146, 148, 149, 150, 151, 153, 154, 155, 156, 158, 164, 165, 166, 167, 168, 169, 170, 171, 172, 173, 174, 175, 176, 177, 178, 179, 180, 181, 182, 183, 184, 185, 186, 187, 189, 190, 191, 192, 193, 194, 195, 196, 197, 198, 199, 200, 201, 202, 203, 204, 205, 206, 207, 208, 209, 210, 211, 212

The following compounds showed an $EC_{50}$ value below 0.1 μM: 5, 7, 8, 19, 20, 43, 51, 52, 53, 53, 54, 54, 84, 86, 90, 91, 92, 93, 94, 95, 96, 100, 101, 102, 103, 108, 109, 110, 113, 114, 115, 116, 117, 118, 119, 120, 121, 123, 124, 125, 126, 128, 129, 130, 131, 133, 134, 135, 136, 138, 139, 140, 141, 143, 144, 145, 146, 148, 149, 150, 151, 153, 154, 155, 156, 164, 165, 166, 167, 168, 169, 170, 171, 172, 173, 174, 175, 176, 177, 178, 179, 180, 181, 182, 183, 184, 185, 186, 187, 189, 190, 191, 192, 193, 194, 195, 196, 197, 198, 199, 202, 203, 204, 205, 206, 207, 208, 209, 210

In Vitro Assay: Agonistic Activity at *C. elegans* Slo-1a

A CHO K1 cell line stably transfected with the *Caenorhabditis elegans* slo-1a (accession no Y51A2D.19a) was established. Cells were seeded in microtiter plates (black 384-well MTP, clear bottom) in a concentration of 10,000 cells/well in 25 μl medium and cultured for 20 to 24 hours at 37° C. and 5% $CO_2$. The cell medium was removed, and the cells washed with Tyrode's solution. 1 of FMP-dye Blue-Tyrode's was added to each well and incubated at room temperature for 30 min.

For the membrane potential measurements, the prepared cell plate and substance plate were placed in the FLIPR Tetra (Molecular Devices). The baseline measurement of the fluorescence was stared for 20 sec (Exc. 510-545 nm, Emm. 565-625 nm). The cells were depolarized by addition of 25p of the diluted test compounds (final assay concentration of the KCl-Tyrode: 70 mM KCl, 2 mM CaCl2), 1 mM MgCl2, 0.8 mM NaH2PO4, 5 mM Glucose, 28 mM Hepes, pH 7.4, including the voltage sensitive dye). The complete measurement takes 150 s.

$EC_{50}$ values were determined in triplicate utilizing compound dilution series. The data were determined at least in two independent tests. The data were proceeded by using the ActivityBase XE Runner software (IDBS) for curve fitting and calculation of the half-maximal effective concentration.

The following compounds showed an $EC_{50}$ value below 10 μM: 1, 3, 7, 8, 9, 10, 12, 13, 14, 15, 16, 19, 20, 21, 22, 23, 24, 25, 26, 27, 29, 30, 31, 33, 34, 35, 36, 37, 38, 39, 40, 41, 42, 43, 44, 45, 46, 47, 48, 49, 54, 54, 55, 56, 57, 58, 62, 65, 67, 68, 69, 70, 71, 73, 74, 75, 77, 79, 82, 83, 84, 85, 90, 92, 94, 95, 100, 102, 103, 105, 107, 108, 109, 110, 113, 115, 116, 118, 119, 120, 121, 123, 124, 125, 126, 128, 129, 130, 131, 135, 136, 138, 139, 140, 141, 144, 145, 146, 148, 149, 150, 151, 153, 154, 155, 156, 160, 164, 165, 166, 167, 168, 169, 170, 171, 172, 173, 174, 175, 176, 177, 178, 179, 180, 181, 182, 183, 184, 185, 186, 187, 190, 191, 192, 193, 194, 195, 196, 197, 199, 201, 202, 203, 204

The following compounds showed an $EC_{50}$ value below 1 μM: 8, 9, 12, 13, 14, 15, 16, 19, 20, 23, 31, 33, 37, 40, 41, 42, 43, 45, 47, 54, 54, 55, 56, 57, 58, 62, 67, 68, 69, 74, 75, 82, 83, 94, 95, 100, 102, 103, 105, 108, 109, 110, 113, 115, 116, 118, 119, 120, 121, 123, 124, 125, 126, 128, 129, 130, 131, 135, 138, 139, 140, 141, 145, 146, 148, 149, 150, 151, 154, 155, 156, 165, 166, 167, 168, 169, 170, 171, 174, 176, 177, 178, 179, 180, 182, 183, 184, 185, 186, 187, 191, 195, 197, 201, 202, 203, 204

In Vitro Assay: Agonistic Activity at the Human Maxi K Channel (BK Channel)

A CHO K1 cell line was stably transfected with the KCNMA1 (KCa1.1, U11058) and beta1 (KCNMB1) subunits of the human Maxi K channel (Ponte et al, Molecular Pharmacology 2012, 81(4), 567-577).

Cells were seeded in microtiter plates (black 384-well MTP, clear bottom) in a concentration of 10,000 cells/well in 25 μl medium and cultured for 20 to 24 hours at 37° C. and 5% $CO_2$. The cell medium was removed, and the cells washed with Tyrode's solution. 25 1 of FMP-dye Blue-Tyrode's was added to each well and incubated at room temperature for 30 min.

For the membrane potential measurements, the prepared cell plate and substance plate were placed in the FLIPR Tetra (Molecular Devices). The baseline measurement of the fluorescence was stared for 20 sec (Exc. 510-545 nm, Emm. 565-625 nm). The cells were depolarized by addition of 25 μl of the diluted test compounds (final assay concentration of the KCl-Tyrode: 70 mM KCl, 2 mM $CaCl_2$), 1 mM $MgCl_2$, 0.8 mM $NaH_2PO_4$, 5 mM Glucose, 28 mM Hepes, pH 7.4, including the voltage sensitive dye). The complete measurement takes 150 s.

$EC_{50}$ values were determined in triplicate utilizing compound dilution series. The data were determined at least in two independent tests. The data were proceeded by using the ActivityBase XE Runner software (IDBS) for curve fitting and calculation of the half-maximal effective concentration.

The following compounds showed an $EC_{50}$ value between 1 and 10 μM: 13, 19, 20, 53, 100, 120, 121, 131, 141, 151

The following compounds showed an $EC_{50}$ value between 10 and 30 μM: 8, 33, 37, 45, 74, 82, 95, 96, 101, 102, 130, 140, 146, 150, 169, 178, 184, 185

The following compounds showed an $EC_{50}$ value above 30 μM: 1, 3, 5, 7, 9, 10, 11, 12, 14, 15, 16, 17, 18, 21, 22, 23, 24, 25, 26, 27, 28, 29, 30, 31, 32, 34, 35, 36, 38, 39, 40, 41, 42, 43, 44, 46, 47, 48, 49, 50, 54, 54, 55, 56, 57, 58, 59, 60, 61, 62, 63, 64, 65, 66, 67, 68, 69, 70, 71, 72, 73, 75, 76, 77, 78, 79, 80, 81, 83, 84, 85, 86, 87, 88, 89, 90, 91, 92, 93, 94, 97, 98, 99, 103, 104, 105, 106, 107, 108, 109, 110, 111, 112, 113, 114, 115, 116, 117, 118, 119, 122, 123, 124, 125, 126, 127, 128, 129, 132, 133, 134, 135, 136, 137, 138, 139, 142, 143, 144, 145, 147, 148, 149, 152, 153, 154, 155, 156, 157, 158, 159, 160, 161, 162, 163, 164, 165, 166, 167, 168, 170, 171, 172, 173, 174, 175, 176, 177, 179, 180, 181, 182, 183, 186, 187, 189, 190, 191, 192, 193, 194, 195, 196, 197, 198, 199, 200, 201, 202, 203, 204

Thus, it can be seen from the present results that the present compound are effective as far as the treatment of helminths, such as nematodes, especially *Dirofilaria*, is concerned, while the potential for target-related adverse reactions in the host such as mammal (e.g. a human being) is low.

In Vivo Assay: Efficacy Against *Haemonchus contortus* in Jirds

Compounds according to this invention were tested in vivo using *Haemonchus contortus* in jirds (*Meriones unguiculatus*). The jirds were orally infected with approximately 1500 third-stage larvae of *Haemonchus contortus*. Ten days after infection, the jirds in the treatment groups were treated once either orally or subcutaneously with compounds at a dose of 10 mg bodyweight. For treatment, compounds were dissolved in a mixture of 10% Transcutol, 10% Cremophor EL and 80% physiological sodium chloride solution. Three days after treatment, the jirds were necropsied, and the larvae burden in the stomach was determined. The efficacy was defined as the reduction of the mean larvae count in the infected jirds of the treatment group in comparison to the infected jirds in an untreated control group (negative control).

Compound 151 reduced the *Haemonchus contortus* count by at least 80% when administered orally or subcutaneously at 10 mg/kg bw.

The invention claimed is:

1. Compound of Formula (I)

Formula (I)

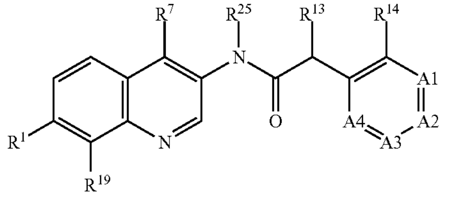

wherein $R^1$ is independently selected from the group consisting of hydrogen, $C_{1-6}$-alkyl, $C_{2-6}$-alkenyl, $C_{2-6}$-alkynyl, $C_{3-10}$-cycloalkyl, 5- to 10-membered heterocyclyl, $C_{6-10}$ aryl, 5- to 10-membered heteroaryl, $C_{1-6}$-alkoxy, $C_{1-6}$-alkylmercapto, halogen, cyano, nitro, hydroxy, mercapto, $NR^2R^3$, COOH, $C(=O)OR^4$, $SR^4$, $SOR^4$, $SO_2R^4$, $SO_2NR^5R^6$ and $C(=O)NR^5R^6$, wherein each $C_{1-6}$-alkyl, $C_{2-6}$-alkenyl, $C_{2-6}$-alkynyl, $C_{3-10}$-cycloalkyl, 5- to 10-membered heterocyclyl, $C_{6-10}$ aryl, 5- to 10-membered heteroaryl, $C_{1-6}$-alkoxy or $C_{1-6}$-alkylmercapto, is optionally substituted with one or more substituent(s) independently selected from the group consisting of $C_{1-6}$-alkyl, $C_{2-6}$-alkenyl, $C_{2-6}$-alkynyl, $C_{3-10}$-cycloalkyl, 5- to 10-membered heterocyclyl, $C_{6-10}$-aryl, 5- to 10-membered heteroaryl, $C_{1-6}$-alkoxy, $C_{1-6}$-alkylmercapto, halogen, cyano, nitro, hydroxy, mercapto, $NR^{2'}R^{3'}$, $C(=O)OR^{4'}$, $SR^{4'}$, $SOR^{4'}$, $SO_2R^{4'}$, $SO_2NR^{5'}R^{6'}$ and $C(=O)NR^{5'}R^{6'}$, $R^2$ and $R^3$ are independently selected from the group consisting of hydrogen, $C_{1-6}$-alkyl, $C_{2-6}$-alkenyl, $C_{2-6}$-alkynyl, $C_{3-10}$-cycloalkyl, 5- to 10-membered heterocyclyl, $C_{6-10}$-aryl, 5- to 10-membered heteroaryl, $C_{1-6}$-alkoxy-$C_{1-6}$-alkyl, $C_{1-6}$-alkyl substituted with $C_{3-10}$-cycloalkyl, $C_{1-6}$-alkyl substituted with 5- to 10-membered heterocyclyl, $C_{1-6}$-alkyl substituted with $C_{6-10}$-aryl and $C_{1-6}$-alkyl substituted with 5- to 10-membered heteroaryl, or $R^2$ and $R^3$ together with the N atom to which they are attached form a saturated or unsaturated heterocyclic ring having 3 to 12 ring atoms, wherein 0, 1, 2 or 3 further ring atoms are selected from N, S and O, wherein each $C_{1-6}$-alkyl, $C_{2-6}$-alkenyl, $C_{2-6}$-alkynyl, $C_{3-10}$-cycloalkyl, 5- to 10-membered heterocyclyl, $C_{6-10}$-aryl, 5- to 10-membered heteroaryl, $C_{1-6}$-alkoxy-$C_1$-6-alkyl, $C_{1-6}$-alkyl substituted with $C_{3-10}$-cycloalkyl, $C_{1-6}$-alkyl substituted with 5- to 10-membered heterocyclyl, $C_{1-6}$-alkyl substituted with $C_{6-10}$-aryl or $C_{1-6}$-alkyl substituted with 5- to 10-membered heteroaryl or the heterocyclic ring formed by $R^2$ and $R^3$ together with the N atom to which they are attached is optionally substituted with one or more substituent(s) independently selected from the group consisting of $C_{1-6}$-alkyl, $C_{2-6}$-alkenyl, $C_{2-6}$-alkynyl, $C_{3-10}$-cycloalkyl, 5- to 10-membered heterocyclyl, $C_{6-10}$-aryl, 5- to 10-membered heteroaryl, $C_{1-6}$-alkoxy, carbonyl, halogen, cyano, hydroxy, mercapto, $NR^{2''}R^{3''}$, $C(=O)OR^{4''}$, $SR^{4''}$, $SOR^4$, $SO_2R^{4''}$, $SO_2NR^{5''}R^{6''}$ and $C(=O)NR^{5''}R^{6''}$;

$R^4$, $R^5$ and $R^6$ are independently selected from hydrogen and $C_{1-6}$-alkyl, $R^{2'}$, $R^{3'}$, $R^{4'}$, $R^{5'}$ and $R^{6'}$ are independently selected from hydrogen and $C_{1-6}$-alkyl, $R^{2''}$, $R^{3''}$, $R^{4''}$, $R^{5''}$ and $R^{6''}$ are independently selected from hydrogen and $C_{1-6}$-alkyl, $R^7$ is independently selected from the group consisting of hydrogen, $C_{1-6}$-alkyl, $C_{2-6}$-alkenyl, $C_{2-6}$-alkynyl, $C_{3-10}$-cycloalkyl, 4- to 10-membered heterocyclyl, $C_{6-10}$ aryl, 5- to 10-membered heteroaryl, $C_{1-6}$-alkoxy, $C_{1-6}$-alkylmercapto, halogen, cyano, nitro, hydroxy, mercapto, $NR^8R^9$, COOH, $C(=O)OR^{10}$, $SR^{10}$, $SOR^{10}$, $SO_2R^{10}$, $SO_2NR^{11}R^{12}$ and $C(=O)NR^{11}R^{12}$, wherein each $C_{1-6}$-alkyl, $C_{2-6}$-alkenyl, $C_{2-6}$-alkynyl, $C_{3-10}$-cycloalkyl, 4- to 10-membered heterocyclyl, $C_{6-10}$ aryl, 5- to 10-membered heteroaryl, $C_{1-6}$-alkoxy or $C_{1-6}$-alkylmercapto, is optionally substituted with one or more substituent(s) independently selected from the group consisting of $C_{1-6}$-alkyl, $C_{2-6}$-alkenyl, $C_{2-6}$-alkynyl, $C_{3-10}$-cycloalkyl, 5- to 10-membered heterocyclyl, $C_{6-10}$-aryl, 5- to 10-membered heteroaryl, $C_{1-6}$-alkoxy, $C_{1-6}$-alkylmercapto, halogen, cyano, nitro, hydroxy, mercapto, $NR^{8'}R^{9'}$, $C(=O)OR^{10'}$, $SR^{10'}$, $SOR^{10'}$, $SO_2R^{10'}$, $SO_2NR^{11'}R^{12'}$ and $C(=O)NR^{11'}R^{12'}$, $R^8$ and $R^9$ are independently selected from the group consisting of hydrogen, $C_{1-6}$-alkyl, $C_{2-6}$-alkenyl, $C_{2-6}$-alkynyl, $C_{3-10}$-cycloalkyl, 5- to 10-membered heterocyclyl, $C_{6-10}$-aryl, 5- to 10-membered heteroaryl, $C_{1-6}$-alkoxy-$C_{1-6}$-alkyl, $C_{1-6}$-alkyl substituted with $C_{3-10}$-cycloalkyl, $C_{1-6}$-alkyl substituted with 5- to 10-membered heterocyclyl, $C_{1-6}$-alkyl substituted with $C_{6-10}$-aryl, $C_{1-6}$-alkyl substituted with 5- to 10-membered heteroaryl, or $R^8$ and $R^9$ together with the N atom to which they are attached form a saturated or unsaturated heterocyclic ring having 3 to 12 ring atoms, wherein 0, 1, 2, or 3 further ring atoms are selected from N, S and O, wherein each $C_{1-6}$-alkyl, $C_{2-6}$-alkenyl, $C_{2-6}$-alkynyl, $C_{3-10}$-cycloalkyl, 5- to 10-membered heterocyclyl, $C_{6-10}$-aryl, 5- to 10-membered heteroaryl, $C_{1-6}$-alkoxy-$C_1$-6-alkyl, $C_{1-6}$-alkyl substituted with $C_{3-10}$-cycloalkyl, $C_{1-6}$-alkyl substituted with 5- to 10-membered heterocyclyl, $C_{1-6}$-alkyl substituted with $C_{6-10}$-aryl or $C_{1-6}$-alkyl substituted with 5- to 10-membered heteroaryl or the heterocyclic ring formed by $R^8$ and $R^9$ together with the N atom to which they are attached is optionally substituted with one or more substituent(s) independently selected from the group consisting of $C_{1-6}$-alkyl, $C_{2-6}$-alkenyl, $C_{2-6}$-alkynyl, $C_{3-10}$-cycloalkyl, 5- to 10-membered heterocyclyl, $C_{6-10}$-aryl, 5- to 10-membered heteroaryl, $C_{1-6}$-alkoxy, carbonyl, halogen, cyano, hydroxy, mercapto, $NR^{8''}R^{9''}$, $C(=O)OR^{10''}$, $SR^{10''}$, $SOR^{10''}$, $SO_2R^{10''}$, $SO_2NR^{11''}R^{12''}$ and $C(=O)NR^{11''}R^{12''}$;

$R^{10}$, $R^{11}$ and $R^{12}$ are independently selected from hydrogen and $C_{1-6}$-alkyl, $R^{8'}$, $R^{9'}$, $R^{10'}$, $R^{11'}$ and $R^{12'}$ are independently selected from hydrogen and $C_{1-6}$-alkyl, $R^{8''}$, $R^{9''}$, $R^{10''}$, $R^{11''}$ and $R^{12''}$ are independently selected from hydrogen and $C_{1-6}$-alkyl, $R^{13}$ is hydrogen or $C_{1-3}$ alkyl, $R^{14}$ is hydrogen, $C_{1-3}$ alkyl, $C_{1-3}$ alkoxy, $NR^{14'}R^{14''}$, wherein $R^{14'}$ and $R^{14''}$ are independently $C_{1-3}$-alkyl or $R^{13}$ and $R^{14}$ together with the atoms to which they are attached form a 5 or 6-carbon atoms containing aromatic ring, wherein the 5 or 6-carbon atoms containing ring is optionally substituted with one or more $C_{1-3}$-alkyl, and/or wherein one or more of the ring forming carbon atoms are optionally replaced by —NH—, —N=, =N—, —O— or —S—, A1 is N or $CR^{15}$, wherein $R^{15}$ is independently hydrogen, halogen, $C_{1-3}$ alkyl, $C_{1-3}$ alkoxy, or $NR^{15'}R^{15''}$, wherein $R^{15'}$ and $R^{15''}$ are independently $C_{1-3}$-alkyl, A2 is N or $CR^{16}$, wherein $R^{16}$ is independently hydrogen, halogen, $C_{1-3}$ alkyl, $C_{1-3}$ alkoxy, or $NR^{16'}R^{16''}$, wherein $R^{16'}$ and $R^{16''}$ are independently $C_{1-3}$-alkyl, A3 is N or $CR^{17}$, wherein $R^{17}$ is independently hydrogen, halogen, $C_{1-3}$ alkyl, $C_{1-3}$ alkoxy, or $NR^{17'}R^{17''}$, wherein $R^{17}$ and $R^{17''}$ are independently $C_{1-3}$-alkyl, A4 is N or $CR^{18}$, wherein $R^{18}$ is independently hydrogen, halogen $C_{1-3}$ alkyl, $C_{1-3}$ alkoxy, or $NR^{18'}R^{18''}$, wherein $R^{18'}$ and $R^{18''}$ are independently $C_{1-3}$-alkyl, $R^{19}$ is independently selected from the group consisting of $C_{6-10}$-aryl and 5- to 10-membered heteroaryl, wherein each $C_{6-10}$-aryl or 5- to 10-membered heteroaryl is optionally substituted with one or more substituent(s) independently selected from the group consisting of $C_{1-6}$-alkyl, $C_{2-6}$-alkenyl, $C_{3-10}$-cycloalkyl, 5- to 10-membered heterocyclyl, $C_{6-10}$-aryl, 5- to 10-membered heteroaryl, $C_{1-6}$-alkoxy, $C_{1-6}$-alkylmercapto, halogen, cyano, nitro, hydroxy, mercapto, $NR^{20}R^{21}$, $C(=O)OR^{22}$, $SR^{22}$, $SOR^{22}$, $SO_2R^{22}$, $SO_2NR^{23}R^{24}$ and $C(=O)NR^{23}R^{24}$, $R^{20}$ and $R^{21}$ are independently selected from the group consisting of hydrogen, $C_{1-6}$-alkyl, $C_{3-10}$-cycloalkyl, $C_{6-10}$-aryl, 5- to 10-membered heteroaryl, $C_{1-6}$-alkoxy-$C_{1-6}$-alkyl, $C_1$-$C_6$-alkyl substituted with $C_{6-10}$-aryl, $C_{1-6}$-alkyl substituted with 5- to 10-membered heteroaryl, or $R^{20}$ and $R^{21}$ together with the N atom to which they are attached form a saturated or unsaturated heterocyclic ring having 3 to 12 ring atoms, wherein 0, 1, 2, or 3 further ring atoms are selected from N, S and O;

wherein each $C_{1-6}$-alkyl, $C_{2-6}$-alkenyl, $C_{3-10}$-cycloalkyl, 5- to 10-membered heterocyclyl, $C_{6-10}$-aryl, 5- to 10-membered heteroaryl, $C_{1-6}$-alkoxy or $C_{1-6}$-alkylmercapto or the heterocyclic ring formed by $R^{20}$ and $R^{21}$ together with the N atom to which they are attached is optionally substituted with one or more substituents independently selected from the group consisting of $C_{1-6}$-alkyl, $C_{2-6}$-alkenyl, $C_{2-6}$-alkynyl, $C_{3-10}$-cycloalkyl, 5- to 10-membered heterocyclyl, $C_{6-10}$-aryl, 5- to 10-membered heteroaryl, $C_{1-6}$-alkoxy, carbonyl, halogen, cyano, hydroxy, mercapto, $NR^{20'}R^{21'}$, $C(=O)OR^{22'}$, $SR^{22'}$, $SOR^{22'}$, $SO_2R^{22'}$, $SO_2NR^{23'}R^{24'}$, and $C(=O)NR^{23'}R^{24'}$ $R^{22}$, $R^{23}$ and $R^{24}$ are independently selected from hydrogen and $C_{1-6}$-alkyl, $R^{20'}$, $R^{21'}$, $R^{22'}$, $R^{23'}$ and $R^{24'}$ are independently selected from hydrogen and $C_{1-6}$-alkyl, $R^{25}$ is independently selected from hydrogen and $C_{1-6}$-alkyl, or a stereoisomer, physiologically acceptable salt, ester, and mixtures thereof.

2. The compound according to claim 1, wherein $R^1$ is independently selected from the group consisting of hydrogen, $C_{1-6}$-alkyl, $C_{1-6}$-alkoxy, halogen, cyano, nitro, hydroxy, $NR^2R^3$, $C(=O)OR^4$ and $C(=O)NR^5R^6$, wherein each $C_{1-6}$-alkyl or $C_{1-6}$-alkoxy is optionally substituted with one or more substituents independently selected from the group consisting of $C_{1-6}$-alkyl, $C_{1-6}$-alkoxy, halogen, cyano, nitro, hydroxy and $NR^{2'}R^{3'}$, $R^2$ and $R^3$ are independently selected from the group consisting of hydrogen, $C_{1-6}$-alkyl, $C_{3-10}$-cycloalkyl, $C_{6-10}$-aryl and 5 to 10-membered heteroaryl, or $R^2$ and $R^3$ together with the N atom to which they are attached form a saturated or unsaturated heterocyclic ring having 3 to 12 ring atoms, wherein 1 ring atom is N and wherein 0, 1, 2 or 3 further ring atoms are selected from N, S and O;

wherein each $C_{1-6}$-alkyl, $C_{3-10}$-cycloalkyl, $C_{6-10}$-aryl or 5 to 10-membered heteroaryl or the heterocyclic ring formed by $R^2$ and $R^3$ together with the N atom to which they are attached is optionally substituted with one or more substituent(s) independently selected from the group consisting of $C_{1-6}$-alkyl, $C_{3-10}$-cycloalkyl and $C_{1-6}$-alkoxy, $R^4$, $R^5$ and $R^6$ are independently selected from hydrogen and $C_{1-6}$-alkyl, $R^{2'}$ and $R^{3'}$ are independently selected from hydrogen and $C_{1-6}$-alkyl.

3. The compound according to claim 1, wherein $R^1$ is independently selected from the group consisting of hydrogen, $C_{1-6}$-alkyl, $C_{1-6}$-alkoxy and halogen, wherein each $C_{1-6}$-alkyl or $C_{1-6}$-alkoxy is optionally substituted with one or more substituent(s) independently selected from the group consisting of $C_{1-6}$-alkyl, $C_{1-6}$-alkoxy, halogen, cyano, hydroxy and $NR^{2'}R^{3'}$, wherein $R^{2'}$ and $R^{3'}$ are independently selected from hydrogen and $C_{1-3}$-alkyl.

4. The compound according to claim 1, wherein $R^1$ is independently selected from the group consisting of hydrogen, methyl, trifluoromethyl, ethyl, methoxy, ethoxy, fluoride and chloride.

5. The compound according to claim 1, wherein $R^7$ is independently selected from the group consisting of hydrogen, $C_{1-6}$-alkyl, $C_{2-6}$-alkenyl, $C_{3-10}$-cycloalkyl, 4- to 10 membered heterocyclyl, $C_{1-6}$-alkoxy, halogen, cyano, hydroxy, $NR^8R^9$, $C(=O)OR^{10}$, $SR^{10}$, $SOR^{10}$, $SO_2R^{10}$ and $C(=O)NR^{11}R^{12}$, wherein each $C_{1-6}$-alkyl, $C_{2-6}$-alkenyl, $C_{3-10}$-cycloalkyl, 4- to 10 membered heterocyclyl or $C_{1-6}$-alkoxy is optionally substituted with one or more substituent(s) independently selected from the group consisting of $C_{1-6}$-alkyl, $C_{3-10}$-cycloalkyl, 5- to 10 membered heterocyclyl, $C_{1-6}$-alkoxy, halogen, cyano, hydroxy, $NR^{8'}R^{9'}$, $C(=O)OR^{10'}$ and $C(=O)NR^{11'}R^{12'}$, $R^8$ and $R^9$ are independently selected from the group consisting of hydrogen, $C_{1-6}$-alkyl, $C_{3-10}$-cycloalkyl, $C_{6-10}$-aryl, 5- to 10 membered heterocyclyl and 5- to 10 membered heteroaryl, or $R^8$ and $R^9$ together with the N atom to which they are attached form a saturated or unsaturated heterocyclic ring having 3 to 12 ring atoms, wherein 1 ring atom is N and wherein 0, 1, 2, or 3 further ring atoms are selected from N, S and O;

wherein each $C_{1-6}$-alkyl, $C_{3-10}$-cycloalkyl, $C_{6-10}$-aryl, 5- to 10 membered heterocyclyl, and 5- to 10 membered heteroaryl or the heterocyclic ring formed by $R^8$ and $R^9$ together with the N atom to which they are attached is optionally substituted with one or more substituent(s) independently selected from the group consisting of $C_{1-6}$-alkyl, $C_{1-6}$-alkoxy, halogen, cyano, hydroxy, $NR^{8''}R^{9''}$, $C(=O)-OR^{10''}$ and $C(=O)NR^{11''}R^{12''}$;

$R^{10}$, $R^{11}$ and $R^{12}$ are independently selected from hydrogen and $C_{1-6}$-alkyl, $R^{8'}$, $R^{9'}$, $R^{10'}$, $R^{11'}$ and $R^{12'}$ are independently selected from hydrogen and $C_{1-6}$-alkyl, $R^{8''}$, $R^{9''}$, $R^{10''}$, $R^{11''}$ and $R^{12''}$ are independently selected from hydrogen and $C_{1-6}$-alkyl.

6. The compound according to claim 1, wherein $R^7$ is independently selected from the group consisting of hydrogen, $C_{1-6}$-alkyl, $C_{2-6}$-alkenyl, 4- to 10 membered heterocyclyl, $C_{1-6}$-alkoxy, hydroxy, $NR^8R^9$, $C(=O)OR^{10}$, $SR^{10}$, $SOR^{10}$, $SO_2R^{10}$ and $C(=O)NR^{11}R^{12}$, wherein each $C_{1-6}$-alkyl, $C_{2-6}$-alkenyl, 4- to 10 membered heterocyclyl or $C_{1-6}$-alkoxy is optionally substituted with one or more substituent(s) independently selected from the group consisting of $C_{1-6}$-alkyl, 5- to 10 membered heterocyclyl, $C_{1-6}$-alkoxy, halogen, cyano, hydroxy, $NR^{8'}R^{9'}$, C(═O)$OR^{10'}$ and C(═O)$NR^{11'}R^{12'}$, $R^8$ and $R^9$ are independently selected from the group consisting of hydrogen, $C_{1-6}$-alkyl, $C_{6-10}$-aryl, and 5- to 10 membered heteroaryl, or $R^8$ and $R^9$ together with the N atom to which they are attached form a saturated or unsaturated heterocyclic ring having 3 to 12 ring atoms, wherein 1 ring atom is N and wherein 0, 1, 2, or 3 further ring atoms are selected from N, S and O;

wherein the $C_{1-6}$-alkyl, $C_{6-10}$-aryl, and 5- to 10 membered heteroaryl or the heterocyclic ring formed by $R^8$ and $R^9$ together with the N atom to which they are attached is optionally substituted with one or more substituent(s) independently selected from the group consisting of $C_{1-6}$-alkyl, $C_{1-6}$-alkoxy, hydroxy and $NR^{8''}R^{9''}$;

$R^{10}$, $R^{11}$ and $R^{12}$ are independently selected from hydrogen or $C_{1-6}$-alkyl, $R^{8'}$, $R^{9'}$, $R^{10'}$, $R^{11'}$ and $R^{12'}$ are independently selected from hydrogen or $C_{1-6}$-alkyl, $R^{8''}$ are $R^{9''}$ are independently selected from hydrogen or $C_{1-6}$-alkyl.

7. The compound according to claim 1, wherein $R^7$ is independently selected from the group consisting of methyl, ethyl, propyl, isopropyl, isopropenyl, methoxy, ethoxy, isopropoxy, hydroxy, methyl sulfoxyl, methyl sulfonyl, methylthio, amino, methylamino, ethylamino, (ethyl)(methyl) amino isopropylamino, dimethylamino, (isopropyl)(methyl) amino, hydroxyethylamino, (hydroxyethyl)(methyl)amino, methoxyethylamino, (methoxyethyl)(methyl)amino, morpholin-4-yl, pyrrolidin-1-yl, 3-hydroxy-pyrrolidin-1-yl 3-fluoroazetidinyl and 3,3-difluoroazetidinyl.

8. The compound according to claim 1, wherein $R^{13}$ and $R^{14}$ together with the atoms to which they are attached form a 5 or 6-carbon atoms containing aromatic ring, wherein the 5 or 6-carbon atoms containing ring is optionally substituted with one or more $C_{1-3}$-alkyl and/or wherein one or more of the ring forming carbon atoms are optionally replaced by —NH—, —N═, ═N—, —O— or —S—, A1 is N or $CR^{15}$, wherein $R^{15}$ is independently hydrogen, halogen $C_{1-3}$ alkyl, $C_{1-3}$ alkoxy or $NR^{15'}R^{15''}$, wherein $R^{15'}$ and $R^{15''}$ are independently $C_{1-3}$-alkyl, A2 is N or $CR^{16}$, wherein $R^{16}$ is independently hydrogen, halogen, $C_{1-3}$ alkyl, $C_{1-3}$ alkoxy or $NR^{16'}R^{16''}$, wherein $R^{16'}$ and $R^{16''}$ are independently $C_{1-3}$-alkyl, A3 is N or $CR^{17}$, wherein $R^{17}$ is independently hydrogen, halogen, $C_{1-3}$ alkyl, $C_{1-3}$ alkoxy or $NR^{15'}R^{15''}$, wherein $R^{15'}$ and $R^{15''}$ are independently $C_{1-3}$-alkyl, A4 is N or $CR^{18}$, wherein $R^{18}$ is independently hydrogen, halogen, $C_{1-3}$ alkyl, $C_{1-3}$ alkoxy or $NR^{15'}R^{15''}$, wherein $R^{15'}$ and $R^{15''}$ are independently $C_{1-3}$-alkyl.

9. The compound according to claim 1, wherein none, one or two of residues A1, A2, A3 and A4 is N.

10. The compound according to claim 1, wherein A1 is $CR^{15}$, A2 is $CR^{16}$, A3 is $CR^{17}$ and A4 is $CR^{18}$.

11. The compound according to claim 1, wherein $R^{19}$ is independently selected from the group consisting of $C_{6-10}$-aryl and 5- to 10-membered heteroaryl, wherein each $C_{6-10}$-aryl or 5- to 10-membered heteroaryl is optionally substituted with one or more substituent(s) independently selected from the group consisting of $C_{1-6}$-alkyl, $C_{3-10}$-cycloalkyl, 5- to 10-membered heterocyclyl, $C_{6-10}$-aryl, 5- to 10-membered heteroaryl, $C_{1-6}$-alkoxy, halogen, cyano, nitro, hydroxy, $NR^{20}R^{21}$, C(═O)$OR^{22}$ and C(═O)$NR^{23}R^{24}$, $R^{20}$ and $R^{21}$ are independently selected from the group consisting of hydrogen, $C_{1-6}$-alkyl, $C_{3-10}$-cycloalkyl and $C_{6-10}$-aryl or $R^{20}$ and $R^{21}$ together with the N atom to which they are attached form a saturated or unsaturated heterocyclic ring having 3 to 12 ring atoms, wherein 0, 1, 2, or 3 further ring atoms are selected from N, S and O;

wherein each $C_{1-6}$-alkyl, $C_{3-10}$-cycloalkyl or $C_{6-10}$-aryl or the heterocyclic ring formed by $R^{20}$ and $R^{21}$ together with the N atom to which they are attached is optionally substituted with one or more substituents independently selected from the group consisting of $C_{1-6}$-alkyl, $C_{3-10}$-cycloalkyl, 5- to 10-membered heterocyclyl, $C_{6-10}$-aryl, 5- to 10-membered heteroaryl, $C_{1-6}$-alkoxy, halogen, cyano, hydroxy, $NR^{20'}R^{21'}$, C(═O)$OR^{22'}$ and C(═O)$NR^{23'}R^{24''}$ $R^{22}$, $R^{23}$ and $R^{24}$ are independently selected from hydrogen and $C_{1-6}$-alkyl, $R^{20'}$, $R^{21'}$, $R^{22'}$, $R^{23'}$ and $R^{24'}$ are independently selected from hydrogen and $C_{1-6}$-alkyl.

12. The compound according to claim 1, wherein $R^{19}$ is independently selected from the group consisting of $C_{6-10}$-aryl and 5- to 10-membered heteroaryl, wherein each $C_{6-10}$-aryl or 5- to 10-membered heteroaryl is optionally substituted with one or more substituent(s) independently selected from the group consisting of $C_{1-6}$-alkyl, $C_{1-6}$-alkoxy, halogen, cyano, nitro and hydroxy.

13. The compound according to claim 1, wherein $R^{19}$ is $C_{6-10}$-aryl, wherein the $C_{6-10}$-aryl is optionally substituted with one or more substituent(s) independently selected from the group consisting of $C_{1-6}$-alkyl, halogen, cyano and nitro.

14. The compound according to claim 1, wherein $R^{19}$ is $C_{6-10}$-aryl, wherein the $C_{6-10}$-aryl is phenyl substituted with one, two or three substituents independently selected from the group consisting of fluoride, chloride and bromide.

15. The compound according to claim 1 being present in form of the(S)-enantiomer.

16. Process for preparing the compound according to Formula (I) comprising the step of reacting a compound of Formula (A)

Formula (A)

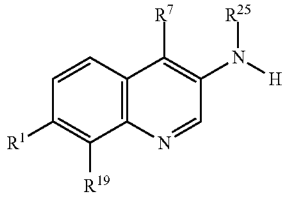

with a compound of Formula (B)

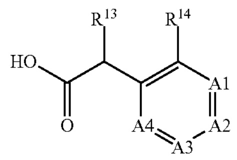

wherein $R^1$, $R^7$, $R^{13}$, $R^{14}$, A1, A2, A3, A4, $R^{19}$ and $R^{25}$ are defined as in claim 1, to obtain the compound according to Formula (I).

17. A Veterinary composition comprising a compound according to Formula (I) according to claim 1, and one or more physiologically acceptable excipient(s).

18. A Veterinary composition according to claim 17, wherein the one or more physiologically acceptable excipient(s) are selected from carriers, fillers, flavours, binders, antioxidants, buffers, sugar components, lubricants, surfactants, stabilizers, flow agents, disintegration agents and preservatives and mixtures thereof.

19. A method of treating a disorder or disease caused by helminths comprising administering the veterinary composition of claim 17 to an animal in need thereof.

20. The method of claim 19 wherein the disease is the heartworm disease.

21. The method of claim 19 wherein the helminths are *Dirofilaria immitis*.

* * * * *